(12) United States Patent
Stubenrauch et al.

(10) Patent No.: US 12,291,561 B2
(45) Date of Patent: May 6, 2025

(54) ANTIGEN BINDING RECEPTORS SPECIFIC FOR MUTATED Fc DOMAINS

(71) Applicant: Hoffmann-La Roche Inc., Little Falls, NJ (US)

(72) Inventors: Kay-Gunnar Stubenrauch, Penzberg (DE); Ekkehard Moessner, Schlieren (CH); Christian Klein, Schlieren (CH); Diana Darowski, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 182 days.

(21) Appl. No.: 18/312,339

(22) Filed: May 4, 2023

(65) Prior Publication Data

US 2023/0390338 A1    Dec. 7, 2023

Related U.S. Application Data

(60) Division of application No. 16/576,546, filed on Sep. 19, 2019, now Pat. No. 11,679,127, which is a continuation of application No. PCT/EP2018/057566, filed on Mar. 26, 2018.

(30) Foreign Application Priority Data

Mar. 27, 2017 (EP) ..................... 17163090

(51) Int. Cl.
| | |
|---|---|
| A61K 35/17 | (2015.01) |
| A61K 39/00 | (2006.01) |
| C07K 14/705 | (2006.01) |
| C07K 14/71 | (2006.01) |
| C07K 14/725 | (2006.01) |
| C07K 16/28 | (2006.01) |
| C07K 16/30 | (2006.01) |
| C07K 16/40 | (2006.01) |
| A61K 38/00 | (2006.01) |

(52) U.S. Cl.
CPC .... *C07K 14/70517* (2013.01); *A61K 39/4611* (2023.05); *A61K 39/464424* (2023.05); *A61K 39/464482* (2023.05); *C07K 14/7051* (2013.01); *C07K 14/70521* (2013.01); *C07K 14/70578* (2013.01); *C07K 14/71* (2013.01); *C07K 16/283* (2013.01); *C07K 16/2887* (2013.01); *C07K 16/3007* (2013.01); *C07K 16/40* (2013.01); *A61K 38/00* (2013.01); *A61K 2239/48* (2023.05); *A61K 2239/50* (2023.05); *C07K 2317/32* (2013.01); *C07K 2317/565* (2013.01); *C07K 2317/732* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 5,571,894 | A | 11/1996 | Wels et al. |
| 5,580,859 | A | 12/1996 | Felgner et al. |
| 5,587,458 | A | 12/1996 | King et al. |
| 5,589,466 | A | 12/1996 | Felgner et al. |
| 5,750,373 | A | 5/1998 | Garrard et al. |
| 5,821,337 | A | 10/1998 | Carter et al. |
| 6,248,516 | B1 | 6/2001 | Winter et al. |
| 6,737,056 | B1 | 5/2004 | Presta |
| 7,332,581 | B2 | 2/2008 | Presta |
| 7,785,903 | B2 | 8/2010 | Bond et al. |
| 7,985,840 | B2 | 7/2011 | Fuh et al. |
| 8,679,490 | B2 | 3/2014 | Dennis et al. |
| 2005/0079574 | A1 | 4/2005 | Bond |
| 2007/0117126 | A1 | 5/2007 | Sidhu et al. |

(Continued)

FOREIGN PATENT DOCUMENTS

| | | |
|---|---|---|
| CN | 106163547 A | 11/2016 |
| EP | 0404097 B1 | 9/1996 |

(Continued)

OTHER PUBLICATIONS

Bazan et al., "Phage display -- a powerful technique for immunotherapy: 1. Introduction and potential of therapeutic applications," Hum Vaccin Immunother. 8(12):1817-28 (2012).

(Continued)

*Primary Examiner* — Sharon X Wen
(74) *Attorney, Agent, or Firm* — Clark & Elbing LLP; Thomas J. Takara

(57) ABSTRACT

The present invention generally relates to antigen binding receptors capable of specific binding to mutated Fc domains with reduced Fc receptor binding and T cells expressing these antigen binding receptors. More precisely, the present invention relates to T cells, transfected/transduced with an antigen binding receptor which is recruited by specifically binding to/interacting with the mutated Fc domain of therapeutic antibodies. Furthermore, the invention relates to a kit comprising the T cells of the invention and/or nucleic acid molecules, vectors expressing antigen binding receptors of the present invention and (a) tumor targeting antibody/antibodies comprising a mutated Fc domain. The invention also provides the production and use of T cells in a method for the treatment of particular diseases in conjunction with tumor-specific antibodies as well as pharmaceutical compositions/medicaments comprising T cells and/or therapeutic antibodies, wherein T cells are to be administered in combination with therapeutic-tumor targeting antibody/antibodies comprising a mutated Fc domain with reduced Fc receptor binding.

28 Claims, 29 Drawing Sheets

Specification includes a Sequence Listing.

(56) References Cited

U.S. PATENT DOCUMENTS

| | | |
|---|---|---|
| 2007/0237764 A1 | 10/2007 | Birtalan et al. |
| 2007/0292936 A1 | 12/2007 | Barthelemy et al. |
| 2009/0002360 A1 | 1/2009 | Chen et al. |
| 2011/0280894 A1 | 11/2011 | Krackhardt et al. |
| 2015/0139943 A1 | 5/2015 | Campana et al. |
| 2016/0068613 A1 | 3/2016 | Regula et al. |

FOREIGN PATENT DOCUMENTS

| | | |
|---|---|---|
| WO | WO-93/01161 A1 | 1/1993 |
| WO | WO-93/16185 A2 | 8/1993 |
| WO | WO-94/20627 A1 | 9/1994 |
| WO | WO-94/29469 A2 | 12/1994 |
| WO | WO-97/00957 A1 | 1/1997 |
| WO | WO-2004/056312 A2 | 7/2004 |
| WO | WO-2005/113595 A3 | 12/2005 |
| WO | WO-2006/082515 A2 | 8/2006 |
| WO | WO-2012/130831 A1 | 10/2012 |
| WO | WO-2014/177460 A1 | 11/2014 |
| WO | WO-2015/142675 A2 | 9/2015 |
| WO | WO-2015/179833 A1 | 11/2015 |
| WO | WO-2016/040441 A1 | 3/2016 |
| WO | WO-2016/090369 A1 | 6/2016 |
| WO | WO-2017/072210 A1 | 5/2017 |
| WO | WO-2018/177967 A1 | 10/2018 |

OTHER PUBLICATIONS

Brunger et al., "Scaffold-mediated lentiviral transduction for functional tissue engineering of cartilage," Proc Natl Acad Sci U S A. 111(9):E798-E806 (2014).
Brüggemann et al., "Comparison of the Effector Functions of Human Immunoglobulins Using a Matched Set of Chimeric Antibodies," J Exp Med. 166(5):1351-61 (1987).
Anderson, "Human Gene Therapy," Science. 256(5058):808-13 (1992).
Campeau et al., "A Versatile Viral System for Expression and Depletion of Proteins in Mammalian Cells," Plos One. 4(8):e6529 (2009).
Cao et al., "Design of Switchable Chimeric Antigen Receptor T Cells Targeting Breast Cancer," Angew Chem Int Ed Engl. 55(26):7520-24 (2016).
Cartellieri et al. (Journal of Biomedicine and Biotechnology, vol. 2010, Article ID 956304, 13 pages).
Chang et al., "E1B-55 kD-Deleted Adenovirus Driven by Murine Oct-3/4 Promoter for Bladder Cancer Therapy," Mole Ther. 9(S1):S367 (2004).
Chen et al., "Retroviral Transduction of Protein Kinase C-gamma into Tumor Specific T Cells Allows Antigen-Independent Long-Term Growth in IL-2 with Retention of Functional Specificity In Vitro and Ability to Mediate Tumor Therapy In Vivo 1," J Immunol. 153(8):3630-38 (1994).
Cherf et al., "Applications of yeast surface display for protein engineering," Methods Mol Bio. 1319:155-175 (2015).
Chicaybam et al. (International Reviews of Immunology, 2011, 30:294-311).
Chothia et al., "Canonical structures for the hypervariable regions of immunoglobulins," J Mol Biol. 196(4):901-17 (1987) (18 pages).
Chothia et al., "Conformations of immunoglobulin hypervariable regions," Nature. 342(6252):877-83 (1989).
Chu et al., "Genetic Modification of T Cells Redirected toward CS1 Enhances Eradication of Myeloma Cells," Clin Cancer Res. 20(15):3989-4000 (2014) (13 pages).
Clackson et al., "Making antibody fragments using phage display libraries," Nature. 352(6336):624-8 (1991).
Clay et al., "Efficient transfer of a tumor antigen-reactive TCR to human peripheral blood lymphocytes confers anti-tumor reactivity," J Immunol. 163(1):507-13 (1999).
Clynes et al., "Fc receptors are required in passive and active immunity to melanoma," Proc Natl Acad Sci U S A. 95(2):652-6 (1998).
Cochlovius et al., "Stable expression of a retrovirally transferred adhesion molecule in a human melanoma-specific cytotoxic T lymphocyte clone," Cancer Immunol Immunother. 46(1):61-6 (1998).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
De Witte et al., "Requirements for Effective Antitumor Responses of TCR Transduced T Cells," J Immunol. 181(7):5128-5136 (2008).
Desiderio, S., et al., "Rearrangement of Exogenous Immunoglobulin Vh and DJh Gene Segments after Retroviral Transduction into Immature Lymphoid Cell Lines" J Exp Med. 167(2):372-388 (1988).
Dudley et al., "Adoptive Cell Therapy for Patients With Metastatic Melanoma: Evaluation of Intensive Myeloablative Chemoradiation Preparative Regimens," J Clin Oncol. 26(32):5233-5239 (2008).
Dudley et al., "Generation of Tumor-Infiltrating Lymphocyte Cultures for Use in Adoptive Transfer Therapy for Melanoma Patients," J Immunother. 26(4):332-342 (2003).
Duewell et al., "RIG-I-like helicases induce immunogenic cell death of pancreatic cancer cells and sensitize tumors toward killing by CD8+ T cells," Cell Death Differ. 21(12):1825-37 (2014).
Duewell et al., Erratum: "RIG-I-like helicases induce immunogenic cell death of pancreatic cancer cells and sensitize tumors toward killing by CD8+ T cells," Cell Death Differ. 21(12):161 (2014).
Ekkens et al., "Th1 and Th2 Cells Help CD8 T-Cell Responses" Infect Immun. 75(5):2291-6 (2007).
Engels et al., "Retroviral vectors for high-level transgene expression in T lymphocytes," Hum Gene Ther. 14(12):1155-68 (2003).
Fellouse et al., "Synthetic antibodies from a four-amino-acid code: A dominant role for tyrosine in antigen recognition," Proc Natl Acad Sci U S A. 101(34):12467-72 (2004).
Frenzel et al., "Phage display-derived human antibodies in clinical development and therapy," MABS. 8(7):1177-1194 (2016).
Gallardo et al., "Recombinant Retroviruses Pseudotyped With the Vesicular Stomatitis Virus G Glycoprotein Mediate Both Stable Gene Transfer and Pseudotransduction in Human Peripheral Blood Lymphocytes," Blood. 90(3):952-957 (1997).
Gazzano-Santoro et al., "A non-radioactive complement-dependent cytotoxicity assay for anti-CD20 monoclonal antibody," J Immunol Methods. 202(2):163-71 (1997).
Ge et al., "Homeostatic T cell proliferation in a T cell-dendritic cell coculture system," Proc Natl Acad Sci U S A. 99(5):2983-2988 (2002).
Gerdes et al., "Green flourescent protein: application in cell biology," Febs Lett. 389(1):44-47 (1996).
Giacomin et al., "Expression of a PAL1 promoter luciferase gene fusion in Arabidopsis thaliana in response to infection by phytopathogenic bacteria," Plant Sci. 116(1):59-72 (1996).
Gilham et al., "Primary Polyclonal Human T Lymphocytes Targeted to Carcino-Embryonic Antigens and Neural Cell Adhesion Molecule Tumor Antigens by CD3zeta-Based Chimeric Immune Receptors," J Immunother. 25(2):139-151 (2002).
Giordano et al., "Intracoronary gene transfer of fibroblast growth factor-5 increases blood flow and contractile function in an ischemic region of the heart," Nat Med. 2(5):534-539 (1996).
Gorchakov et al., "Chimeric antigen receptors for adoptive T-cell therapy," Russian Journal of Biotherapy. 15(1):25-26 (2016) (1 page) (English Translation).
Grevys et al., "Fc Engineering of Human IgG1 for Altered Binding to the Neonatal Fc Receptor Affects Fc Effector Functions," J Immunol. 194(11):5497-5508 (2015).
Griffiths et al., "Human anti-self antibodies with high specificity from phage display libraries," EMBO J. 12(2):725-34 (1993).
Grupp et al., "Chimeric Antigen Receptor-Modified T Cells for Acute Lymphoid Leukemia," New England J Med. 368(16):1509-1518 (2013).
Hanes et al., "In vitro selection and evolution of functional proteins by using ribosome display," Proc Natl Acad Sci USA. 94(10):4937-42 (1997).

(56) References Cited

OTHER PUBLICATIONS

Hartman et al., "Two dominant-acting selectable markers for gene transfer studies in mammalian cells," Proc Natl Acad Sci U S A. 85(21):8047-51 (1988).
He et al., "Antibody-ribosome-mRNA (ARM) complexes as efficient selection particles for in vitro display and evolution of antibody combining sites," Nucleic Acids Res. 25(24):5132-5134 (1997).
Heeley et al., "Mutations Flanking the Polyglutamine Repeat in the Modulatory Domain of Rat Glucocorticoid Receptor Lead to an Increase in Affinity for Hormone," Endocr Res. 28(3):217-229 (2002).
Heemskerk et al., "Inhibition of T-Cell nad Promotion of Natural Killer Cell Development by the Dominant Negative Helix Loop Helix Factor Id3," J Exp Med. 186(9):1597-1602 (1997).
Hellström et al., "Antitumor effects of L6, an IgG2a antibody that reacts with most human carcinomas," Proc Natl Acad Sci USA. 83(18):7059-63 (1986).
Herrera-Estrella et al., "Chimeric genes as dominant selectable markers in plant cells," Embo J. 2(6):987-995 (1983).
Holliger et al., "Diabodies': Small bivalent and bispecific antibody fragments," Proc Natl Acad Sci USA. 90(14):6444-8 (1993).
Hoogenboom et al., "By-passing immunisation. Human antibodies from synthetic repertoires of germline VH gene segments rearranged in vitro," J Mol Biol. 227(2):381-388 (1992).
Hoogenboom et al., "Overview of Antibody Phage-Display Technology and Its Applications," Methods Mol Biol. 178:1-37 (2002).
Hotta et al., "Isolation of human iPS cells using EOS lentiviral vectors to select for pluripotency," Nat Methods. 6(5):370-378 (2009).
Hu et al., "Fibulin-3 Is Uniquely Upregulated in Malignant Gliomas and Promotes Tumor Cell Motility and Invasion," Mol Cancer Res. 7(11):1756-1770 (2009).
Hudson et al., "Engineered antibodies," Nat Med. 9(1):129-134 (2003).
Isner et al., "Clinical evidence of angiogenesis after arterial gene transfer of phVEGF165 in patient with ischaemic limb," Lancet. 348(9024):370-374 (1996).
Jefferson et al., "GUS fusions: beta-glucuronidase as a sensitive and versatile gene fusion marker in higher plants," Embo J. 6(13):3901-7 (1987).
Kang et al., "Simultaneous Profiling of 194 Distinct Receptor Transcripts in Human Cells," SCI Signal. 6(297):rs13 (2013).
Kantoff et al., "Correction of adenosine deaminase deficiency in cultured human T and B celss by retrovirus-mediated gene transfer," Proc Natl Acad Sci U S A . 83(17):6563-67 (1986).
Kasid et al., "Human gene transfer: Characterization of human tumor-infiltrating lymphocytes as vehicles for retroviral-mediated gene transfer in man," Proc Natl Acad Sci USA. 87(1):473-7 (1990).
Keiler et al., "C-terminal specific protein degradation: Activity and substrate specificity of the Tsp protease," Protein Sci. 4(8):1507-15 (1995).
Kim et al., "Redirection of Genetically Engineered CAR-T Cells Using Bifunctional Small Molecules," J Am Chem Soc. 137(8):2832-2835 (2015).
Kindt et al., "Antigens and Antibodies," Chapter 4, Kuby Immunology. 91 (2007).
Klein et al., "The use of CrossMAb technology for the generation of bi- and multispecific antibodies," MAbs. 8(6):1010-20 (2016).
Kochenderfer et al., "Chemotherapy-Refractory Diffuse Large B-Cell Lymphoma and Indolent B-Cell Malignancies Can Be Effectively Treated ith Autologous T Cells Expressin an Anti-CD19 Chimeric Antigen Receptor," J Clin Oncol. 33(6):540-9 (2015).
Krutzik et al., "Chapter 9: Phospho Flow Cytometry Methods for the Analysis of Kinase Signaling in Cell Lines and Primary Human Blood Samples," Methods Mol Biol. 699:179-202 (2011).
Laver et al., "Epitopes on Protein Antigens: Misconceptions and Realities," Cell. 61(4):553-6 (1990).

Lazebnik et al., "Determination and Functional Analysis of the Consensus Binding Site for TFII-I Family Member BEN, Implicated in William-Bueren Syndrome," J Biol Chem. 283(17):11078-82 (2008).
Lee et al., "Bivalent antibody phage display mimics natural immunoglobulin," J Immunol Methods. 284(1-2):119-32 (2004).
Lee et al., "High-affinity human antibodies from phage-displayed synthetic fab libraries with a single framework scaffold", J Mol Biol. 340(5):1073-1093 (2004).
Lemoine et al., "Efficient transduction and selection of human T-lymphocytes with bicistronic Thy1/HSV1-TK retroviral vector produced by a human packaging cell line," J Gene Med. 6(4):374-86 (2004).
Lerner, "Combinatorial antibody libraries: new advances, new immunological insights," Nat Rev Immunol. 16(8):498-508 (2016).
Liljeblad et al., "Analysis of agalacto-lgG in rheumatoid arthritis using surface plasmon resonance," Glycoconj J. 17(5):323-9 (2000).
Lois et al., "Germline transmission and tissue-specific expression of transgenes delivered by lentiviral vectors," Science. 295(5556):868-72 (2002).
Ma et al., "Versatile strategy for controlling the specificity and activity of engineered T cells," Proc Natl Acad Sci USA. 113(4):E450-E458 (2016).
Mack et al., "A small biospecific antibody construct expressed as a functional single-chain molecule with high tumor cell cytotoxicity," Proc Natl Acad Sci U S A. 92(15):7021-25 (1995).
Marks et al., "By-passing immunization, human antibodies from V-gene libraries displayed on phage," J Mol Biol. 222(3): 581-97 (1991).
Marks et al., "Selection of Human Antibodies from Phage Display Libraries," Methods Mol Biol. 248:161-176 (2004).
Marr et al., "Neprilysin Regulates Amyloid Beta Peptide Levels," J Mol Neurosci. 22(1-2):5-11 (2004).
Marsch et al., "The pIC plasmid and phage vectors with versatile cloning sites for recombinant selection by insertional inactivation," Gene. 32(3):481-85 (1984).
Maude et al., "Chimeric Antigen Receptor T Cells for Sustained Remissions in Leukemia," N Engl J Med. 371(16):1507-17 (2014).
Mccafferty et al., "Phage antibodies: filamentous phage displaying antibody variable domains," Nature. 348(6301):552-4 (1990).
Miyoshi et al., "Development of a self-inactivating lentivirus vector," J Virol. 72(10):8150-7 (1998).
Morgan et al., "High efficiency TCR gene transfer into primary human lymphocytes affords avid recognition of melanoma tumor antigen glycoprotein 100 and does not alter the recognition of autologous melanoma antigens," J Immunol. 171(6):3287-95 (2003).
Morozova et al., "Prospectives of T-cells genetic programming in adoptive immunotherapy of malignancies," Sechenov Medical Journal. 3(25):23-28 (2016) (English Translation).
Muhlhauser et al., "VEGF165 Expressed by a Replication-Deficient Recombinant Adenovirus Vector Induces Angiogenesis In Vivo," Circ Res. 77(6):1077-86 (1995).
Mullen et al., "Molecular Analysis of T Lymphocyte-Directed Gene Therapy for Adenosine Deaminase Deficiency: Long-Term Expression in Vivo of Genes Introduced with a Retroviral Vector," Hum Gene Ther. 7(9):1123-29 (1996).
Nabel et al., "In Vivo Gene Transfer: A Biological Tool," Ann NY Acad Sci. 811:289-292 (1997).
Neil et al., "Transduction and rearrangement of the myc gene by feline leukaemia virus in naturally occurring T-cell leukaemias," Nature. 308(5962):814-20 (1984).
Onodera et al., "Successful Peripheral T-Lymphocyte-Directed Gene Transfer for a Patient With Severe Combined Immune Deficiency Caused by Adenosine Deaminase," Blood. 91(1):30-6 (1998).
Pluckthun et al., "Chapter 11: Antibodies from Escherichia coli," The Pharmacology of Monoclonal Antibodies. 113:269-315 (1994).
Qin et al., "Systematic Comparison of Constitutive Promoters and the Doxycycline-Inducible Promoter," Plos One. 5(5):e10611 (2010).
Raissi et al., "Sema4D localizes to synapses and regulates GABAergic synapse development as a membrane-bound molecule in the mammalian hippocampus," Mol Cell Neurosci. 57:23-32 (2013).
Raum et al., "Anti-self antibodies selected from a human IgD heavy chain repertoire: a novel approach to generate therapeutic human

(56) References Cited

OTHER PUBLICATIONS antibodies against tumor-associated differentiation antigens," Cancer Immunol Immunother. 50(3):141-50 (2001).
Reiss et al., "A family of binary gene vectors with low inter-transformant variation," Plant Physiol Life Sci Adv. 13:143-49 (1994).
Ritz-Laser et al., "Ectopic expression of the beta-cell specific trnscription factor Pdx1 inhibits glucagon gene transcription," Diabetologia. 46(6):810-21 (2003).
Rodgers et al., "Switch-mediated activation and retargeting of CAR-T cells for B-cell malignancies," Proc Natl Acad Sci U S A. 113(4):E459-E468 (2016).
Rosenberg et al., "Adoptive cell transfer as personalized immunotherapy for human cancer," Science. 348(6230):62-8 (2015).
Schaper et al., "Molecular Mechanisms of Coronary Collateral Vessel Growth," Circ Res. 79(5):911-19 (1996).
Schlothauer et al., "Novel Human IgG1 and lgG4 Fc-engineered Antibodies with Completely Abolished Immune Effector Functions," Protein Engineering, Design & Selection. 29(10):457-466 (2016).
Sela, "Antigenicity: Some Molecular Aspects," Science. 166(3911):1365-74 (1969).
Shields et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," J Biol Chem. 276(9):6591-604 (2001).
Sidhu et al., "Phage-displayed antibody libraries of synthetic heavy chain complementarity determining regions," J Mol Biol. 338(2):299-310 (2004).
Solomon et al., "Frequent truncating mutations of STAG2 in bladder cancer," Nat Genet. 45(12):1428-30 (2013).
Srikantha et al., "The Sea Pansy Renilla reinformis Luciferase Serves as a Sensitive Bioluminescent Reporter for Differential Gene Expression in Candida albicans," J Bacteriol. 178(1):121-29 (1996).
Sun et al., "Construction of Retroviral Vectors Carrying Human CD3gamma cDNA and Reconstitution of CD3gamma Expression and T Cell Receptor Surface Expression and Function in a CD3gamma-Deficient Mutant T Cell Line," Hum Gene Ther. 8(9):1041-48 (1997).
Tamada et al., "Redirecting Gene-Modified T Cells toward Various Cancer Types Using Tagged Antibodies," Clin Cancer Res. 18(23):6436-45 (2012).
Tamura et al., "Blasticidin S Deaminase Gene (BSD): a New Selection Marker Gene for Transformation of *Arabidopsis thaliana* and *Nicotiana tabacum*," Biosci Biotechnol Biochem. 59(12):2336-38 (1995).
Taylor et al., "Reconstitution of T Cell Receptor Signaling in ZAP-70-deficient Cells by Retroviral Transduction of the ZAP-70 Gene," J Exp Med. 184(5):2031-36 (1996).
Thakur et al., "Real time monitoring of the cell viability during treatment with tumor-targeted toxins and saponins using impedance measurement," Biosens Bioelectron. 35(1):503-6 (2012).
Tiberghien et al., "Ganciclovir Treatment of Herpes Simplex Thymidine Kinase-Transduced Primary T Lymphocytes: An Approach for Specific In Vivo Donor T-Cell Depletion After Bone Marrow Transplantation?," Blood. 84(4):1333-41 (1994).
Verma et al., "Gene therapy—promises, problems and prospects," Nature 389(6648): 239-42 (1997).
Verma et al., "Gene transfer into human umbilical cord blood-derived CD34+ cells by particle-mediated gene transfer," Gene Ther. 5(5):692-9 (1998).
Verzeletti et al., "Herpes simplex virus thymidine kinase gene transfer for controlled graft-versus-host disease and graft-versus-leukemia: clinical follow-up and improved new vectors," Hum Gene Ther. 9(15):2243-51 (1998).
Vieillard et al., "Interferon β transduction of peripheral blood lymphocytes from HIV-infected donors increases Th1-type cytokine production and improves the proliferative response to recall antigens," Proc Natl Acad Sci U S A. 94(21):11595-11600 (1997).
Wang et al., "A time- and matrix-dependent TGFBR3-JUND-KRT5 regulatory circuit in single breast epithelial cells and basal-like premalignancies," Nat Cell Biol. 16(4):345-56 (2014).
Wang et al., "Second-generation adenovirus vectors," Nat Med. 2(6):714-16 (1996).
Weijtens et al., "A retroviral vector system 'STITCH' in combination with an optimized single chain antibody chimeric receptor gene structure allows efficient gene transduction and expression in human T lymphocytes," Gene Ther. 5(9):1195-1203 (1998).
Winter et al., "Making Antibodies by Phage Display Technology," Annu Rev Immunol. 12:433-55 (1994).
Wu et al., "Improvement of Gene Transduction Efficiency in T Lymphocytes Using Retroviral Vectors," Hum Gene Ther. 10(6):977-82 (1999).
Wu et al., "Isolation and characterization of the murine Nanog gene promoter," Cell Res. 15(5):317-24 (2005).
Xie et al., "Akt isoforms differentially protect against stroke-induced neuronal injury by regulating mTOR activities," J Cereb Blood F Metab. 33(12):1875-85 (2013).
Yarilin, Chapter 3: Molecular and cellular basis of adaptive immunity. *Immunology Basics: Manual*. Medicina, (1999) (12 pages).
Zhao et al., "Chapter 5: Yeast Display of Engineered Antibody Domains," *Methods Mol Biol*. 899:73-84 (2012).
Zhao et al., "High-efficiency transfection of primary human and mouse T lymphocytes using RNA electroporation," Mol Ther. 13(1):151-9 (2006).
Zhao et al., "Phage antibody display libraries: a powerful antibody discovery platform for immunotherapy," Crit Rev Biotechnol. 36(2):276-89 (2016).
Zhao et al., "Primary human lymphocytes transduced with NY-ESO-1 antigen-specific TCR genes recognize and kill diverse human tumor cell lines," J Immunol. 174(7):4415-23 (2005).
English Translation of Office Action for Russian Patent Application No. 2019133202, dated Jul. 19, 2021 (10 pages).
International Preliminary Report on Patentability for International Application No. PCT/EP2018/057566, issued Oct. 1, 2019 (10 pages).
International Search Report for International Application No. PCT/EP2018/057566, mailed on May 11, 2018 (7 pages).
Office Action for Chinese Patent Application No. 201880034376.0 dated Feb. 28, 2023, including English language summary of the search report (7 pages).
Kudo et al., "T Lymphocytes Expressing a CD16 Signaling Receptor Exert Antibody-Dependent Cancer Cell Killing," Cancer Res., 74(1):93-103 (2014).

ATM = anchoring transmembrane domain
CSD = co-stimulatory signaling domain
SSD = stimulatory signaling domain

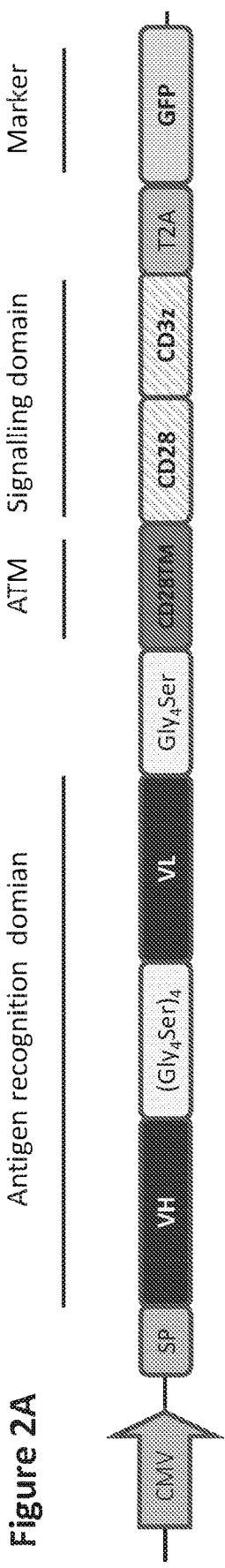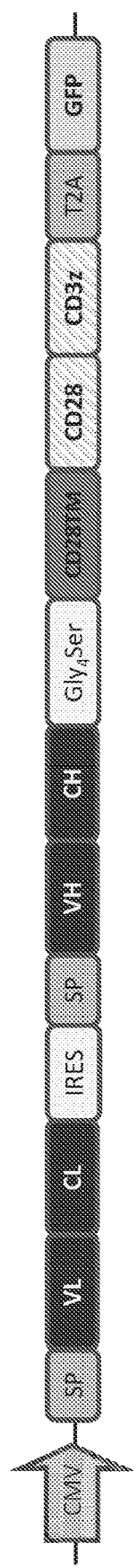
Figure 2A
Figure 2B
CMV = Cytomegalovirus promotor
SP = Signal peptide
VH = variable heavy chain
VL = variable light chain
TM = transmembrane domain
IRES = internal ribosomal entry site

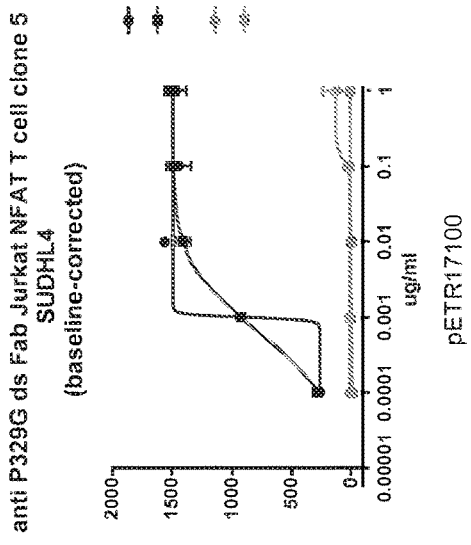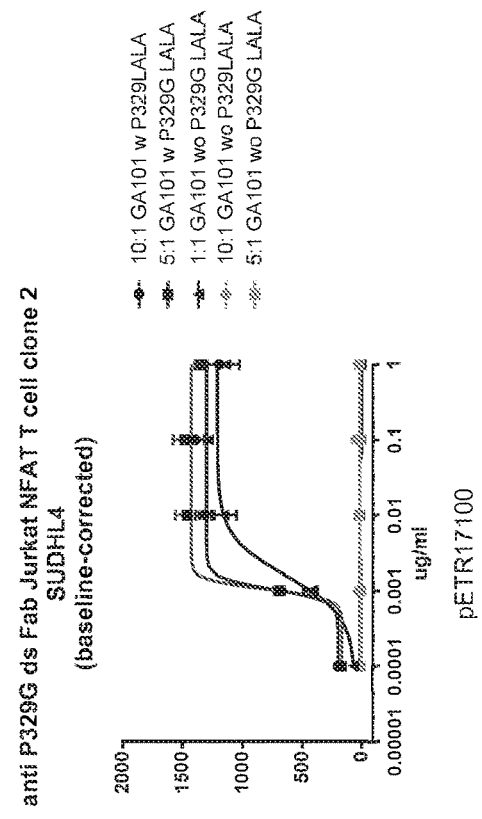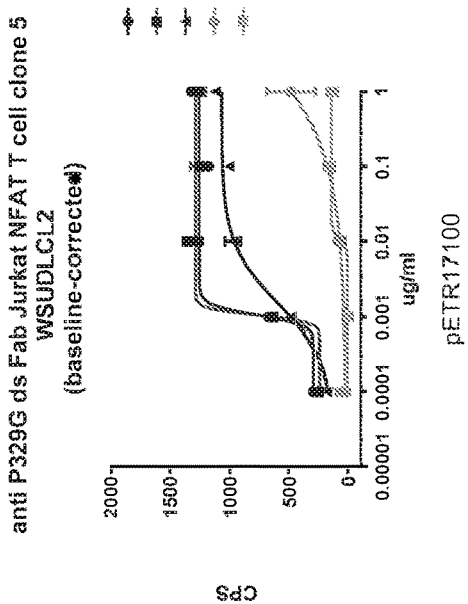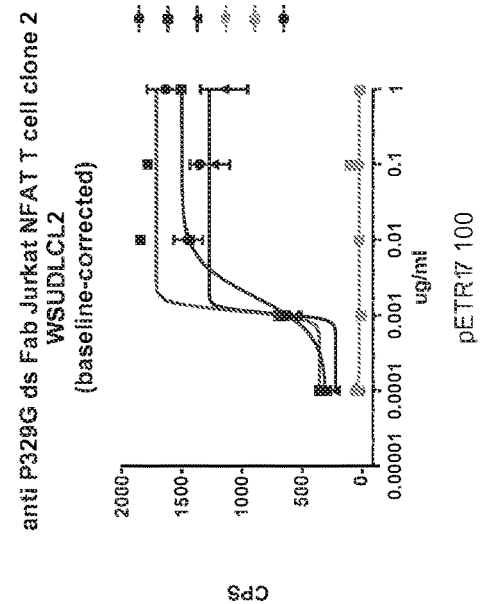

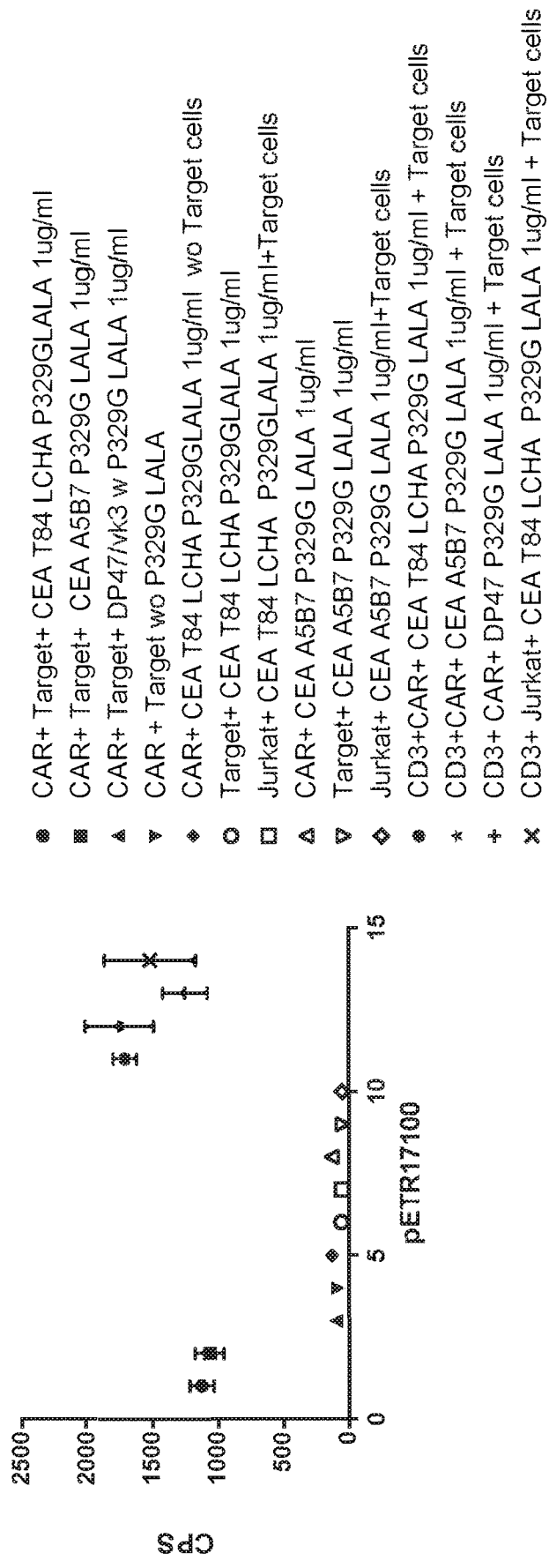

SEQUENCE LISTING

```
Sequence total quantity: 130
SEQ ID NO: 1              moltype = AA  length = 5
FEATURE                   Location/Qualifiers
source                    1..5
                          mol_type = protein
                          note = Anti-P329G CDR H1 Kabat
                          organism = synthetic construct
SEQUENCE: 1
RYWMN                                                                   5

SEQ ID NO: 2              moltype = AA  length = 17
FEATURE                   Location/Qualifiers
source                    1..17
                          mol_type = protein
                          note = Anti-P329G CDR H2 Kabat
                          organism = synthetic construct
SEQUENCE: 2
EITPDSSTIN YTPSLKD                                                      17

SEQ ID NO: 3              moltype = AA  length = 10
FEATURE                   Location/Qualifiers
source                    1..10
                          mol_type = protein
                          note = Anti-P329G CDR H3 Kabat
                          organism = synthetic construct
SEQUENCE: 3
PYDYGAWFAS                                                              10

SEQ ID NO: 4              moltype = AA  length = 14
FEATURE                   Location/Qualifiers
source                    1..14
                          mol_type = protein
                          note = Anti-P329G CDR L1 Kabat
                          organism = synthetic construct
SEQUENCE: 4
RSSTGAVTTS NYAN                                                         14

SEQ ID NO: 5              moltype = AA  length = 7
FEATURE                   Location/Qualifiers
```

```
source                  1..7
                        mol_type = protein
                        note = Anti-P329G CDR L2 Kabat
                        organism = synthetic construct
SEQUENCE: 5
GTNKRAP                                                                         7

SEQ ID NO: 6            moltype = AA  length = 9
FEATURE                 Location/Qualifiers
source                  1..9
                        mol_type = protein
                        note = Anti-P329G CDR L3 Kabat
                        organism = synthetic construct
SEQUENCE: 6
ALWYSNHWV                                                                       9

SEQ ID NO: 7            moltype = AA  length = 433
FEATURE                 Location/Qualifiers
source                  1..433
                        mol_type = protein
                        note = Anti-P329G-ds-scFv-CD28ATM-CD28CSD-CD3zSSD fusion
                         pETR17096
                        organism = synthetic construct
SEQUENCE: 7
EVKLLESGGG LVQPGGSLKL SCAASGFDFS RYWMNWVRQA PGKCLEWIGE ITPDSSTINY          60
TPSLKDKFII SRDNAKNTLY LQMIKVRSED TALYYCVRPY DYGAWFASWG QGTLVTVSAG          120
GGGSGGGGSG GGGSGGGGSQ AVVTQESALT TSPGETVTLT CRSSTGAVTT SNYANWVQEK          180
PDHLFTGLIG GTNKRAPGVP ARFSGSLIGD KAALTITGAQ TEDEAIYFCA LWYSNHWVFG          240
CGTKLTVLGG GGSFWVLVVV GGVLACYSLL VTVAFIIFWV RSKRSRLLHS DYMNMTPRRP          300
GPTRKHYQPY APPRDFAAYR SRVKFSRSAD APAYQQGQNQ LYNELNLGRR EEYDVLDKRR          360
GRDPEMGGKP RRKNPQEGLY NELQKDKMAE AYSEIGMKGE RRRGKGHDGL YQGLSTATKD          420
TYDALHMQAL PPR                                                            433

SEQ ID NO: 8            moltype = AA  length = 119
FEATURE                 Location/Qualifiers
source                  1..119
                        mol_type = protein
                        note = Anti-P329G-ds VH
                        organism = synthetic construct
SEQUENCE: 8
EVKLLESGGG LVQPGGSLKL SCAASGFDFS RYWMNWVRQA PGKCLEWIGE ITPDSSTINY          60
TPSLKDKFII SRDNAKNTLY LQMIKVRSED TALYYCVRPY DYGAWFASWG QGTLVTVSA           119

SEQ ID NO: 9            moltype = AA  length = 109
FEATURE                 Location/Qualifiers
source                  1..109
                        mol_type = protein
                        note = Anti-P329G-ds VL
                        organism = synthetic construct
SEQUENCE: 9
QAVVTQESAL TTSPGETVTL TCRSSTGAVT TSNYANWVQE KPDHLFTGLI GGTNKRAPGV          60
PARFSGSLIG DKAALTITGA QTEDEAIYFC ALWYSNHWVF GCGTKLTVL                     109

SEQ ID NO: 10           moltype = AA  length = 248
FEATURE                 Location/Qualifiers
source                  1..248
                        mol_type = protein
                        note = Anti-P329G-ds-scFv
                        organism = synthetic construct
SEQUENCE: 10
EVKLLESGGG LVQPGGSLKL SCAASGFDFS RYWMNWVRQA PGKCLEWIGE ITPDSSTINY          60
TPSLKDKFII SRDNAKNTLY LQMIKVRSED TALYYCVRPY DYGAWFASWG QGTLVTVSAG          120
GGGSGGGGSG GGGSGGGGSQ AVVTQESALT TSPGETVTLT CRSSTGAVTT SNYANWVQEK          180
PDHLFTGLIG GTNKRAPGVP ARFSGSLIGD KAALTITGAQ TEDEAIYFCA LWYSNHWVFG          240
CGTKLTVL                                                                  248

SEQ ID NO: 11           moltype = AA  length = 27
FEATURE                 Location/Qualifiers
source                  1..27
                        mol_type = protein
                        note = CD28ATM
                        organism = synthetic construct
SEQUENCE: 11
FWVLVVVGGV LACYSLLVTV AFIIFWV                                             27

SEQ ID NO: 12           moltype = AA  length = 41
FEATURE                 Location/Qualifiers
source                  1..41
                        mol_type = protein
```

```
                        note = CD28CSD
                        organism = synthetic construct
SEQUENCE: 12
RSKRSRLLHS DYMNMTPRRP GPTRKHYQPY APPRDFAAYR S                      41

SEQ ID NO: 13           moltype = AA   length = 112
FEATURE                 Location/Qualifiers
source                  1..112
                        mol_type = protein
                        note = CD3zSSD
                        organism = synthetic construct
SEQUENCE: 13
RVKFSRSADA PAYQQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR          112

SEQ ID NO: 14           moltype = AA   length = 180
FEATURE                 Location/Qualifiers
source                  1..180
                        mol_type = protein
                        note = CD28ATM-CD28-CD3z
                        organism = synthetic construct
SEQUENCE: 14
FWVLVVVGGV LACYSLLVTV AFIIFWVRSK RSRLLHSDYM NMTPRRPGPT RKHYQPYAPP   60
RDFAAYRSRV KFSRSADAPA YQQGQNQLYN ELNLGRRREY DVLDKRRGRD PEMGGKPRRK   120
NPQEGLYNEL QKDKMAEAYS EIGMKGERRR GKGHDGLYQG LSTATKDTYD ALHMQALPPR   180

SEQ ID NO: 15           moltype = AA   length = 238
FEATURE                 Location/Qualifiers
source                  1..238
                        mol_type = protein
                        note = eGFP
                        organism = synthetic construct
SEQUENCE: 15
VSKGEELFTG VVPILVELDG DVNGHKFSVS GEGEGDATYG KLTLKFICTT GKLPVPWPTL   60
VTTLTYGVQC FSRYPDHMKQ HDFFKSAMPE GYVQERTIFF KDDGNYKTRA EVKFEGDTLV   120
NRIELKGIDF KEDGNILGHK LEYNYNSHNV YIMADKQKNG IKVNFKIRHN IEDGSVQLAD   180
HYQQNTPIGD GPVLLPDNHY LSTQSALSKD PNEKRDHMVL LEFVTAAGIT LGMDELYK    238

SEQ ID NO: 16           moltype = AA   length = 20
FEATURE                 Location/Qualifiers
source                  1..20
                        mol_type = protein
                        note = (G4S)4 linker
                        organism = synthetic construct
SEQUENCE: 16
GGGGSGGGGS GGGGSGGGGS                                              20

SEQ ID NO: 17           moltype = AA   length = 5
FEATURE                 Location/Qualifiers
source                  1..5
                        mol_type = protein
                        note = G4S linker
                        organism = synthetic construct
SEQUENCE: 17
GGGGS                                                              5

SEQ ID NO: 18           moltype = AA   length = 19
FEATURE                 Location/Qualifiers
source                  1..19
                        mol_type = protein
                        note = T2A linker
                        organism = synthetic construct
SEQUENCE: 18
GEGRGSLLTC GDVEENPGP                                               19

SEQ ID NO: 19           moltype = DNA   length = 1356
FEATURE                 Location/Qualifiers
source                  1..1356
                        mol_type = other DNA
                        note = Anti-P329G-ds-scFv-CD28ATM-CD28CSD-CD3zSSD fusion
                          pETR17096
                        organism = synthetic construct
SEQUENCE: 19
atgggatgga gctgtatcat cctcttcttg gtagcaacag ctaccggtgt gcattccgag   60
gtgaagctgc tggagagcgg cggcggcctg gtgcagcccg gcggcagcct gaagctgagc   120
tgcgccgcca gcggcttcga cttcagcagg tactggatga actgggtgag caggccccc    180
ggcaagtgtc tggagtggat cggcgagatc acccccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag ccctacgac   360
```

```
tacggcgcct ggttcgccag ctggggccag ggcaccctgg tgaccgtgag cgccggaggg   420
ggcggaagtg gtggcggggg aagcggcggg ggtggcagcg gaggggggcgg atctcaggcc   480
gtggtgaccc aggagagcgc cctgaccacc agccccggcg agaccgtgac cctgacctgc   540
aggagcagca ccggcgccgt gaccaccagc aactacgcca actgggtgca ggagaagccc   600
gaccacctgt tcaccggcct gatcggcggc accaacaaga ggccccccgg cgtgcccgcc   660
aggttcagcg gcagcctgat cggcgacaag gccgccctga ccatcaccgg cgcccagacc   720
gaggacgagg ccatctactt ctgcgccctg tggtacagca accactgggt gttcggctgt   780
ggcaccaagc tgaccgtgct ggggaggggc ggatccttct gggtgctggt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccag gaggcccggc   960
cccaccagga agcactacca gccctacgcc ccccccaggg acttcgccgc ctacaggagc  1020
agggtgaagt tcagcaggag cgccgacgcc cccgcctacc agcagggcca gaaccagctg  1080
tataacgagc tgaacctggg caggaggagg gagtacgacg tgctggacaa gaggaggggc  1140
agggaccccg agatgggcgg caagcccagg aggaagaacc cccaggaggg cctgtataac  1200
gagctgcaga aggacaagat ggccgaggcc tacagcgaga tcggcatgaa gggcgagagg  1260
aggaggggca agggccacga cggcctgtac cagggcctga gcaccgccac caaggacacc  1320
tacgacgccc tgcacatgca ggccctgccc cccagg                            1356

SEQ ID NO: 20          moltype = DNA  length = 357
FEATURE                Location/Qualifiers
source                 1..357
                       mol_type = other DNA
                       note = Anti-P329G-ds VH
                       organism = synthetic construct
SEQUENCE: 20
gaggtgaagc tgctggagag cggcggcggc ctggtgcagc ccggcggcag cctgaagctg   60
agctgcgccg ccagcggctt cgacttcagc aggtactgga tgaactgggt gaggcaggcc  120
cccggcaagt gtctggagtg gatcggcgag atcaccccg acagcagcac catcaactac  180
accccagctg tgaaggacaa gttcatcatc agcagggaca cgccaagaa caccctgtac  240
ctgcagatga tcaaggtgag gagcgaggac accgccctgt actactgcgt gaggccctac  300
gactacggcg cctggttcgc cagctggggc cagggcaccc tggtgaccgt gagcgcc    357

SEQ ID NO: 21          moltype = DNA  length = 327
FEATURE                Location/Qualifiers
source                 1..327
                       mol_type = other DNA
                       note = Anti-P329G-ds VL
                       organism = synthetic construct
SEQUENCE: 21
caggccgtgg tgacccagga gagcgccctg accaccagcc ccggcgagac cgtgaccctg   60
acctgcagga gcagcaccgg cgccgtgacc accagcaact acgccaactg ggtgcaggag  120
aagcccgacc acctgttcac cggcctgatc ggcggcacca caagagggc ccccggcgtg  180
cccgccaggt tcagcggcag cctgatcggc gacaaggccg ccctgaccat caccggcgcc  240
cagaccgagg acgaggccat ctacttctgt gccctgtggt acagcaacca ctgggtgttc  300
ggctgtggca ccaagctgac cgtgctg                                      327

SEQ ID NO: 22          moltype = DNA  length = 799
FEATURE                Location/Qualifiers
source                 1..799
                       mol_type = other DNA
                       note = Anti-P329G-ds-scFv
                       organism = synthetic construct
SEQUENCE: 22
atgggatgga gctgtatcat cctcttcttg gtagcaacag ctaccggtgt gcattccgag   60
gtgaagctgc tggagagcgg cggcggcctg gtgcagcccg gcggcagcct gaagctgagc  120
tgcgccgcca gcggcttcga cttcagcagg tactgatga actgggtgag gcaggccccc  180
ggcaagtgtc tggagtggat cggcgagatc accccgaca gcagcaccat caactacacc  240
cccagcctga aggacaagtt catcatcagc agggacaacg ccaagaacac cctgtacctg  300
cagatgatca aggtgaggag cgaggacacc gccctgtact actgcgtgag gccctacgac  360
tacggcgcct ggttcgccag ctggggccag ggcaccctgg tgaccgtgag cgccggaggg  420
ggcggaagtg gtggcggggg aagcggcggg ggtggcagcg gaggggggcgg atctcaggcc  480
gtggtgaccc aggagagcgc cctgaccacc agccccggcg agaccgtgac cctgacctgc  540
aggagcagca ccggcgccgt gaccaccagc aactacgcca actgggtgca ggagaagccc  600
gaccacctgt tcaccggcct gatcggcggc accaacaaga ggccccccgg cgtgcccgcc  660
aggttcagcg gcagcctgat cggcgacaag gccgccctga ccatcaccgg cgcccagacc  720
gaggacgagg ccatctactt ctgcgccctg tggtacagca accactgggt gttcggctgt  780
ggcaccaagc tgaccgtgc                                                799

SEQ ID NO: 23          moltype = DNA  length = 647
FEATURE                Location/Qualifiers
source                 1..647
                       mol_type = other DNA
                       note = IRES EV71, internal ribosomal entry side
                       organism = synthetic construct
SEQUENCE: 23
cccgaagtaa cttagaagct gtaaatcaac gatcaatagc aggtgtggca caccagtcat   60
accttgatca agcacttctg tttccccgga ctgagtatca ataggctgct cgcgcggctg  120
aaggagaaaa cgttcgttac ccgaccaact acttcgagaa gcttagtacc accatgaacg  180
aggcagggtg tttcgctcag cacaaccca gtgtagatca ggctgatgag tcactgcaac  240
```

```
ccccatgggc gaccatggca gtggctgcgt tggcggcctg cccatggaga aatccatggg   300
acgctctaat tctgacatgg tgtgaagtgc ctattgagct aactggtagt cctccggccc   360
ctgattgcgg ctaatcctaa ctgcggagca catgctcaca aaccagtggg tggtgtgtcg   420
taacgggcaa ctctgcagcg gaaccgacta ctttgggtgt ccgtgtttcc ttttattcct   480
atattggctg cttatggtga caatcaaaaa gttgttacta tatagctatt ggattggcca   540
tccggtgtgc aacagggcaa ctgtttacct atttattggt tttgtaccat tatcactgaa   600
gtctgtgatc actctcaaat tcattttgac cctcaacaca atcaaac                 647

SEQ ID NO: 24           moltype = DNA   length = 81
FEATURE                 Location/Qualifiers
source                  1..81
                        mol_type = other DNA
                        note = CD28ATM
                        organism = synthetic construct
SEQUENCE: 24
ttttgggtgc tggtggtggt tggtggagtc ctggcttgct atagcttgct agtaacagtg    60
gcctttatta ttttctgggt g                                              81

SEQ ID NO: 25           moltype = DNA   length = 123
FEATURE                 Location/Qualifiers
source                  1..123
                        mol_type = other DNA
                        note = CD28CSD
                        organism = synthetic construct
SEQUENCE: 25
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

SEQ ID NO: 26           moltype = DNA   length = 336
FEATURE                 Location/Qualifiers
source                  1..336
                        mol_type = other DNA
                        note = CD3z SSD
                        organism = synthetic construct
SEQUENCE: 26
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac caggtctca gtacagccac caaggacacc   300
tacgacgccc ttcacatgca ggccctgccc cctcgc                             336

SEQ ID NO: 27           moltype = DNA   length = 540
FEATURE                 Location/Qualifiers
source                  1..540
                        mol_type = other DNA
                        note = CD28ATM-CD28-CD3z
                        organism = synthetic construct
SEQUENCE: 27
ttctgggtgc tggtggtggt gggcggcgtg ctggcctgct acagcctgct ggtgaccgtg    60
gccttcatca tctttctgggt gaggagcaag aggagcaggc tgctgcacag cgactacatg   120
aacatgaccc ccaggaggcc cggccccacc aggaagcact accagcccta cgccccccc   180
agggacttcg ccgcctacag gagcagggtg aagttcagca ggagcgccga cgcccccgcc   240
taccagcagg gccagaacca gctgtataac agctgcaatc tgggcaggag gagagtac   300
gacgtgctgg acaagaggag gggcagggac cccgagatgg gcggcaagcc caggaggaag   360
aaccccagg agggcctgta taacgagctg cagaaggaca gatggccga ggcctacagc   420
gagatcggca tgaagggcga gaggaggagg gcaagggcc acgacggcct gtaccaggc   480
ctgagcaccg ccaccaagga cacctacgac gccctgcaca tgcaggccct gccccccagg   540

SEQ ID NO: 28           moltype = DNA   length = 63
FEATURE                 Location/Qualifiers
source                  1..63
                        mol_type = other DNA
                        note = T2A element
                        organism = synthetic construct
SEQUENCE: 28
tccggagagg gcagaggaag tcttctaaca tgcggtgacg tggaggagaa tcccggccct    60
agg                                                                  63

SEQ ID NO: 29           moltype = DNA   length = 717
FEATURE                 Location/Qualifiers
source                  1..717
                        mol_type = other DNA
                        note = eGFP
                        organism = synthetic construct
SEQUENCE: 29
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
```

```
aagctgaccc tgaagttcat ctgcaccacc ggcaagctgc ccgtgccctg gcccacccte   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatcac atggtcctg    660
ctggagttcg tgaccgccgc cgggatcact ctcggcatgg acgagctgta caagtga     717

SEQ ID NO: 30             moltype = DNA  length = 2136
FEATURE                   Location/Qualifiers
source                    1..2136
                          mol_type = other DNA
                          note = Anti-P329G-ds-scFv-CD28ATM-CD28CSD-CD3zSSD-eGFP
                            fusion pETR17096
                          organism = synthetic construct
SEQUENCE: 30
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga actgggtgcg ggccccca    180
ggcaagtgtc tggagtggat cggcgagatc accccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag ccctacgac    360
tacggcgcct ggttcgccag ctggggccag ggcaccctgg tgaccgtgag cgccggaggg   420
ggcggaagtg gtggcggggg aagcggcggg ggtggcagcg aggggggcgg atctcaggcc   480
gtggtgaccc aggagagcgc cctgaccacc agccccggcg agaccgtgac cctgacctgc   540
aggagcagca ccggcgccgt gaccaccagc aactacgcca actgggtgca ggagaagccc   600
gaccacctgt tcaccggcct gatcggcggc accaacaagg cccccgggg cgtgcccgcc   660
aggttcagcg gcagcctgat cggcgacaag gccgccctga ccatcaccgg cgcccagacc   720
gaggacgagg ccatctactt ctgcgcctg tggtacagca accactgggt gttcggctgt   780
ggcaccaagc tgaccgtgct ggggagggc ggatccttct gggtgctggt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccag gaggcccggc   960
cccaccagga agcactacca gccctacgcc ccccccaggg acttcgccgc ctacaggagc  1020
agggtgaagt tcagcaggag cgccgacgcc cccgcctacc agcagggcca gaaccagctg  1080
tataacgagc tgaacctggg caggagggag gagtacgacg tgctggacaa gaggagggc    1140
agggacccg agatgggcgg caagcccagg aggaagaacc cccagggagg cctgtataac   1200
gagctgcaga aggacaagat ggccgaggcc tacagcgaga tcggcatgaa gggcgagagg   1260
aggaggggca agggccacga cggcctgtac cagggcctga gcaccgccac caaggacacc   1320
tacgacgccc tgcacatgca ggccctgccc ccaggtccg gagagggcag aggaagtctt   1380
ctaacatgcg gtgacgtgga ggagaatccc ggccctagtg agcaaggg cgaggagctg    1440
ttcaccggg tggtgcccat cctggtcgag ctggacggcg acgtaaacgg ccacaagttc   1500
agcgtgtccg gcgagggcga gggcgatgcc acctacggca agctgaccct gaagttcatc   1560
tgcaccaccg gcaagctgcc cgtgccctgg cccaccctcg tgaccaccct gacctacggc   1620
gtgcagtgct tcagccgcta ccccgaccac atgaagcagc acgacttcct caagtccgcc   1680
atgcccgaag gctacgtcca ggagcgcacc atcttcttca aggacgacgg caactacaag   1740
acccgcgcc aggtgaagtt cgagggcgac accctggtga accgcatcga gctgaagggc   1800
atcgacttca aggaggacgg caacatcctg ggcacaagc tggagtacaa ctacaacagc   1860
cacaacgtct atatcatggc cgacaagcag aagaacggca tcaaggtgaa cttcaagatc   1920
cgccacaaca tcgaggacgg cagcgtgcag ctcgccgacc actaccagca gaacaccccc   1980
atcggcgacg gccccgtgct gctgcccgac aaccactacc tgagcaccca gtccgccctg   2040
agcaaagacc ccaacgagaa gcgcgatcac atggtcctgc tggagttcgt gaccgccgcc   2100
gggatcactc tcggcatgga cgagctgtac aagtga                              2136

SEQ ID NO: 31             moltype = AA  length = 433
FEATURE                   Location/Qualifiers
source                    1..433
                          mol_type = protein
                          note = Anti-P329G-scFv- CD28ATM-CD28CSD-CD3zSSD fusion
                          organism = synthetic construct
SEQUENCE: 31
EVKLLESGGG LVQPGGSLKL SCAASGFDFS RYWMNWVRQA PGKGLEWIGE ITPDSSTINY    60
TPSLKDKFII SRDNAKNTLY LQMIKVRSED TALYYCVRPY DYGAWFASWG QGTLVTVSAG   120
GGGSGGGGSG GGGSGGGGSQ AVVTQESALT TSPGETVTLT CRSSTGAVTT SNYANWVQEK   180
PDHLFTGLIG GTNKRAPGVP ARFSGSLIGD KAALTITGAQ TEDEAIYFCA LWYSNHWVFG   240
GGTKLTVLGG GGSFWVLVVV GGVLACYSLL VTVAFIIFWV RSKRSRLLHS DYMNMTPRRP   300
GPTRKHYQPY APPRDFAAYR SRVKFSRSAD APAYQQGQNQ LYNELNLGRR EEYDVLDKRR   360
GRDPEMGGKP RRKNPQEGLY NELQKDKMAE AYSEIGMKGE RRRGKGHDGL YQGLSTATKD   420
TYDALHMQAL PPR                                                      433

SEQ ID NO: 32             moltype = AA  length = 119
FEATURE                   Location/Qualifiers
source                    1..119
                          mol_type = protein
                          note = Anti-P329G VH
                          organism = synthetic construct
SEQUENCE: 32
```

```
EVKLLESGGG LVQPGGSLKL SCAASGFDFS RYWMNWVRQA PGKGLEWIGE ITPDSSTINY    60
TPSLKDKFII SRDNAKNTLY LQMIKVRSED TALYYCVRPY DYGAWFASWG QGTLVTVSA    119

SEQ ID NO: 33           moltype = AA  length = 109
FEATURE                 Location/Qualifiers
source                  1..109
                        mol_type = protein
                        note = Anti-P329G VL
                        organism = synthetic construct
SEQUENCE: 33
QAVVTQESAL TTSPGETVTL TCRSSTGAVT TSNYANWVQE KPDHLFTGLI GGTNKRAPGV    60
PARFSGSLIG DKAALTITGA QTEDEAIYFC ALWYSNHWVF GGGTKLTVL              109

SEQ ID NO: 34           moltype = AA  length = 248
FEATURE                 Location/Qualifiers
source                  1..248
                        mol_type = protein
                        note = Anti-P329G-scFv
                        organism = synthetic construct
SEQUENCE: 34
EVKLLESGGG LVQPGGSLKL SCAASGFDFS RYWMNWVRQA PGKGLEWIGE ITPDSSTINY    60
TPSLKDKFII SRDNAKNTLY LQMIKVRSED TALYYCVRPY DYGAWFASWG QGTLVTVSAG   120
GGGSGGGGSG GGGSGGGGSQ AVVTQESALT TSPGETVTLT CRSSTGAVTT SNYANWVQEK   180
PDHLFTGLIG GTNKRAPGVP ARFSGSLIGD KAALTITGAQ TEDEAIYFCA LWYSNHWVFG   240
GGTKLTVL                                                          248

SEQ ID NO: 35           moltype = DNA  length = 1356
FEATURE                 Location/Qualifiers
source                  1..1356
                        mol_type = other DNA
                        note = Anti-P329G-scFv-CD28ATM-CD28CSD-CD3zSSD fusion
                        organism = synthetic construct
SEQUENCE: 35
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga actgggtgag gcaggccccc   180
ggcaagggtc tggagtggat cggcgagatc accccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag gccctacgac   360
tacggcgcct ggttcgccag ctggggccag ggcaccctgg tgaccgtgag cgccggaggg   420
ggcggaagtg gtggcggggg aagcggcggg ggtggcagcg aggggggcgg atctcaggcc   480
gtggtgaccc aggagagcgc cctgaccacc agccccggcg agaccgtgac cctgacctgc   540
aggagcagca ccggcgccgt gaccaccagc aactacgcca actgggtgca ggagaagccc   600
gaccaccgtg tcaccggcct gatcggcggc accaacaaga gggcccccgg cgtgcccgcc   660
aggttcagcg gcagcctgat cggcgacaag gccgccctga ccatcaccgg cgcccagacc   720
gaggacgagg ccatctactt ctgcgccctg tggtacagca accactgggt gttcggcggt   780
ggcaccaagc tgaccgtgct gggaggggc ggatccttct ggtgctggtt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccag gaggcccggc   960
cccaccagga agcactacca gccctacgcc ccccccaggg acttcgccgc ctacaggagc  1020
agggtgaagt tcagcaggag cgccgacgcc ccgcctacc agcagggcca gaaccagctg  1080
tataacgagc tgaacctggg caggagggag gagtacgacg tgctggacaa gaggaggggc  1140
agggaccccg agatgggcgg caagcccagg aggaagaacc cccaggaggg cctgtataac  1200
gagctgcaga aggacaagat ggccgaggcc tacagcgaga tcggcatgaa gggcgagagg  1260
aggaggggca agggccacga cggcctgtac caggcctga gcaccgccac caaggacacc  1320
tacgacgccc tgcacatgca ggccctgccc cccagg                           1356

SEQ ID NO: 36           moltype = DNA  length = 357
FEATURE                 Location/Qualifiers
source                  1..357
                        mol_type = other DNA
                        note = Anti-P329G VH
                        organism = synthetic construct
SEQUENCE: 36
gaggtgaagc tgctggagag cggcggcggc ctggtgcagc ccggcggcag cctgaagctg    60
agctgcgccg ccagcggctt cgacttcagc aggtactgga tgaactgggt gaggcaggcc   120
cccggcaagg gtctggagtg gatcggcgag atcaccccg acagcagcac catcaactac   180
accccccagcc tgaaggacaa gttcatcatc agcagggaca acgccaagaa caccctgtac   240
ctgcagatga tcaaggtgag gagcgaggac accgccctgt actactgcgt gaggccctac   300
gactacggcg cctggttcgc cagctgggc agggcaccc tggtgaccgt gagcgcc      357

SEQ ID NO: 37           moltype = DNA  length = 327
FEATURE                 Location/Qualifiers
source                  1..327
                        mol_type = other DNA
                        note = Anti-P329G VL
                        organism = synthetic construct
SEQUENCE: 37
caggccgtgg tgacccagga gagcgccctg accaccagcc ccggcgagac cgtgaccctg    60
```

```
acctgcagga gcagcaccgg cgccgtgacc accagcaact acgccaactg ggtgcaggag   120
aagcccgacc acctgttcac cggcctgatc ggcggcacca acaagagggc ccccggcgtg   180
cccgccaggt tcagcggcag cctgatcggc gacaaggccg ccctgaccat caccggcgcc   240
cagaccgagg acgaggccat ctacttctgc gccctgtggt acagcaacca ctgggtgttc   300
ggcggtggca ccaagctgac cgtgctg                                       327

SEQ ID NO: 38         moltype = DNA   length = 2136
FEATURE               Location/Qualifiers
source                1..2136
                      mol_type = other DNA
                      note = Anti-P329G-scFv-CD28ATM-CD28CSD-CD3zSSD-eGFP fusion
                      organism = synthetic construct
SEQUENCE: 38
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga actgggtgag gcaggccccc   180
ggcaagggtc tggagtggat cggcgagatc accccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag ggcctacgac   360
tacggcgcct ggttcgccag ctgggggcag ggcaccctgg tgaccgtgag cgccggaggg   420
ggcggaagtg gtggcggggg aagcggcggg ggtggcagcg aggggggcgg atctcaggcc   480
gtggtgaccc aggagagcgc cctgaccacc agccccggcg agaccgtgac cctgacctgc   540
aggagcagca ccgcgccgt gaccaccagc aactacgcca actgggtgca ggagaagccc   600
gaccacctgt tcaccggcct gatcggcggc accaacaaga gggcccccgg cgtgcccgcc   660
aggttcagcg gcagcctgat cggcgacaag gccgccctga ccatcaccgg cgcccagacc   720
gaggacgagg ccatctactt ctgcgccctg tggtacagca accactgggt gttcggcggt   780
ggcaccaagc tgaccgtgct ggggaggggc ggatccttct gggtgctggt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccccag gaggcccggc   960
cccaccagga agcactacca gccctacgcc cccccaggg acttcgccgc ctacaggagc  1020
agggtgaagt tcagcaggag cgccgacgcc cccgcctacc agcagggcca gaaccagctg  1080
tataacgagc tgaacctggg caggagggag gagtacgacg tgctgacaa gaggaggggc  1140
agggaccccg agatgggcgg caagcccagg aggaagaacc cccaggaggg cctgtataac  1200
gagctgcaga aggacaagat ggccgaggcc tacagcgaga tcggcatgaa gggcgagagg  1260
aggaggggca aggccacga cggcctgtac caggggcctga gcaccgccac caaggacacc  1320
tacgacgccc tgcacatgca ggccctgccc ccaggtccgg agagggcag aggaagtctt  1380
ctaacatgcg gtgacgtgga ggagaatccc ggccctaggg tgagcaaggg cgaggagctg  1440
ttcaccgggg tggtgcccat cctggtcgag ctggacggcg acgtaaacgg ccacaagttc  1500
agcgtgtccg gcgaggcga ggcgatgcc acctacggca agctgaccct gaagttcatc  1560
tgcaccaccg gcaagctgcc cgtgccctgg cccaccctcg tgaccaccct gacctacggc  1620
gtgcagtgct tcagcgcta cccgaccac atgaagcagc acgacttctt caagtccgcc  1680
atgcccgaag gctacgtcca ggagcgcacc atcttcttca aggacgacgg caactacaag  1740
acccgcgccg aggtgaagtt cgagggcgac acctggtga accgcatcga gctgaagggc  1800
atcgacttca aggaggacgg caacatcctg gggcacaagc tggagtacaa ctacaacagc  1860
cacaacgtct atatcatggc cgacaagcag aagaacggca tcaaggtgaa cttcaagatc  1920
cgccacaaca tcgaggacgg cagcgtgcag ctcgccgacc actaccagca gaacacccccc  1980
atcggcgacg gccccgtgct gctgcccgac aaccactacc tgagcaccca gtccgccctg  2040
agcaaagacc ccaacgagaa gcgcgatcac atggtcctgc tggagttcgt gaccgccgcc  2100
gggatcactc tcggcatgga cgagctgtac aagtga                           2136

SEQ ID NO: 39         moltype = AA   length = 407
FEATURE               Location/Qualifiers
source                1..407
                      mol_type = protein
                      note = Anti-P329G-ds-Fab- heavy
                        chain-CD28ATM-CD28CSD-CD3zSSD fusion pETR17100
                      organism = synthetic construct
SEQUENCE: 39
EVKLLESGGG LVQPGGSLKL SCAASGFDFS RYWMNWVRQA PGKCLEWIGE ITPDSSTINY    60
TPSLKDKFII SRDNAKNTLY LQMIKVRSED TALYYCVRPY DYGAWFASWG QGTLVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCGGGGSFWV LVVVGGVLAC   240
YSLLVTVAFI IFWVRSKRSR LLHSDYMNMT PRRPGPTRKH YQPYAPPRDF AAYRSRVKFS   300
RSADAPAYQQ GQNQLYNELN LGRREEYDVL DKRRGRDPEM GGKPRRKNPQ EGLYNELQKD   360
KMAEAYSEIG MKGERRRGKG HDGLYQGLST ATKDTYDALH MQALPPR                 407

SEQ ID NO: 40         moltype = AA   length = 222
FEATURE               Location/Qualifiers
source                1..222
                      mol_type = protein
                      note = Anti-P329G-ds-Fab heavy chain
                      organism = synthetic construct
SEQUENCE: 40
EVKLLESGGG LVQPGGSLKL SCAASGFDFS RYWMNWVRQA PGKCLEWIGE ITPDSSTINY    60
TPSLKDKFII SRDNAKNTLY LQMIKVRSED TALYYCVRPY DYGAWFASWG QGTLVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SC                      222

SEQ ID NO: 41         moltype = AA   length = 216
```

```
FEATURE                 Location/Qualifiers
source                  1..216
                        mol_type = protein
                        note = Anti P329G-ds-Fab light chain
                        organism = synthetic construct
SEQUENCE: 41
QAVVTQESAL TTSPGETVTL TCRSSTGAVT TSNYANWVQE KPDHLFTGLI GGTNKRAPGV    60
PARFSGSLIG DKAALTITGA QTEDEAIYFC ALWYSNHWVF GCGTKLTVLR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 42           moltype = AA   length = 107
FEATURE                 Location/Qualifiers
source                  1..107
                        mol_type = protein
                        note = CL
                        organism = synthetic construct
SEQUENCE: 42
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 43           moltype = AA   length = 103
FEATURE                 Location/Qualifiers
source                  1..103
                        mol_type = protein
                        note = CH1
                        organism = synthetic construct
SEQUENCE: 43
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSC                     103

SEQ ID NO: 44           moltype = DNA  length = 2645
FEATURE                 Location/Qualifiers
source                  1..2645
                        mol_type = other DNA
                        note = Anti-P329G-ds-Fab-heavy
                          chain-CD28ATM-CD28CSD-CD3zSSD fusion pETR17100
                        organism = synthetic construct
SEQUENCE: 44
atgggatgga gctgtatcat cctcttcttg gtagcaacag ctacgggtgt gcattcccag    60
gccgtggtga cccaggagag cgccctgacc accagccccg gcgagaccgt gaccctgacc   120
tgcaggagca gcaccggcgc cgtgaccacc agcaactacg ccaactgggt gcaggagaag   180
cccgaccacc tgttcaccgg cctgatcggc ggcaccaaca gagggcccc cggcgtgccc   240
gccaggttca gcggcagcct gatcggcgac aaggccgccc tgaccatcac cggcgcccag   300
accgaggacg aggccatcta cttctgcgcc ctgtggtaca gcaaccactg ggtgttcggc   360
tgtggcacca agctgaccgt gctgcgtacg gtggctgcac atctgtcttt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtgttagga attccccgaa   720
gtaacttaga agctgtaaat caacgatcaa tagcaggtgt ggcacaccag tcataccttg   780
atcaagcact tctgtttccc cggactgagt caataggc tgctcgcgcg gctgaaggag   840
aaaacgttcg ttacccgacc aactacttcg agaagcttag taccaccatg aacgaggcag   900
ggtgttttcg c tcagcacaac cccagtgtag atcaggctga tgagtcactg caaccccgat   960
gggcgaccat ggcagtggct gcgttggcgc cctgcccatg agaaaatcca tgggacgctc  1020
taattctgac atggtgtgaa gtgccattg agctaactgg tagtcctccg gcccctgatt  1080
gcggctaatc ctaactgcgg agcacatgct cacaaaccag tgggtggtgt gtcgtaacgg  1140
gcaactctgc agcggaaccg actactttgg gtgtccgtgt ttcctttat tcctatattg  1200
gctgcttatg gtgacaatca aaaagttgtt accatatagc tattggattg gccatccggt  1260
gtgcaacagg gcaactgttt acctatttat tggttttgta ccattatcac tgaagtctgt  1320
gatcactctc aaattcattt tgaccctcaa cacaatcaaa cgccaccatg ggatggagct  1380
gtatcatcct cttcttggta gcaacagcta ccggtgtgca ctccgaggtg aagctgctgg  1440
agagcggggg cggcctggtg cagcccggcg gcagcctgcg gctgagctgc gccgccagcg  1500
gcttcgactt cagcaggtac tggatgaact gggtgaggca ggccccggc aagtgtctgg  1560
agtggatcgg cgagatcacc cccgacagca gcaccatcaa ctaccccccc agcctgaagg  1620
acaagttcat catcagcagg gacaacgcca agaacaccct gtacctgcag atgatcaagg  1680
tgaggagcga ggacaccgcc ctgtactact gcgtgagggc ctacgactac ggcgcctggt  1740
tcgccagctg ggggcagggc accctggtga cccgtgagcgc cgctagcacc aagggcccct  1800
ccgtgttccc cctggccccc agcagcaaga gcaccagcgg cggcacagcc gctctgggct  1860
gcctggtcaa ggactacttc cccgagcccg tgaccgtgtc ctggaacagc ggagccctga  1920
cctccggcgt gcacaccttc cccgccgtgc tgcagttc tggcctgtat agcctgagca  1980
gcgtggtcac cgtgccttct agcagcctgg gcacccagac ctacatcgc aacgtgaacc  2040
acaagcccag caacaccaag gtggacaaga aggtggagcc caagagcctgc  2100
gatcttctcg ggtgctggtg gtggtgggcg gcgtgctggc ctgctacagc ctgctgggtga  2160
ccgtggcctt catcatcttc tgggtgagga gcaagaggag caggctgctg cacagcgact  2220
acatgaacat gaccccacgg aggccgcc ccaccaggaa gcactaccag ccctacgccc  2280
cccccaggga cttcgccgcc tacaggagaca gggtgaagtt cagcaggagc gccgacgccc  2340
ccgcctacca gcagggccag aaccagctgt ataacgagct gaacctgggc aggagggagg  2400
```

-continued

```
agtacgacgt gctggacaag aggaggggca gggaccccga gatgggcggc aagcccagga   2460
ggaagaaccc ccaggagggc ctgtataacg agctgcagaa ggacaagatg gccgaggcct   2520
acagcgagat cggcatgaag ggcgagagga ggaggggcaa gggccacgac ggcctgtacc   2580
agggcctgag caccgccacc aaggacacct acgacgccct gcacatgcag gccctgcccc   2640
ccagg                                                               2645

SEQ ID NO: 45          moltype = DNA   length = 324
FEATURE                Location/Qualifiers
source                 1..324
                       mol_type = other DNA
                       note = CL
                       organism = synthetic construct
SEQUENCE: 45
cgtacggtgg ctgcaccatc tgtcttcatc ttcccgccat ctgatgagca gttgaaatct   60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                          324

SEQ ID NO: 46          moltype = DNA   length = 309
FEATURE                Location/Qualifiers
source                 1..309
                       mol_type = other DNA
                       note = CH1
                       organism = synthetic construct
SEQUENCE: 46
gctagcacca agggcccctc cgtgttcccc ctggccccca gcagcaagag caccagcggc   60
ggcacagccg ctctgggctg cctggtcaag gactacttcc ccgagcccgt gaccgtgtcc   120
tggaacagcg gagccctgac ctccggcgtg cacaccttcc cagccgtgct gcagagttct   180
ggcctgtata gcctgagcag cgtggtcacc gtgccttcta gcagcctggg cacccagacc   240
tacatctgca acgtgaacca caagcccagc aacaccaagg tggacaagaa ggtggagccc   300
aagagctgc                                                           309

SEQ ID NO: 47          moltype = DNA   length = 3425
FEATURE                Location/Qualifiers
source                 1..3425
                       mol_type = other DNA
                       note = Anti-P329G-ds-Fab-heavy
                         chain-CD28TM-CD28CSD-CD3ZSSD-eGFP fusion pETR17100
                       organism = synthetic construct
SEQUENCE: 47
atgggatgga gctgtatcat cctcttcttg gtagcaacag ctacgggtgt gcattcccag   60
gccgtggtga cccaggagag cgccctgacc accagcccccg cgagaccgt gaccctgacc   120
tgcaggagca gcaccggcgc cgtgaccacc agcaactacg ccaactgggt gcaggagaag   180
cccgaccacc tgttcaccgg cctgatcggc ggcaccaaca gagggcccc cggcgtgccc   240
gccaggttca gcggcagcct gatcggcgac aaggccgacc tgaccatcac cggcgcccag   300
accgaggacg aggccatcta cttctgcgcc ctgtggtaca gcaaccactg ggtgttcggc   360
tgtggcacca agctgaccgt gctgcgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgttagga attccccgaa   720
gtaacttaga agctgtaaat caacgatcaa tagcaggtgt ggcacaccag tcataccttg   780
atcaagcact tctgtttccc cggactgagt atcaataggc tgctcgcgcg gctgaaggag   840
aaaacgttcg ttacccgacc aactacttcg agaagcttag taccaccatg aacgaggcag   900
ggtgtttcgc tcagcacaac cccagtgtag atcaggctga tgagtcactg caaccccccat   960
gggcgaccat ggcagtggct gcgttggcgg cctgcccatg gagaaatcca tgggacgctc   1020
taattctgac atggtgtgaa gtgcctattg agctaactgg tagtcctccg gcccctgatt   1080
gcggctaatc ctaactgcgg agcacatgct cacaaaccag tgggtggtgt gtcgtaacgg   1140
gcaactctgc agcggaaccg actactttgg gtgtccgtgt ttccttttat tcctatattg   1200
gctgcttatg gtgacaatca aaaagttgtt accatatagc tattggattg gccatccggt   1260
gtgcaacagg gcaactgttt acctatttat tggttttgta ccattatcac tgaagtctgt   1320
gatcactctc aaattcattt tgaccctcaa cacaatcaaa gccaccatg ggatggagct   1380
gtatcatcct cttcttggta gcaacagcta ccggtgtgca ctccgaggtg aagctgctgg   1440
agagcggcgc cggcctggtg cagcccggcg gcagcctgaa gctgagctgc gccgccagcg   1500
gcttcgactt cagcaggtac tggatgaact gggtgaggca ggccccggc aagtgtctgg   1560
agtggatcgg cgagatcacc cccgacagca gcaccatcaa ctacaccccc agcctgaagg   1620
acaagttcat catcagcagg gacaacgcca gaaacaccct gtacctgcag atgatcaagg   1680
tgaggagcga ggacaccgcc ctgtactact gcgtgaggcc ctacgactac ggcgcctggt   1740
tcgccagctg gggccagggc accctggtga ccgtgagcgc cgctagcacc aagggcccct   1800
ccgtgttccc cctggccccc agcagcaaga gcaccagcgg cggcacagcc gctctgggct   1860
gcctggtcaa ggactacttc cccgagcccg tgaccgtgtc ctggaacagc ggagccctga   1920
cctccggcgt gcacaccttc ccagccgtgc tgcagagttc tggcctgtat agcctgagca   1980
gcgtggtcac cgtgccttct agcagcctgg gcacccagac ctacatctgc aacgtgaacc   2040
acaagcccag caacaccaag gtggacaaga aggtggagcc caagagctgc ggaggggcg   2100
gatccttctg ggtgctggtg gtggtgggcg gcgtgctggc ctgctacagc ctgctggtga   2160
ccgtggcctt catcatcttc tgggtgagga gcaagaggag caggctgctg cacagcgact   2220
```

```
acatgaacat gacccccagg aggcccggcc ccaccaggaa gcactaccag ccctacgccc   2280
cccccaggga cttcgccgcc tacaggagca gggtgaagtt cagcaggagc gccgacgccc   2340
ccgcctacca gcagggccag aaccagctgt ataacgagct gaacctgggc aggagggagg   2400
agtacgacgt gctggacaag aggaggggca gggaccccga gatgggcggc aagcccagga   2460
ggaagaaccc ccaggagggc ctgtataacg agctgcagaa ggacaagatg gccgaggcct   2520
acagcgagat cggcatgaag ggcgagagga ggaggggcaa gggccacgac ggcctgtacc   2580
agggcctgag caccgccacc aaggacacct acgacgccct gcacatgcag gccctgcccc   2640
ccaggtccgg agagggcaga ggaagtcttc taacatgcgg tgacgtggag gagaatcccg   2700
gccctagggt gagcaagggc gaggagctgt tcaccggggt ggtgcccatc ctggtcgagc   2760
tggacggcga cgtaaacggc cacaagttca gcgtgtccgg cgagggcgag ggcgatgcca   2820
cctacggcaa gctgaccctg aagttcatct gcaccaccgg caagctgccc gtgccctggc   2880
ccaccctcgt gaccaccctg acctacgcgt gcagtgcttc agccgctac cccgaccaca   2940
tgaagcagca cgacttcttc aagtccgcca tgcccgaagg ctacgtccag gagcgcacca   3000
tcttcttcaa ggacgacggc aactacaaga cccgcgccga ggtgaagttc gagggcgaca   3060
ccctggtgaa ccgcatcgag ctgaagggca tcgacttcaa ggaggacggc aacatcctgg   3120
ggcacaagct ggagtacaac tacaacagcc acaacgtcta tatcatggcc gacaagcaga   3180
agaacggcat caaggtgaac ttcaagatcc gccacaacat cgaggacggc agcgtgcagc   3240
tcgccgacca ctaccagcag aacacccca tcggcgacgg ccccgtgctg ctgcccgaca   3300
accactacct gagcacccag tccgccctga gcaaagaccc caacgagaag cgcgatcaca   3360
tggtcctgct ggagttcgtg accgccgccg ggatcactct cggcatggac gagctgtaca   3420
agtga                                                              3425

SEQ ID NO: 48           moltype = AA   length = 407
FEATURE                 Location/Qualifiers
source                  1..407
                        mol_type = protein
                        note = Anti-P329G-Fab-heavy chain-CD28ATM-CD28CSD-CD3zSSD
                         fusion pETR17594
                        organism = synthetic construct
SEQUENCE: 48
EVKLLESGGG LVQPGGSLKL SCAASGFDFS RYWMNWVRQA PGKGLEWIGE ITPDSSTINY   60
TPSLKDKFII SRDNAKNTLY LQMIKVRSED TALYYCVRPY DYGAWFASWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCGGGGSFWV LVVVGGVLAC  240
YSLLVTVAFI IFWVRSKRSR LLHSDYMNMT PRRPGPTRKH YQPYAPPRDF AAYRSRVKFS  300
RSADAPAYQQ GQNQLYNELN LGRREEYDVL DKRRGRDPEM GGKPRRKNPQ EGLYNELQKD  360
KMAEAYSEIG MKGERRRGKG HDGLYQGLST ATKDTYDALH MQALPPR                407

SEQ ID NO: 49           moltype = AA   length = 222
FEATURE                 Location/Qualifiers
source                  1..222
                        mol_type = protein
                        note = Anti-P329G-Fab heavy chain
                        organism = synthetic construct
SEQUENCE: 49
EVKLLESGGG LVQPGGSLKL SCAASGFDFS RYWMNWVRQA PGKGLEWIGE ITPDSSTINY   60
TPSLKDKFII SRDNAKNTLY LQMIKVRSED TALYYCVRPY DYGAWFASWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SC                     222

SEQ ID NO: 50           moltype = AA   length = 216
FEATURE                 Location/Qualifiers
source                  1..216
                        mol_type = protein
                        note = Anti-P329G-Fab light chain
                        organism = synthetic construct
SEQUENCE: 50
QAVVTQESAL TTSPGETVTL TCRSSTGAVT TSNYANWVQE KPDHLFTGLI GGTNKRAPGV   60
PARFSGSLIG DKAALTITGA QTEDEAIYFC ALWYSNHWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 51           moltype = DNA   length = 2645
FEATURE                 Location/Qualifiers
source                  1..2645
                        mol_type = other DNA
                        note = Anti-P329G-Fab-heavy chain-CD28ATM-CD28CSD-CD3zSSD
                         fusion pETR17594
                        organism = synthetic construct
SEQUENCE: 51
atgggatgga gctgtatcat cctcttcttg gtagcaacag ctacgggtgt gcattcccag    60
gccgtgtgta cccaggagag cgccctgacc accagccccg gcgagaccgt gaccctgacc   120
tgcaggagca gcaccggcgc cgtgaccacc agcaactacg ccaactgggt gcaggagaag   180
cccgaccacc tgttcaccgg cctgatcggc ggcaccaaca agagggcccc cggcgtgccc   240
gccaggttca gcggcagcct gatcggcgac aaggccgccc tgaccatcac cggcgcccag   300
accgaggacg aggccatcta cttctgcgcc ctgtggtaca gcaaccactg ggtgttcggc   360
ggtggcacca agctgaccgt gctgcgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
```

```
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttagga attccccgaa    720
gtaacttaga agctgtaaat caacgatcaa tagcaggtgt ggcacaccag tcataccttg    780
atcaagcact tctgtttccc cggactgagt atcaataggc tgctcgcgcg gctgaaggag    840
aaaacgttcg ttacccgacc aactacttcg agaagcttag taccaccatg aacgaggcag    900
ggtgtttcgc tcagcacaac cccagtgtag atcaggctga tgagtcactg caaccccat    960
gggcgaccat ggcagtggct cgcgttggcgg cctgcccatg agaaatcca tgggacgctc   1020
taattctgac atggtgtgaa gtgcctattg agctaactgg tagtcctccg gcccctgatt   1080
gcggctaatc ctaactgcgg agcacatgct cacaaaccag tgggtggtgt gtcgtaacgg   1140
gcaactctgc agcggaaccg actacttggg gtgtccgtgt ttcctttat tcctatattg    1200
gctgcttatg gtgacaatca aaaagttgtt accatatagc tattggattg gccatccggt    1260
gtgcaacagg gcaactgttt acctatttat tggttttgta ccattatcac tgaagtctgt    1320
gatcactctc aaattcattt tgaccctcaa cacaatcaaa cgccaccatg ggatggagct    1380
gtatcatcct cttcttggta gcaacagcta ccggtgtgca ctccgaggtg aagctgctgg    1440
agagcggcgg cggcctggtg cagcccggcg gcagcctgaa gctgagctgc gccgccagcg    1500
gcttcgactt cagcaggtac tggatgaact gggtgaggca ggcccccggc aagggtctgg    1560
agtggatcgg cgagatcacc cccgacagca gcaccatcaa ctacaccccc agcctgaagg    1620
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc cccgccgtgc tgcagagttc tggcctgtat agcctgagca    1980
gcgtggtcac cgtgccttct agcagcctgg gcacccagac ctacatctgc aacgtgaacc    2040
acaagcccag caacaccaag gtggacaaga aggtgggagc caagagctgc ggggacgccc    2100
gatccttctg ggtgctggtg gtggtgggcg gcgtgctggc ctgctacagc ctgctggtga    2160
ccgtggcctt catcatcttc tgggtgagga gcaagaggag caggctgctg cacagcgact    2220
acatgaacat gaccccccagg aggcccggcc caccaggaa gcactaccag ccctacgccc    2280
ccccagggga cttcgccgcc tacaggagca gggtgaagtt cagcaggagc gccgacgccc    2340
ccgcctacca gcagggccag aaccagctgt ataacgagct gaacctgggc aggagggagg    2400
agtacgacgt gctggacaag aggagggggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga ggagggggcca gggccacgac ggcctgtacc    2580
agggcctgag caccgccacc aaggacacct acgacgccct gcacatgcag gccctgcccc    2640
ccagg                                                                2645
```

| SEQ ID NO: 52 | moltype = DNA length = 3425 |
|---|---|
| FEATURE | Location/Qualifiers |
| source | 1..3425 |
| | mol_type = other DNA |
| | note = Anti-P329G-Fab-heavy chain-CD28ATM-CD28CSD-CD3zSSD-eGFP fusion pETR17594 |
| | organism = synthetic construct |

SEQUENCE: 52
```
atgggatgga gctgtatcat cctcttcttg gtagcaacag ctacgggtgt gcattcccag     60
gccgtggtga cccaggagag cgccctgacc accagccgag accgt gaccctgacc          120
tgcaggagca gcaccggcgc cgtgaccacc agcaactacg ccaactgggt gcaggagaag    180
cccgaccacc tgttcaccgg cctgatcggc ggcaccaaca gaggccccc cggcgtgccc     240
gccaggttca gcggcagcct gatcggcgac aaggccgccc tgaccatcac cggcgcccag    300
accgggacg aggccatcta cttctgcgcc ctgtggtaca gcaaccactg ggtgttcggc     360
ggtggcacca agctgaccgt gctgcgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttagga attccccgaa    720
gtaacttaga agctgtaaat caacgatcaa tagcaggtgt ggcacaccag tcataccttg    780
atcaagcact tctgtttccc cggactgagt atcataggc tgctcgcgcg gctgaaggag     840
aaaacgttcg ttacccgacc aactacttcg agaagcttag taccaccatg aacgaggcag    900
ggtgtttcgc tcagcacaac cccagtgtag atcaggctga tgagtcactg caaccccat    960
gggcgaccat ggcagtggct cgcgttggcgg cctgcccatg agaaatcca tgggacgctc   1020
taattctgac atggtgtgaa gtgcctattg agctaactgg tagtcctccg gcccctgatt   1080
gcggctaatc ctaactgcgg agcacatgct cacaaaccag tgggtggtgt gtcgtaacgg   1140
gcaactctgc agcggaaccg actacttggg gtgtccgtgt ttcctttat tcctatattg    1200
gctgcttatg gtgacaatca aaaagttgtt accatatagc tattggattg gccatccggt    1260
gtgcaacagg gcaactgttt acctatttat tggttttgta ccattatcac tgaagtctgt    1320
gatcactctc aaattcattt tgaccctcaa cacaatcaaa cgccaccatg ggatggagct    1380
gtatcatcct cttcttggta gcaacagcta ccggtgtgca ctccgaggtg aagctgctgg    1440
agagcggcgg cggcctggtg cagcccggcg gcagcctgaa gctgagctgc gccgccagcg    1500
gcttcgactt cagcaggtac tggatgaact gggtgaggca ggcccccggc aagggtctgg    1560
agtggatcgg cgagatcacc cccgacagca gcaccatcaa ctacaccccc agcctgaagg    1620
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc cccgccgtgc tgcagagttc tggcctgtat agcctgagca    1980
gcgtggtcac cgtgccttct agcagcctgg gcacccagac ctacatctgc aacgtgaacc    2040
```

```
acaagcccag caacaccaag gtggacaaga aggtggagcc caagagctgc ggagggggcg    2100
gatccttctg ggtgctggtg gtggtgggcg gcgtgctggc ctgctacagc ctgctggtga    2160
ccgtggcctt catcatcttc tgggtgagga gcaagaggag caggctgctg cacagcgact    2220
acatgaacat gaccccgagg aggcccggcc ccaccaggaa gcactaccag ccctacgccc    2280
ccccagggga cttcgccgcc tacaggagca gggtgaagtt cagcaggagc gccgacgccc    2340
ccgcctacca gcagggccag aaccagctgt ataacgagct gaacctgggc aggagggagg    2400
agtacgacgt gctggacaag aggaggggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga ggaggggcaa gggccacgac ggcctgtacc    2580
agggcctgag caccgccacc aaggacacct acgacgccct gcacatgcag gccctgcccc    2640
ccaggtccgg agagggcaga ggaagtcttc taacatgcgg tgacgtggag gagaatcccg    2700
gccctagggt gagcaaggcc gaggagctgt tcaccgggt ggtgcccatc ctggtcgagc    2760
tggacggcga cgtaaacggc cacaagttca gcgtgtccgg cgagggcgag ggcgatgcca    2820
cctacggcaa gctgaccctg aagttcatct gcaccacccc caagctgccc gtgccctgcc    2880
ccaccctcgt gaccaccctg acctacggct gcagtgctt cagccgctac ccgaccaca    2940
tgaagcagca cgacttcttc aagtccgcca tgcccgaagg ctacgtccag gagcgcacca    3000
tcttcttcaa ggacgacggc aactacaaga cccgcgccga ggtgaagttc gagggcgaca    3060
ccctggtgaa ccgcatcgag ctgaagggca tcgacttcaa ggaggacggc aacatcctgg    3120
ggcacaagct ggagtacaac tacaacagcc acaacgtcta tatcatggcc gacaagcaga    3180
agaacggcat caaggtgaac ttcaagatcc gccacaacat cgaggacggc agcgtgcagc    3240
tcgccgacca ctaccagcag aacacccca tcggcgacgg ccccgtgctg ctgcccgaca    3300
accactacct gagcacccag tccgccctga gcaaagaccc caacgagaag cgcgatcaca    3360
tggtcctgct ggagttcgtg accgccgcgg ggatcactct cggcatggac gagctgtaca    3420
agtga                                                                3425

SEQ ID NO: 53        moltype = AA    length = 5
FEATURE              Location/Qualifiers
source               1..5
                     mol_type = protein
                     note = Anti-AAA CDR H1 Kabat
                     organism = synthetic construct
SEQUENCE: 53
SYGMS                                                                5

SEQ ID NO: 54        moltype = AA    length = 6
FEATURE              Location/Qualifiers
source               1..6
                     mol_type = protein
                     note = Anti-AAA CDR H2 Kabat
                     organism = synthetic construct
SEQUENCE: 54
SSGGSY                                                               6

SEQ ID NO: 55        moltype = AA    length = 12
FEATURE              Location/Qualifiers
source               1..12
                     mol_type = protein
                     note = Anti-AAA CDR H3 Kabat
                     organism = synthetic construct
SEQUENCE: 55
LGMITTGYAM DY                                                        12

SEQ ID NO: 56        moltype = AA    length = 16
FEATURE              Location/Qualifiers
source               1..16
                     mol_type = protein
                     note = Anti-AAA CDR L1 Kabat
                     organism = synthetic construct
SEQUENCE: 56
RSSQTIVHST GHTYLE                                                    16

SEQ ID NO: 57        moltype = AA    length = 7
FEATURE              Location/Qualifiers
source               1..7
                     mol_type = protein
                     note = Anti-AAA CDR L2 Kabat
                     organism = synthetic construct
SEQUENCE: 57
KVSNRFS                                                              7

SEQ ID NO: 58        moltype = AA    length = 9
FEATURE              Location/Qualifiers
source               1..9
                     mol_type = protein
                     note = Anti-AAA CDR L3 Kabat
                     organism = synthetic construct
SEQUENCE: 58
FQGSHVPYT                                                            9
```

```
SEQ ID NO: 59            moltype = AA  length = 457
FEATURE                  Location/Qualifiers
source                   1..457
                         mol_type = protein
                         note = Anti-AAA-scFv-CD28ATM-CD28CSD-CD3zSSD fusion
                         organism = synthetic construct
SEQUENCE: 59
MNFGLSLVFL ALILKGVQCE VQLVESGGDL VKPGGSLKLS CAASGFTFSS YGMSWVRQTP    60
DKRLEWVATI SSGGSYIYYP DSVKGRFTIS RDNAKNTLYL QMSSLKSEDT AMYYCARLGM   120
ITTGYAMDYW GQGTSVTVSS GGGGSGGGGS GGGGSGGGGS DVLMTQTPLS LPVSLGDQAS   180
ISCRSSQTIV HSTGHTYLEW FLQKPGQSPK LLIYKVSNRF SGVPDRFSGS GSGTDFTLKI   240
SRVEAEDLGV YYCFQGSHVP YTFGGGTKLE IKGGGGSFWV LVVVGGVLAC YSLLVTVAFI   300
IFWVRSKRSR LLHSDYMNMT PRRPGPTRKH YQPYAPPRDF AAYRSRVKFS RSADAPAYQQ   360
GQNQLYNELN LGRREEYDVL DKRRGRDPEM GGKPRRKNPQ EGLYNELQKD KMAEAYSEIG   420
MKGERRRGKG HDGLYQGLST ATKDTYDALH MQALPPR                           457

SEQ ID NO: 60            moltype = AA  length = 272
FEATURE                  Location/Qualifiers
source                   1..272
                         mol_type = protein
                         note = Anti-AAA-scFv
                         organism = synthetic construct
SEQUENCE: 60
MNFGLSLVFL ALILKGVQCE VQLVESGGDL VKPGGSLKLS CAASGFTFSS YGMSWVRQTP    60
DKRLEWVATI SSGGSYIYYP DSVKGRFTIS RDNAKNTLYL QMSSLKSEDT AMYYCARLGM   120
ITTGYAMDYW GQGTSVTVSS GGGGSGGGGS GGGGSGGGGS DVLMTQTPLS LPVSLGDQAS   180
ISCRSSQTIV HSTGHTYLEW FLQKPGQSPK LLIYKVSNRF SGVPDRFSGS GSGTDFTLKI   240
SRVEAEDLGV YYCFQGSHVP YTFGGGTKLE IK                                272

SEQ ID NO: 61            moltype = AA  length = 140
FEATURE                  Location/Qualifiers
source                   1..140
                         mol_type = protein
                         note = Anti-AAA VH
                         organism = synthetic construct
SEQUENCE: 61
MNFGLSLVFL ALILKGVQCE VQLVESGGDL VKPGGSLKLS CAASGFTFSS YGMSWVRQTP    60
DKRLEWVATI SSGGSYIYYP DSVKGRFTIS RDNAKNTLYL QMSSLKSEDT AMYYCARLGM   120
ITTGYAMDYW GQGTSVTVSS                                              140

SEQ ID NO: 62            moltype = AA  length = 112
FEATURE                  Location/Qualifiers
source                   1..112
                         mol_type = protein
                         note = Anti-AAA VL
                         organism = synthetic construct
SEQUENCE: 62
DVLMTQTPLS LPVSLGDQAS ISCRSSQTIV HSTGHTYLEW FLQKPGQSPK LLIYKVSNRF    60
SGVPDRFSGS GSGTDFTLKI SRVEAEDLGV YYCFQGSHVP YTFGGGTKLE IK          112

SEQ ID NO: 63            moltype = AA  length = 428
FEATURE                  Location/Qualifiers
source                   1..428
                         mol_type = protein
                         note = Anti-AAA-Fab-heavy chain-CD28ATM-CD28CSD-CD3zSSD
                           fusion
                         organism = synthetic construct
SEQUENCE: 63
MNFGLSLVFL ALILKGVQCE VQLVESGGDL VKPGGSLKLS CAASGFTFSS YGMSWVRQTP    60
DKRLEWVATI SSGGSYIYYP DSVKGRFTIS RDNAKNTLYL QMSSLKSEDT AMYYCARLGM   120
ITTGYAMDYW GQGTSVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSCGGGGSFW VLVVVGGVLA CYSLLVTVAF IIFWVRSKRL LLHSDYMNM TPRRPGPTRK   300
HYQPYAPPRD FAAYRSRVKF SRSADAPAYQ QGQNQLYNEL NLGRREEYDV LDKRRGRDPE   360
MGGKPRRKNP QEGLYNELQK DKMAEAYSEI GMKGERRRGK GHDGLYQGLS TATKDTYDAL   420
HMQALPPR                                                           428

SEQ ID NO: 64            moltype = AA  length = 243
FEATURE                  Location/Qualifiers
source                   1..243
                         mol_type = protein
                         note = Anti-AAA-Fab heavy chain
                         organism = synthetic construct
SEQUENCE: 64
MNFGLSLVFL ALILKGVQCE VQLVESGGDL VKPGGSLKLS CAASGFTFSS YGMSWVRQTP    60
DKRLEWVATI SSGGSYIYYP DSVKGRFTIS RDNAKNTLYL QMSSLKSEDT AMYYCARLGM   120
ITTGYAMDYW GQGTSVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
KSC                                                                243
```

```
SEQ ID NO: 65             moltype = AA  length = 219
FEATURE                   Location/Qualifiers
source                    1..219
                          mol_type = protein
                          note = Anti-AAA-Fab light chain
                          organism = synthetic construct
SEQUENCE: 65
DVLMTQTPLS LPVSLGDQAS ISCRSSQTIV HSTGHTYLEW FLQKPGQSPK LLIYKVSNRF   60
SGVPDRFSGS GSGTDFTLKI SRVEAEDLGV YYCFQGSHVP YTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 66             moltype = DNA  length = 780
FEATURE                   Location/Qualifiers
source                    1..780
                          mol_type = genomic DNA
                          organism = Homo sapiens
SEQUENCE: 66
atggcgcgcc cgcatccgtg gtggctgtgc gtgctgggca ccctggtggg cctgagcgcg   60
accccggcgc cgaaaagctg cccggaacgc cattattggg cgcagggcaa actgtgctgc  120
cagatgtgcg aaccgggcac cttttctggtg aaagattgcg atcagcatcg caaagcgcg  180
cagtgcgatc cgtgcattcc gggcgtgagc tttagcccgg atcatcatac ccgcccgcat  240
tgcgaaagct gccgccattg caacagcggc ctgctggtgc gcaactgcac cattaccgcg  300
aacgcggaat gcgcgtgccg caacggctgg cagtgccgcg ataaagaatg caccgaatgc  360
gatccgctgc cgaacccgag cctgaccgcg cgcagcaggc aggcgctgag cccgcatccg  420
cagccgaccc atctgccgta tgtgagcgaa atgctggaag cgcgcaccgc gggccatatg  480
cagaccctgg cggattttcg ccagctgccg gcgcgcaccc tgagcaccca ttggccgccg  540
cagcgcagcc tgtgcagcag cgatttttatt cgcattctgg tgatttttag cggcatgttt  600
ctggtgttta ccctggcggg cgcgctgttt ctgcatcagc gccgcaaata tcgcagcaac  660
aaaggcgaaa gcccggtgga accggcgaa ccgtgccatt atgcctgccc gcgcgaagaa  720
gaaggcagca ccattccgat tcaggaagat tatcgcaaac cggaaccggc gtgcagcccg  780

SEQ ID NO: 67             moltype = AA  length = 260
FEATURE                   Location/Qualifiers
source                    1..260
                          mol_type = protein
                          organism = Homo sapiens
SEQUENCE: 67
MARPHPWWLC VLGTLVGLSA TPAPKSCPER HYWAQGKLCC QMCEPGTFLV KDCDQHRKAA   60
QCDPCIPGVS FSPDHHTRPH CESCRHCNSG LLVRNCTITA NAECACRNGW QCRDKECTEC  120
DPLPNPSLTA RSSQALSPHP QPTHLPYVSE MLEARTAGHM QTLADFRQLP ARTLSTHWPP  180
QRSLCSSDFI RILVIFSGMF LVFTLAGALF LHQRRKYRSN KGESPVEPAE PCHYSCPREE  240
EGSTIPIQED YRKPEPACSP                                              260

SEQ ID NO: 68             moltype = DNA  length = 750
FEATURE                   Location/Qualifiers
source                    1..750
                          mol_type = genomic DNA
                          organism = Mus musculus
SEQUENCE: 68
atggcgtggc cgccgccgta ttggctgtgc atgctgggca ccctggtggg cctgagcgcg   60
accctggcgc cgaacagctg cccggataaa cattattgga ccggcggcgg cctgtgctgc  120
cgcatgtgcg aaccgggcac cttttttgtg aaagattgcg aacaggatcg caccgcggcg  180
cagtgcgatc cgtgcattcc gggcaccagc tttagcccgg attatcatac ccgcccgcat  240
tgcgaaagct gccgccattg caacagcggc tttctgattc gcaactgcac cgtgaccgcg  300
aacgcggaat gcagctgcag caaaaactgg cagtgccgcg atcaggaatg caccgaatgc  360
gatccgccgc tgaacccggc gctgacccgc cagccgagcg aaaccccgag cccgcagccg  420
ccgccgaccc atctgccgca tggcaccgaa aaaccgagct ggccgctgca tcgccagctg  480
ccgaacagca ccgtgtatag ccagcgcagc agccatcgcc cgctgtgcag cagcgattgc  540
attcgcattt ttgtgacctt tagcagcatg tttctgattt ttgtgctggg cgcgattctg  600
tttttttcatc agcgccgcaa ccatggcccg aacgaagatc gccaggcggt gccggaagaa  660
ccgtgcccgt atagctgccc gcgcgaagaa gaaggcagcg cgattccgat tcaggaagat  720
tatcgcaaac cggaaccggc gttttatccg                                    750

SEQ ID NO: 69             moltype = AA  length = 250
FEATURE                   Location/Qualifiers
source                    1..250
                          mol_type = protein
                          organism = Mus musculus
SEQUENCE: 69
MAWPPPYWLC MLGTLVGLSA TLAPNSCPDK HYWTGGGLCC RMCEPGTFFV KDCEQDRTAA   60
QCDPCIPGTS FSPDYHTRPH CESCRHCNSG FLIRNCTVTA NAECSCSKNW QCRDQECTEC  120
DPPLNPALTR QPSETPSPQP PPTHLPHGTE KPSWPLHRQL PNSTVYSQRS SHRPLCSSDC  180
IRIFVTFSSM FLIFVLGAIL FFHQRRNHGP NEDRQAVPEE PCPYSCPREE EGSAIPIQED  240
YRKPEPAFYP                                                         250

SEQ ID NO: 70             moltype = DNA  length = 660
FEATURE                   Location/Qualifiers
```

| | | |
|---|---|---|
| source | 1..660<br>mol_type = genomic DNA<br>organism = Homo sapiens | |

SEQUENCE: 70

```
atgctgcgcc tgctgctggc gctgaacctg tttccgagca ttcaggtgac cggcaacaaa   60
attctggtga aacagagccc gatgctggtg gcgtatgata acgcggtgaa cctgagctgc  120
aaatatagct ataacctgtt tagccgcgaa tttcgcgcga gcctgcataa aggcctggat  180
agcgcggtgg aagtgtgcgt ggtgtatggc aactatagcc agcagctgca ggtgtatagc  240
aaaaccggct ttaactgcga tggcaaactg ggcaacgaaa gcgtgacctt ttatctgcag  300
aacctgtatg tgaaccagac cgatatttat ttttgcaaaa ttgaagtgat gtatccgccg  360
ccgtatctgg ataacgaaaa aagcaacggc accattattc atgtgaaagg caaacatctg  420
tgcccgagcc cgctgtttcc gggcccgagc aaaccgtttt gggtgctggt ggtgggtggc  480
ggcgtgctgg cgtgctatag cctgctggtg accgtggcgt ttattatttt tgggtgcgc   540
agcaaacgca gccgcctgct gcatagcgat tatatgaaca tgaccccgcg ccgcccgggc  600
ccgacccgca aacattatca gccgtatgcg ccgccgcgcg atttttgcgg cgtatcgcagc  660
```

| | | |
|---|---|---|
| SEQ ID NO: 71<br>FEATURE<br>source | moltype = AA length = 220<br>Location/Qualifiers<br>1..220<br>mol_type = protein<br>organism = Homo sapiens | |

SEQUENCE: 71

```
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                       220
```

| | | |
|---|---|---|
| SEQ ID NO: 72<br>FEATURE<br>source | moltype = DNA length = 654<br>Location/Qualifiers<br>1..654<br>mol_type = genomic DNA<br>organism = Mus musculus | |

SEQUENCE: 72

```
atgaccctgc gcctgctgtt tctggcgctg aacttttta gcgtgcaggt gaccgaaaac   60
aaaattctgg tgaaacagag cccgctgctg gtggtggata gcaacgaagt gagcctgagc  120
tgccgctata gctataacct gctggcgaaa gaatttcgcg cgagcctgta taaaggcgtg  180
aacagcgatg tggaagtgtg cgtgggcaac ggcaacttta cctatcagcc gcagtttcgc  240
agcaacgcgg aatttaactg cgatggcgat tttgataacg aaaccgtgac cttttcgctg  300
tggaacctgc atgtgaacca taccgatatt tatttttgca aaattgaatt tatgtatccg  360
ccgccgtatc tggataacga acgcagcaac ggcaccatta ttcatattaa agaaaaacat  420
ctgtgccata cccagagcag cccgaaactg ttttgggcgc tggtggtggt ggcgggcgtg  480
ctgttttgct atggcctgct ggtgaccgtg gcgctgtgcg tgatttggac caacagccgc  540
cgcaaccgcc tgctgcagag cgattatatg aacatgaccc cgcgccgccc gggcctgacc  600
cgcaaaccgt atcagccgta tgcgccggcg cgcgattttg cggcgtatcg cccg         654
```

| | | |
|---|---|---|
| SEQ ID NO: 73<br>FEATURE<br>source | moltype = AA length = 218<br>Location/Qualifiers<br>1..218<br>mol_type = protein<br>organism = Mus musculus | |

SEQUENCE: 73

```
MTLRLLFLAL NFFSVQVTEN KILVKQSPLL VVDSNEVSLS CRYSYNLLAK EFRASLYKGV   60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                         218
```

| | | |
|---|---|---|
| SEQ ID NO: 74<br>FEATURE<br>source | moltype = DNA length = 768<br>Location/Qualifiers<br>1..768<br>mol_type = genomic DNA<br>organism = Homo sapiens | |

SEQUENCE: 74

```
atgggaaaca gctgttacaa catagtagcc actctgttgc tggtcctcaa ctttgagagg   60
acaagatcat tgcaggatcc ttgtagtaac tgcccagctg gtacattctg tgataataac  120
aggaatcaga tttgcagtcc ctgtcctcca aatagtttct ccagcgcagg tggacaaagg  180
acctgtgaca tatgcaggca gtgtaaaggt gttttcagga ccaggaagga gtgttcctcc  240
accagcaatg cagagtgtga ctgcactcca gggtttcact gcctggggc aggatgcagc  300
atgtgtgaac aggattgtaa acaaggtcaa gaactgacaa aaaaaggttg taaagactgt  360
tgctttggga catttaacga tcagaaacgt ggcatctgtc gaccctggac aaactgtctt  420
ttggatggaa agtctgtgct tgtgaatggg acgaaggaga gggacgtggt ctgtggacca  480
tctccagccg acctctctcc gggagcatcc tctgtgaccc cgcctgcccc tgcgagagag  540
ccaggacact ctccgcagat catctccttc tttcttgcgc tgacgtcgac tgcgttgctc  600
ttcctgctgt tcttcctcac gctccgtttc tctgttgtta acggggcag aaagaaactc  660
ctgtatatat tcaaacaacc atttatgaga ccagtacaaa ctactcaaga ggaagatggc  720
tgtagctgcc gatttccaga agaagaagaa ggaggatgtg aactgtga              768
```

| | | |
|---|---|---|
| SEQ ID NO: 75<br>FEATURE<br>source | moltype = AA length = 255<br>Location/Qualifiers<br>1..255 | |

```
                        mol_type = protein
                        organism = Homo sapiens
SEQUENCE: 75
MGNSCYNIVA TLLLVLNFER TRSLQDPCSN CPAGTFCDNN RNQICSPCPP NSFSSAGGQR      60
TCDICRQCKG VFRTRKECSS TSNAECDCTP GFHCLGAGCS MCEQDCKQGQ ELTKKGCKDC     120
CFGTFNDQKR GICRPWTNCS LDGKSVLVNG TKERDVVCGP SPADLSPGAS SVTPPAPARE     180
PGHSPQIISF FLALTSTALL FLLFFLTLRF SVVKRGRKKL LYIFKQPFMR PVQTTQEEDG     240
CSCRFPEEEE GGCEL                                                     255

SEQ ID NO: 76           moltype = DNA  length = 768
FEATURE                 Location/Qualifiers
source                  1..768
                        mol_type = genomic DNA
                        organism = Mus musculus
SEQUENCE: 76
atgggcaaca actgctataa cgtggtggtg attgtgctgc tgctggtggg ctgcgaaaaa      60
gtgggcgcgc tgcagaacag ctgcgataac tgccagccgg gcaccttttg ccgcaaatat     120
aacccggtgt gcaaaagctg cccgccgagc acctttagca gcattggcgg ccagccgaac     180
tgcaacattt gccgcgtgtg cgcgggctat tttcgcttta aaaattttg cagcagcacc      240
cataacgcgg aatgcgaatg cattgaaggc tttcattgcc tgggcccgca gtgcacccgc     300
tgcgaaaaag attgccgccc gggccaggaa ctgaccaaac agggctgcaa aacctgcagc     360
ctgggcacct taacgatca gaacggcacc ggcgtgtgcc gcccgtggac caactgcagc      420
ctggatggcc gcagcgtgct gaaaaccggc accaccgaaa agatgtggt gtgcggcccg      480
ccggtggtga gctttagccc gagcaccacc attagcgtga ccccggaagg cggcccgggc     540
ggccatagcc tgcaggtgct gaccctgttt ctggcgctga ccagcgcgct gctgctggcg     600
ctgattttta ttacctgct gtttagcgtg ctgaaatgga ttcgcaaaaa atttccgcat      660
attttaaaac agccgtttaa aaaaaccacc ggcgcggcgc aggaagaaga tgcgtgcagc     720
tgccgctgcc cgcaggaaga agaaggcgg ggcggcggct atgaactg                   768

SEQ ID NO: 77           moltype = AA  length = 256
FEATURE                 Location/Qualifiers
source                  1..256
                        mol_type = protein
                        organism = Mus musculus
SEQUENCE: 77
MGNNCYNVVV IVLLLVGCEK VGAVQNSCDN CQPGTFCRKY NPVCKSCPPS TFSSIGGQPN      60
CNICRVCAGY FRFKKFCSST HNAECECIEG FHCLGPQCTR CEKDCRPGQE LTKQGCKTCS     120
LGTFNDQNGT GVCRPWTNCS LDGRSVLKTG TTEKDVVCGP PVVSFSPSTT ISVTPEGGPG     180
GHSLQVLTLF LALTSALLLA LIFITLLLFSV LKWIRKKFPH IFKQPFKKTT GAAQEEDACS    240
CRCPQEEEGG GGGYEL                                                    256

SEQ ID NO: 78           moltype = DNA  length = 831
FEATURE                 Location/Qualifiers
source                  1..831
                        mol_type = genomic DNA
                        organism = Homo sapiens
SEQUENCE: 78
atgtgcgtgg gcgcgcgccg cctgggccgc ggcccgtgcg cggcgctgct gctgctgggc      60
ctgggcctga gcaccgtgac cggcctgcat tgcgtgggcg ataccatcc gagcaacgat     120
cgctgctgcc atgaatgccg ccccgggcaac ggcatggtga gccgctgcag ccgcagccag    180
aacaccgtgt gccgccccgtg cggccccggc ttttataacg atgtggtgag cagcaaaccg    240
tgcaaaccgt gcacctggtg caacctgcgc agcggcagcg aacgcaaaca gctgtgcacc    300
gcgacccagg atacccgtgtg ccgctgccgc gcgggcaccc agccgctgga tagctataaa   360
ccgggcgtgg attgcgcgcc gtgcccgccg ggccattttta gcccgggcga taaccaggcg   420
tgcaaaccgt ggaccaactg cacccctggcg caaaacatca cctgcagcc ggcgagcaac     480
agcagcgatg cgatttgcga agatcgcgat ccgccggcga cccagccgca ggaaacccag    540
ggcccgccgg cgcgccccgat taccgtgcag ccgaccgaag cgtggccgcg caccagccag    600
ggcccgagca cccgccccggt ggaagtgccg ggcggccgcg cggtggcggc gattctgggc   660
ctgggcctgg tgctgggcct gctgggcccg ctggcgattc tgctggcgct gtatctgctg   720
cgccgcgatc agcgcctgcc gccggatgcg cataaaccgc cgggcggcgg cagctttcgc    780
acccgattc aggaagaaca ggcggatgcg catagcctga tggcgaaaat t              831

SEQ ID NO: 79           moltype = AA  length = 277
FEATURE                 Location/Qualifiers
source                  1..277
                        mol_type = protein
                        organism = Homo sapiens
SEQUENCE: 79
MCVGARRLGR GPCAALLLLG LGLSTVTGLH CVGDTYPSND RCCHECRPGN GMVSRCSRSQ      60
NTVCRPCGPG FYNDVVSSKP CKPCTWCNLR SGSERKQLCT ATQDTVCRCR AGTQPLDSYK    120
PGVDCAPCPP GHFSPGDNQA CKPWTNCTLA GKHTLQPASN SSDAICEDRD PPATQPQETQ    180
GPPARPITVQ PTEAWPRTSQ GPSTRPVEVP GGRAVAAILG LGLVLGLLGP LAILLALYLL    240
RRDQRLPPDA HKPPGGGSFR TPIQEEQADA HSTLAKI                             277

SEQ ID NO: 80           moltype = DNA  length = 816
FEATURE                 Location/Qualifiers
source                  1..816
                        mol_type = genomic DNA
                        organism = Mus musculus
```

```
SEQUENCE: 80
atgtatgtgt gggtgcagca gccgaccgcg ctgctgctgc tggcgctgac cctgggcgtg    60
accgcgcgcc gcctgaactg cgtgaaacat acctatccga gcggccataa atgctgccgc   120
gaatgccagc cggcccatgg catggtgagc cgctgcgatc ataccgcga taccctgtgc    180
catccgtgcg aaaccggctt ttataacgaa gcggtgaact atgatacctg caaacagtgc   240
acccagtgca accatcgcag cggcagcgaa ctgaaacaga actgcacccc gacccaggat   300
accgtgtgcc gctgccgccc gggcacccag ccgcgcagg atagcggcta taaactgggc    360
gtggattgcg tgccgtgccc gccgggccat tttagcccgg caacaacca ggcgtgcaaa    420
ccgtggacca actgcaccct gagcggcaaa cagacccgc atccggcgag cgatagcctg    480
gatgcggtgt gcgaagatcg cagcctgctg gcgaccctgc tgtggaaac ccagcgcccg    540
acctttcgcc cgaccaccgt gcagagcacc accgtgtggc cgcgcaccag cgaactgccg    600
agcccgccga ccctggtgac cccggaaggc ccggcgtttg cggtgctgct gggcctgggc    660
ctgggcctgc tggcgccgct gaccgtgctg ctggcgctgt atctgctgcg caaagcgtgg    720
cgcctgccga cacccgaa accgtgctgg ggcaacagct ttcgcacccc gattcaggaa     780
gaacataccg atgcgcattt taccctggcg aaaatt                              816

SEQ ID NO: 81           moltype = AA  length = 272
FEATURE                 Location/Qualifiers
source                  1..272
                        mol_type = protein
                        organism = Mus musculus
SEQUENCE: 81
MYVWVQQPTA LLLLALTLGV TARRLNCVKH TYPSGHKCCR ECQPGHGMVS RCDHTRDTLC    60
HPCETGFYNE AVNYDTCKQC TQCNHRSGSE LKQNCTPTQD TVCRCRPGTQ PRQDSGYKLG   120
VDCVPCPPGH FSPGNNQACK PWTNCTLSGK QTRHPASDSL DAVCEDRSLL ATLLWETQRP   180
TFRPTTVQST TVWPRTSELP SPPTLVTPEG PAFAVLLGLG LGLLAPLTVL LALYLLRKAW   240
RLPNTPKPCW GNSFRTPIQE EHTDAHFTLA KI                                  272

SEQ ID NO: 82           moltype = DNA  length = 597
FEATURE                 Location/Qualifiers
source                  1..597
                        mol_type = genomic DNA
                        organism = Homo sapiens
SEQUENCE: 82
atgaaaagcg gcctgtggta tttttttctg ttttgcctgc gcattaaagt gctgaccggc    60
gaaattaacg gcagcgcgaa ctatgaaatg tttattttc ataacggcgg cgtgcagatt    120
ctgtgcaaat atccggatat tgtgcagcag tttaaaatgc agctgctgaa aggcggccag   180
attctgtgcg atctgaccaa aaccaaaggc agcggcaaca ccgtgagcat taaaagcctg    240
aaattttgcc atagccagct gagcaacaac agcgtgagct ttttctgta taacctggat    300
catagccatg cgaactatta ttttttgcaac ctgagcattt ttgatccgcc gccgtttaaa    360
gtgaccctga ccggcggcta tctgcatatt tatgaaagcc agctgtgctg ccagctgaaa    420
ttttggctgc cgattggctg cgcggcgttt gtggtggtgt gcattctggg ctgcattctg    480
atttgctggc tgaccaaaaa aaaatatagc agcagcgtgc atgatccgaa cggcgaatat    540
atgtttatgc gcgcggtgaa caccgcgaaa aaaagccgc tgaccgatgt gaccctg       597

SEQ ID NO: 83           moltype = AA  length = 199
FEATURE                 Location/Qualifiers
source                  1..199
                        mol_type = protein
                        organism = Homo sapiens
SEQUENCE: 83
MKSGLWYFFL FCLRIKVLTG EINGSANYEM FIFHNGGVQI LCKYPDIVQQ FKMQLLKGGQ    60
ILCDLTKTKG SGNTVSIKSL KFCHSQLSNN SVSFFLYNLD HSHANYYFCN LSIFDPPPFK   120
VTLTGGYLHI YESQLCCQLK FWLPIGCAAF VVVCILGCIL ICWLTKKKYS SSVHDPNGEY   180
MFMRAVNTAK KSRLTDVTL                                                 199

SEQ ID NO: 84           moltype = DNA  length = 600
FEATURE                 Location/Qualifiers
source                  1..600
                        mol_type = genomic DNA
                        organism = Mus musculus
SEQUENCE: 84
atgaaaccgt attttttgccg cgtgtttgtg ttttgctttc tgattcgcct gctgaccggc    60
gaaattaacg gcagcgcgga tcatcgcatg tttagcttc ataacggcgg cgtgcagatt    120
agctgcaaat atccggaaac cgtgcagcag ctgaaaatgc agctgtttcg gaacgcgaa    180
gtgctgtgcg aactgaccaa aaccaaaggc agcggcaacg cggtgagcat taaaaacccg    240
atgctgtgcc tgtatcatct gagcaacaac agcgtgagct ttttttctgaa caccccggat    300
agcagcagg gcagctatta tttttgcagc ctgagcattt ttgatccgcc gccgtttcag    360
gaacgcaacc tgagcggcgg ctatctgcat atttatgaa gccagctgtg ctgccagctg    420
aaactgtggc tgccggtggg ctgcgcggcg tttgtggtgg tgctgctgtt tggctgcatt    480
ctgattattt ggtttagcaa aaaaaaatat ggcagcagcg tgcatgatcc gaacagcgaa    540
tatatgttta tggcggcggt gaacaccaac aaaaaaagcc gcctggcggg cgtgaccagc    600

SEQ ID NO: 85           moltype = AA  length = 200
FEATURE                 Location/Qualifiers
source                  1..200
                        mol_type = protein
                        organism = Mus musculus
SEQUENCE: 85
```

```
MKPYFCRVFV FCFLIRLLTG EINGSADHRM FSFHNGGVQI SCKYPETVQQ LKMRLFRERE    60
VLCELTKTKG SGNAVSIKNP MLCLYHLSNN SVSFFLNNPD SSQGSYYFCS LSIFDPPPFQ   120
ERNLSGGYLH IYESQLCCQL KLWLPVGCAA FVVVLLFGCI LIIWFSKKKY GSSVHDPNSE   180
YMFMAAVNTN KKSRLAGVTS                                              200

SEQ ID NO: 86           moltype = DNA   length = 279
FEATURE                 Location/Qualifiers
source                  1..279
                        mol_type = genomic DNA
                        organism = Homo sapiens
SEQUENCE: 86
atgattcatc tgggccatat tctgtttctg ctgctgctgc cggtggcggc ggcgcagacc    60
acccccgggcg aacgcagcag cctgccggcg ttttatccgg gcaccagcgg cagctgcagc  120
ggctgcggca gcctgagcct gccgctgctg cggggctggg tggcggcgga tgcggtggcg   180
agcctgctga ttgtgggcgc ggtgtttctg tgcgcgcgcc cgcgccgcag cccggcgcag   240
gaagatggca aagtgtatat taacatgccg ggccgcggc                          279

SEQ ID NO: 87           moltype = AA   length = 93
FEATURE                 Location/Qualifiers
source                  1..93
                        mol_type = protein
                        organism = Homo sapiens
SEQUENCE: 87
MIHLGHILFL LLLPVAAAQT TPGERSSLPA FYPGTSGSCS GCGSLSLPLL AGLVAADAVA    60
SLLIVGAVFL CARPRRSPAQ EDGKVYINMP GRG                                 93

SEQ ID NO: 88           moltype = DNA   length = 237
FEATURE                 Location/Qualifiers
source                  1..237
                        mol_type = genomic DNA
                        organism = Mus musculus
SEQUENCE: 88
atggatccgc cgggctatct gctgtttctg ctgctgctgc cggtggcggc gagccagacc    60
agcgcgggca gctgcagcgg ctgcggcacc ctgagcctgc cgctgctggc gggcctggtg   120
gcggcggatg cggtgatgag cctgctgatt gtgggcgtgg tgtttgtgtg catgcgcccg   180
catggccgcc cggcgcagga agatggccgc gtgtatatta acatgccggg ccgcggc      237

SEQ ID NO: 89           moltype = AA   length = 79
FEATURE                 Location/Qualifiers
source                  1..79
                        mol_type = protein
                        organism = Mus musculus
SEQUENCE: 89
MDPPGYLLFL LLLPVAASQT SAGSCSGCGT LSLPLLAGLV AADAVMSLLI VGVVFVCMRP    60
HGRPAQEDGR VYINMPGRG                                                 79

SEQ ID NO: 90           moltype = DNA   length = 342
FEATURE                 Location/Qualifiers
source                  1..342
                        mol_type = genomic DNA
                        organism = Homo sapiens
SEQUENCE: 90
atgggggggac ttgaaccctg cagcaggctc ctgctcctgc ctctcctgct ggctgtaagt   60
ggtctccgtc ctgtccaggc ccaggcccag agcgattgca gttgctctac ggtgagcccg   120
ggcgtgctgg cagggatcgt gatgggagac ctggtgctga cagtgctcat tgccctggcc   180
gtgtacttcc tgggccggct ggtccctcgg gggcgagggg ctgcggaggc agcgacccgg   240
aaacagcgta tcactgagac cgagtcgcct atcaggagc tccagggtca gaggtcggat    300
gtctacagcg acctcaacac acagaggccg tattacaaat ga                      342

SEQ ID NO: 91           moltype = AA   length = 113
FEATURE                 Location/Qualifiers
source                  1..113
                        mol_type = protein
                        organism = Homo sapiens
SEQUENCE: 91
MGGLEPCSRL LLLPLLLAVS GLRPVQAQAQ SDCSCSTVSP GVLAGIVMGD LVLTVLIALA    60
VYFLGRLVPR GRGAAEAATR KQRITETESP YQELQGQRSD VYSDLNTQRP YYK          113

SEQ ID NO: 92           moltype = DNA   length = 345
FEATURE                 Location/Qualifiers
source                  1..345
                        mol_type = genomic DNA
                        organism = Mus musculus
SEQUENCE: 92
atggggggctc tggagccctc ctggtgcctt ctgttcttc ctgtcctcct gactgtggga    60
ggattaagtc cgtacaggc ccagagtgac actttcccaa gatgcgactg ttcttccgtg    120
agccctggtg tactggctgg gattgttctg ggtgacttgg tgttgactct gctgattgcc   180
ctggctgtgt actctctggg ccgcctggtc tcccgaggtc aagggacagc ggaagggacc   240
cggaaacaac acattgctga gactgagtcg ccttatcagg agcttcaggg tcagagacca   300
```

```
gaagtataca gtgacctcaa cacacagagg caatattaca gatga           345

SEQ ID NO: 93           moltype = AA  length = 114
FEATURE                 Location/Qualifiers
source                  1..114
                        mol_type = protein
                        organism = Mus musculus
SEQUENCE: 93
MGALEPSWCL LFLPVLLTVG GLSPVQAQSD TFPRCDCSSV SPGVLAGIVL GDLVLTLLIA    60
LAVYSLGRLV SRGQGTAEGT RKQHIAETES PYQELQGQRP EVYSDLNTQR QYYR         114

SEQ ID NO: 94           moltype = AA  length = 164
FEATURE                 Location/Qualifiers
source                  1..164
                        mol_type = protein
                        organism = Homo sapiens
SEQUENCE: 94
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPR                    164

SEQ ID NO: 95           moltype = DNA  length = 492
FEATURE                 Location/Qualifiers
source                  1..492
                        mol_type = genomic DNA
                        organism = Homo sapiens
SEQUENCE: 95
atgaagtgga aggcgctttt caccgcggcc atcctgcagg cacagttgcc gattacagag    60
gcacagagct ttggcctgct ggatcccaaa ctctgctacc tgctggatgg aatcctcttc   120
atctatggtg tcattctcac tgccttgttc ctgagagtga agttcagcag gagcgcagag   180
cccccccgcgt accagcaggg ccagaaccag ctctataacg agctcaatct aggacgaaga   240
gaggagtacg atgttttgga caagagacgt ggccgggacc ctgagatggg gggaaagccg   300
agaaggaaga accctcagga aggcctgtac aatgaactgc agaaagataa gatggcggag   360
gcctacagtg agattgggat gaaaggcgag cgccggaggg gcaaggggca cgatggcctt   420
taccagggtc tcagtacagc caccaaggac acctacgacg cccttcacat gcaggccctg   480
ccccctcgct aa                                                      492

SEQ ID NO: 96           moltype = AA  length = 164
FEATURE                 Location/Qualifiers
source                  1..164
                        mol_type = protein
                        organism = Mus musculus
SEQUENCE: 96
MKWKVSVLAC ILHVRFPGAE AQSFGLLDPK LCYLLDGILF IYGVIITALY LRAKFSRSAE    60
TAANLQDPNQ LYNELNLGRR EEYDVLEKKR ARDPEMGGKQ QRRRNPQEGV YNALQKDKMA   120
EAYSEIGTKG ERRRGKGHDG LYQGLSTATK DTYDALHMQT LAPR                    164

SEQ ID NO: 97           moltype = DNA  length = 495
FEATURE                 Location/Qualifiers
source                  1..495
                        mol_type = genomic DNA
                        organism = Mus musculus
SEQUENCE: 97
atgaagtgga aagtgtctgt tctcgcctgc atcctccacg tgcggttccc aggagcagag    60
gcacagagct ttggtctgct ggatcccaaa ctctgctact tgctagatgg aatcctcttc   120
atctacggag tcatcatcac agccctgtac ctgagagcaa aattcagcag gagtgcagag   180
actgctgcca acctgcagga ccccaaccag ctctacaatg agctcaatct agggcgaaga   240
gaggaatatg acgtcttgga gaagaagcgg gctcgggatc cagagatggg aggcaaacag   300
cagaggagga ggaaccccca ggaaggcgta tacaatgcac tgcagaaaga caagatggca   360
gaagcctaca gtgagatcgg cacaaaaggc gagaggcgga ggcaagggg gcacgatggc   420
ctttaccagg gtctcagcac tgccaccaag gacacctatg atgccctgca tatgcagacc   480
ctggcccctc gctaa                                                   495

SEQ ID NO: 98           moltype = AA  length = 254
FEATURE                 Location/Qualifiers
source                  1..254
                        mol_type = protein
                        organism = Homo sapiens
SEQUENCE: 98
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLFGSKN   180
VSSETVNITI TQGLAVSTIS SFFPPGYQVS FCLVMVLLFA VDTGLYFSVK TNIRSSTRDW   240
KDHKFKWRKD PQDK                                                    254

SEQ ID NO: 99           moltype = DNA  length = 762
FEATURE                 Location/Qualifiers
source                  1..762
                        mol_type = genomic DNA
```

```
                       organism = Homo sapiens
SEQUENCE: 99
atgtggcagc tgctgctgcc gaccgcgctg ctgctgctgg tgagcgcggg catgcgcacc    60
gaagatctgc cgaaagcggt ggtgtttctg aaccgcagt  ggtatcgcgt gctggaaaaa   120
gatagcgtga ccctgaaatg ccagggcgcg tatagcccgg aagataacag cacccagtgg   180
tttcataacg aaagcctgat tagcagccag gcgagcagct attttattga tgcggcgacc   240
gtggatgata cgcggcgaata tcgctgccag accaacctga gcaccctgag cgatccggtg   300
cagctggaag tgcatattgg ctggctgctg ctgcaggcgc cgcgctgggt gtttaaagaa   360
gaagatccga ttcatctgcg ctgccatagc tggaaaaaca ccgcgctgca taaagtgacc   420
tatctgcaga acggcaaagg ccgcaaatat tttcatcata acagcgattt ttatattccg   480
aaagcgaccc tgaaagatag cggcagctat ttttgccgcg gcctgtttgg cagcaaaaac   540
gtgagcagca aaaccgtgaa cattaccatt ccccagggcc tggcggtgag caccattagc   600
agcttttttc cgccgggcta tcaggtgagc ttttgcctgg tgatggtgct gctgtttgcg   660
gtggataccg gcctgtattt tagcgtgaaa accaacattc gcagcagcac ccgcgattgg   720
aaagatcata aatttaaatg gcgcaaagat ccgcaggata aa                        762

SEQ ID NO: 100        moltype = AA  length = 261
FEATURE               Location/Qualifiers
source                1..261
                      mol_type = protein
                      organism = Mus musculus
SEQUENCE: 100
MFQNAHSGSQ WLLPPLTILL LFAFADRQSA ALPKAVVKLD PPWIQVLKED MVTLMCEGTH     60
NPGNSSTQWF HNGRSIRSQV QASYTFKATV NDSGEYRCQM EQTRLSDPVD LGVISDWLLL   120
QTPQRVFLEG ETITLRCHSW RNKLLNRISF FHNEKSVRYH HYKSNFSIPK ANHSHSGDYY   180
CKGSLGSTQH QSKPVTITVQ DPATTSSISL VWYHTAFSLV MCLLFAVDTG LYFYVRRNLQ   240
TPREYWRKSL SIRKHQAPQD K                                              261

SEQ ID NO: 101        moltype = DNA  length = 786
FEATURE               Location/Qualifiers
source                1..786
                      mol_type = genomic DNA
                      organism = Mus musculus
SEQUENCE: 101
atgtttcaga atgcacactc tggaagccaa tggctactc  caccactgac aattctgctg    60
ctgtttgctt ttgcagacag gcagagtgca gctcttccga aggctgtggt gaaactggac   120
ccccccatgga tccaggtgct caaggaagac atggtgacac tgatgtgcga agggaccac   180
aaccctggga actcttctac ccagtggttc acaacgggga ggtccatccg gagccaggtc   240
caagccagtt acacgtttaa ggccacagtc aatgacagtg gagaatatcg tgtgcaaatg   300
gagcagaccc gcctcagcga ccctgtagat ctgggagtga tttctgactg gctgctgctc   360
cagacccctc agcgggtgtt tctggaaggg gaaaccatca cgctaaggtg ccatagctgg   420
aggaacaaac tactgaacag gatctcattc ttccataatg aaaaatccgt gaggtatcat   480
cactacaaaa gtaatttctc tatcccaaaa gccaaccaca gtcacagtgg ggactactac   540
tgcaaaggaa gtctaggaag tacacagcac cagtccaagc ctgtcaccat cactgtccaa   600
gatccagcaa ctacatcctc catctctcta gtctggtacc acactgcttt ctccctagtg   660
atgtgcctcc tgtttgcagt ggacacgggc ctttatttct acgtacgag  aaatcttcaa   720
accccgaggg agtactggag gaagtccctg tcaatcagaa agcaccaggc tcctcaagac   780
aagtga                                                              786

SEQ ID NO: 102        moltype = AA  length = 216
FEATURE               Location/Qualifiers
source                1..216
                      mol_type = protein
                      organism = Homo sapiens
SEQUENCE: 102
MGWIRGRRSR HSWEMSEFHN YNLDLKKSDF STRWQKQRCP VVKSKCRENA SPFFFCCFIA     60
VAMGIRFIIM VAIWSAVFLN SLFNQEVQIP LTESYCGPCP KNWICYKNNC YQFFDESKNW   120
YESQASCMSQ NASLLKVYSK EDQDLLKLVK SYHWMGLVHI PTNGSWQWED GSILSPNLLT   180
IIEMQKGDCA LYASSFKGYI ENCSTPNTYI CMQRTV                              216

SEQ ID NO: 103        moltype = DNA  length = 648
FEATURE               Location/Qualifiers
source                1..648
                      mol_type = genomic DNA
                      organism = Homo sapiens
SEQUENCE: 103
atgggctgga ttcgcggccg ccgcagccgc catagctggg aaatgagcga atttcataac     60
tataacctgg atctgaaaaa aagcgatttt agcacccgct ggcagaaaca gcgctgcccg   120
gtggtgaaaa gcaaatgccg cgaaaacgcg agccgtttt  ttttttgctg ctttattgcg   180
gtggcgatgg gcattcgctt tattattatg gtggcgattt ggagcgcggt gtttctgaac   240
agcctgttta accaggaagt gcagattccg ctgaccgaaa gctattcggg cccgtgcccg   300
aaaaactgga tttgctataa aaacaactgc tatcagtttt ttgatgaaag caaaaactgg   360
tatgaaagcc aggcgagctg catgagccag aacgcgagcc tgctgaaagt gtatagcaaa   420
gaagatcagg atctgctgaa actggtgaaa agctatcatt ggatgggcct ggtgcatatt   480
ccgaccaacg gcagctggca gtgggaagat ggcagcattc tgagcccgaa cctgctgacc   540
attattgaaa tgcagaaagg cgattgcgcg ctgtatgcga gctttaa   aggctatatt   600
gaaaactgca gcaccccgaa cacctatatt tgcatgcagc gcaccgtg                648

SEQ ID NO: 104        moltype = AA  length = 232
```

```
FEATURE                 Location/Qualifiers
source                  1..232
                        mol_type = protein
                        organism = Mus musculus
SEQUENCE: 104
MALIRDRKSH HSEMSKCHNY DLKPAKWDTS QEQQKQRLAL TTSQPGENGI IRGRYPIEKL    60
KISPMFVVRV LAIALAIRFT LNTLMWLAIF KETFQPVLCN KEVPVSSREG YCGPCPNNWI   120
CHRNNCYQFF NEEKTWNQSQ ASCLSQNSSL LKIYSKEEQD FLKLVKSYHW MGLVQIPANG   180
SWQWEDGSSL SYNQLTLVEI PKGSCAVYGS SFKAYTEDCA NLNTYICMKR AV           232

SEQ ID NO: 105          moltype = DNA   length = 696
FEATURE                 Location/Qualifiers
source                  1..696
                        mol_type = genomic DNA
                        organism = Mus musculus
SEQUENCE: 105
atggcgctga ttcgcgatcg caaaagccat catagcgaaa tgagcaaatg ccataactat    60
gatctgaaac cggcgaaatg ggataccagc caggaacagc aaaaacagcg cctggcgctg   120
accaccagcc agccgggcga aaacggcatt attcgcggcc gctatccgat tgaaaaactg   180
aaaattagcc cgatgtttgt ggtgcgcgtg ctggcgattg cgctggcgat tcgctttacc   240
ctgaacaccc tgatgtggct ggcgattttt aaagaaacct ttcagccggt gctgtgcaac   300
aaagaagtgc cggtgagcag ccgcgaaggc tattgcccga acaactggatt             360
tgccatcgca acaactgcta tcagtttttt aacgaagaaa aaacctggaa ccagagccag   420
gcgagctgcc tgagccagaa cagcagcctg ctgaaaattt atagcaaaga agaacaggat   480
tttctgaaac tggtgaaaag ctatcattgg atgggcctgg tgcagattcc ggcgaacggc   540
agctggcagt gggaagatgg cagcagcctg agctataacc agctgaccct ggtgaaaatt   600
ccgaaaggcg gctgcgcggt gtatggcagc agctttaaag cgtataccga agattgcgcg   660
aacctgaaca cctatatttg catgaaacgc gcggtg                             696

SEQ ID NO: 106          moltype = AA    length = 4
FEATURE                 Location/Qualifiers
source                  1..4
                        mol_type = protein
                        note = CD28 YMNM
                        organism = synthetic construct
SEQUENCE: 106
YMNM                                                                  4

SEQ ID NO: 107          moltype = AA    length = 4
FEATURE                 Location/Qualifiers
source                  1..4
                        mol_type = protein
                        note = CD28 PYAP
                        organism = synthetic construct
SEQUENCE: 107
PYAP                                                                  4

SEQ ID NO: 108          moltype = AA    length = 4
FEATURE                 Location/Qualifiers
source                  1..4
                        mol_type = protein
                        note = CD28 FMNM
                        organism = synthetic construct
SEQUENCE: 108
FMNM                                                                  4

SEQ ID NO: 109          moltype = AA    length = 4
FEATURE                 Location/Qualifiers
source                  1..4
                        mol_type = protein
                        note = CD28 AYAA
                        organism = synthetic construct
SEQUENCE: 109
AYAA                                                                  4

SEQ ID NO: 110          moltype = AA    length = 21
FEATURE                 Location/Qualifiers
source                  1..21
                        mol_type = protein
                        note = Signal peptide
                        organism = synthetic construct
SEQUENCE: 110
ATMGWSCIIL FLVATATGVH S                                              21

SEQ ID NO: 111          moltype = DNA   length = 57
FEATURE                 Location/Qualifiers
source                  1..57
                        mol_type = other DNA
                        note = Signal peptide DNA sequence
```

-continued

```
                        organism = synthetic construct
SEQUENCE: 111
atgggatgga gctgtatcat cctcttcttg gtagcaacag ctaccggtgt gcactcc      57

SEQ ID NO: 112          moltype = AA   length = 449
FEATURE                 Location/Qualifiers
source                  1..449
                        mol_type = protein
                        note = Anti-CD20 (GA101) heavy chain
                        organism = synthetic construct
SEQUENCE: 112
QVQLVQSGAE VKKPGSSVKV SCKASGYAFS YSWINWVRQA PGQGLEWMGR IFPGDGDTDY   60
NGKFKGRVTI TADKSTSTAY MELSSLRSED TAVYYCARNV FDGYWLVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 113          moltype = AA   length = 219
FEATURE                 Location/Qualifiers
source                  1..219
                        mol_type = protein
                        note = Anti-CD20 (GA101) light chain
                        organism = synthetic construct
SEQUENCE: 113
DIVMTQTPLS LPVTPGEPAS ISCRSSKSLL HSNGITYLYW YLQKPGQSPQ LLIYQMSNLV   60
SGVPDRFSGS GSGTDFTLKI SRVEAEDVGV YYCAQNLELP YTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 114          moltype = AA   length = 447
FEATURE                 Location/Qualifiers
source                  1..447
                        mol_type = protein
                        note = Anti-FAP(4B9) PGLALA heavy chain
                        organism = synthetic construct
SEQUENCE: 114
EVQLLESGGG LVQPGGSLRL SCAASGFTFS SYAMSWVRQA PGKGLEWVSA IIGSGASTYY   60
ADSVKGRFTI SRDNSKNTLY LQMNSLRAED TAVYYCAKGW FGGFNYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 115          moltype = AA   length = 215
FEATURE                 Location/Qualifiers
source                  1..215
                        mol_type = protein
                        note = Anti-FAP(4B9) light chain
                        organism = synthetic construct
SEQUENCE: 115
EIVLTQSPGT LSLSPGERAT LSCRASQSVT SSYLAWYQQK PGQAPRLLIN VGSRRATGIP   60
DRFSGSGSGT DFTLTISRLE PEDFAVYYCQ QGIMLPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 116          moltype = AA   length = 451
FEATURE                 Location/Qualifiers
source                  1..451
                        mol_type = protein
                        note = Anti-CEA (A5B7) PGLALA heavy chain
                        organism = synthetic construct
SEQUENCE: 116
EVQLVESGGG LVQPGRSLRL SCAASGFTVS SYWMHWVRQA PGKGLEWVGF IRNKANGGTT   60
EYAASVKGRF TISRDDSKNT LYLQMNSLRA EDTAVYYCAR DRGLRFYFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 117          moltype = AA   length = 223
FEATURE                 Location/Qualifiers
source                  1..223
```

```
                          mol_type = protein
                          note = Anti-CEA (A5B7) light chain
                          organism = synthetic construct
SEQUENCE: 117
QAVLTQPASL SASPGASASL TCTLRRGINV GAYSIYWYQQ KPGSPPQYLL RYKSDSDKQQ    60
GSGVSSRFSA SKDASANAGI LLISGLQSED EADYYCMIWH SGASAVFGGG TKLTVLRTVA   120
APSVFIFPPS DEQLKSGTAS VVCLLNNFYP REAKVQWKVD NALQSGNSQE SVTEQDSKDS   180
TYSLSSTLTL SKADYEKHKV YACEVTHQGL SSPVTKSFNR GEC                     223

SEQ ID NO: 118            moltype = AA   length = 451
FEATURE                   Location/Qualifiers
source                    1..451
                          mol_type = protein
                          note = Anti-CEA (T84.66LCHA) PGLALA heavy chain
                          organism = synthetic construct
SEQUENCE: 118
QVQLVQSGAE VKKPGSSVKV SCKASGFNIK DTYMHWVRQA PGQGLEWMGR IDPANGNSKY    60
VPKFQGRVTI TADTSTSTAY MELSSLRSED TAVYYCAPFG YYVSDYAMAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 119            moltype = AA   length = 218
FEATURE                   Location/Qualifiers
source                    1..218
                          mol_type = protein
                          note = Anti-CEA (T84.66LCHA) light chain
                          organism = synthetic construct
SEQUENCE: 119
EIVLTQSPAT LSLSPGERAT LSCRAGESVD IFGVGFLHWY QQKPGQAPRL LIYRASNRAT    60
GIPARFSGSG SGTDFTLTIS SLEPEDFAVY YCQQTNEDPY TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 120            moltype = AA   length = 451
FEATURE                   Location/Qualifiers
source                    1..451
                          mol_type = protein
                          note = Anti-CEA (CH1A1A98/992F1) PGLALA heavy chain
                          organism = synthetic construct
SEQUENCE: 120
QVQLVQSGAE VKKPGASVKV SCKASGYTFT EFGMNWVRQA PGQGLEWMGW INTKTGEATY    60
VEEFKGRVTF TTDTSTSTAY MELRSLRSDD TAVYYCARWD FAYYVEAMDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVCTLPPSRD   360
ELTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                  451

SEQ ID NO: 121            moltype = AA   length = 215
FEATURE                   Location/Qualifiers
source                    1..215
                          mol_type = protein
                          note = Anti-CEA (CH1A1A98/992F1) light chain
                          organism = synthetic construct
SEQUENCE: 121
DIQMTQSPSS LSASVGDRVT ITCKASAAVG TYVAWYQQKP GKAPKLLIYS ASYRKRGVPS    60
RFSGSGSGTD FTLTISSLQP EDFATYYCHQ YYTYPLFTFG QGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 122            moltype = AA   length = 449
FEATURE                   Location/Qualifiers
source                    1..449
                          mol_type = protein
                          note = Anti-CEA (hMN14) PGLALA heavy chain
                          organism = synthetic construct
SEQUENCE: 122
EVQLVESGGG VVQPGRSLRL SCSASGFDFT TYWMSWVRQA PGKGLEWIGE IHPDSSTINY    60
APSLKDRFTI SRDNAKNTLF LQMDSLRPED TGVYFCASLY FGFPWFAYWG QGTPVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL GAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
```

```
QGNVFSCSVM HEALHNHYTQ KSLSLSPGK                                449

SEQ ID NO: 123         moltype = AA   length = 213
FEATURE                Location/Qualifiers
source                 1..213
                       mol_type = protein
                       note = Anti-CEA (hMN14) light chain
                       organism = synthetic construct
SEQUENCE: 123
DIQLTQSPSS LSASVGDRVT ITCKASQDVG TSVAWYQQKP GKAPKLLIYW TSTRHTGVPS   60
RFSGSGSGTD FTFTISSLQP EDIATYYCQQ YSLYRSFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 124         moltype = AA   length = 451
FEATURE                Location/Qualifiers
source                 1..451
                       mol_type = protein
                       note = Anti-TNC (2B10) PGLALA heavy chain
                       organism = synthetic construct
SEQUENCE: 124
QVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCARLY GYAYYGAFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSPG K                                451

SEQ ID NO: 125         moltype = AA   length = 214
FEATURE                Location/Qualifiers
source                 1..214
                       mol_type = protein
                       note = Anti-TNC (2B10) light chain
                       organism = synthetic construct
SEQUENCE: 125
DIQMTQSPSS LSASVGDRVT ITCRASQGIR NDLGWYQQKP GKAPKRLIYA ASSLQSGVPS   60
RFSGSGSGTE FTLTISSLQP EDFATYYCLQ NGLQPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 126         moltype = AA   length = 449
FEATURE                Location/Qualifiers
source                 1..449
                       mol_type = protein
                       note = Anti-HER2 (PER) PG LALA heavy chain 1
                       organism = synthetic construct
SEQUENCE: 126
EVQLVESGGG LVQPGGSLRL SCAASGFTFT DYTMDWVRQA PGKGLEWVAD VNPNSGGSIY   60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL GAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 127         moltype = AA   length = 214
FEATURE                Location/Qualifiers
source                 1..214
                       mol_type = protein
                       note = Anti-HER2 (PER) light chain 1
                       organism = synthetic construct
SEQUENCE: 127
DIQMTQSPSS LSASVGDRVT ITCKASQDVS IGVAWYQQKP GKAPKLLIYS ASYRYTGVPS   60
RFSGSGSGTD FTLTISSLQP EDFATYYCQQ YYIYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 128         moltype = AA   length = 449
FEATURE                Location/Qualifiers
source                 1..449
                       mol_type = protein
                       note = Anti-HER2 (PER) PG LALA heavy chain 2
                       organism = synthetic construct
SEQUENCE: 128
EVQLVESGGG LVQPGGSLRL SCAASGFTFT DYTMDWVRQA PGKGLEWVAD VNPNSGGSIY   60
NQRFKGRFTL SVDRSKNTLY LQMNSLRAED TAVYYCARNL GPSFYFDYWG QGTLVTVSSA  120
```

-continued

```
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL GAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 129          moltype = AA  length = 214
FEATURE                 Location/Qualifiers
source                  1..214
                        mol_type = protein
                        note = Anti-HER2 (PER) light chain 2
                        organism = synthetic construct
SEQUENCE: 129
DIQMTQSPSS LSASVGDRVT ITCKASQDVS IGVAWYQQKP GKAPKLLIYS ASYRYTGVPS   60
RFSGSGSGTD FTLTISSLQP EDFATYYCQQ YYIYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 130          moltype = AA  length = 330
FEATURE                 Location/Qualifiers
source                  1..330
                        mol_type = protein
                        organism = Homo sapiens
SEQUENCE: 130
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330
```

ANTIGEN BINDING RECEPTORS SPECIFIC FOR MUTATED Fc DOMAINS

CROSS REFERENCE TO RELATED APPLICATIONS

This application is a division of U.S. patent application Ser. No. 16/576,546, which is a continuation of International Application No. PCT/EP2018/057566, filed Mar. 26, 2018, the content of which is herein incorporated by reference in its entirety, which claims priority to EP Application No. 17163090.8 filed Mar. 27, 2017.

SEQUENCE LISTING

The instant application contains a Sequence Listing which has been submitted electronically in XML format and is hereby incorporated by reference in its entirety. Said XML copy, created on May 2, 2023, is named "50474-228003_Sequence_Listing_5_2_23.xml" and is 182,766 bytes in size.

FIELD OF THE INVENTION

The present invention generally relates to antigen binding receptors capable of specific binding to mutated Fc domains with reduced Fc receptor binding and T cells expressing these antigen binding receptors. More precisely, the present invention relates to T cells, transfected/transduced with an antigen binding receptor which is recruited by specifically binding to/interacting with the mutated Fc domain of therapeutic antibodies. Furthermore, the invention relates to a kit comprising the T cells of the invention and/or nucleic acid molecules, vectors expressing antigen binding receptors of the present invention and (a) tumor targeting antibody/antibodies comprising a mutated Fc domain. The invention also provides the production and use of T cells in a method for the treatment of particular diseases in conjunction with tumor-specific antibodies as well as pharmaceutical compositions/medicaments comprising T cells and/or therapeutic antibodies, wherein T cells are to be administered in combination with therapeutic-tumor targeting antibody/antibodies comprising a mutated Fc domain with reduced Fc receptor binding.

BACKGROUND

Adoptive T cell therapy (ACT) is a powerful treatment approach using cancer-specific T cells (Rosenberg and Restifo, Science 348(6230) (2015), 62-68). ACT may use naturally occurring tumor-specific cells or T cells rendered specific by genetic engineering using T cell or chimeric antigen receptors (Rosenberg and Restifo, Science 348 (6230) (2015), 62-68). ACT can successfully treat and induce remission in patients suffering even from advanced and otherwise treatment refractory diseases such as acute lymphatic leukemia, non-hodgkins lymphoma or melanoma (Dudley et al., J Clin Oncol 26(32) (2008), 5233-5239; Grupp et al., N Engl J Med 368 (16) (2013), 1509-1518; Kochenderfer et al., J Clin Oncol. (2015) 33(6):540-549, doi: 10.1200/JCO.2014.56.2025. Epub 2014 Aug. 25).

However, despite impressive clinical efficacy, ACT is limited by treatment-related toxicities. The specificity, and resulting on-target and off-target effects, of engineered T cells used in ACT is mainly driven by the tumor targeting antigen binding moiety implemented in the chimeric antigen receptor (CAR). Non-exclusive expression of the tumor antigen or temporal difference in the expression level can result with serious side effects or even abortion of ACT due to non-tolerable toxicity of the treatment.

Additionally, the availability of tumor-specific T cells for efficient tumor cells lysis is dependent on the long-term survival and proliferation capacity of engineered T cells in vivo. On the other hand, in vivo survival and proliferation of T cells may result with unwanted long-term effects due to the persistence of an uncontrolled CAR-T response (Grupp et al. 2013 N Engl J Med 368(16):1509-18, Maude et al. 2014 2014 N Engl J Med 371(16):1507-17).

One approach for limiting serious treatment-related toxicities and to improve safety of ACT is to restrict the activation and proliferation of CAR-T cells by introducing adaptor molecules in the immunological synapse. Such adaptor molecules comprise small molecular bimodular switches as e.g. recently described folate-FITC switch (Kim et al. J Am Chem Soc 2015; 137:2832-2835). A further approach included artificially modified antibodies comprising a tag to guide and direct the specificity of CAR-T cells to target tumor cells (Ma et al. PNAS 2016; 113(4):E450-458, Cao et al. Angew Chem 2016; 128:1-6, Rogers et al. PNAS 2016; 113(4):E459-468, Tamada et al. Clin Cancer Res 2012; 18(23):6436-6445).

However, existing approaches have several limitations. Immunological synapses relying on molecular switches require introduction of additional elements which might elicit an immune response or result with non-specific off-target effects. Furthermore, the complexity of such multi-component systems may limit treatment efficacy and tolerability. On the other hand, the introduction of tag structure in existing therapeutic monoclonal antibodies may affect the efficacy and safety profile of these constructs.

Accordingly, the targeted tumor therapy, particularly the adoptive T cell therapy needs to be improved in order to suffice the needs of the cancer patients. Thus, there is still a need to provide improved means having the potential to improve safety and efficacy of ACT and overcome the above disadvantages.

SUMMARY OF THE INVENTION

The present invention generally relates to antigen binding receptors capable of specific binding to mutated Fc domains with reduced Fc receptor binding and T cells expressing these antigen binding receptors.

In one aspect the invention relates to an antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain.

In one embodiment, Fc receptor binding of the mutated Fc domain is reduced compared to Fc receptor binding of the non-mutated parent Fc domain, particularly wherein the Fc receptor is a Fcγ receptor or neonatal Fc receptor (FcRn). In one embodiment, Fc receptor binding is measured by Surface Plasmon Resonance (SPR) at 25° C.

In one embodiment, the antigen binding moiety is a scFv, a Fab, a crossFab, or a scFab. In a preferred embodiment, the antigen binding moiety is a scFv. In another preferred embodiment, the antigen binding moiety is a Fab or a crossFab.

In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

In one embodiment, the anchoring transmembrane domain is the CD28 transmembrane domain, in particular wherein the anchoring transmembrane domain comprises the amino acid sequence of SEQ ID NO:11.

In one embodiment, the antigen binding receptor further comprises at least one stimulatory signaling domain and/or at least one co-stimulatory signaling domain. In one embodiment, the at least one stimulatory signaling domain is individually selected from the group consisting of the intracellular domain of CD3z, of FCGR3A and of NKG2D, or fragments thereof. In one embodiment, the at least one stimulatory signaling domain is a fragment of the intracellular domain of CD3z, in particular wherein the at least one stimulatory signaling domain comprises the amino acid sequence of SEQ ID NO:13. In one embodiment, the at least one co-stimulatory signaling domain is individually selected from the group consisting of the intracellular domain of CD27, of CD28, of CD137, of OX40, of ICOS, of DAP10 and of DAP12, or fragments thereof. In one embodiment, the at least one co-stimulatory signaling domain is a fragment of the CD28 intracellular domain. In one embodiment, the antigen binding receptor comprises one stimulatory signaling domain comprising the intracellular domain of CD3z, or a fragment thereof, and wherein the antigen binding receptor comprises one co-stimulatory signaling domain comprising the intracellular domain of CD28, or a fragment thereof. In one embodiment, the stimulatory signaling domain comprises the amino acid sequence of SEQ ID NO:13 and the co-stimulatory signaling domain comprises the amino acid sequence of SEQ ID NO:12.

In one embodiment, the extracellular domain is connected to the anchoring transmembrane domain, optionally through a peptide linker. In one embodiment, the peptide linker comprises the amino acid sequence GGGGS (SEQ ID NO:17). In one embodiment, the anchoring transmembrane domain is connected to a co-signaling domain or to a signaling domain, optionally through a peptide linker. In one embodiment, the signaling and/or co-signaling domains are connected, optionally through at least one peptide linker.

In one embodiment, the antigen binding moiety is a scFv fragment, wherein the scFv fragment is connected at the C-terminus to the N-terminus of the anchoring transmembrane domain, optionally through a peptide linker.

In one embodiment, the antigen binding moiety is a Fab fragment or a crossFab fragment, wherein the Fab or crossFab fragment is connected at the C-terminus of the heavy chain to the N-terminus of the anchoring transmembrane domain, optionally through a peptide linker.

In one embodiment, the antigen binding receptor comprises one co-signaling domain, wherein the co-signaling domain is connected at the N-terminus to the C-terminus of the anchoring transmembrane domain. In one embodiment, the antigen binding receptor comprises one stimulatory signaling domain, wherein the stimulatory signaling domain is connected at the N-terminus to the C-terminus of the co-stimulatory signaling domain.

In one embodiment, the non-mutated parent Fc domain is an IgG1 or an IgG4 Fc domain, particularly a human IgG1 Fc domain. In one embodiment, the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

In one embodiment, the mutated Fc domain comprises at least one amino acid mutation at a position selected from the group consisting of L234, L235 and P329 according to EU numbering, in particular the amino acid mutations L234A, L235A and P329G ("PGLALA").

In one embodiment, the mutated Fc domain comprises the amino acid mutation P329G according to EU numbering, wherein Fcγ receptor binding of the mutated Fc domain is reduced compared to Fcγ receptor binding of the non-mutated parent Fc domain, in particular wherein the Fcγ receptor is human FcγRIIIa and/or FcγRIIa.

In one embodiment, the mutated Fc domain comprises at least one amino acid mutation at a position selected from the group consisting of I253, H310 and H435 according to EU numbering, in particular the amino acid mutations I253A, H310A and H435A ("AAA"), wherein FcRn binding of the mutated Fc domain is reduced compared to FcRn binding of the non-mutated parent Fc domain.

In one embodiment, the at least one antigen binding moiety is capable of specific binding to a mutated Fc domain comprising the P329G mutation but not capable of specific binding to the non-mutated parent Fc domain, wherein the antigen binding moiety comprises:
  (i) a heavy chain variable region (VH) comprising
    (a) the heavy chain complementarity-determining region (CDR H) 1 amino acid sequence RYWMN (SEQ ID NO:1);
    (b) the CDR H2 amino acid sequence EITPDSSTI-NYTPSLKD (SEQ ID NO:2); and
    (c) the CDR H3 amino acid sequence PYDYGAWFAS (SEQ ID NO:3); and
  (ii) a light chain variable region (VL) comprising
    (d) the light chain complementary-determining region (CDR L) 1 amino acid sequence RSST-GAVTTSNYAN (SEQ ID NO:4);
    (e) the CDR L2 amino acid sequence GTNKRAP (SEQ ID NO:5); and
    (f) the CDR L3 amino acid sequence ALWYSNHWV (SEQ ID NO:6).

In one embodiment, the at least one antigen binding moiety is capable of specific binding to a mutated Fc domain comprising the P329G mutation but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to an amino acid sequence selected from the group consisting of SEQ ID NO:8 and SEQ ID NO:32, and a light chain variable region (VL) comprising an amino acid sequence that is at least about 95%, 96%, 97%, 98%, 99% or 100% identical to an amino acid sequence selected from the group consisting of SEQ ID NO:9 and SEQ ID NO:33.

In one embodiment, the at least one antigen binding moiety comprises the heavy chain variable region (VH) of SEQ ID NO:8 and the light chain variable region (VL) of SEQ ID NO:9. In one embodiment, the at least one antigen binding moiety is a scFv capable of specific binding to a mutated Fc domain comprising the P329G mutation but not capable of specific binding to the non-mutated parent Fc domain, wherein the antigen binding receptor comprises an amino acid sequence that is at least about 95%, 96%, 97%, 98%, 99% or 100% identical to an amino acid sequence selected from the group consisting of SEQ ID NO:7 and SEQ ID NO:31. In one embodiment, the antigen binding receptor comprises the amino acid sequence of SEQ ID NO:7. In one embodiment, the at least one antigen binding moiety is a Fab fragment capable of specific binding to a mutated Fc domain comprising the P329G mutation but not capable of specific binding to the non-mutated parent Fc domain, wherein the antigen binding receptor comprises
   a) a heavy chain fusion polypeptide that is at least about 95%, 96%, 97%, 98%, 99% or 100% identical to an amino acid sequence selected from the group consisting of SEQ ID NO:39 and SEQ ID NO:48; and
   b) a light chain polypeptide that is at least about 95%, 96%, 97%, 98%, 99% or 100% identical to an amino acid sequence selected from the group consisting of SEQ ID NO:41 and SEQ ID NO:50.

In one embodiment, the antigen binding receptor comprises
   a) the heavy chain fusion polypeptide of SEQ ID NO:39; and
   b) the light chain polypeptide of SEQ ID NO:41.

In one embodiment, the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises:
   (i) a heavy chain variable region (VH) comprising
      (a) the heavy chain complementarity-determining region (CDR H) 1 amino acid sequence SYGMS (SEQ ID NO:53);
      (b) the CDR H2 amino acid sequence SSGGSY (SEQ ID NO:54); and
      (c) the CDR H3 amino acid sequence LGMITTG-YAMDY (SEQ ID NO:55); and
   (ii) a light chain variable region (VL) comprising
      (d) the light chain complementary-determining region (CDR L) 1 amino acid sequence RSSQTIVH-STGHTYLE (SEQ ID NO:56);
      (e) the CDR L2 amino acid sequence KVSNRFS (SEQ ID NO:57); and
      (f) the CDR L3 amino acid sequence FQGSHVPYT (SEQ ID NO:58).

In one embodiment, the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence of SEQ ID NO:62.

In one embodiment, the at least one antigen binding moiety comprises
   a) the heavy chain variable region (VH) of SEQ ID NO:61; and
   b) the light chain variable region (VL) of SEQ ID NO:62.

In one embodiment, the at least one antigen binding moiety is a scFv capable of specific binding to a mutated Fc domain comprising the I253A, H310A and H435A ("AAA") mutations but not capable of specific binding to the non-mutated parent Fc domain, wherein the antigen binding receptor comprises an amino acid sequence that is at least about 95%, 96%, 97%, 98%, 99% or 100% identical to the amino acid sequence of SEQ ID NO:59. In one embodiment, the antigen binding receptor comprises the amino acid sequence of SEQ ID NO:59.

In one embodiment, the at least one antigen binding moiety is a Fab fragment capable of specific binding to a mutated Fc domain comprising the P329G mutation but not capable of specific binding to the non-mutated parent Fc domain, wherein the antigen binding receptor comprises
   a) a heavy chain fusion polypeptide that is at least about 95%, 96%, 97%, 98%, 99% or 100% identical to the amino acid sequence of SEQ ID NO:39; and
   b) a light chain polypeptide that is at least about 95%, 96%, 97%, 98%, 99% or 100% identical to the amino acid sequence of SEQ ID NO:41.

In one embodiment, the antigen binding receptor comprises
   a) the heavy chain fusion polypeptide of SEQ ID NO:39; and
   b) the light chain polypeptide of SEQ ID NO:41.

In one embodiment, provided is an isolated polynucleotide encoding the antigen binding receptor as described herein. In one embodiment, provided is an isolated polynucleotide encoding a heavy chain fusion polypeptide or a light chain polypeptide of the antigen binding receptor as described herein. In one embodiment, provided is a composition encoding the antigen binding receptor as described herein, comprising a first isolated polynucleotide encoding a heavy chain fusion polypeptide, and a second isolated polynucleotide encoding a light chain polypeptide.

In one embodiment, provided is a polypeptide encoded by the polynucleotide as described herein or by the composition as described herein.

In one embodiment, provided is a vector, particularly an expression vector, comprising the polynucleotide(s) as described herein.

In one embodiment, provided is a transduced T cell comprising the polynucleotide(s) as described herein or the vector as described herein. In one embodiment, provided is a transduced T cell capable of expressing the antigen binding receptor as described herein. In one embodiment, provided is the transduced T cell as described herein, wherein the transduced T cell is co-transduced with a T cell receptor (TCR) capable of specific binding of a target antigen.

In one embodiment, provided is a kit comprising
   (A) a transduced T cell capable of expressing the antigen binding receptor as described herein; and
   (B) an antibody comprising a mutated Fc domain;
   wherein the antigen binding receptor is capable of specific binding to the mutated Fc domain but not capable of specific binding to the non-mutated parent Fc domain.

In one embodiment, provided is a kit comprising
   (A) an isolated polynucleotide encoding the antigen binding receptor as described herein; and
   (B) an antibody comprising a mutated Fc domain;
   wherein the antigen binding receptor is capable of specific binding to the mutated Fc domain but not capable of specific binding to the non-mutated parent Fc domain.

In one embodiment, provided is a kit comprising
   (A) the composition or the vector as described herein encoding the antigen binding receptor as described herein; and
   (B) an antibody comprising a mutated Fc domain;
   wherein the antigen binding receptor is capable of specific binding to the mutated Fc domain but not capable of specific binding to the non-mutated parent Fc domain.

In one embodiment, the non-mutated parent Fc domain is an IgG1 or an IgG4 Fc domain, particularly a human IgG1

Fc domain. In one embodiment, provided is a mutated Fc domain comprising at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A. In one embodiment, the mutated Fc domain comprises at least one amino acid mutation at a position selected from the group consisting of L234, L235 and P329 according to EU numbering, in particular the amino acid mutations L234A, L235A and P329G ("PGLALA").

In one embodiment, the mutated Fc domain comprises the amino acid mutation P329G according to EU numbering. In one embodiment, the mutated Fc domain comprises at least one amino acid mutation at a position selected from the group consisting of I253, H310 and H435 according to EU numbering, in particular the amino acid mutations I253A, H310A and H435A ("AAA").

In one embodiment, the antibody comprising the mutated Fc domain is capable of specific binding to an antigen on the surface of a tumor cell, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

In one embodiment, the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

In one embodiment, provided is the kit as described herein for use as a medicament.

In one embodiment, provided is the antigen binding receptor or the transduced T cell as described herein for use as a medicament, wherein the transduced T cell expressing the antigen binding receptor is administered before, simultaneously with or after administration of an antibody comprising a mutated Fc domain wherein the antigen binding receptor is capable of specific binding to the mutated Fc domain but not capable of specific binding to the non-mutated parent Fc domain.

In one embodiment, provided is the kit as described herein for use in the treatment of a malignant disease. In one embodiment, provided is the antigen binding receptor or the transduced T cell as described herein for use in the treatment of a malignant disease, wherein the treatment comprises administration of a transduced T cell expressing the antigen binding receptor before, simultaneously with or after administration of an antibody comprising a mutated Fc domain wherein the antigen binding receptor is capable of specific binding to the mutated Fc domain but not capable of specific binding to the non-mutated parent Fc domain.

In one embodiment, said malignant disease is selected from cancer of epithelial, endothelial or mesothelial origin and cancer of the blood.

In one embodiment, the transduced T cell is derived from a cell isolated from the subject to be treated. In one embodiment, the transduced T cell is not derived from a cell isolated from the subject to be treated.

In one embodiment, provided is a method of treating a disease in a subject, comprising administering to the subject a transduced T cell capable of expressing the antigen binding receptor as described herein and administering before, simultaneously with or after administration of the transduced T cell a therapeutically effective amount of an antibody comprising a mutated Fc domain, wherein the antigen binding receptor is capable of specific binding to the mutated Fc domain but not capable of specific binding to the non-mutated parent Fc domain. In one embodiment, the T cell is additionally isolated from the subject and the transduced T cell is generated by transducing the isolated T cell with the polynucleotide, the composition or the vector as described herein. In one embodiment, the T cell is transduced with a retroviral or lentiviral vector construct or with a non-viral vector construct. In one embodiment, the non-viral vector construct is a sleeping beauty minicircle vector.

In one embodiment, the transduced T cell is administered to the subject by intravenous infusion.

In one embodiment, the transduced T cell is contacted with anti-CD3 and/or anti-CD28 antibodies prior to administration to the subject. In one embodiment, the transduced T cell is contacted with at least one cytokine prior to administration to the subject, preferably with interleukin-2 (IL-2), interleukin-7 (IL-7), interleukin-15 (IL-15), and/or interleukin-21, or variants thereof.

In one embodiment, the disease is a malignant disease. In one embodiment, the malignant disease is selected from cancer of epithelial, endothelial or mesothelial origin and cancer of the blood.

In one embodiment, provided is a method for inducing lysis of a target cell, comprising contacting the target cell with a transduced T cell capable of expressing the antigen binding receptor as described herein in the presence of an antibody comprising a mutated Fc domain wherein the antigen binding receptor is capable of specific binding to the mutated Fc domain but not capable of specific binding to the non-mutated parent Fc domain.

In one embodiment, the target cell is a cancer cell. In one embodiment, the target cell expresses an antigen selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX. In one embodiment, the target cell expresses an antigen selected from the group consisting of carcinoembryonic antigen (CEA), mesothelin (MSLN), CD20, folate receptor 1 (FOLR1), and tenascin (TNC).

In one embodiment, the polynucleotides or the transduced T cell as described herein is used for the manufacture of a medicament. In one embodiment, the medicament is for treatment of a malignant disease.

BRIEF DESCRIPTION OF THE DRAWINGS

FIG. 1A shows the architecture of the anti-P329G-scFv-CD28ATD-CD28CSD-CD3zSSD format and anti-P329G-ds-scFv-CD28ATD-CD28CSD-CD3zSSD format. Depicted is the extracellular domain comprising an antigen binding moiety capable of specific binding to a mutated Fc domain comprising the P329G mutation. The antigen binding moiety consists of a variable heavy and a variable light chain. Both are connected by a $(Gly_4Ser)_4$ linker. Attached to the variable light chain, a $Gly_4Ser$ linker connects the antigen recognition domain with the CD28 transmembrane Domain™ which is fused to the intracellular co-stimulatory signaling domain (CSD) of CD28 which in turn is fused to the stimulatory signaling domain (SSD) of CD3z. FIG. 1B shows the architecture of the anti-P329G-Fab-CD28ATD-CD28CSD-CD3zSSD and anti-P329G-ds-Fab-CD28ATD-CD28CSD-CD3zSSD format. Depicted is the extracellular domain comprising an antigen binding moiety capable of specific binding to a mutated Fc domain comprising the P329G mutation. The antigen binding moiety consists of an Ig heavy chain and an Ig light chain. Attached to the heavy chain, a Gly4Ser linker connects the antigen recognition domain with the CD28 transmembrane domain which is fused to the intracellular co-stimulatory signaling domain of CD28 which in turn is fused to the stimulatory signaling domain of CD3z.

FIG. 2A and FIG. 2B depict a schematic representation illustrating the modular composition of exemplary expression constructs encoding antigen binding receptors of the invention. FIG. 2A depicts a P392G-targeted scFv format. FIG. 2B depicts a P392G-targeted Fab format.

In FIG. 6A a sorted pool of anti-P329G-ds-Fab-CD28ATD-CD28CSD-CD3zSSD expressing Jurkat NFAT T cells was used as effector cells. In FIG. 6B a sorted pool of anti-P329G-ds-scFv-CD28ATD-CD28CSD-CD3zSSD expressing Jurkat NFAT T cells was used as effector cells.

FIGS. 7A-7D depict the Jurkat NFAT T cell reporter assay using CD20 tumor cells as target cells. An anti-CD20 IgG antibody (GA101) harboring the P329G mutation was used which recognizes the tumor associated antigen and is recognized by the Jurkat NFAT T cells expressing antigen binding receptors according to the invention. In FIG. 7A the single clone 5 of anti-P329G-ds-Fab-CD28ATD-CD28CSD-CD3zSSD expressing Jurkat NFAT T cells were used as effector cells and WSUDLCL2 cells as tumor cells. In FIG. 7B the single clone 2 of anti-P329G-ds-Fab-CD28ATD-CD28CSD-CD3zSSD expressing Jurkat NFAT T cells were used as effector cells and WSUDLCL2 cells as tumor cells. In FIG. 7C the single clone 5 of anti-P329G-ds-Fab-CD28ATD-CD28CSD-CD3zSSD expressing Jurkat NFAT T cells were used as effector cells and SUDHL4 cells as tumor cells. In FIG. 7D the single clone 2 of anti-P329G-ds-Fab-CD28ATD-CD28CSD-CD3zSSD expressing Jurkat NFAT T cells were used as effector cells and SUDHL4 as tumor cells.

In FIG. 8A a sorted pool of anti-P329G-ds-Fab-CD28ATD-CD28CSD-CD3zSSD expressing Jurkat NFAT T cells was used as effector cells. In FIG. 8B a sorted pool of anti-P329G-ds-scFv-CD28ATD-CD28CSD-CD3zSSD expressing Jurkat NFAT T cells was used as effector cells. In FIG. 8C a sorted pool of anti-P329G-ds-Fab-CD28ATD-CD28CSD-CD3zSSD expressing Jurkat NFAT T cells was used as effector cells. In FIG. 8D a sorted pool of anti-P329G-ds-scFv-CD28ATD-CD28CSD-CD3zSSD expressing Jurkat NFAT T cells was used as effector cells FIGS. 9A-9D depict the Jurkat NFAT T cell reporter assay using adherent CEA expressing MKN45 tumor cells as target cells. Either the anti-CEA IgG clone A5B7 or the anti-CEA IgG clone T84 LCHA both harboring the P329G mutation were used which recognize the tumor associated antigen and are recognized by the Jurkat NFAT T cells expressing antigen binding receptors according to the invention. Further IgG DP47/vk3 harboring the P329G mutation was included as isotype control. In FIG. 9A and in FIG. 9B a sorted pool of anti-P329G-ds-Fab-CD28ATD-CD28CSD-CD3zSSD expressing NFAT T cells was used as effector cells. In FIG. 9C and in FIG. 9D a sorted pool of anti-P329G-ds-scFv-CD28ATD-CD28CSD-CD3zSSD expressing NFAT T cells was used as effector cells.

In FIG. 10A and in FIG. 10B a sorted pool of anti-P329G-ds-scFv-CD28ATD-CD28CSD-CD3zSSD expressing NFAT T cells was used as effector cells. In FIG. 10C and in FIG. 10D a sorted pool of anti-P329G-ds-Fab-CD28ATD-CD28CSD-CD3zSSD expressing NFAT T cells was used as effector cells.

In FIG. 11A and in FIG. 11B a sorted pool of anti-P329G-ds-scFv-CD28ATD-CD28CSD-CD3zSSD expressing NFAT T cells was used as effector cells. In FIG. 11C and in FIG. 11D a sorted pool of anti-P329G-ds-Fab-CD28ATD-CD28CSD-CD3zSSD expressing NFAT T cells was used as effector cells

In FIG. 13A the pool of cells of anti-P329G-ds-scFv-CD28ATD-CD28CSD-CD3zSSD expressing Jurkat NFAT T cells were used as effector cells and SUDHL4 cells as tumor cells. In FIG. 13B the pool of cells of anti-P329G-ds-Fab-CD28ATD-CD28CSD-CD3zSSD expressing Jurkat NFAT T cells were used as effector cells and SUDHL4 cells as tumor cells.

In FIG. 14A the pool of cells of anti-P329G-ds-scFv-CD28ATD-CD28CSD-CD3zSSD expressing Jurkat NFAT T cells were used as effector cells and SUDHL4 cells as tumor cells. In FIG. 14B the pool of cells of anti-P329G-ds-Fab-CD28ATD-CD28CSD-CD3zSSD expressing Jurkat NFAT T cells were used as effector cells and SUDHL4 cells as tumor cells.

DETAILED DESCRIPTION

Definitions

Figure 1B:
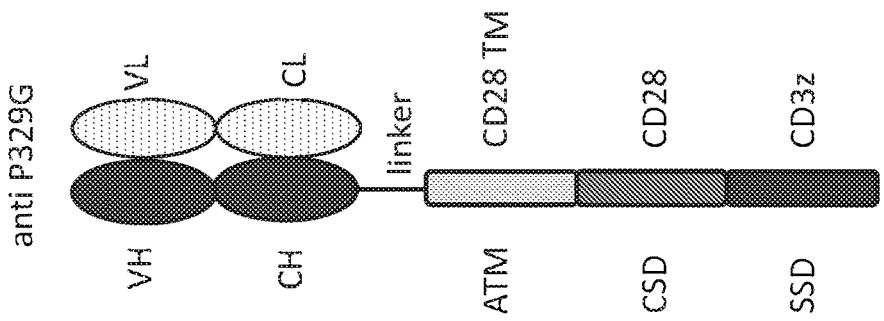
FIG. 1A and FIG. 1B depict the architecture of exemplary antigen binding receptors according to the invention.

Terms are used herein as generally used in the art, unless otherwise defined in the following. An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity ("ADCC") is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been mutated. For example the reduction in ADCC mediated by an antibody comprising in its Fc domain an amino acid mutation that reduces ADCC, is relative to the ADCC mediated by the same antibody without this amino acid mutation in the Fc domain. Suitable assays to measure ADCC are well known in the art (see e.g., PCT publication no. WO 2006/082515 or PCT publication no. WO 2012/130831).

An "effective amount" of an agent (e.g., an antibody) refers to the amount that is necessary to result in a physiological change in the cell or tissue to which it is administered.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen and/or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A preferred method for measuring affinity is Surface Plasmon Resonance (SPR) and a preferred temperature for the measurement is 25° C.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, 7-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering e.g., the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

The term "antibody" herein is used in the broadest sense and encompasses various antibody structures, including but not limited to monoclonal antibodies, polyclonal antibodies, and antibody fragments so long as they exhibit the desired antigen-binding activity. Accordingly, in context of the present invention, the term antibody relates to full immunoglobulin molecules as well as to parts of such immunoglobulin molecules. Furthermore, the term relates, as discussed herein, to modified and/or altered antibody molecules, in particular to mutated antibody molecules. The term also relates to recombinantly or synthetically generated/synthesized antibodies. In the context of the present invention the term antibody is used interchangeably with the term immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g., scFv), and single-domain antibodies. For a review of certain antibody fragments, see Hudson et al., Nat Med 9, 129-134 (2003). For a review of scFv fragments, see e.g., Pluckthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody (Domantis, Inc., Waltham, MA; see e.g., U.S. Pat. No. 6,248,516 B1). Antibody fragments can be made by various techniques, including but not limited to proteolytic digestion of an intact antibody as well as production by recombinant host cells (e.g., *E. coli* or phage), as described herein.

As used herein, the term "antigen binding molecule" refers in its broadest sense to a molecule that specifically binds an antigenic determinant. Examples of antigen binding molecules are immunoglobulins and derivatives, e.g., fragments, thereof as well as antigen binding receptors and derivatives thereof.

As used herein, the term "antigen binding moiety" refers to a polypeptide molecule that specifically binds to an antigenic determinant. In one embodiment, an antigen binding moiety is able to direct the entity to which it is attached (e.g., an immunoglobulin or an antigen binding receptor) to a target site, for example to a specific type of tumor cell or tumor stroma bearing the antigenic determinant or to an immunoglobulin binding to the antigenic determinant on a tumor cell. In another embodiment an antigen binding moiety is able to activate signaling through its target antigen, for example signaling is activated upon binding of an antigenic determinant to an antigen binding receptor on a T cell. In the context of the present invention, antigen binding moieties may be included in antibodies and fragments thereof as well as in antigen binding receptors and fragments thereof as further defined herein. Antigen binding moieties include an antigen binding domain, comprising an immunoglobulin heavy chain variable region and an immunoglobulin light chain variable region. In certain embodiments, the antigen binding moieties may comprise immunoglobulin constant regions as further defined herein and known in the art. Useful heavy chain constant regions include any of the five isotypes: α, δ, ε, γ, or μ. Useful light chain constant regions include any of the two isotypes: κ and λ.

In the context of the present invention the term "antigen binding receptor" relates to an antigen binding molecule comprising an anchoring transmembrane domain and an extracellular domain comprising at least one antigen binding moiety. An antigen binding receptor can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details on the antigen binding receptors of the present invention are described herein below. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to the intracellular signaling domains of CD3z and CD28.

An "antigen binding site" refers to the site, i.e. one or more amino acid residues, of an antigen binding molecule which provides interaction with the antigen. For example, the antigen binding site of an antibody or an antigen binding receptor comprises amino acid residues from the complementarity determining regions (CDRs). A native immunoglobulin molecule typically has two antigen binding sites, a Fab or a scFv molecule typically has a single antigen binding site.

The term "antigen binding domain" refers to the part of an antibody or an antigen binding receptor that comprises the area which specifically binds to and is complementary to part or all of an antigen. An antigen binding domain may be provided by, for example, one or more immunoglobulin variable domains (also called variable regions). Particularly, an antigen binding domain comprises an immunoglobulin light chain variable region (VL) and an immunoglobulin heavy chain variable region (VH).

The term "variable region" or "variable domain" refers to the domain of an immunoglobulin heavy or light chain that is involved in binding the antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, $6^{th}$ ed., W.H. Freeman and Co, page 91 (2007). A single VH or VL domain is usually sufficient to confer antigen-binding specificity.

The term "ATD" as used herein refers to "anchoring transmembrane domain" which defines a polypeptide stretch capable of integrating in (the) cellular membrane(s) of a cell. The ATM can be fused to further extracellular and/or intracellular polypeptide domains wherein these extracellular and/or intracellular polypeptide domains will be confined to the cell membrane as well. In the context of the antigen binding receptors of the present invention the ATM confers membrane attachment and confinement of the antigen binding receptor of the present invention. The antigen binding receptors of the present invention comprise at least one ATM and an extracellular domain comprising an antigen binding moiety. Additionally, the ATM may be fused to further intracellular signaling domains.

The term "binding to" as used in the context of the antigen binding receptors of the present invention defines a binding (interaction) of an "antigen-interaction-site" and an antigen with each other. The term "antigen-interaction-site" defines, in accordance with antigen binding receptors of the present invention, a motif of a polypeptide which shows the capacity of specific interaction with a specific antigen or a specific group of antigens (i.e. mutated Fc domains).

Said binding/interaction is also understood to define a "specific recognition". The term "specifically recognizing" means in accordance with this invention that the antigen binding receptor is capable of specifically interacting with and/or binding to a modified molecule as defined herein whereas the non-modified molecule is not recognized. The antigen binding moiety of an antigen binding receptor can recognize, interact and/or bind to different epitopes on the same molecule. This term relates to the specificity of the antigen binding receptor, i.e., to its ability to discriminate between the specific regions of a modified molecule, i.e. a mutated Fc domain, as defined herein. The specific interaction of the antigen-interaction-site with its specific antigen may result in an initiation of a signal, e.g. due to the induction of a change of the conformation of the polypeptide comprising the antigen, an oligomerization of the polypeptide comprising the antigen, an oligomerization of the antigen binding receptor, etc. Thus, a specific motif in the amino acid sequence of the antigen-interaction-site and the antigen bind to each other as a result of their primary, secondary or tertiary structure as well as the result of secondary modifications of said structure. Accordingly, the term binding to does not only relate to a linear epitope but may also relate to a conformational epitope, a structural epitope or a discontinuous epitope consisting of two regions of the target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with". The ability of the antigen binding moiety (e.g. a Fab or scFv domain) of an antigen binding receptor or an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the target antigen as measured, in particular by SPR. In certain embodiments, an antigen binding moiety that binds to the target antigen, has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). The term "specific binding" as used in accordance with the present invention means that the molecules of the invention do not or do not essentially cross-react with (poly-) peptides of similar structures, i.e. with a non-mutated parent Fc domain wherein an antigen binding receptor of the invention is capable of specific binding to a mutated Fc domain. Accordingly, the antigen binding receptor of the invention specifically binds to/interacts with a mutated Fc domain. Cross-reactivity of a panel of constructs under investigation may be tested, for example, by assessing binding of a panel of antigen binding moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the mutated Fc domain of interest as well as to parent non-mutated Fc domain. Only those constructs (i.e. Fab fragments, scFvs and the like) that bind to the mutated Fc domain of interest but do not or do not essentially bind to a non-mutated parent Fe domain are considered specific for the mutated Fc domain of interest and selected for further studies in accordance with the method provided herein. These methods may comprise, inter alia, binding studies, blocking and competition studies with structurally and/or functionally closely related Fc domains. The binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays.

The term "CDR" as employed herein relates to "complementary determining region", which is well known in the art. The CDRs are parts of immunoglobulins or antigen binding receptors that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g. a single chain antibody domain) fused by a spacer sequence to the intracellular signaling domains of CD3z and CD28. The invention additionally provides antigen binding receptors wherein the antigen binding moiety is a Fab or a crossFab fragment. The term "CAR" is understood in its broadest form to comprise antigen binding receptors constituted of an extracellular portion comprising an antigen binding moiety fused to CD3z and fragment thereof and to CD28 and fragments thereof, optionally through one or several peptide linkers.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, IgG$_3$, IgG$_4$, IgA$_1$, and IgA$_2$. The heavy chain constant domains that correspond to the different classes of immunoglobulins are called α, δ, ε, γ, and μ, respectively.

By a "crossover Fab molecule" (also termed "crossFab" or "crossover Fab fragment") is meant a Fab molecule wherein either the variable regions or the constant regions of the Fab heavy and light chain are exchanged, i.e. the crossFab fragment comprises a peptide chain composed of the light chain variable region and the heavy chain constant region, and a peptide chain composed of the heavy chain variable region and the light chain constant region. For clarity, in a crossFab fragment wherein the variable regions of the Fab light chain and the Fab heavy chain are exchanged, the peptide chain comprising the heavy chain constant region is referred to herein as the heavy chain of the crossover Fab molecule. Conversely, in a crossFab fragment wherein the constant regions of the Fab light chain and the Fab heavy chain are exchanged, the peptide chain comprising the heavy chain variable region is referred to herein as the heavy chain of the crossFab fragment. Accordingly, a crossFab fragment comprises a heavy or light chain composed of the heavy chain variable and the light chain constant regions (VH-CL), and a heavy or light chain composed of the light chain variable and the heavy chain constant regions (VL-CH1). In contrast thereto, by a "conventional Fab" molecule is meant a Fab molecule in its natural format, i.e. comprising a heavy chain composed of the heavy chain variable and constant regions (VH-CH1), and a light chain composed of the light chain variable and constant regions (VL-CL).

The term "CSD" as used herein refers to co-stimulatory signaling domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer", "engineered", "engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment.

Typically, the recombinant expression cassette portion of an expression vector includes, among other sequences, a nucleic acid sequence to be transcribed and a promoter. In certain embodiments, the expression cassette of the invention comprises polynucleotide sequences that encode antigen binding molecules of the invention or fragments thereof.

A "Fab molecule" refers to a protein consisting of the VH and CH1 domain of the heavy chain (the "Fab heavy chain") and the VL and CL domain of the light chain (the "Fab light chain") of an antigen binding molecule.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the "EU numbering" system, also called the EU index, as described in Kabat et al., Sequences of Proteins of Immunological Interest, 5th Ed. Public Health Service, National Institutes of Health, Bethesda, M D, 1991. A subunit of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE.) The full length antibodies used according to the invention can be from a single species e.g. human, or they can be chimerized or humanized antibodies. In some embodiments, the full length antibodies used according to the invention, i.e. a therapeutic antibody comprising a mutated Fc domain, comprise two antigen binding sites each formed by a pair of VH and VL, which both specifically bind to the same antigen. In further embodiments, the full length antibodies used according to the invention comprise two antigen binding sites each formed by a pair of VH and VL, wherein the two antigen binding sites bind to different antigens, e.g. wherein the antibodies are bispecific. The C-terminus of the heavy or light chain of said full length antibody denotes the last amino acid at the C-terminus of said heavy or light chain.

By "fused" is meant that the components (e.g., a Fab and a transmembrane domain) are linked by peptide bonds, either directly or via one or more peptide linkers.

The terms "host cell", "host cell line" and "host cell culture" are used interchangeably and refer to cells into which exogenous nucleic acid has been introduced, including the progeny of such cells. Host cells include "transformants" and "transformed cells" which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate an antibody used according to the present invention. Host cells include cultured cells, e.g., mammalian cultured cells, such as CHO cells, BHK cells, NS0 cells, SP2/0 cells, Y0 myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody and/or an antigen binding receptor or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |

TABLE 1-continued

| CDR Definitions[1] | | | |
|---|---|---|---|
| CDR | Kabat | Chothia | AbM[2] |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of Kabat numbering to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety variable region are according to the Kabat numbering system. The polypeptide sequences of the sequence listing are not numbered according to the Kabat numbering system. However, it is well within the ordinary skill of one in the art to convert the numbering of the sequences of the Sequence Listing to Kabat numbering.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both sense and antisense strands. Moreover, the herein described nucleic acid molecule may contain non-natural or derivatized nucleotide bases, as will be readily appreciated by those skilled in the art.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. As used herein, term "polypeptide" refers to a molecule composed of monomers (amino acids) linearly linked by amide bonds (also known as peptide bonds). The term polypeptide refers to any chain of two or more amino acids, and does not refer to a specific length of the product. Thus, peptides, dipeptides, tripeptides, oligopeptides, protein, amino acid chain, or any other term used to refer to a chain of two or more amino acids, are included within the definition of polypeptide, and the term polypeptide may be used instead of, or interchangeably with any of these terms. The term polypeptide is also intended to refer to the products of postexpression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

The term "regulatory sequence" refers to DNA sequences, which are necessary to affect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, the term "single-chain" refers to a molecule comprising amino acid monomers linearly linked by peptide bonds. In certain embodiments, one of the antigen binding moieties is a scFv fragment, i.e. a VH domain and a VL domain connected by a peptide linker. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. The term "SSD" as used herein refers to stimulatory signaling domain.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, cells expressing antigen binding receptors of the invention are used together with therapeutic antibodies comprising a mutated Fc domain to delay development of a disease or to slow the progression of a disease.

As used herein, the term "target antigenic determinant" is synonymous with "target antigen", "target epitope" and "target cell antigen" and refers to a site (e.g., a contiguous stretch of amino acids or a conformational configuration made up of different regions of non-contiguous amino acids) on a polypeptide macromolecule to which an antibody binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., CD20, CEA, FAP, TNC) can be any native form of the proteins from any vertebrate source, including mammals such as primates (e.g., humans) and rodents (e.g., mice and rats), unless otherwise indicated. In a particular embodiment the target antigen is a human protein. Where reference is made to a specific target protein herein, the term encompasses the "full-length", unprocessed target protein as well as any form of the target protein that results from processing in the target cell. The term also encompasses naturally occurring variants of the target protein, e.g., splice variants or allelic variants. Exemplary human target proteins useful as antigens include, but are not limited to: CD20, CEA, FAP, TNC, MSLN, FolR1, HER1 and HER2. The ability of an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)).

In one embodiment, the extent of binding of the antibody to an unrelated protein is less than about 10% of the binding of the antibody to the target antigen as measured, e.g., by SPR. In certain embodiments, the antibody binds to the target antigen with an affinity dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

"Antibodies comprising a mutated Fc domain" according to the present invention, i.e. therapeutic antibodies may have one, two, three or more binding domains and may be monospecific, bispecific or multispecific. The antibodies can be full length from a single species, or be chimerized or humanized. For an antibody with more than two antigen binding domains, some binding domains may be identical and/or have the same specificity.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The antigen binding receptors of the invention are capable of inducing T cell activation. Suitable assays to measure T cell activation are known in the art described herein.

In accordance with this invention, the term "T cell receptor" or "TCR" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T cell receptors which fulfill the above mentioned three criteria are known in the art such as receptors recognizing NY-ESO-1 (for sequence information(s) see, e.g., PCT/GB2005/001924) and/or HER2neu (for sequence information(s) see WO-A1 2011/0280894).

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode antigen binding receptors of the invention or fragments thereof.

Antigen Binding Receptors Capable of Specific Binding to (a) Mutated Fc Domain(s)

The present invention relates to antigen binding receptors capable of specific binding to the mutated Fc domain of an antibody, i.e. a therapeutic antibody targeting a cancer cell. In particular, the present invention relates to antigen binding receptors comprising an extracellular domain comprising at least one antigen binding moiety capable of specific binding to a mutated Fc domain but not capable of specific binding to the parent non-mutated Fc domain. In preferred embodiments, the mutated Fc domain comprises at least one amino acid substitution compared to the non-mutated parent Fc domain, wherein Fc receptor binding by the mutated Fc domain is reduced compared to Fc receptor binding by the non-mutated Fc domain. In particular embodiments, the present invention relates to antigen binding receptors comprising an extracellular domain comprising at least one antigen binding moiety capable of specific binding to a mutated Fc domain, wherein the at least one antigen binding moiety is not capable of specific binding to the parent non-mutated Fc domain, wherein the mutated Fc domain comprises at least one amino acid substitution selected from the group consisting of L234, L235, I253, H310, P331, P329 and H435, in particular wherein the amino acid mutation is L234A, L235A, I253A, N297A, H310A, P329G and/or H435A, compared to the non-mutated parent Fc domain, wherein Fc receptor binding by the mutated Fc domain is reduced compared to Fc receptor binding by the non-mutated Fc domain. In one preferred embodiment, the amino acid mutation is P329G wherein binding to Fcγ receptor is reduced as measured by SPR at 25° C. In a further preferred embodiment, the amino acid mutations are I253A, H310A and H435A wherein binding to the neonatal Fc receptor (FcRn) is reduced as measured by SPR at 25° C.

The present invention further relates to the transduction of T cells, such as CD8+ T cells, CD4+ T cells, CD3+ T cells, ᵧδ T cells or natural killer (NK) T cells, preferably CD8+ T cells, with an antigen binding receptor as described herein and their targeted recruitment, e.g., to a tumor, by an antibody molecule, e.g. a therapeutic antibody, comprising a mutated Fc domain. In one embodiment, the antibody is capable of specific binding to a tumor-specific antigen that is naturally occurring on the surface of a tumor cell.

As shown in the appended Examples, as a proof of the inventive concept, the antigen binding receptor comprising an anchoring transmembrane domain and an extracellular domain according to the invention pETR17096 (SEQ ID NO:7 as encoded by the DNA sequence shown in SEQ ID NO:19) was constructed which is capable of specific binding to a therapeutic antibody (represented by the anti-CD20 antibody comprising a heavy chain of SEQ ID NO ID: 112 and a light chain of SEQ ID NO:113) comprising the P329G mutation. Transduced T cells (Jurkat NFAT T cells) expressing the Anti-P329G-scFv-CD28ATD-CD28CSD-CD3zSSD protein (SEQ ID NO:7 as encoded by the DNA sequence shown in SEQ ID NO:19) could be strongly activated by co-incubation with the anti-CD20 antibody comprising the P329G mutation in the Fc domain together with CD20 positive tumor cells. The inventors further provided multiple formats of the antigen binding receptor capable of specific binding to a mutated Fc domain but not capable of specific binding to the non-mutated parent Fc domain to support the proof of the inventive concept.

The treatment of tumor cells by the combination of an antibody directed against a tumor antigen wherein the antibody comprises the P329G mutation together with transduced T cells expressing the Anti-P329G-Fab-ds-CD28ATD-CD28CSD-CD3zSSD protein (SEQ ID NOs: 44 (DNA) and 39, 41 (protein)) surprisingly leads to stronger activation of the transduced T cell compared to the transduced T cells expressing the Anti-P329G-scFv-CD28ATD-CD28CSD-CD3zSSD (SEQ ID NOs: 19 (DNA) and 7 (protein)) fusion protein. (see e.g. FIGS. 6 and 8 to 11).

Accordingly, it was surprisingly and unexpectedly found that T cells, preferably CD8+ T cells, that were transduced with an antigen binding receptor of the present invention can be specifically stimulated by the use of a tumor-specific antibody comprising a mutated Fc domain and recruited by the tumor-specific antibody as linking element to the tumor cell. Thus, it was surprisingly and unexpectedly shown in the present invention that pairing a tumor-specific antibody, i.e. a therapeutic antibody, comprising a mutated Fc domain with T cells transduced with an antigen binding receptor which comprise/consist of an extracellular domain comprising an antigen binding moiety capable of specific binding to the mutated Fc domain would result in a specific activation of the T cells and subsequent lysis of the tumor cell. This approach bears significant safety advantages over conventional T cell based approaches, as the T cell would be inert in the absence of the antibody comprising the mutated Fc domain and their availability may be controlled by the antibody molecule format chosen (i.e. smaller molecules for shorter half-life and vice-versa). Accordingly, the invention provides a versatile therapeutic platform wherein IgG type antibodies may be used to mark or label tumor cells as a guidance for T cell and wherein transduced T cells are specifically targeted toward the tumor cells by providing specificity for a mutated Fc domain of the IgG type antibody. After binding to the mutated Fc domain of the antibody on the surface of a tumor cell, the transduced T cell as described herein becomes activated and the tumor cell will subsequently be lysed. The platform is flexible and specific by allowing the use of diverse (existing or newly developed) target antibodies or co-application of multiple antibodies with different antigen specificity but comprising the same mutation in the Fc domain. The degree of T cell activation can further be adjusted by adjusting the dosage of the co-applied therapeutic antibody or by switching to different antibody specificities or formats. Transduced T cell according to the invention are inert without co-application of a targeting antibody comprising a mutated Fc domain because mutations to the Fc domain as described herein do not occur in natural or non-mutated immunoglobulins. Accordingly, in one embodiment, the mutated Fc domain does not naturally occur in wild type immunoglobulins.

Accordingly, the present invention relates to an antigen binding receptor comprising an extracellular domain comprising at least one antigen binding moiety capable of specific binding to a mutated Fc domain, wherein the at least one antigen binding moiety is not capable of specific binding to the parent non-mutated Fc domain, wherein the mutated Fc domain comprises at least one amino acid mutation compared to the non-mutated parent Fc domain, wherein Fc receptor binding by the mutated Fc domain and/or effector function induced by the mutated Fc domain is reduced compared to Fc receptor binding and/or effector function induced by the non-mutated Fc domain. It may be particularly desirable to use therapeutic antibodies with reduced effector function in cancer therapy since effector function may lead to severe side effects of antibody-based tumor therapies as further described herein.

In the context of the present invention, the antigen binding receptor comprises an extracellular domain that does not naturally occur in or on T cells. Thus, the antigen binding receptor is capable of providing tailored binding specificity to cells expressing the antigen binding receptor according to the invention. Cells, e.g. T cells, transduced with (an) antigen binding receptor(s) of the invention become capable of specific binding to a mutated Fc domain but not to the non-mutated parent Fc domain. Specificity is provided by the antigen binding moiety of the extracellular domain of the antigen binding receptor, such antigen binding moieties are considered to be specific for the mutated Fc domain as defined herein. In the context of the present invention and as explained herein, the antigen binding moiety capable of specific binding to a mutated Fc domain bind to/interact with the mutated Fc domain but not to/with the non-mutated parent Fc domain.

Antigen Binding Moieties

In an illustrative embodiment of the present invention, as a proof of concept, antigen binding receptors are provided comprising an anchoring transmembrane domain and an extracellular domain comprising at least one antigen binding moiety, wherein the at least one antigen binding moiety is capable of specific binding to a mutated Fc domain but not capable of specific binding to the non-mutated parent Fc domain, wherein the mutated Fc domain comprises at least one amino acid substitution compared to the non-mutated parent Fc.

In certain embodiment, at least one of the antigen binding moieties is a conventional Fab fragment, i.e. a Fab molecule consisting of a Fab light chain and a Fab heavy chain. In certain embodiment, at least one of the antigen binding moieties is a crossFab fragment, i.e. a Fab molecule consisting of a Fab light chain and a Fab heavy chain, wherein either the variable regions or the constant regions of the Fab heavy and light chain are exchanged. In certain embodiments, at least one of the antigen binding moieties is a scFv fragment. In a particular such embodiment, the C-terminus of the variable heavy chain (VH) is connected to the N-terminus of the variable light chain (VL) in the scFv molecule, optionally through a peptide linker. In certain embodiments, at least one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule, optionally through a peptide linker.

Accordingly, in the context of the present invention, the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain.

Antigen binding moieties capable of specific binding to a mutated Fc domain may be generated by immunization of e.g. a mammalian immune system. Such methods are known in the art and e.g. are described in Burns in Methods in Molecular Biology 295:1-12 (2005). Alternatively, antigen binding moieties of the invention may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antigen binding moieties possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178:1-37 (O'Brien et al., ed., Human Press, Totowa, N J, 2001) and further described, e.g., in the McCafferty et al., Nature 348:552-554; Clackson et al., Nature 352: 624-628 (1991); Marks et al., J. Mol. Biol. 222: 581-597 (1992) and in Marks and Bradbury in Methods in Molecular Biology 248:161-175 (Lo, ed., Human Press, Totowa, N J, 2003). Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antigen binding moieties to the immunogen without the requirement of constructing hybridomas. Alternatively, the naive repertoire can be cloned (e.g., from human) to provide a single source of antigen binding moieties to a wide range of non-self and also self antigens without any immunization as described by Griffiths et al. in EMBO Journal 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. and 2009/0002360. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319:155-175

(2015) as well as in the Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

In the context of the present invention, provided herein are antigen binding receptors comprising at least one antigen binding moiety capable of specific binding to a mutated Fc domain. Accordingly, transduced cells, i.e. T cells, expressing an antigen binding receptor according to the invention are capable of specific binding to the mutated Fc domain of an antibody, i.e. of a therapeutic antibody. The Fc domain confers to antibodies, i.e. therapeutic antibodies, favorable pharmacokinetic properties, including a long serum half-life which contributes to good accumulation in the target tissue and a favorable tissue-blood distribution ratio. At the same time it may, however, lead to undesirable targeting of therapeutic antibodies to cells expressing Fc receptors rather than to the preferred antigen-bearing cells. Moreover, the co-activation of Fc receptor signaling pathways may lead to cytokine release which results in excessive activation of cytokine receptors and severe side effects upon systemic administration of therapeutic antibodies. Activation of (Fc receptor-bearing) immune cells other than T cells may even reduce efficacy of therapeutic antibodies due to the potential destruction of immune cells. Accordingly, therapeutic antibodies known in the art may be engineered or mutated to exhibit reduced binding affinity to an Fc receptor and/or reduced effector function, as compared to, e.g., a native $IgG_1$ Fc domain. The antigen binding receptors according to the invention may be used to target effector cells, e.g. T cells, expressing the antigen binding receptors according to the invention in vitro and/or in vivo to target cells, i.e. tumor cells, which are labeled with an antibody capable of specific binding to the target cells, wherein the antibody comprise an engineered and/or mutated Fc domain as described herein.

In an illustrative embodiment of the present invention, as a proof of concept, provided are antigen binding receptors capable of specific binding to a mutated Fc domain comprising the amino acid mutation P329G and effector cells expressing said antigen binding receptors. The P329G mutation reduces binding to Fcγ receptors and associated effector function. Accordingly, the mutated Fc domain comprising the P329G mutation binds to Fcγ receptors with reduced or abolished affinity compared to the non-mutated Fc domain. In an alternative illustrative embodiment of the present invention, as a proof of concept provided are antigen binding receptors capable of specific binding to a mutated Fc domain comprising the amino acid mutations I253A, H310A and H435A ("AAA"). The AAA mutations essentially abolishes binding to the FcRn.

However, antibodies with reduced with improved or diminished binding to Fc receptors (FcRs) and/or effector function comprising a mutated Fc domain are widely used in the art. Accordingly, herein provided are antigen binding receptors capable of specific binding to antibodies comprising a mutated Fc domain, such antibodies are herein also referred to as target antibodies. Accordingly, in one embodiment the antigen binding receptor of the present invention is capable of specific binding to a target antibody comprising a mutated Fc domain with reduced binding affinity to an Fc receptor and/or reduced effector function. Target antibodies with reduced effector function include those with mutation of one or more of Fc region residues 238, 265, 269, 270, 297, 327 and 329 (U.S. Pat. No. 6,737,056). Such Fc mutants include Fc mutants with mutations at two or more of amino acid positions 265, 269, 270, 297 and 327, including the so-called "DANA" Fc mutant with mutation of residues 265 and 297 to alanine (U.S. Pat. No. 7,332,581). Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).) In certain embodiments, an antigen binding receptor is provided capable of specific binding to an antibody variant comprises an Fc region with one or more amino acid mutations which improve ADCC, e.g., mutations at positions 298, 333, and/or 334 of the Fc region (EU numbering of residues). In certain embodiments, a target antibody variant comprises an Fc region with one or more amino acid mutations, which reduce or diminish FcRn binding, e.g., mutations at positions 253, and/or 310, and/or 435 of the Fc region (EU numbering of residues). In certain embodiments, the target antibody variant comprises an Fc region with the amino acid mutations at positions 253, 310 and 435. In one embodiment the mutations are I253A, H310A and H435A in an Fc region derived from a human IgG1 Fc region. See e.g., Grevys, A., et al., J. Immunol. 194 (2015) 5497-5508.

In certain embodiments, an antigen binding receptor is provided capable of specific binding to an antibody variant comprising an Fc region with one or more amino acid mutations, which reduced or diminished FcRn binding, e.g., mutations at one of the positions 310 and/or, 433 and/or 436 of the Fc region (EU numbering of residues). In certain embodiments, the target antibody variant comprises an Fc region with the amino acid mutations at positions 310, 433 and 436. In one embodiment the mutations are H310A, H433A and Y436A in an Fc region derived from a human IgG1 Fc region. In certain embodiments, a target antibody variant comprises an Fc region with one or more amino acid mutations, which increased FcRn binding, e.g., mutations at positions 252 and/or, 254 and/or 256 of the Fc region (EU numbering of residues). In certain embodiments, the target antibody variant comprises an Fc region with the amino acid mutations at positions 252, 254, and 256. In one embodiment the mutations are M252Y, S254T and T256E in an Fc region derived from a human IgG1 Fc region. In certain embodiments, an antigen binding receptor is provided capable of specific binding to an antibody variant comprising an Fc region with amino acid mutations, which diminish FcγR binding, e.g., mutations at positions 234, 235 and 329 of the Fc region (EU numbering of residues). In one embodiment the mutations are L234A and L235A (LALA). In certain embodiments, the target antibody variant further comprises D265A and/or P329G in an Fc region derived from a human IgG1 Fc region. In one embodiment the mutation is P329G ("PG") in an Fc region derived from a human IgG1 Fc region. In another embodiment, the mutations are I253A, H310A and H435A ("AAA") in an Fc region derived from a human IgG1 Fc region.

In one embodiment the antigen binding moiety is capable of specific binding to a mutated Fe domain composed of a first and a second subunit capable of stable association. In one embodiment the Fc domain is an IgG, specifically an $IgG_1$ or IgG4, Fc domain. In one embodiment the Fc domain is a human Fc domain. In one embodiment the mutated Fc domain exhibits reduced binding affinity to an Fc receptor and/or reduced effector function, as compared to a native $IgG_1$ Fc domain. In one embodiment the Fc domain comprises one or more amino acid mutations that reduce binding to an Fc receptor and/or effector function.

In one preferred embodiment the one or more amino acid mutation is at one or more position selected from the group of L234, L235, and P329 (Kabat numbering). In one particular embodiment each subunit of the Fc domain comprises three amino acid mutations that reduce binding to an activating Fc receptor and/or effector function wherein said amino acid mutations are L234A, L235A and P329G. In one particular embodiment the Fc receptor is an Fc receptor.

In one embodiment the effector function is antibody-dependent cell-mediated cytotoxicity (ADCC).

In a particular embodiment, the mutated Fc domain comprises the P329G mutation. Accordingly, the mutated Fc domain comprising the P329G mutation binds to Fcγ receptors with reduced or abolished affinity compared to the non-mutated Fc domain. In one embodiment, the extracellular domain of the antigen binding receptor comprises an antigen binding moiety capable of specific binding to an Fc domain comprising the P329G mutation, wherein the antigen binding moiety comprises a heavy chain variable region comprising at least one of:

(a) a heavy chain complementarity determining region (CDR H) 1 amino acid sequence of RYWMN (SEQ ID NO:1);
(b) a CDR H2 amino acid sequence of EITPDSSTINYTPSLKD (SEQ ID NO:2); and
(c) a CDR H3 amino acid sequence of PYDYGAWFAS (SEQ ID NO:3).

In one embodiment the extracellular domain of the antigen binding receptor comprises an antigen binding moiety capable of specific binding to an Fc domain comprising the P329G mutation, wherein the antigen binding moiety comprises a light chain variable region comprising at least one of:

(d) a light chain (CDR L)1 amino acid sequence of RSSTGAVTTSNYAN (SEQ ID NO:4);
(e) a CDR L2 amino acid sequence of GTNKRAP (SEQ ID NO:5); and
(f) a CDR L3 amino acid sequence of ALWYSNHWV (SEQ ID NO:6).

In one embodiment the extracellular domain of the antigen binding receptor comprises an antigen binding moiety capable of specific binding to an Fc domain comprising the P329G mutation, wherein the antigen binding moiety comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:1, SEQ ID NO:2 and SEQ ID NO:3 and at least one light chain CDR selected from the group of SEQ ID NO:4, SEQ ID NO:5 and SEQ ID NO:6.

In one embodiment the extracellular domain of the antigen binding receptor comprises an antigen binding moiety capable of specific binding to an Fc domain comprising the P329G mutation, wherein the antigen binding moiety comprises the heavy chain complementarity determining region (CDRs) of SEQ ID NO:1, SEQ ID NO:2 and SEQ ID NO:3 and the light chain CDRs of SEQ ID NO:4, SEQ ID NO:5 and SEQ ID NO:6.

In one preferred embodiment the extracellular domain of the antigen binding receptor comprises an antigen binding moiety capable of specific binding to an Fc domain comprising the P329G mutation, wherein the antigen binding moiety comprises a heavy chain variable region comprising:

(a) a heavy chain complementarity determining region (CDR H) 1 amino acid sequence of RYWMN (SEQ ID NO:1);
(b) a CDR H2 amino acid sequence of EITPDSSTINYTPSLKD (SEQ ID NO:2);
(c) a CDR H3 amino acid sequence of PYDYGAWFAS (SEQ ID NO:3); and a light chain variable region comprising:
(d) a light chain (CDR L)1 amino acid sequence of RSSTGAVTTSNYAN (SEQ ID NO:4);
(e) a CDR L2 amino acid sequence of GTNKRAP (SEQ ID NO:5); and
(f) a CDR L3 amino acid sequence of ALWYSNHWV (SEQ ID NO:6).

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising an amino acid sequence that is at least about 95%, 96%, 97%, 98%, 99% or 100% identical to an amino acid sequence selected from SEQ ID NO:8 and SEQ ID NO:32 and a light chain variable region (VL) comprising an amino acid sequence that is at least about 95%, 96%, 97%, 98%, 99% or 100% identical to an amino acid sequence selected from SEQ ID NO:9 and SEQ ID NO:33.

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising an amino acid sequence selected from SEQ ID NO:8 and SEQ ID NO:32, and a light chain variable region (VL) comprising an amino acid sequence selected from SEQ ID NO:9 and SEQ ID NO:33.

In one embodiment the extracellular domain of the antigen binding receptor comprises an antigen binding moiety capable of specific binding to an Fc domain comprising the P329G mutation, wherein the antigen binding moiety comprises a heavy chain variable region (VH) comprising the amino acid sequence of SEQ ID NO:32 and a light chain variable region (VL) comprising the amino acid sequence of SEQ ID NO:33.

In one preferred embodiment the extracellular domain of the antigen binding receptor comprises an antigen binding moiety capable of specific binding to an Fc domain comprising the P329G mutation, wherein the antigen binding moiety comprises a heavy chain variable region (VH) comprising the amino acid sequence of SEQ ID NO:8 and a light chain variable region (VL) comprising the amino acid sequence of SEQ ID NO:9.

In one embodiment, the at least one antigen binding moiety is a scFv, a Fab, a crossFab or a scFab fragment. In one embodiment the extracellular domain of the antigen binding receptor comprises an antigen binding moiety capable of specific binding to an Fc domain comprising the P329G mutation, wherein the antigen binding moiety is a Fab fragment.

In a preferred embodiment the extracellular domain of the antigen binding receptor comprises an antigen binding moiety capable of specific binding to an Fc domain comprising the P329G mutation, wherein the Fab fragment comprising a heavy chain of SEQ ID NO:40 and a light chain of SEQ ID NO:41.

In one embodiment the extracellular domain of the antigen binding receptor comprises an antigen binding moiety capable of specific binding to an Fc domain comprising the P329G mutation, wherein the at least one antigen binding moiety is a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the extracellular domain of the antigen binding receptor comprises an antigen binding moiety capable of specific binding to an Fc domain comprising the P329G mutation, wherein the scFv fragment comprises the amino acid sequence of SEQ ID NO:10.

In an alternative particular embodiment, the mutated Fc domain comprises the I253A, H310A and H435A ("AAA") mutations. The AAA mutations reduce binding to the neonatal Fc receptor (FcRn). Accordingly, the mutated Fc domain comprising the AAA mutations binds to FcRn with reduced or abolished affinity compared to the non-mutated Fc domain.

Accordingly, in one embodiment, the extracellular domain of the antigen binding receptor comprises an antigen binding moiety capable of specific binding to an Fc domain comprising the I253A, H310A and H435A mutations, wherein the antigen binding moiety comprises a heavy chain variable region comprising at least one of:
  (a) a heavy chain complementarity determining region (CDR H) 1 amino acid sequence of SYGMS (SEQ ID NO:53);
  (b) a CDR H2 amino acid sequence of SSGGSY (SEQ ID NO:54); and
  (c) a CDR H3 amino acid sequence of LGMITTG-YAMDY (SEQ ID NO:55).

In one embodiment the extracellular domain of the antigen binding receptor comprises an antigen binding moiety capable of specific binding to an Fc domain comprising the I253A, H310A and H435A mutations, wherein the antigen binding moiety comprises a light chain variable region comprising at least one of:
  (d) a light chain (CDR L)1 amino acid sequence of RSSQTIVHSTGHTYLE (SEQ ID NO:56);
  (e) a CDR L2 amino acid sequence of KVSNRFS (SEQ ID NO:57); and
  (f) a CDR L3 amino acid sequence of FQGSHVPYT (SEQ ID NO:58).

In one embodiment the extracellular domain of the antigen binding receptor comprises an antigen binding moiety capable of specific binding to an Fc domain comprising the I253A, H310A and H435A mutations, wherein the antigen binding moiety comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:53, SEQ ID NO:54 and SEQ ID NO:55 and at least one light chain CDR selected from the group of SEQ ID NO:56, SEQ ID NO:57 and SEQ ID NO:58.

In one embodiment the extracellular domain of the antigen binding receptor comprises an antigen binding moiety capable of specific binding to an Fc domain comprising the P329G mutation, wherein the antigen binding moiety comprises the heavy chain complementarity determining region (CDRs) of SEQ ID NO:53, SEQ ID NO:54 and SEQ ID NO:55 and the light chain CDRs of SEQ ID NO:56, SEQ ID NO:57 and SEQ ID NO:58.

In a preferred embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region comprising:
  (a) a heavy chain complementarity determining region (CDR H) 1 amino acid sequence of SYGMS (SEQ ID NO:53);
  (b) a CDR H2 amino acid sequence of SSGGSY (SEQ ID NO:54);
  (c) a CDR H3 amino acid sequence of LGMITTG-YAMDY (SEQ ID NO:55); and a light chain variable region comprising:
  (d) a light chain (CDR L)1 amino acid sequence of RSSQTIVHSTGHTYLE (SEQ ID NO:56);
  (e) a CDR L2 amino acid sequence of KVSNRFS (SEQ ID NO:57); and
  (f) a CDR L3 amino acid sequence of FQGSHVPYT (SEQ ID NO:58).

In one embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence selected of SEQ ID NO:62.

In one embodiment the extracellular domain of the antigen binding receptor comprises an antigen binding moiety capable of specific binding to an Fc domain comprising the I253A, H310A and H435A mutations, wherein the antigen binding moiety comprises a heavy chain variable region (VH) comprising the amino acid sequence of SEQ ID NO:61, and a light chain variable region (VL) comprising the amino acid sequence of SEQ ID NO:62.

In one embodiment, the at least one antigen binding moiety is a scFv, a Fab, a crossFab or a scFab fragment. In one embodiment the extracellular domain of the antigen binding receptor comprises an antigen binding moiety capable of specific binding to an Fc domain comprising the I253A, H310A and H435A mutations, wherein the at least the antigen binding moiety is a Fab fragment. In a particular embodiment the extracellular domain of the antigen binding receptor comprises an antigen binding moiety capable of specific binding to an Fc domain comprising the I253A, H310A and H435A mutations, wherein the Fab fragment comprising a heavy chain of SEQ ID NO:64 and a light chain of SEQ ID NO:65.

In one embodiment the extracellular domain of the antigen binding receptor comprises an antigen binding moiety capable of specific binding to an Fc domain comprising the I253A, H310A and H435A mutations, wherein the at least one antigen binding moiety is a scFv fragment. In a particular embodiment the extracellular domain of the antigen binding receptor comprises an antigen binding moiety capable of specific binding to an Fc domain comprising the I253A, H310A and H435A mutations, wherein the scFv fragment comprises the amino acid sequence of SEQ ID NO:60.

In further embodiments according to the invention the antigen binding moiety comprised in the extracellular domain is a single chain Fab fragment or scFab.

Fab and scFab fragments are stabilized via the natural disulfide bond between the CL domain and the CH1 domain. Antigen binding moieties comprising a heavy chain variable domain (VH) and a light chain variable domain (VL), such as the Fab, crossFab, scFv and scFab fragments as described herein might be further stabilized by introducing interchain disulfide bridges between the VH and the VL domain. Accordingly, in one embodiment, the Fab fragment(s), the crossFab fragment(s), the scFv fragment(s) and/or the scFab fragment(s) comprised in the antigen binding receptors according to the invention might be further stabilized by generation of interchain disulfide bonds via insertion of cysteine residues (e.g., position 44 in the variable heavy chain and position 100 in the variable light chain according to Kabat numbering). Such stabilized antigen binding moieties are referred to by the term "ds" within the appended examples and Figures.

Anchoring Transmembrane Domain

In the context of the present invention, the anchoring transmembrane domain of the antigen binding receptors of the present invention may be characterized by not having a cleavage site for mammalian proteases. In the context of the present invention, proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate the antigen binding receptors of the invention, which activate T cells, preferably CD8+ T cells, upon binding to a mutated Fc domain as defined herein.

Accordingly, in the context of the present invention, the anchoring transmembrane domain may comprise part of a murine/mouse or preferably of a human transmembrane domain. An example for such an anchoring transmembrane domain is a transmembrane domain of CD28, for example, having the amino acid sequence as shown herein in SEQ ID NO:11 (as encoded by the DNA sequence shown in SEQ ID NO:24). In the context of the present invention, the transmembrane domain of the antigen binding receptor of the present invention may comprise/consist of an amino acid sequence as shown in SEQ ID NO:11 (as encoded by the DNA sequence shown in SEQ ID NO:24).

In an illustrative embodiment of the present invention, as a proof of concept, an antigen binding receptor is provided which comprises an antigen binding moiety comprising an amino acid sequence of SEQ ID NO: 10 (as encoded by the DNA sequence shown in SEQ ID NO:22), and a fragment/polypeptide part of CD28 (the UniProt Entry number of the human CD28 is P10747 (with the version number 173 and version 1 of the sequence)) as shown herein as SEQ ID NO:71 (as encoded by the DNA sequence shown in SEQ ID NO:70). Alternatively, any protein having a transmembrane domain, as provided among others by the CD nomenclature, may be used as an anchoring transmembrane domain of the antigen binding receptor protein of the invention.

As described above, the herein provided antigen binding receptor may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:71 (as encoded by the cDNA shown in SEQ ID NO:70). Accordingly, in context of the present invention the anchoring transmembrane domain may comprise or consist of an amino acid sequence as shown in SEQ ID NO:11 (as encoded by the DNA sequence shown in SEQ ID NO:24).

In one embodiment provided is an antigen binding receptor comprising an anchoring transmembrane domain and an extracellular domain comprising a Fab fragment capable of specific binding to an Fc domain comprising the I253A, H310A and H435A mutations, wherein antigen binding receptor comprises a
(a) a heavy chain comprising the amino acid sequence of SEQ ID NO:64 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:65.

In one embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising an amino acid sequence selected from SEQ ID NO:40 and SEQ ID NO:49 fused at the C-terminus to the N-terminus of the anchoring transmembrane domain of SEQ ID NO:11, optionally through the peptide linker of SEQ ID NO:17; and
(b) a light chain comprising an amino acid sequence selected from SEQ ID NO:41 and SEQ ID NO:50.

In one embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising the amino acid sequence of SEQ ID NO:40 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:41.

In one preferred embodiment provided is an antigen binding receptor comprising an anchoring transmembrane domain and an extracellular domain comprising a Fab fragment capable of specific binding to an Fc domain comprising the P329G mutation, wherein the antigen binding receptor comprises a
(a) a heavy chain comprising the amino acid sequence of SEQ ID NO:49 fused at the C-terminus to the N-terminus of the anchoring transmembrane domain of SEQ ID NO:11, optionally through the peptide linker of SEQ ID NO:17; and
(b) a light chain comprising the amino acid sequence of SEQ ID NO:50.

In one embodiment provided is an antigen binding receptor comprising an anchoring transmembrane domain and an extracellular domain comprising a scFv fragment capable of specific binding to an Fc domain comprising the I253A, H310A and H435A mutations but not capable of specific binding to the non-mutated parent Fc domain, wherein the antigen binding receptor comprises the amino acid of SEQ ID NO:60 fused at the C-terminus to the N-terminus of the anchoring transmembrane domain of SEQ ID NO:11, optionally through the peptide linker of SEQ ID NO:17.

In one embodiment provided is an antigen binding receptor comprising an anchoring transmembrane domain and an extracellular domain comprising a scFv fragment capable of specific binding to an Fc domain comprising the P329G mutation but not capable of specific binding to the non-mutated parent Fc domain, wherein the antigen binding receptor comprises an amino acid sequence selected from SEQ ID NO:10 and SEQ ID NO:34 fused at the C-terminus to the N-terminus of the anchoring transmembrane domain of SEQ ID NO:11, optionally through the peptide linker of SEQ ID NO:17.

In one preferred embodiment provided is an antigen binding receptor comprising an anchoring transmembrane domain and an extracellular domain comprising a scFv fragment capable of specific binding to an Fc domain comprising the P329G mutation but not capable of specific binding to the non-mutated parent Fc domain, wherein the antigen binding receptor comprises the amino acid sequence of SEQ ID NO:10 fused at the C-terminus to the N-terminus of the anchoring transmembrane domain of SEQ ID NO:11, optionally through a peptide linker of SEQ ID NO:17.

In one embodiment provided is an antigen binding receptor comprising an anchoring transmembrane domain and an extracellular domain comprising a scFab fragment capable of specific binding to an Fc domain comprising the P329G mutation but not capable of specific binding to the non-mutated parent Fc domain, wherein the scFv fragment comprises the amino acid sequence of SEQ ID NO:34 fused at the C-terminus to the N-terminus of the anchoring transmembrane domain of SEQ ID NO:11, optionally through a peptide linker of SEQ ID NO:17.

Stimulatory Signaling Domain (SSD) and Co-Stimulatory Signaling Domain (CSD)

Preferably, the antigen binding receptor of the present invention comprises at least one stimulatory signaling domain and/or at least one co-stimulatory signaling domain. Accordingly, the herein provided antigen binding receptor preferably comprises a stimulatory signaling domain, which provides T cell activation. The herein provided antigen binding receptor may comprise a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is O54709 (version number 132 with sequence number 2)).

Thus, the stimulatory signaling domain which is comprised in the herein provided antigen binding receptor may be a fragment/polypeptide part of the full length of CD3z, FCGR3A or NKG2D. The amino acid sequences of the murine/mouse full length of CD3z, or NKG2D are shown herein as SEQ ID NOs: 96 (CD3z), 100 (FCGR3A) or 104 (NKG2D) (murine/mouse as encoded by the DNA sequences shown in SEQ ID NOs:97 (CD3z), 101 (FCGR3A) or 105 (NKG2D). The amino acid sequences of the human full length CD3z, FCGR3A or NKG2D are shown herein as SEQ ID NOs:94 (CD3z), 98 (FCGR3A) or 102 (NKG2D) (human as encoded by the DNA sequences shown in SEQ ID NOs:95 (CD3z), 99 (FCGR3A) or 103 (NKG2D)). The antigen binding receptor of the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the antigen binding receptor of the present invention comprises polypeptides which are derived from human origin. Thus, more preferably, the herein provided antigen binding receptor comprises the amino acid sequences as shown herein as SEQ ID NOs:94 (CD3z), 98 (FCGR3A) or 102 (NKG2D) (human as encoded by the DNA sequences shown in SEQ ID NOs:95 (CD3z), 99 (FCGR3A) or 103 (NKG2D)). For example, the fragment/polypeptide part of the human CD3z which may be comprised in the antigen binding receptor of the present invention may comprise or consist of the amino acid sequence shown in SEQ ID NO:13 (as encoded by the DNA sequence shown in SEQ ID NO:26). Accordingly, in one embodiment the antigen binding receptor comprises the sequence as shown in SEQ ID NO:13 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:13 and which is characterized by having a stimulatory signaling activity. Specific configurations of antigen binding receptors comprising a stimulatory signaling domain (SSD) are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

Furthermore, the herein provided antigen binding receptor preferably comprises at least one co-stimulatory signaling domain which provides additional activity to the T cell. The herein provided antigen binding receptor may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the UniProt Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/mouse DAP10 is Q9QUJ0 (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is O054885 (primary citable accession number) or Q9R1E7 (secondary citable accession number) with the version number 123 and the sequence number 1). In certain embodiments of the present invention the antigen binding receptor of the present invention may comprise one or more, i.e. 1, 2, 3, 4, 5, 6 or 7 of the herein defined co-stimulatory signaling domains.

Accordingly, in the context of the present invention, the antigen binding receptor of the present invention may comprise a fragment/polypeptide part of a murine/mouse or preferably of a human CD28 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the antigen binding receptor of the present invention comprises a co-stimulatory signaling domain which is derived from a human origin. Thus, more preferably, the co-stimulatory signaling domain(s) which is (are) comprised in the antigen binding receptor of the present invention may comprise or consist of the amino acid sequence as shown in SEQ ID NO:12 (as encoded by the DNA sequence shown in SEQ ID NO:25).

Thus, the co-stimulatory signaling domain which may be optionally comprised in the herein provided antigen binding receptor is a fragment/polypeptide part of the full length CD27, CD28, CD137, OX40, ICOS, DAP10 and DAP12. The amino acid sequences of the murine/mouse full length CD27, CD28, CD137, OX40, ICOS, CD27, DAP10 or DAP12 are shown herein as SEQ ID NOs:69 (CD27), 73 (CD28), 77 (CD137), 81 (OX40), 85 (ICOS), 89 (DAP10) or 93 (DAP12) (murine/mouse as encoded by the DNA sequences shown in SEQ ID NOs:68 (CD27), 72 (CD28), 76 (CD137), 80 (OX40), 84 (ICOS), 88 (DAP10) or 92 (DAP12)). However, because human sequences are most preferred in the context of the present invention, the co-stimulatory signaling domain which may be optionally comprised in the herein provided antigen binding receptor protein is a fragment/polypeptide part of the human full length CD27, CD28, CD137, OX40, ICOS, DAP10 or DAP12. The amino acid sequences of the human full length CD27, CD28, CD137, OX40, ICOS, DAP10 or DAP12 are shown herein as SEQ ID NOs: 67(CD27), 71 (CD28), 75 (CD137), 79 (OX40), 83 (ICOS), 87 (DAP10) or 91 (DAP12) (human as encoded by the DNA sequences shown in SEQ ID NOs: 66 (CD27), 70 (CD28), 74 (CD137), 78 (OX40), 82 (ICOS), 86 (DAP10) or 90 (DAP12)).

In one preferred embodiment, the antigen binding receptor comprises CD28 or a fragment thereof as co-stimulatory signaling domain. The herein provided antigen binding receptor may comprise a fragment of CD28 as co-stimulatory signaling domain, provided that at least one signaling domain of CD28 is comprised. In particular, any part/fragment of CD28 is suitable for the antigen binding receptor of the invention as long as at least one of the signaling motives of CD28 is comprised. For example, the CD28 polypeptide which is comprised in the antigen binding receptor protein of the present invention may comprise or consist of the amino acid sequence shown in SEQ ID NO:12 (as encoded by the DNA sequence shown in SEQ ID NO:25). In the present invention the intracellular domain of CD28, which functions as a co-stimulatory signaling domain, may comprise a sequence derived from the intracellular domain of the CD28 polypeptide having the sequence(s) YMNM (SEQ ID NO:106) and/or PYAP (SEQ ID NO:107). Preferably, the antigen binding receptor of the present invention comprises polypeptides which are derived from human origin. For example, the fragment/polypeptide part of the human CD28 which may be comprised in the antigen binding receptor of the present invention may comprise or consist of the amino acid sequence shown in SEQ ID NO:12 (as encoded by the DNA sequence shown in SEQ ID NO:25). Accordingly, in the context of the present invention the antigen binding receptor comprises the sequence as shown in SEQ ID NO:12 or a sequence which has up to 1, 2, 3, 4, 5, 6, 7, 8, 9 or 10 substitutions, deletions or insertions in comparison to SEQ ID NO:12 and which is characterized by having a co-stimulatory signaling activity. Specific configurations of antigen binding receptors comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory signaling domain of the antigen binding receptor may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2), proliferation of T cells measured e.g. by ki67-measurement, cell quantification by flow cytometry, or lytic activity as assessed by real time impedance measurement of the target cell (by using e.g. an ICELLligence instrument as described e.g. in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Duwell et al., Cell Death Differ. 21(12) (2014), 1825-1837, Erratum in: Cell Death Differ. 21(12) (2014), 161). The co-stimulatory signaling domains PYAP (AA 208 to 211 of SEQ ID NO:107) and YMNM (AA 191 to 194 of SEQ ID NO:106) are beneficial for the function of the CD28 polypeptide and the functional effects enumerated above. The amino acid sequence of the YMNM domain is shown in SEQ ID NO:106; the amino acid sequence of the PYAP domain is shown in SEQ ID NO:107. Accordingly, in the antigen binding receptor of the present invention, the CD28 polypeptide preferably comprises a sequence derived from intracellular domain of a CD28 polypeptide having the sequences YMNM (SEQ ID NO:106) and/or PYAP (SEQ ID NO:107). In the context of the present invention an intracellular domain of a CD28 polypeptide having the sequences YMNM (SEQ ID NO:106) and/or PYAP (SEQ ID NO:107) characterized by a CD28 activity, defined as cytokine production, proliferation and lytic activity of a transduced cell described herein, like e.g. a transduced T cell. Accordingly, in the context of the present invention the co-stimulatory signaling domain of the antigen binding receptors of the present invention has the amino acid sequence of SEQ ID NO:12 (human) (as encoded by the DNA sequence shown in SEQ ID NO:25). However, in the antigen binding receptor of the present invention, one or both of these domains may be mutated to FMNM (SEQ ID NO:108) and/or AYAA (SEQ ID NO:109), respectively. Either of these mutations reduces the ability of a transduced cell comprising the antigen binding receptor to release cytokines without affecting its ability to proliferate and can advantageously be used to prolong the viability and thus the therapeutic potential of the transduced cells. Or, in other words, such a non-functional mutation preferably enhances the persistence of the cells which are transduced with the herein provided antigen binding receptor in vivo.

These signaling motives may, however, be present at any site within the intracellular domain of the herein provided antigen binding receptor.

Linker and Signal Peptides

Moreover, the herein provided antigen binding receptor may comprise at least one linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein provided antigen binding receptor may comprise a linker between the extracellular domain comprising at least one antigen binding moiety capable of specific binding to a mutated Fc domain, the anchoring transmembrane domain, the co-stimulatory signaling domain and/or the stimulatory signaling domain. Such linkers have the advantage that they increase the probability that the different polypeptides of the antigen binding receptor (i.e. the extracellular domain comprising at least one antigen binding moiety capable of specific binding to a mutated Fc domain, the anchoring transmembrane domain, the co-stimulatory signaling domain and/or the stimulatory signaling domain) fold independently and behave as expected. Thus, in the context of the present invention, the extracellular domain comprising at least one antigen binding moiety capable of specific binding to a mutated Fc domain, the anchoring transmembrane domain that does not have a cleavage site for mammalian proteases, the co-stimulatory signaling domain and the stimulatory signaling domain may be comprised in a single-chain multi-functional polypeptide.

A single-chain fusion construct e.g. may consist of (a) polypeptide(s) comprising (an) extracellular domain(s) comprising at least one antigen binding moiety capable of specific binding to a mutated Fc domain, (an) anchoring transmembrane domain(s), (a) co-stimulatory signaling domain(s) and/or (a) stimulatory signaling domain(s). In alternative embodiments, the antigen binding receptor comprises a antigen binding moiety which is not a single chain fusion construct, i.e. the antigen binding moiety is a Fab or a crossFab fragment. In such embodiments the antigen binding receptor is not a single chain fusion construct comprising only one polypeptide chain. Preferably such constructs will comprise a single chain heavy chain fusion polypeptide combined with an immunoglobulin light chain as described herein, e.g., heavy chain fusion polypeptide comprises (an) immunoglobulin heavy chain(s), (an) anchoring transmembrane domain(s), (a) co-stimulatory signaling domain(s) and/or (a) stimulatory signaling domain(s) and is combined with (an) immunoglobulin light chain(s). Accordingly, the antigen binding moiety, the anchoring transmembrane domain, the co-stimulatory signaling domain and the stimulatory signaling domain may be connected by one or more identical or different peptide linker as described herein. For example, in the herein provided antigen binding receptor the linker between the extracellular domain comprising at least one antigen binding moiety capable of specific binding to a mutated Fc domain and the anchoring transmembrane domain may comprise or consist of the amino and amino acid sequence as shown in SEQ ID NO:17. Accordingly, the anchoring transmembrane domain, the co-stimulatory signaling domain and/or the stimulatory domain may be connected to each other by peptide linkers or alternatively, by direct fusion of the domains.

In some embodiments according to the invention the antigen binding moiety comprised in the extracellular domain is a single-chain variable fragment (scFv) which is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. For example, in the herein provided antigen binding receptor the linker may have the amino and amino acid sequence as shown in SEQ ID NO:16. The scFv antigen binding moiety as described herein retains the specificity of the original antibody, despite removal of the constant regions and the introduction of the linker. scFv antibodies are, e.g. described in Houston, J. S., Methods in Enzymol. 203 (1991) 46-96).

In some embodiments according to the invention the antigen binding moiety comprised in the extracellular domain is a single chain Fab fragment or scFab which is a polypeptide consisting of an heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain.

In some embodiments according to the invention the antigen binding moiety comprised in the extracellular domain is a crossover single chain Fab fragment which is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids.

The herein provided antigen binding receptor or parts thereof may comprise a signal peptide. Such a signal peptide will bring the protein to the surface of the T cell membrane. For example, in the herein provided antigen binding receptor the signal peptide may have the amino and amino acid sequence as shown in SEQ ID NO:110 (as encoded by the DNA sequence shown in SEQ ID NO:111).

T Cell Activating Antigen Binding Receptors Capable of Specific Binding to Mutated Fc Domains The components of the antigen binding receptors as described herein can be fused to each other in a variety of configurations to generate T cell activating antigen binding receptors.

In some embodiments, the antigen binding receptor comprises an extracellular domain composed of a heavy chain variable domain (VH) and a light chain variable domain (VL) connected to an anchoring transmembrane domain. In some embodiments, the VH domain is fused at the C-terminus to the N-terminus of the VL domain, optionally through a peptide linker. In other embodiments, the antigen binding receptor further comprises a stimulatory signaling domain and/or a co-stimulatory signaling domain. In a specific such embodiment, the antigen binding receptor essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain. Optionally, the antigen binding receptor further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the antigen binding receptor essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

In preferred embodiments, one of the binding moieties is a Fab fragment or a crossFab fragment. In one preferred embodiment, the antigen binding moiety is fused at the C-terminus of the Fab or crossFab heavy chain to the N-terminus of the anchoring transmembrane domain, optionally through a peptide linker. In an alternative embodiment, the antigen binding moiety is fused at the C-terminus of the Fab or crossFab light chain to the N-terminus of the anchoring transmembrane domain, optionally through a peptide linker. In other embodiments, the antigen binding receptor further comprises a stimulatory signaling domain and/or a co-stimulatory signaling domain. In a specific such embodiment, the antigen binding receptor essentially consists of a Fab or crossFab fragment, an anchoring transmembrane domain, and optionally a stimulatory signaling domain connected by one or more peptide linkers, wherein the Fab or crossFab fragment is fused at the C-terminus of the heavy or light chain to the N-terminus of the anchoring transmembrane domain, wherein the anchoring transmembrane domain is fused at the C-terminus to the N-terminus of the stimulatory signaling domain. Preferably, the antigen binding receptor further comprises a co-stimulatory signaling domain. In one such embodiment, the antigen binding receptor essentially consists of a Fab or crossFab fragment, an anchoring transmembrane domain, a stimulatory signaling domain and a co-stimulatory signaling domain connected by one or more peptide linkers, wherein the Fab or crossFab fragment is fused at the C-terminus of the heavy or light chain to the N-terminus of the anchoring transmembrane domain, wherein the stimulatory signaling domain is fused at the C-terminus to the N-terminus of the co-stimulatory signaling domain. In a preferred embodiment, the co-stimulatory signaling domain is connected to the anchoring transmembrane domain instead of the stimulatory signaling domain. In a most preferred embodiment, the antigen binding receptor essentially consists of a Fab or crossFab fragment, an anchoring transmembrane domain, a co-stimulatory signaling domain and a stimulatory signaling domain, wherein the Fab or crossFab fragment is fused at the C-terminus of the heavy chain to the N-terminus of the anchoring transmembrane domain through a peptide linker, wherein the anchoring transmembrane domain is fused at the C-terminus to the N-terminus of the co-stimulatory signaling domain, wherein the co-stimulatory signaling domain is fused at the C-terminus to N-terminus of the stimulatory signaling domain.

The antigen binding moiety, the anchoring transmembrane domain and the stimulatory signaling and/or co-stimulatory signaling domains may be fused to each other directly or through one or more peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers, wherein "n" is generally a number between 1 and 10, typically between 2 and 4. A preferred peptide linker for connecting the antigen binding moiety and the anchoring transmembrane moiety is GGGGS ($G_4S$) according to SEQ ID NO 17. An exemplary peptide linker suitable for connecting variable heavy chain (VH) and the variable light chain (VL) is GGGSGGGSGGGSGGGS ($G_4S$)$_4$ according to SEQ ID NO 16.

Additionally, linkers may comprise (a portion of) an immunoglobulin hinge region. Particularly where an antigen binding moiety is fused to the N-terminus of an anchoring transmembrane domain, it may be fused via an immunoglobulin hinge region or a portion thereof, with or without an additional peptide linker.

As described herein, the antigen binding receptors of the present invention comprise an extracellular domain comprising at least one antigen binding moiety. An antigen binding receptor with a single antigen binding moiety capable of specific binding to a target cell antigen is useful and preferred, particularly in cases where high expression of the antigen binding receptor is needed. In such cases, the presence of more than one antigen binding moiety specific for the target cell antigen may limit the expression efficiency of the antigen binding receptor. In other cases, however, it will be advantageous to have an antigen binding receptor comprising two or more antigen binding moieties specific for a target cell antigen, for example to optimize targeting to the target site or to allow crosslinking of target cell antigens.

In one particular embodiment, the antigen binding receptor comprises one antigen binding moiety capable of specific binding to a mutated Fc domain, in particular an IgG1 Fc domain, comprising the P329G mutation. In one embodiment, the antigen binding moiety capable of specific binding to a mutated Fc domain but not capable of specific binding to the non-mutated parent Fc domain is a scFv, a Fab or a crossFab.

In one embodiment, the antigen binding moiety is fused at the C-terminus of the scFv fragment or at the C-terminus of the Fab or crossFab heavy chain to the N-terminus of an anchoring transmembrane domain, optionally through a peptide linker. In one embodiment the peptide linker comprises the amino acid sequence GGGGS (SEQ ID NO:16). In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

In a preferred embodiment, the anchoring transmembrane domain is the CD28 transmembrane domain or a fragment thereof. In a particular embodiment, the anchoring transmembrane domain comprises or consist of the amino acid sequence of FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, of CD28, of CD137, of OX40, of ICOS, of DAP10 and of DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence RSKRSRLLHSDYMNMTPRRPGPTRKHYQPYAPPRD-FAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

```
                                      (SEQ ID NO: 13)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) according to SEQ ID NO:18.

In a particular embodiment, the antigen binding receptor comprises an anchoring transmembrane domain and an extracellular domain comprising at least one antigen binding moiety, wherein the at least one antigen binding moiety is a scFv fragment capable of specific binding to a mutated Fc domain but not capable of specific binding to the non-mutated parent Fc domain, wherein the mutated Fc domain comprises the P329G mutation. The P329G mutation reduces Fcγ receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration scFv-ATD-CSD-SSD. In a preferred embodiment, the antigen binding receptor has the configuration scFv-G$_4$S-ATD-CSD-SSD, wherein G$_4$S is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is a scFv fragment capable of specific binding to a mutated Fc domain comprising the P329G mutation, wherein the antigen binding moiety comprises at least one heavy chain complementarity determining region (CDR) selected from the group consisting of SEQ ID NO:1, SEQ ID NO:2 and SEQ ID NO:3 and at least one light chain CDR selected from the group of SEQ ID NO:4, SEQ ID NO:5, SEQ ID NO:6.

In a preferred embodiment, the antigen binding moiety is a scFv capable of specific binding to a mutated Fc domain comprising the P329G mutation, wherein the antigen binding moiety comprises the complementarity determining region (CDR H) 1 amino acid sequence RYWMN (SEQ ID NO:1), the CDR H2 amino acid sequence EITPDSSTI-NYTPSLKD (SEQ ID NO:2), the CDR H3 amino acid sequence PYDYGAWFAS (SEQ ID NO:3), the light chain complementary-determining region (CDR L) 1 amino acid sequence RSSTGAVTTSNYAN (SEQ ID NO:4), the CDR L2 amino acid sequence GTNKRAP (SEQ ID NO:5) and the CDR L3 amino acid sequence ALWYSNHWV (SEQ ID NO:6).

In one embodiment the present invention provides an antigen binding receptor comprising in order from the N-terminus to the C-terminus:
- (i) an antigen binding moiety which is a scFv fragment capable of specific binding to a mutated Fc domain comprising the P329G mutation, wherein the scFv fragment comprises a heavy chain variable region (VH) comprising the heavy chain complementarity determining region (CDR) 1 of SEQ ID NO:1, the heavy chain CDR 2 of SEQ ID NO:2, the heavy chain CDR 3 of SEQ ID NO:3, and a light chain variable region (VH) comprising the light chain CDR 1 of SEQ ID NO:4, the light chain CDR 2 of SEQ ID NO:5 and the light chain CDR 3 of SEQ ID NO:6;
- (ii) a peptide linker, in particular the peptide linker of SEQ ID NO:17;
- (iii) an anchoring transmembrane domain, in particular the anchoring transmembrane domain of SEQ ID NO:11;
- (iii) a co-stimulatory signaling domain, in particular the co-stimulatory signaling domain of SEQ ID NO:12; and
- (iv) a stimulatory signaling domain, in particular the stimulatory signaling domain of SEQ ID NO:13.

In one embodiment, the present invention provides an antigen binding receptor comprising in order from the N-terminus to the C-terminus:
- (i) an antigen binding moiety which is a scFv molecule capable of specific binding to a mutated Fc domain comprising the P329G mutation, wherein the scFv comprises a heavy chain variable domain (VH) selected from SEQ ID NO:8 and SEQ ID NO:32 and the light chain variable domain (VL) selected from SEQ ID NO:9 and SEQ ID NO:33;
- (ii) a peptide linker, in particular the peptide linker of SEQ ID NO:17;
- (iii) an anchoring transmembrane domain, in particular the anchoring transmembrane domain of SEQ ID NO:11;
- (iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In a preferred embodiment, the present invention provides an antigen binding receptor comprising in order from the N-terminus to the C-terminus
  (i) an antigen binding moiety which is a scFv molecule capable of specific binding to a mutated Fc domain comprising the P329G mutation, wherein the scFv comprises the heavy chain variable domain (VH) SEQ ID NO:8 and the light chain variable domain (VL) SEQ ID NO:9;
  (ii) a peptide linker, in particular the peptide linker of SEQ ID NO:17;
  (iii) an anchoring transmembrane domain, in particular the anchoring transmembrane domain of SEQ ID NO:11;
  (iii) a co-stimulatory signaling domain, in particular the co-stimulatory signaling domain of SEQ ID NO:12; and
  (iv) a stimulatory signaling domain, in particular the stimulatory signaling domain of SEQ ID NO:13.

In a preferred embodiment, the present invention provides an antigen binding receptor comprising in order from the N-terminus to the C-terminus
  (i) an antigen binding moiety which is a scFv molecule capable of specific binding to a mutated Fc domain comprising the P329G mutation, wherein the scFv comprises an amino acid sequence of SEQ ID NO:10 or SEQ ID NO:34;
  (ii) a peptide linker, in particular the peptide linker of SEQ ID NO:17;
  (iii) an anchoring transmembrane domain, in particular the anchoring transmembrane domain of SEQ ID NO:11;
  (iii) a co-stimulatory signaling domain, in particular the co-stimulatory signaling domain of SEQ ID NO:12; and
  (iv) a stimulatory signaling domain, in particular the stimulatory signaling domain of SEQ ID NO:13.

In a particular embodiment, the antigen binding moiety is capable of specific binding to a mutated Fc domain comprising the P329G mutation, wherein the antigen binding receptor comprises an amino acid sequence that is at least about 95%, 96%, 97%, 98%, 99% or 100% identical to the amino acid sequence of: SEQ ID NO:31.

In a preferred embodiment, the antigen binding moiety is capable of specific binding to a mutated Fc domain comprising the P329G mutation, wherein the antigen binding receptor comprises the amino acid sequence of: SEQ ID NO:31 In a preferred embodiment, the antigen binding moiety is a Fab fragment. In one embodiment, the antigen binding moiety is fused at the C-terminus of the Fab heavy chain to the N-terminus of an anchoring transmembrane domain. In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof.

In a particular embodiment, the anchoring transmembrane domain is FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, CD28, CD137, OX40, ICOS, DAP10 and DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence: RSKRSRLLHSDYMNMT-PRRPGPTRKHYQPYAPPRDFAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists

```
                                              (SEQ ID NO: 13)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) of SEQ ID NO:18.

In a particular embodiment, the antigen binding receptor comprises an anchoring transmembrane domain and an extracellular domain comprising at least one antigen binding moiety, wherein the at least one antigen binding moiety is a Fab fragment capable of specific binding to a mutated Fc domain but not capable of specific binding to the non-mutated parent Fc domain, wherein the mutated Fc domain comprises the P329G mutation, wherein the P329G mutation reduces Fcγ receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration Fab-ATD-CSD-SSD. In a preferred embodiment, the antigen binding receptor has the configuration Fab-G₄S-ATD-CSD-SSD, wherein G₄S is a linker comprising the sequence GGGGS of SEQ ID NO:17. Optionally, a reporter protein can be added to the C-terminus of the antigen binding receptor, optionally through a peptide linker. In a particular embodiment, the antigen binding moiety is capable of specific binding to a mutated Fc domain comprising the P329G mutation, wherein the antigen binding moiety is a Fab fragment comprising at least one heavy chain complementarity determining region (CDR) selected from the group consisting of SEQ ID NO:1, SEQ ID NO:2 and SEQ ID NO:3 and at least one light chain CDR selected from the group of SEQ ID NO:4, SEQ ID NO:5, SEQ ID NO:6.

In one embodiment, the antigen binding moiety is a Fab fragment capable of specific binding to a mutated Fc domain comprising the P329G mutation, wherein the antigen binding moiety comprises the complementarity determining region (CDR H) 1 amino acid sequence RYWMN (SEQ ID NO:1), the CDR H2 amino acid sequence EITPDSSTINYTPSLKD (SEQ ID NO:2), the CDR H3 amino acid sequence PYDYGAWFAS (SEQ ID NO:3), the light chain complementary-determining region (CDR L) 1 amino acid sequence RSSTGAVTTSNYAN (SEQ ID NO:4), the CDR L2 amino acid sequence GTNKRAP (SEQ ID NO:5) and the CDR L3 amino acid sequence ALWYSNHWV (SEQ ID NO:6).

In one embodiment the present invention provides an antigen binding receptor comprising in order from the N-terminus to the C-terminus
- (i) an antigen binding moiety which is a Fab molecule capable of specific binding to a mutated Fc domain comprising the P329G mutation, comprising the heavy chain complementarity determining region (CDR) 1 of SEQ ID NO:1, the heavy chain CDR 2 of SEQ ID NO:2, the heavy chain CDR 3 of SEQ ID NO:3, the light chain CDR 1 of SEQ ID NO:4, the light chain CDR 2 of SEQ ID NO:5 and the light chain CDR 3 of SEQ ID NO:6;
- (ii) a peptide linker, in particular the peptide linker of SEQ ID NO:17;
- (iii) an anchoring transmembrane domain, in particular the anchoring transmembrane domain of SEQ ID NO:11;
- (iii) a co-stimulatory signaling domain, in particular the co-stimulatory signaling domain of SEQ ID NO:12; and
- (iv) a stimulatory signaling domain, in particular the stimulatory signaling domain of SEQ ID NO:13.

In one embodiment the present invention provides an antigen binding receptor comprising:
a) a heavy chain fusion polypeptide comprising in order from the N-terminus to the C-terminus;
- (i) a heavy chain comprising the heavy chain complementarity determining region (CDR) 1 of SEQ ID NO:1, the heavy chain CDR 2 of SEQ ID NO:2, the heavy chain CDR 3 of SEQ ID NO:3;
- (ii) a peptide linker, in particular the peptide linker of SEQ ID NO:17;
- (iii) an anchoring transmembrane domain, in particular the anchoring transmembrane domain of SEQ ID NO:11;
- (iii) a co-stimulatory signaling domain, in particular the co-stimulatory signaling domain of SEQ ID NO:12; and
- (iv) a stimulatory signaling domain, in particular the stimulatory signaling domain of SEQ ID NO:13 and
b) a light chain comprising the light chain CDR 1 of SEQ ID NO:4, the light chain CDR 2 of SEQ ID NO:5 and the light chain CDR 3 of SEQ ID NO:6.

In one embodiment the present invention provides an antigen binding receptor comprising:
a) a heavy chain fusion polypeptide comprising in order from the N-terminus to the C-terminus;
- (i) the heavy chain variable domain (VH) SEQ ID NO:8;
- (ii) a peptide linker, in particular the peptide linker of SEQ ID NO:17;
- (iii) an anchoring transmembrane domain, in particular the anchoring transmembrane domain of SEQ ID NO:11;
- (iii) a co-stimulatory signaling domain, in particular the co-stimulatory signaling domain of SEQ ID NO:12; and
- (iv) a stimulatory signaling domain, in particular the stimulatory signaling domain of SEQ ID NO:13 and
b) the light chain variable domain (VL) SEQ ID NO:9.

In one embodiment the antigen binding moiety is a Fab fragment comprising a heavy chain comprising or consisting of an amino acid sequence of SEQ ID NO:40 or SEQ ID NO:49, and a light chain comprising or consisting of the amino acid sequence of SEQ ID NO:41 or SEQ ID NO:50. In a preferred embodiment the antigen binding moiety is a Fab fragment comprising a heavy chain comprising or consisting of an amino acid sequence of SEQ ID NO:40 and a light chain comprising or consisting of the amino acid sequence of SEQ ID NO:41.

In a particular embodiment, the antigen binding moiety is a Fab fragment capable of specific binding to a mutated Fc domain comprising the P329G mutation, wherein the antigen binding receptor comprises a heavy chain fusion polypeptide comprising an amino acid sequence that is at least about 95%, 96%, 97%, 98%, 99% or 100% identical to an amino acid sequence selected from the group of SEQ ID NO:39 and SEQ ID NO:48 and a light chain polypeptide comprising an amino acid sequence that is at least about 95%, 96%, 97%, 98%, 99% or 100% identical to an amino acid sequence selected from the group of SEQ ID NO:41 and SEQ ID NO:50.

In a preferred embodiment, the antigen binding moiety is a Fab fragment capable of specific binding to a mutated Fc domain comprising the P329G mutation, wherein the antigen binding receptor comprises a heavy chain fusion polypeptide comprising the amino acid sequence of SEQ ID NO:39 and a light chain polypeptide comprising the amino acid sequence of SEQ ID NO:41.

In an alternative embodiment, the antigen binding receptor comprises one antigen binding moiety capable of specific binding to a mutated Fc domain, in particular an IgG1 Fc domain, comprising the mutations I253A, H310A and H435A ("AAA"), In one embodiment, antigen binding moiety capable of specific binding to a mutated Fc domain but not capable of specific binding to the non-mutated parent Fc domain is a scFv, a Fab or a crossFab.

In one embodiment, the antigen binding moiety is fused at the C-terminus of the scFv fragment or at the C-terminus of the Fab or crossFab heavy chain to the N-terminus of an anchoring transmembrane domain, optionally through a peptide linker. In one embodiment the peptide linker comprises the amino acid sequence GGGGS (SEQ ID NO:16). In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

In a preferred embodiment, the anchoring transmembrane domain is the CD28 transmembrane domain or a fragment thereof. In a particular embodiment, the anchoring transmembrane domain comprises or consist of the amino acid sequence of FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, of CD28, of CD137, of OX40, of ICOS, of DAP10 and of DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence: RSKRSRLLHSDYMNMTPRRPGPTRKHYQPYAPPRD-FAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists of the sequence:

```
                                          (SEQ ID NO: 13)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGD-VEENPGP (T2A) according to SEQ ID NO:18.

In a particular embodiment, the antigen binding receptor comprises an anchoring transmembrane domain and an extracellular domain comprising at least one antigen binding moiety, wherein the at least one antigen binding moiety is a scFv fragment capable of specific binding to a mutated Fc domain but not capable of specific binding to the non-mutated parent Fc domain, wherein the mutated Fc domain comprises the I253A, H310A and H435A mutations. The I253A, H310A and H435A mutations reduce FcRn receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration scFv-ATD-CSD-SSD. In a preferred embodiment, the antigen binding receptor has the configuration scFv-G$_4$S-ATD-CSD-SSD, wherein G$_4$S is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is a scFv fragment capable of specific binding to a mutated Fc domain comprising the I253A, H310A and H435A mutations, wherein the antigen binding moiety comprises at least one heavy chain complementarity determining region (CDR) selected from the group consisting of SEQ ID NO:53, SEQ ID NO:54 and SEQ ID NO:55 and at least one light chain CDR selected from the group of SEQ ID NO:56, SEQ ID NO:57, SEQ ID NO:58.

In a preferred embodiment, the antigen binding moiety is a scFv capable of specific binding to a mutated Fc domain comprising the I253A, H310A and H435A mutations, wherein the antigen binding moiety comprises the complementarity determining region (CDR H) 1 amino acid sequence SYGMS (SEQ ID NO:53), the CDR H2 amino acid sequence SSGGSY (SEQ ID NO:54), the CDR H3 amino acid sequence LGMITTGYAMDY (SEQ ID NO:55), the light chain complementary-determining region (CDR L) 1 amino acid sequence RSSQTIVHSTGHTYLE (SEQ ID NO:56), the CDR L2 amino acid sequence KVSNRFS (SEQ ID NO:57) and the CDR L3 amino acid sequence FQGSHVPYT (SEQ ID NO:58).

In one embodiment the present invention provides an antigen binding receptor comprising in order from the N-terminus to the C-terminus:
(i) an antigen binding moiety which is a scFv fragment capable of specific binding to a mutated Fc domain comprising the I253A, H310A and H435A mutations, wherein the scFv fragment comprises a heavy chain variable region (VH) comprising the heavy chain complementarity determining region (CDR) 1 of SEQ ID NO:53, the heavy chain CDR 2 of SEQ ID NO:54, the heavy chain CDR 3 of SEQ ID NO:55, and a light chain variable region (VH) comprising the light chain CDR 1 of SEQ ID NO:56, the light chain CDR 2 of SEQ ID NO:57 and the light chain CDR 3 of SEQ ID NO:58;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment, the present invention provides an antigen binding receptor comprising in order from the N-terminus to the C-terminus:
(i) an antigen binding moiety which is a scFv molecule capable of specific binding to a mutated Fc domain comprising the I253A, H310A and H435A mutations, wherein the scFv comprises the heavy chain variable domain (VH) of SEQ ID NO:61 and the light chain variable domain (VL) of SEQ ID NO:62;
(ii) a peptide linker, in particular the peptide linker of SEQ ID NO:17;
(iii) an anchoring transmembrane domain, in particular the anchoring transmembrane domain of SEQ ID NO:11;
(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment, the present invention provides an antigen binding receptor comprising in order from the N-terminus to the C-terminus:
(i) an antigen binding moiety which is a scFv molecule capable of specific binding to a mutated Fc domain comprising the I253A, H310A and H435A mutations, wherein the scFv comprises the amino acid sequence of SEQ ID NO:60;
(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and (iv) a stimulatory signaling domain, in particular the stimulatory signaling domain of SEQ ID NO:13.

In a particular embodiment, the antigen binding moiety is capable of specific binding to a mutated Fc domain comprising the I253A, H310A and H435A mutations, wherein the antigen binding receptor comprises an amino acid sequence that is at least about 95%, 96%, 97%, 98%, 99% or 100% identical to the amino acid sequence of: SEQ ID NO:59.

In a preferred embodiment, the antigen binding moiety is capable of specific binding to a mutated Fc domain comprising the I253A, H310A and H435A mutations, wherein the antigen binding receptor comprises the amino acid sequence of: SEQ ID NO:595 In a preferred embodiment, the antigen binding moiety is a Fab fragment. In one embodiment, the antigen binding moiety is fused at the C-terminus of the Fab heavy chain to the N-terminus of an anchoring transmembrane domain. In one embodiment, the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof. In a preferred embodiment, the anchoring transmembrane domain is the CD28 transmembrane domain or a fragment thereof.

In a particular embodiment, the anchoring transmembrane domain is FWVLVVVGGVLACYSLLVTVAFIIFWV (SEQ ID NO:11). In one embodiment, the antigen binding receptor further comprises a co-stimulatory signaling domain (CSD). In one embodiment, the anchoring transmembrane domain of the antigen binding receptor is fused at the C-terminus to the N-terminus of a co-stimulatory signaling domain. In one embodiment, the co-stimulatory signaling domain is individually selected from the group consisting of the intracellular domain of CD27, CD28, CD137, OX40, ICOS, DAP10 and DAP12, or fragments thereof as described herein before. In a preferred embodiment, the co-stimulatory signaling domain is the intracellular domain of CD28 or a fragment thereof. In a particular embodiment the co-stimulatory signaling domain comprises or consists of the sequence RSKRSRLLHSDYMNMTPRRPGPTRKHYQPYAPPRDFAAYRS (SEQ ID NO:12). In one embodiment, the antigen binding receptor further comprises a stimulatory signaling domain. In one embodiment, the co-stimulatory signaling domain of the antigen binding receptor is fused at the C-terminus to the N-terminus of the stimulatory signaling domain. In one embodiment, the at least one stimulatory signaling domain is individually selected from the group consisting of the intracellular domain of CD3z, FCGR3A and NKG2D, or fragments thereof. In a preferred embodiment, the co-stimulatory signaling domain is the intracellular domain of CD3z or a fragment thereof. In a particular embodiment the co-stimulatory signaling domain comprises or consists

```
                                         (SEQ ID NO: 13)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR.
```

In one embodiment, the antigen binding receptor is fused to a reporter protein, particularly to GFP or enhanced analogs thereof. In one embodiment, the antigen binding receptor is fused at the C-terminus to the N-terminus of eGFP (enhanced green fluorescent protein), optionally through a peptide linker as described herein. In a preferred embodiment, the peptide linker is GEGRGSLLTCGDVEENPGP (T2A) of SEQ ID NO:18.

In a particular embodiment, the antigen binding receptor comprises an anchoring transmembrane domain and an extracellular domain comprising at least one antigen binding moiety, wherein the at least one antigen binding moiety is a Fab fragment capable of specific binding to a mutated Fc domain but not capable of specific binding to the non-mutated parent Fc domain, wherein the mutated Fc domain comprises the I253A, H310A and H435A mutations, wherein the I253A, H310A and H435A mutations reduce FcRn receptor binding. In one embodiment, the antigen binding receptor of the invention comprises an anchoring transmembrane domain (ATD), a co-stimulatory signaling domain (CSD) and a stimulatory signaling domain (SSD). In one such embodiment, the antigen binding receptor has the configuration Fab-ATD-CSD-SSD. In a preferred embodiment, the antigen binding receptor has the configuration Fab-$G_4S$-ATD-CSD-SSD, wherein $G_4S$ is a linker comprising the sequence GGGGS of SEQ ID NO:17. Optionally, a reporter protein can be added to the C-terminus of the antigen binding receptor, optionally through a peptide linker.

In a particular embodiment, the antigen binding moiety is capable of specific binding to a mutated Fc domain comprising the I253A, H310A and H435A mutations, wherein the antigen binding moiety is a Fab fragment comprising at least one heavy chain complementarity determining region (CDR) selected from the group consisting of SEQ ID NO:53, SEQ ID NO:54 and SEQ ID NO:55 and at least one light chain CDR selected from the group of SEQ ID NO:56, SEQ ID NO:57, SEQ ID NO:58.

In a preferred embodiment, the antigen binding moiety is a Fab fragment capable of specific binding to a mutated Fc domain comprising the I253A, H310A and H435A mutations, wherein the antigen binding moiety comprises the complementarity determining region (CDR H) 1 amino acid sequence SYGMS (SEQ ID NO:53), the CDR H2 amino acid sequence SSGGSY (SEQ ID NO:54), the CDR H3 amino acid sequence LGMITTGYAMDY (SEQ ID NO:55), the light chain complementary-determining region (CDR L) 1 amino acid sequence RSSQTIVHSTGHTYLE (SEQ ID NO:56), the CDR L2 amino acid sequence KVSNRFS (SEQ ID NO:57) and the CDR L3 amino acid sequence FQGSHVPYT (SEQ ID NO:58).

In one embodiment the present invention provides an antigen binding receptor comprising in order from the N-terminus to the C-terminus (i) an antigen binding moiety which is a Fab molecule capable of specific binding to a mutated Fc domain comprising the I253A, H310A and H435A mutations, comprising the heavy chain complementarity determining region (CDR) 1 of SEQ ID NO:53, the heavy chain CDR 2 of SEQ ID NO:54, the heavy chain CDR 3 of SEQ ID NO:55, the light chain CDR 1 of SEQ ID NO:56, the light chain CDR 2 of SEQ ID NO:57 and the light chain CDR 3 of SEQ ID NO:58;

(ii) a peptide linker, in particular the peptide linker of SEQ ID NO:17;

(iii) an anchoring transmembrane domain, in particular the anchoring transmembrane domain of SEQ ID NO:11;

(iii) a co-stimulatory signaling domain, in particular the co-stimulatory signaling domain of SEQ ID NO:12; and
(iv) a stimulatory signaling domain, in particular the stimulatory signaling domain of SEQ ID NO:13.

In one embodiment the present invention provides an antigen binding receptor comprising:
a) a heavy chain fusion polypeptide comprising in order from the N-terminus to the C-terminus;
  (i) a heavy chain comprising the heavy chain complementarity determining region (CDR) 1 of SEQ ID NO:53, the heavy chain CDR 2 of SEQ ID NO:54, the heavy chain CDR 3 of SEQ ID NO:55;
  (ii) a peptide linker, in particular the peptide linker of SEQ ID NO:17;
  (iii) an anchoring transmembrane domain, in particular the anchoring transmembrane domain of SEQ ID NO:11;
  (iii) a co-stimulatory signaling domain, in particular the co-stimulatory signaling domain of SEQ ID NO:12; and
  (iv) a stimulatory signaling domain, in particular the stimulatory signaling domain of SEQ ID NO:13 and
b) a light chain comprising the light chain CDR 1 of SEQ ID NO:56, the light chain CDR 2 of SEQ ID NO:57 and the light chain CDR 3 of SEQ ID NO:58.

In one embodiment the present invention provides an antigen binding receptor comprising:
a) a heavy chain fusion polypeptide comprising in order from the N-terminus to the C-terminus;
  (i) the heavy chain variable domain (VH) SEQ ID NO:61;
  (ii) a peptide linker, in particular the peptide linker of SEQ ID NO:17;
  (iii) an anchoring transmembrane domain, in particular the anchoring transmembrane domain of SEQ ID NO:11;
  (iii) a co-stimulatory signaling domain, in particular the co-stimulatory signaling domain of SEQ ID NO:12; and
  (iv) a stimulatory signaling domain, in particular the stimulatory signaling domain of SEQ ID NO:13 and
b) the light chain variable domain (VL) SEQ ID NO:62.

In one particular embodiment the antigen binding moiety is a Fab fragment comprising a heavy chain comprising or consisting of the amino acid sequence of SEQ ID NO:64 and a light chain comprising or consisting of the amino acid sequence of SEQ ID NO:65.

In a particular embodiment, the antigen binding moiety is a Fab fragment capable of specific binding to a mutated Fc domain comprising the I253A, H310A and H435A mutations, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:63 and a light chain polypeptide comprising an amino acid sequence that is at least about 95%, 96%, 97%, 98%, 99% or 100% identical to the amino acid sequence of SEQ ID NO:65.

In a preferred embodiment, the antigen binding moiety is a Fab fragment capable of specific binding to a mutated Fc domain comprising the I253A, H310A and H435A mutations, wherein the antigen binding receptor comprises a heavy chain fusion polypeptide comprising the amino acid sequence of SEQ ID NO:63 and a light chain polypeptide comprising the amino acid sequence of SEQ ID NO:65.

In certain alternative embodiments, the antigen binding receptor of the invention, the Fab light chain polypeptide and the Fab heavy chain fusion polypeptide are fused to each other, optionally via a linker peptide. Fusion of the Fab heavy and light chains can improve pairing of Fab heavy and light chains, and also reduces the number of plasmids needed for expression of some of the antigen binding receptors of the invention. An alternative strategy to reduce the number of plasmids needed for expression of the antigen binding receptor is the use of an internal ribosomal entry side to enable expression of both heavy and light chain constructs from the same plasmid as illustrated e.g. in FIG. 2A and FIG. 2B.

In certain embodiments the antigen binding receptor comprises a polypeptide wherein the Fab light chain variable region of the antigen binding moiety shares a carboxy-terminal peptide bond with the Fab heavy chain constant region of the antigen binding moiety (i.e. a the antigen binding moiety comprises a crossFab heavy chain, wherein the heavy chain variable region is replaced by a light chain variable region), which in turn shares a carboxy-terminal peptide bond with the anchoring transmembrane domain ($VL_{(1)}$-$CH1_{(1)}$-ATD). In some embodiments the antigen binding receptor further comprises a polypeptide wherein the Fab heavy chain variable region of the first antigen binding moiety shares a carboxy-terminal peptide bond with the Fab light chain constant region of the first antigen binding moiety ($VH_{(1)}$-$CL_{(1)}$). In certain embodiments the polypeptides are covalently linked, e.g., by a disulfide bond. In alternative embodiments the antigen binding receptor comprises a polypeptide wherein the Fab heavy chain variable region of the antigen binding moiety shares a carboxy-terminal peptide bond with the Fab light chain constant region of the antigen binding moiety (i.e. the antigen binding moiety comprises a crossFab heavy chain, wherein the heavy chain constant region is replaced by a light chain constant region), which in turn shares a carboxy-terminal peptide bond with an anchoring transmembrane domain ($VH_{(1)}$-$CL_{(1)}$-ATD). In some embodiments the antigen binding receptor further comprises a polypeptide wherein the Fab light chain variable region of the antigen binding moiety shares a carboxy-terminal peptide bond with the Fab heavy chain constant region of the antigen binding moiety ($VL_{(1)}$-$CH1_{(1)}$) In certain embodiments the polypeptides are covalently linked, e.g., by a disulfide bond.

According to any of the above embodiments, components of the antigen binding receptor (e.g., VH and VL, antigen binding moiety, anchoring transmembrane domain, co-stimulatory signaling domain, stimulatory signaling domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally a number between 1 and 10, preferably between 1 and 4.

Exemplary T Cell Activating Antigen Binding Receptors

Figure 1A:
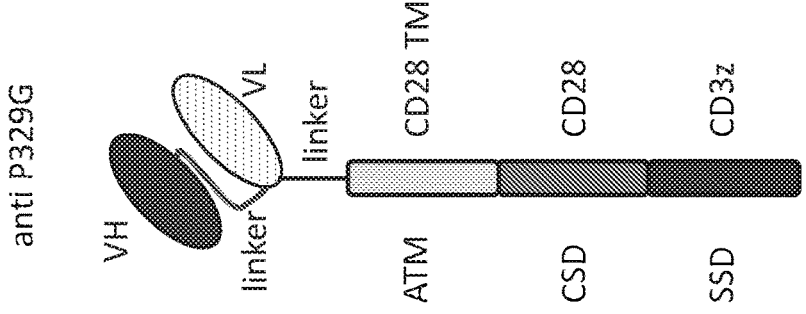
Figure 3:
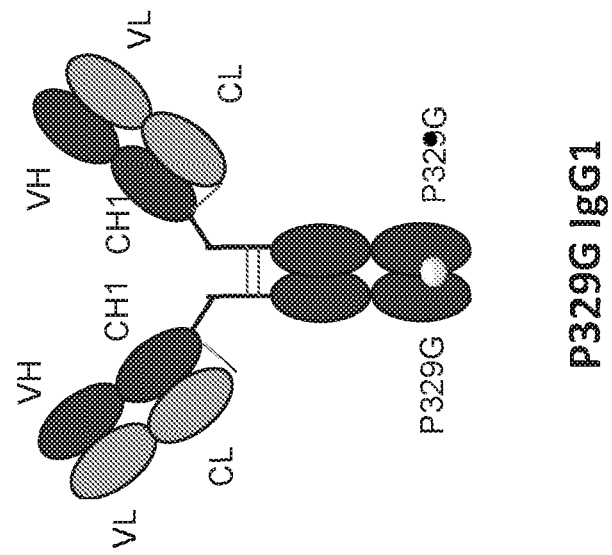
FIG. 3 depicts an exemplary IgG1 molecule harboring the P329G mutation in the Fc domain which is recognized by an anti-P329G antigen binding receptor of the invention.
Figure 4:
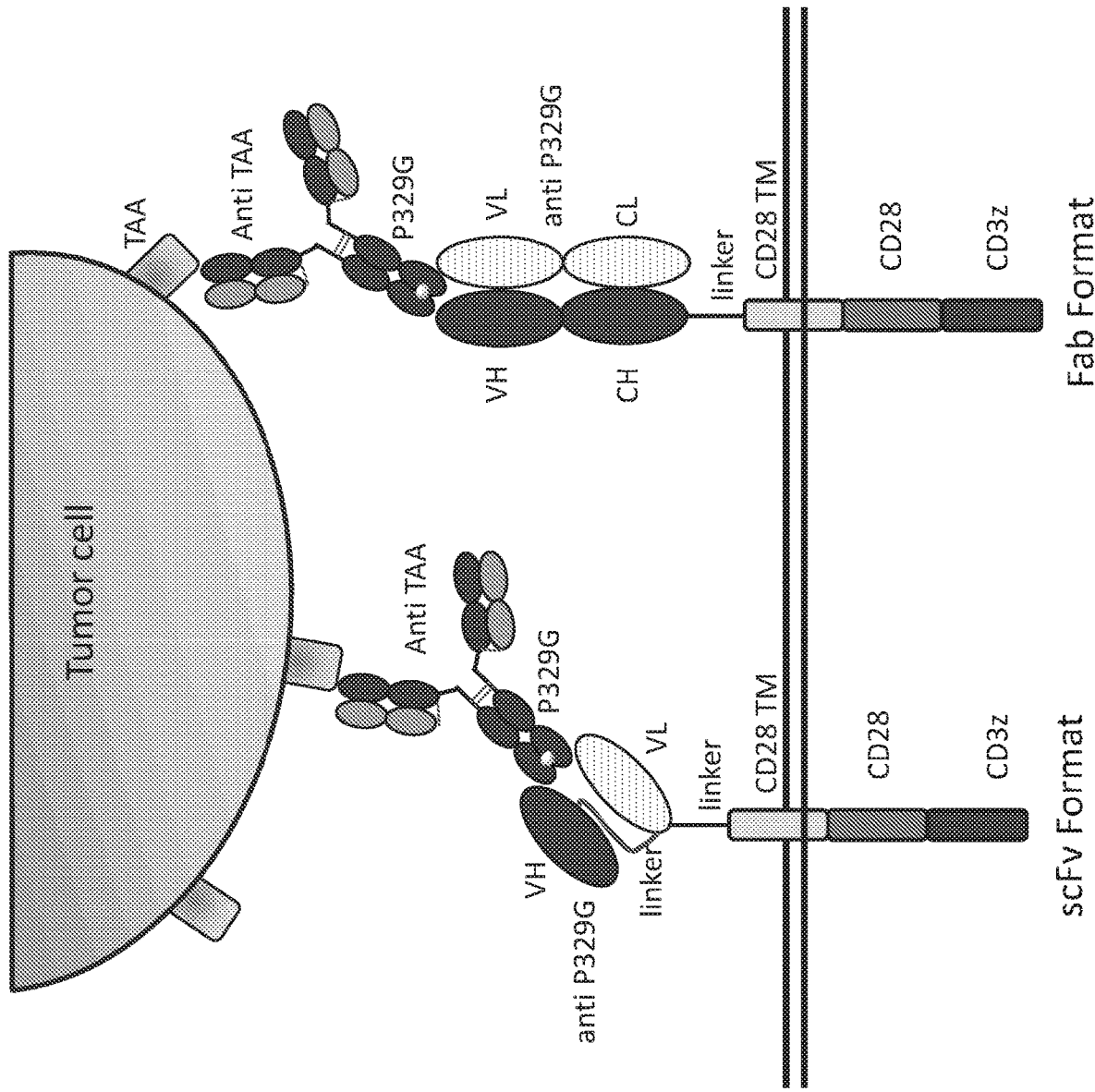
FIG. 4 depicts a schematic representation of a tumor associated antigen (TAA) bound IgG harboring the P329G mutation. This antibody can in turn be recognized by an anti-P329G antigen binding receptor expressing T cell, whereby the T cell gets activated.
Figure 5:
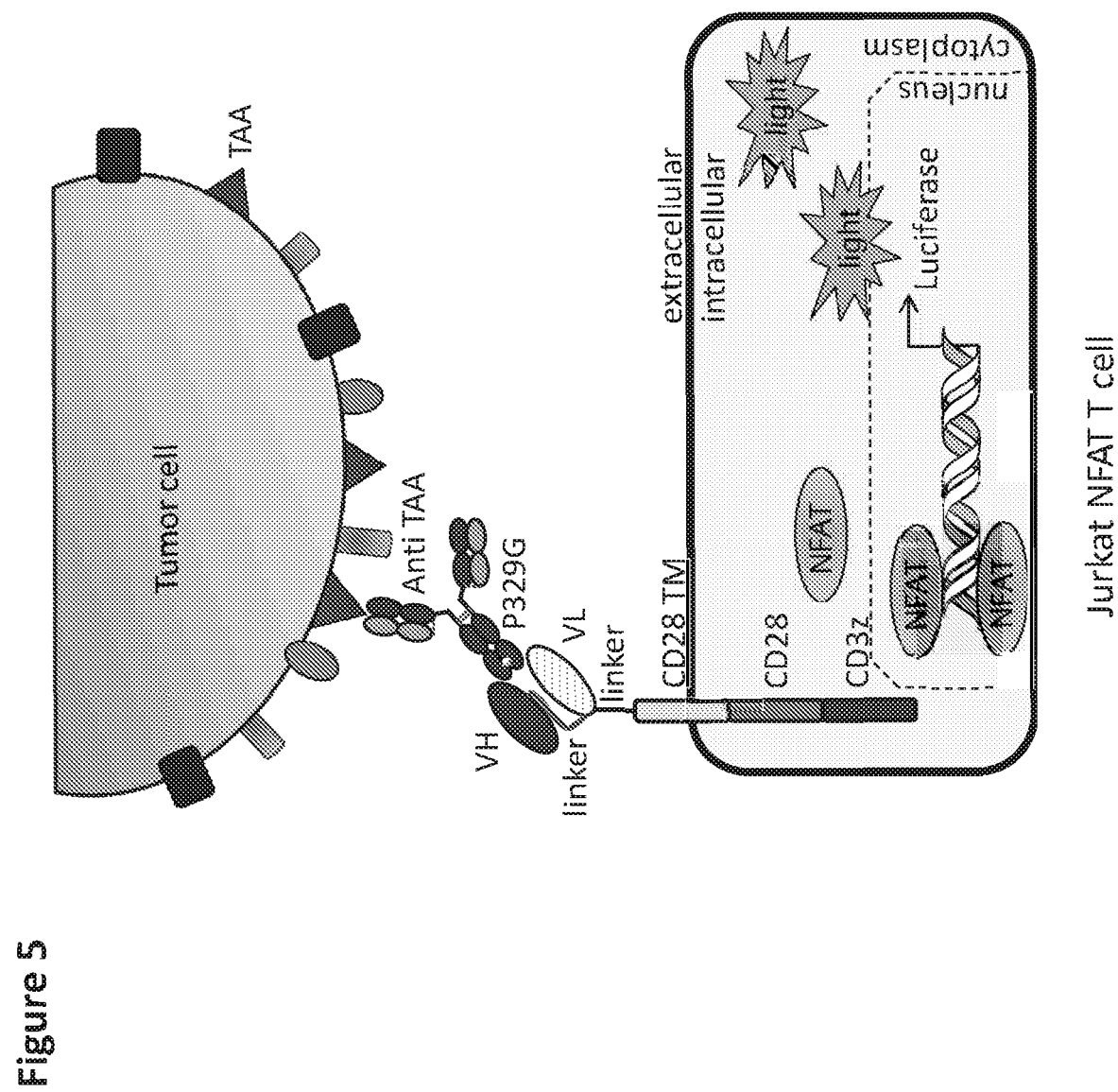
FIG. 5 shows a schematic representation of a Jurkat NFAT T cell reporter assay. TAA bound IgG harboring the P329G mutation can be recognized by the anti-P329G antigen binding receptor expressing Jurkat NFAT T cell. This recognition leads to the activation of the cell which can be detected by measuring luminescence (cps).

As illustratively shown in the appended Examples and in FIG. 1A, as a proof of concept of the present invention, the antigen binding receptor "Anti-P329G-ds-scFv-CD28ATD-CD28CSD-CD3zSSD pETR17096" (SEQ ID NO:7) was constructed which comprises one stabilized scFv antigen binding moiety binding to/directed against/interacting with or on an antibody comprising the P329G mutation in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-P329G-ds-scFv-CD28ATD-CD28CSD-CD3zSSD pETR17096" are shown in Tables 2 and 3.

Furthermore, as illustrated in FIG. 1B, as a further proof of concept of the present invention, the antigen binding receptor "Anti-P329G-ds-Fab-CD28ATD-CD28CSD-CD3zSSD pETR17100" (SEQ ID NOs: 39, 41) was constructed which comprises one stabilized Fab antigen binding moiety binding to/directed against/interacting with or on an antibody comprising the P329G mutations in the Fc domain. The construct further comprises the CD28 transmembrane domain, a fragment of CD28 as co-stimulatory signaling domain and a fragment of CD3z as stimulatory signaling domain. The sequences (amino acid and DNA) of the antigen binding receptor "Anti-P329G-ds-Fab-CD28ATD-CD28CSD-CD3zSSD pETR17100" are shown in Tables 4 and 5.

As a further proof of concept of the present invention, the antigen binding receptor "Anti-P329G-Fab-CD28ATD-CD28CSD-CD3zSSD pETR17594" (SEQ ID NOs: 48, 50) was constructed which comprises one Fab antigen binding moiety binding to/directed against/interacting with or on an antibody comprising the P329G mutations in the Fc domain. The construct further comprises the CD28 transmembrane domain, a fragment of CD28 as co-stimulatory signaling domain and a fragment of CD3z as stimulatory signaling domain. The sequences (amino acid and DNA) of the antigen binding receptor "Anti-P329G-Fab-CD28ATD-CD28CSD-CD3zSSD pETR17594" are shown in Tables 6 and 7.

As a further proof of concept of the present invention, the antigen binding receptor "Anti-AAA scFv" (SEQ ID NO:59) was constructed which comprises one scFv antigen binding moiety binding to/directed against/interacting with or on an antibody comprising the I253A, H310A and H435A mutations in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-AAA scFv" are shown below in Tables 8 and 9.

As a further proof of concept of the present invention, the antigen binding receptor "Anti-AAA Fab" (SEQ ID NOs: 63, 65) was constructed which comprises one Fab antigen binding moiety binding to/directed against/interacting with or on an antibody comprising the I253A, H310A and H435A mutations in the Fc domain. The construct further comprises the CD28 transmembrane domain, a fragment of CD28 as co-stimulatory signaling domain and a fragment of CD3z as stimulatory signaling domain. The sequences (amino acid and cDNA) of the antibody binding molecule "Anti-AAA scFv" are shown below in Tables 10 and 11.

The invention also provides (a) nucleic acid molecule(s) encoding antigen binding receptors of the invention as described herein. Also encompassed by the present invention are (a) nucleic acid molecule(s) encoding the antigen binding receptors of the present invention and kits comprising nucleic acid molecule(s) according to the invention as further described herein.

Kits

A further aspect of the present invention are kits comprising or consisting of a nucleic acid encoding an antigen binding receptor of the invention and/or cells, preferably T cells transduced with antigen binding receptors of the invention and, optionally, (an) antibody/antibodies comprising a mutated Fc domain, wherein the antigen binding receptor is capable of specific binding to the mutated Fc domain.

Accordingly, provided is a kit comprising
(A) a transduced T cell capable of expressing an antigen binding receptor of the invention; and
(B) an antibody comprising a mutated Fc domain;
wherein the antigen binding receptor is capable of specific binding to the mutated Fc domain but not capable of specific binding to the non-mutated parent Fc domain.

Further provided is a kit comprising
(A) an isolated polynucleotide and/or a vector encoding an antigen binding receptor of the invention; and
(B) an antibody comprising a mutated Fc domain;
wherein the antigen binding receptor is capable of specific binding to the mutated Fc domain but not capable of specific binding to the non-mutated parent Fc domain.

In the context of the present invention, the kits of the present invention may comprise transduced T cells, isolated polynucleotides and/or vectors and one or more antibodies comprising a mutated Fc domain. In particular embodiments, the antibody is a therapeutic antibody, e.g. a tumor specific antibody. Tumor specific antigens are known in the art and described herein. In the context of the present invention, the antibody is administered before, simultaneously with or after administration of transduced T cell expressing an antigen binding receptor of the invention. The kits according to the present invention comprise transduced T cells or polynucleotides/vectors to generate transduced T cells. In this context, the transduced T cells are universal T cells since they are not specific for a given tumor but can be targeted to any tumor depending on the therapeutic antibody comprising the mutated Fc domain. Herein provided are examples of antibodies comprising a mutated Fc domain, however, any antibody comprising a mutated Fc domain as described herein may be included in the herein provided kits. In particular embodiments the mutated Fc domain of the antibodies exhibits reduced binding affinity to an Fc receptor and/or reduced effector function, as compared to a native $IgG_1$ Fc domain. In one such embodiment the mutated Fc domain (or the antibody comprising said Fc mutated domain) exhibits less than 50%, preferably less than 20%, more preferably less than 10% and most preferably less than 5% of the binding affinity to an Fc receptor, as compared to a native $IgG_1$ Fc domain (or an antibody comprising a native $IgG_1$ Fc domain), and/or less than 50%, preferably less than 20%, more preferably less than 10% and most preferably less than 5% of the effector function, as compared to a native $IgG_1$ Fc domain (or an antibody comprising a native $IgG_1$ Fc domain). In one embodiment, the mutated Fc domain (or the antibody comprising said mutated Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the mutated Fc domain exhibits substantially altered binding affinity to neonatal Fc receptor (FcRn), as compared to a native $IgG_1$ Fc domain. In one embodiment the antibody comprising mutated Fc domain exhibits less than 20%, particularly less than 10%, more particularly less than 5% of the binding affinity to an Fc receptor as compared to a antibody comprising a non-engineered Fc domain. In a particular embodiment the Fc receptor is an Fcγ receptor. In some embodiments the Fc receptor is a human Fc receptor.

In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced.

In certain embodiments the Fc domain of the antibody is mutated to have reduced effector function, as compared to a non-mutated Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or an antibody comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A.

In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In one embodiment the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid mutations L234A, L235A and optionally P329G, or a human IgG$_4$ Fc domain comprising the amino acid mutations S228P, L235E and optionally P329G.

In certain embodiments N-glycosylation of the Fc domain has been eliminated. In one such embodiment the Fc domain comprises an amino acid mutation at position N297, particularly an amino acid mutation replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with mutation of one or more of Fc domain residues 238, 265, 269, 270, 297, 327 and 329 (U.S. Pat. No. 6,737,056). Such Fc mutants include Fc mutants with mutations at two or more of amino acid positions 265, 269, 270, 297 and 327, including the so-called "DANA" Fc mutant with mutation of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or an antibody comprising an Fc domain, can be measured by methods known in the art. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the antibody is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In one embodiment binding affinity to neonatal Fc receptor (FcRn) is reduced. In particular embodiments a mutated Fc domain according to the invention exhibits reduced binding affinity to FcRn receptor, as compared to a native IgG$_1$ Fc domain. In one such embodiment the Fc domain (or the antibody comprising said Fc domain) exhibits less than 50%, preferably less than 20%, more preferably less than 10% and most preferably less than 5% of the binding affinity to neonatal Fc receptor, as compared to a native IgG$_1$ Fc domain (or an antibody comprising a native IgG$_1$ Fc domain), and/or less than 50%, preferably less than 20%, more preferably less than 10% and most preferably less than 5% of the effector function, as compared to a native IgG$_1$ Fc domain (or an antibody comprising a native IgG$_1$ Fc domain). In one embodiment, the mutated Fc domain (or the antibody comprising said mutated Fc domain) does not substantially bind to neonatal Fc receptor. In a particular embodiment the Fc receptor is an FcRn receptor. In one embodiment the Fc receptor is a human FcRn receptor. In particular embodiments the Fc domain comprises amino acid substitutions at positions I253, H310 and H435. In more particular embodiments the Fc domain comprises the amino acid mutations I253A, H310A and H435A ("AAA"). In one such embodiment, the Fc domain is an IgG$_1$ Fc domain, particularly a human IgG$_1$ Fc domain. The "AAA" combination of amino acid substitutions almost completely abolishes FcRn receptor binding of a human IgG$_1$ Fc domain.

In a specific embodiment, the antibody comprising the mutated Fc region is capable of specific binding to CD20 and comprises the heavy chain sequence of SEQ ID NO:112, and the light chain sequence of SEQ ID NO:113. In one embodiment, the antibody comprising the mutated Fc region is capable of specific binding to FAP and comprises the heavy chain sequence of SEQ ID NO:114, and the light chain sequence of SEQ ID NO:115. In one embodiment, the antibody comprising the mutated Fc region is capable of specific binding to CEA and comprises the heavy chain sequence of SEQ ID NO:116 and the light chain sequence of SEQ ID NO:117, the heavy chain sequence of SEQ ID NO:118 and the light chain sequence of SEQ ID NO:119, the heavy chain sequence of SEQ ID NO:120 and the light chain sequence of SEQ ID NO:121, or the heavy chain sequence of SEQ ID NO:122 and the light chain sequence of SEQ ID NO:123.

In further embodiments, the antibody comprising the mutated Fc region is capable of specific binding to tenascin (TNC) and comprises the heavy chain sequence of SEQ ID NO:124, and the light chain sequence of SEQ ID NO:125.

In a further embodiment, the antibody comprising the mutated Fc region is a bispecific antibody, e.g. a T-cell activating bispecific antibody. In one such embodiment the bispecific antibody comprises a first binding moiety capable of specific binding to a T-cell activating target, in particular CD3, and a second binding moiety capable of specific binding to a tumor antigen as described herein.

In one embodiment, the antibody comprising the mutated Fc region is bispecific and capable of specific binding to Her2, wherein the bispecific antibody comprises a first heavy chain sequence of SEQ ID NO:126, a first light chain sequence of SEQ ID NO:127, a second heavy chain sequence of SEQ ID NO:128 and a second light chain sequence of SEQ ID NO:129.

In and illustrative embodiment of the present invention, as a proof of concept, a kit is provided comprising an amino acid sequence as shown in SEQ ID NO:7 ("Anti-P329G-ds-scFv-CD28ATD-CD28CSD-CD3zSSD" (as encoded by the DNA sequence shown in SEQ ID NO:19)) combined with the antibody comprising a heavy chain of SEQ ID NO:112 and a light chain of SEQ ID NO:113. Alternatively, the kit may comprise an amino acid sequence as shown in SEQ ID NO:31 ("Anti-P329G-scFv-CD28ATD-CD28CSD-CD3zSSD" (as encoded by the DNA sequence shown in SEQ ID NO:35)) combined with the antibody comprising a heavy chain of SEQ ID NO:112 and a light chain of SEQ ID NO:113. Moreover, in the context of the present invention the kit may comprise an amino acid sequence as shown in SEQ ID NO:39 ("Anti-P329G-ds-Fab-CD28ATD-CD28CSD-CD3zSSD" (as encoded by the DNA sequence shown in SEQ ID NO:44)) combined with the antibody comprising a heavy chain of SEQ ID NO:112 and a light chain of SEQ ID NO:113. Alternatively, the kit may comprise an amino acid sequence as shown in SEQ ID NO:48 ("Anti-P329G-Fab-CD28ATD-CD28CSD-CD3zSSD" (as encoded by the DNA sequence shown in SEQ ID NO:51)) combined with an antibody comprising a heavy chain of SEQ ID NO:112 and a light chain of SEQ ID NO:113. Alternatively, the kit may comprise an amino acid sequence as shown in SEQ ID NO:59 ("Anti-AAA-scFv-CD28ATD-CD28CSD-CD3zSSD") combined with an antibody comprising a heavy chain of SEQ ID NO:112 and a light chain of SEQ ID NO:113. Moreover, in the context of the present invention the kit may comprise an amino acid sequence as shown in SEQ ID NO:63 ("Anti-AAA-Fab-CD28ATD-CD28CSD-CD3zSSD") combined with an antibody comprising a heavy chain of SEQ ID NO:112 and a light chain of SEQ ID NO:113. Moreover, in the context of the present invention the kit may comprise at least one antibody molecule comprising a heavy chain and a light chain selected from the group consisting of SEQ ID NO:112 and SEQ ID NO:113, SEQ ID NO:114 and SEQ ID NO:115, SEQ ID NO:116 and SEQ ID NO:117, SEQ ID NO:118 and SEQ ID NO:119, SEQ ID NO:120 and SEQ ID NO:121, SEQ ID NO:122 and SEQ ID NO:123, and SEQ ID NO:124 and SEQ ID NO:125. Moreover, in the context of the present invention the kit may comprise a bispecific antibody molecule, in particular a bispecific antibody comprising a first heavy chain of SEQ ID NO:128, a first light chain of SEQ ID NO:129, a second heavy chain of SEQ ID NO:130 and a second light chain of SEQ ID NO:131.

Furthermore, parts of the kit of the invention can be packaged individually in vials or bottles or in combination in containers or multicontainer units. Additionally, the kit of the present invention may comprise a (closed) bag cell incubation system where patient cells, preferably T cells as described herein, can be transduced with (an) antigen binding receptor(s) of the invention and incubated under GMP (good manufacturing practice, as described in the guidelines for good manufacturing practice published by the European Commission under http://ec.europa.eu/health/documents/eudralex/index_en.htm) conditions. Furthermore, the kit of the present invention comprises a (closed) bag cell incubation system where isolated/obtained patients T cells can be transduced with (an) antigen binding receptor(s) of the invention and incubated under GMP. Furthermore, in the context of the present invention, the kit may also comprise a vector encoding (the) antigen binding receptor(s) as described herein. The kit of the present invention may be advantageously used, inter alia, for carrying out the method of the invention and could be employed in a variety of applications referred to herein, e.g., as research tools or medical tools. The manufacture of the kits preferably follows standard procedures which are known to the person skilled in the art.

In this context, patient derived cells, preferably T cells, can be transduced with an antigen binding receptor of the invention capable of specific binding to a mutated Fc domain as described herein using the kit as described above. The extracellular domain comprising an antigen binding moiety capable of specific binding to a mutated Fc domain does not naturally occur in or on T cells. Accordingly, the patient derived cells transduced with the kits of the invention will acquire the capability of specific binding to a mutated Fc domain of an antibody, e.g. a therapeutic antibody and will become capable of inducing elimination/lysis of target cells via interaction with a therapeutic antibody comprising the mutated Fc domain, wherein the therapeutic antibody is able to bind to a tumor-specific antigen naturally occurring (that is endogenously expressed) on the surface of a tumor cell. Binding of the extracellular domain of the antigen binding receptor as described herein activates that T cell and brings it into physical contact with the tumor cell through the therapeutic antibody comprising the mutated Fc domain.

Non-transduced or endogenous T cells (e.g. CD8+ T cells) are unable to bind to the mutated Fc domain of the therapeutic antibody comprising the mutated Fc domain. The transduced T cells expressing the antigen binding receptor comprising the extracellular domain capable of specific binding to a mutated Fc domain remain unaffected by a therapeutic antibody not comprising the mutations in the Fc domain as described herein. Accordingly, T cells expressing the inventive antigen binding receptor molecule have the ability to lyse target cells in the presence of an antibody comprising the mutations in the Fc domain as described herein in vivo and/or in vitro. Corresponding target cells comprise cells expressing a surface molecule, i.e. a tumor-specific antigen naturally occurring on the surface of a tumor cell, which is recognized by at least one, preferably two, binding domains of the therapeutic antibody as described herein. Such surface molecules are characterized herein below.

Lysis of the target cell can be detected by methods known in the art. Accordingly, such methods comprise, inter alia, physiological in vitro assays. Such physiological assays may monitor cell death, for example by loss of cell membrane integrity (e.g. FACS based propidium Iodide assay, trypan blue influx assay, photometric enzyme release assays (LDH), radiometric 51Cr release assay, fluorometric Europium release and CalceinAM release assays). Further assays comprise monitoring of cell viability, for example by photometric MTT, XTT, WST-1 and alamarBlue assays, radiometric 3H-Thd incorporation assay, clonogenic assay measuring cell division activity, and fluorometric Rhodamine123 assay measuring mitochondrial transmembrane gradient. In addition, apoptosis may be monitored for example by FACS-based phosphatidylserine exposure assay, ELISA-based TUNEL test, caspase activity assay (photometric, fluorometric or ELISA-based) or analyzing changed cell morphology (shrinking, membrane blebbing).

Transduced T Cells Capable of Expressing Antigen Binding Receptors of the Invention A further aspect of the present invention are transduced T cells capable of expressing an antigen binding receptor of the present invention. The antigen binding receptors as described herein relate to molecules which are naturally not comprised in and/or on the surface of T cells and which are not (endogenously) expressed in or on normal (non-transduced) T cells. Thus, the antigen binding receptor of the invention in and/or on T cells is artificially introduced into T cells. In the context of the present invention, said T cells, preferably CD8+ T cells, may be isolated/obtained from a subject to be treated as defined herein. Accordingly, the antigen binding receptors as described herein which are artificially introduced and subsequently presented in and/or on the surface of said T cells comprise domains comprising one or more antigen binding moiety accessible (in vitro or in vivo) to (Ig-derived) immunoglobulins, preferably antibodies, in particular to the Fc domain of the antibodies. In the context of the present invention, these artificially introduced molecules are presented in and/or on the surface of said T cells after (retroviral or lentiviral) transduction as described herein below.

Accordingly, after transduction, T cells according to the invention can be activated by immunoglobulins, preferably (therapeutic) antibodies comprising specific mutations in the Fc domain as described herein.

The invention also relates to transduced T cells expressing an antigen binding receptor encoded by (a) nucleic acid molecule(s) encoding the antigen binding receptor of the present invention.

Accordingly, in the context of the present invention, the transduced cell may comprise a nucleic acid molecule encoding the antigen binding receptor of the present invention or a vector of the present invention which expresses an antigen binding receptor of the present invention.

In the context of the present invention, the term "transduced T cell" relates to a genetically modified T cell (i.e. a T cell wherein a nucleic acid molecule has been introduced deliberately).

The herein provided transduced T cell may comprise the vector of the present invention. Preferably, the herein provided transduced T cell comprises the nucleic acid molecule encoding the antigen binding receptor of the present invention and/or the vector of the present invention.

The transduced T cell of the invention may be a T cell which transiently or stably expresses the foreign DNA (i.e. the nucleic acid molecule which has been introduced into the T cell). In particular, the nucleic acid molecule encoding the antigen binding receptor of the present invention can be stably integrated into the genome of the T cell by using a retroviral or lentiviral transduction. By using mRNA transfection, the nucleic acid molecule encoding the antigen binding receptor of the present invention may be expressed transiently. Preferably, the herein provided transduced T cell has been genetically modified by introducing a nucleic acid molecule in the T cell via a viral vector (e.g. a retroviral vector or a lentiviral vector).

Accordingly, the expression of the antigen binding receptors may be constitutive and the extracellular domain of the antigen binding receptor may be detectable on the cell surface. This extracellular domain of the antigen binding receptor may comprise the complete extracellular domain of an antigen binding receptor as defined herein but also parts thereof. The minimal size required being the antigen binding site of the antigen binding moiety in the antigen binding receptor.

The expression may also be conditional or inducible in the case that the antigen binding receptor is introduced into T cells under the control of an inducible or repressible promoter. Examples for such inducible or repressible promoters can be a transcriptional system containing the alcohol dehydrogenase I (alcA) gene promoter and the transactivator protein AlcR. Different agricultural alcohol-based formulations are used to control the expression of a gene of interest linked to the alcA promoter. Furthermore, tetracycline-responsive promoter systems can function either to activate or repress gene expression system in the presence of tetracycline. Some of the elements of the systems include a tetracycline repressor protein (TetR), a tetracycline operator sequence (tetO) and a tetracycline transactivator fusion protein (tTA), which is the fusion of TetR and a herpes simplex virus protein 16 (VP16) activation sequence.

Further, steroid-responsive promoters, metal-regulated or pathogenesis-related (PR) protein related promoters can be used.

The expression can be constitutive or constitutional, depending on the system used. The antigen binding receptors of the present invention can be expressed on the surface of the herein provided transduced T cell. The extracellular portion of the antigen binding receptor (i.e. the extracellular domain of the antigen binding receptor can be detected on the cell surface, while the intracellular portion (i.e. the co-stimulatory signaling domain(s) and the stimulatory signaling domain) are not detectable on the cell surface. The detection of the extracellular domain of the antigen binding receptor can be carried out by using an antibody which specifically binds to this extracellular domain or by the mutated Fc domain which the extracellular domain is capable to bind. The extracellular domain can be detected using these antibodies or Fc domains by flow cytometry or microscopy.

The transduced cells of the present invention may be any immune cell. These include but are not limited to B-cells, T cells, Natural Killer (NK) cells, Natural Killer (NK) T cells, γδ T cells, innate lymphoid cells, macrophages, monocytes, dendritic cells, or neutrophils. Preferentially, said immune cell would be a lymphocyte, preferentially a NK or T cells. The said T cells include CD4 T cells and CD8 T cells. Triggering of the antigen binding receptor of the present invention on the surface of the leukocyte will render the cell cytotoxic against a target cell in conjunction with a therapeutic antibody comprising a mutated Fc domain irrespective of the lineage the cell originated from. Cytotoxicity will happen irrespective of the stimulatory signaling domain or co-stimulatory signaling domain chosen for the antigen binding receptor and is not dependent on the exogenous supply of additional cytokines. Accordingly, the transduced cell of the present invention may be, e.g., a CD4+ T cell, a CD8+−T cell, a γδ T cell, a Natural Killer (NK) T cell, a Natural Killer (NK) cell, a tumor-infiltrating lymphocyte (TIL) cell, a myeloid cell, or a mesenchymal stem cell. Preferably, the herein provided transduced cell is a T cell (e.g. an autologous T cell), more preferably, the transduced cell is a CD8+ T cell. Accordingly, in the context of the present invention, the transduced cell is a CD8+ T cell. Further, in the context of the present invention, the transduced cell is an autologous T cell. Accordingly, in the context of the present invention, the transduced cell is preferably an autologous CD8+ T cell. In addition to the use of autologous cells (e.g. T cells) isolated from the subject, the present invention also comprehends the use of allogeneic cells. Accordingly, in the context of the present invention the transduced cell may also be an allogeneic cell, such as an allogeneic CD8+ T cell. The use of allogeneic cells is based on the fact that cells, preferably T cells can recognize a specific antigen epitope presented by foreign antigen-presenting cells (APC), provided that the APC express the MHC molecule, class I or class II, to which the specific responding cell population, i.e. T cell population is restricted, along with the antigen epitope recognized by the T cells.

Thus, the term allogeneic refers to cells from an unrelated coming from an unrelated donor individual/subject which is human leukocyte antigen (HLA) compatible to the individual/subject which will be treated by e.g. the herein described antigen binding receptor expressing transduced cell. Autologous cells refer to cells which are isolated/obtained as described herein above from the subject to be treated with the transduced cell described herein.

The transduced cell of the invention may be co-transduced with further nucleic acid molecules, e.g. with a nucleic acid molecule encoding a T cell receptor.

The present invention also relates to a method for the production of a transduced T cell expressing an antigen binding receptor of the invention, comprising the steps of transducing a T cell with a vector of the present invention, culturing the transduced T cell under conditions allowing the expressing of the antigen binding receptor in or on said transduced cell and recovering said transduced T cell.

In the context of the present invention, the transduced cell of the present invention is preferably produced by the following process: cells (e.g., T cells, preferably CD8+ T cells) are isolated/obtained from a subject (preferably a human patient). Methods for isolating/obtaining cells (e.g. T cells, preferably CD8+ T cells) from patients or from donors are well known in the art and in the context of the present the cells (e.g. T cells, preferably CD8+ T cells) from patients or from donors may be isolated by blood draw or removal of bone marrow. After isolating/obtaining cells as a sample of the patient, the cells (e.g. T cells) are separated from the other ingredients of the sample. Several methods for separating cells (e.g. T cells) from the sample are known and include, without being limiting, e.g. leukapheresis for obtaining cells from the peripheral blood sample from a patient or from a donor, isolating/obtaining cells by using a FACSort apparatus, picking living of dead cells from fresh biopsy specimens harboring living cells by hand or by using a micromanipulator (see, e.g., Dudley, Immunother. 26 (2003), 332-342; Robbins, Clin. Oncol. 29 (2011), 917-924 or Leisegang, J. Mol. Med. 86 (2008), 573-58). The isolated/obtained cells T cells, preferably CD8+ T cells, are subsequently cultivated and expanded, e.g., by using an anti-CD3 antibody, by using anti-CD3 and anti-CD28 monoclonal antibodies and/or by using an anti-CD3 antibody, an anti-CD28 antibody and interleukin-2 (IL-2) (see, e.g., Dudley, Immunother. 26 (2003), 332-342 or Dudley, Clin. Oncol. 26 (2008), 5233-5239).

In a subsequent step the cells (e.g. T cells) are artificially/genetically modified/transduced by methods known in the art (see, e.g., Lemoine, J Gene Med 6 (2004), 374-386). Methods for transducing cells (e.g. T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector In the context of the present invention, the methods for transducing cells (e.g. T cells) include retroviral or lentiviral T cell transduction, non-viral vectors (e.g., sleeping beauty minicircle vector) as well as mRNA transfection. "mRNA transfection" refers to a method well known to those skilled in the art to transiently express a protein of interest, like in the present case the antigen binding receptor of the present invention, in a cell to be transduced. In brief cells may be electroporated with the mRNA coding for the antigen binding receptor of the present by using an electroporation system (such as e.g. Gene Pulser, Bio-Rad) and thereafter cultured by standard cell (e.g. T cell) culture protocol as described above (see Zhao et al., Mol Ther. 13(1) (2006), 151-159.) The transduced cell of the invention is a T cell, most preferably a CD8+ T cell, and is generated by lentiviral, or most preferably retroviral T cell transduction.

In this context, suitable retroviral vectors for transducing T cells are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing cells (e.g. T cells) are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The transduced T cell/T cells of the present invention is/are preferably grown under controlled conditions, outside of their natural environment. In particular, the term "culturing" means that cells (e.g. the transduced cell(s) of the invention) which are derived from multi-cellular eukaryotes (preferably from a human patient) are grown in vitro. Culturing cells is a laboratory technique of keeping cells alive which are separated from their original tissue source. Herein, the transduced cell of the present invention is cultured under conditions allowing the expression of the antigen binding receptor of the present invention in or on said transduced cells. Conditions which allow the expression or a transgene (i.e. of the antigen binding receptor of the present invention) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the antigen binding receptor of the present invention in the cultured transduced cell (e.g., a CD8+T), the transduced cell is recovered (i.e. re-extracted) from the culture (i.e. from the culture medium). Accordingly, also encompassed by the invention is a transduced cell, preferably a T cell, in particular a CD8+T expressing an antigen binding receptor encoded by a nucleic acid molecule of the invention obtainable by the method of the present invention.

Nucleic Acid Molecules

A further aspect of the present invention are nucleic acids and vectors encoding one or several antigen binding receptors of the present invention. Exemplary nucleic acid molecules encoding the antigen binding receptors of the present invention are shown in SEQ ID NOs:19, 30, 35, 38, 44, 47, 51 and 52. The nucleic acid molecules of the invention may be under the control of regulatory sequences. For example, promoters, transcriptional enhancers and/or sequences which allow for induced expression of the antigen binding receptor of the invention may be employed. In the context of the present invention, the nucleic acid molecules are expressed under the control of constitutive or inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). The present invention therefore also relates to (a) vector(s) comprising the nucleic acid molecule(s) described in the present invention. Herein the term vector relates to a circular or linear nucleic acid molecule which can autonomously replicate in a host cell (i.e. in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

The invention also relates to (a) vector(s) comprising (a) nucleic acid molecule(s) which is (are) a regulatory sequence operably linked to said nucleic acid molecule(s) encoding an antigen binding receptor as defined herein. In the context of the present invention the vector can be polycistronic. Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) an expression vector(s) comprising the nucleic acid molecule(s) encoding the antigen binding receptor as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in $E.$ $coli$, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode an antigen binding receptor including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR, pEF-ADA or pEF-neo (Raum et al. Cancer Immunol Immunother 50 (2001), 141-150) or pSPORT1 (GIBCO BRL).

In the context of the present invention, the expression control sequences will be eukaryotic promoter systems in vectors capable of transforming or transfecting eukaryotic cells, but control sequences for prokaryotic cells may also be used. Once the vector has been incorporated into the appropriate cell, the cell is maintained under conditions suitable for high level expression of the nucleotide sequences, and as desired. Additional regulatory elements may include transcriptional as well as translational enhancers. Advantageously, the above-described vectors of the invention comprise a selectable and/or scorable marker. Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from $Aspergillus$ $terreus$ which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule(s) can be used alone or as part of (a) vector(s) to express the antigen binding receptors of the invention in cells, for, e.g., adoptive T cell therapy but also for gene therapy purposes. The nucleic acid molecules or vector(s) containing the DNA sequence(s) encoding any one of the herein described antigen binding receptors is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77

(1995), 1077-1086; Onodera, Blood 91(1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957; U.S. Pat. Nos. 5,580,859; 5,589,466; or Schaper, Current Opinion in Biotechnology 7 (1996), 635-640. The recited nucleic acid molecule(s) and vector(s) may be designed for direct introduction or for introduction via liposomes, or viral vectors (e.g., adenoviral, retroviral) into the cell. In the context of the present invention, said cell is a T cells, such as CD8+ T cells, CD4+ T cells, CD3+ T cells, 76 T cells or natural killer (NK) T cells, preferably CD8+ T cells.

In accordance with the above, the present invention relates to methods to derive vectors, particularly plasmids, cosmids and bacteriophages used conventionally in genetic engineering that comprise a nucleic acid molecule encoding the polypeptide sequence of an antigen binding receptor defined herein. In the context of the present invention, said vector is an expression vector and/or a gene transfer or targeting vector. Expression vectors derived from viruses such as retroviruses, vaccinia virus, adeno-associated virus, herpes virus, or bovine papilloma virus, may be used for delivery of the recited polynucleotides or vector into targeted cell populations. Methods which are well known to those skilled in the art can be used to construct (a) recombinant vector(s); see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. The recited vector may, inter alia, be the pEF-DHFR, pEF-ADA or pEF-neo. The vectors pEF-DHFR, pEF-ADA and pEF-neo have been described in the art, e.g. in Mack et al. Proc. Natl. Acad. Sci. USA 92 (1995), 7021-7025 and Raum et al. Cancer Immunol Immunother 50 (2001), 141-150.

The invention also provides for a T cell transformed or transfected with a vector as described herein. Said T cell may be produced by introducing at least one of the above described vector or at least one of the above described nucleic acid molecules into the T cell or its precursor cell. The presence of said at least one vector or at least one nucleic acid molecule in the T cell may mediate the expression of a gene encoding the above described antigen binding receptor comprising an extracellular domain comprising an antigen binding moiety capable of specific binding to a mutated Fc domain. The vector of the present invention can be polycistronic. The described nucleic acid molecule(s) or vector(s) which is (are) introduced in the T cell or its precursor cell may either integrate into the genome of the cell or it may be maintained extrachromosomally.

Tumor Specific Antigens

As mentioned above, the (Ig-derived) domain(s) of the herein-described antibody comprising a mutated Fc domain may comprise an antigen-interaction-site with specificity for a cell surface molecule, i.e. a tumor-specific antigen that naturally occurs on the surface of a tumor cell. In the context of the present invention, such antibodies will bring transduced T cells as described herein comprising the antigen binding receptor of the invention in physical contact with a tumor cell, wherein the transduced T cell becomes activated. Activation of transduced T cells of the present invention can result with lysis of the tumor cell as described herein.

Examples of tumor markers that naturally occur on the surface of tumor cells are given herein below and comprise, but are not limited to FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

Accordingly, in the context of the present invention, the antigen binding receptor as described herein binds to the mutated Fc domain of an antibody, i.e. a therapeutic antibody capable of specific binding to an antigen/marker that naturally occurs on the surface of tumor cells selected from the group consisting of FAP (fibroblast activation protein), CEA (carcinoembryonic antigen), p95 (p95HER2), BCMA (B-cell maturation antigen), EpCAM (epithelial cell adhesion molecule), MSLN (mesothelin), MCSP (melanoma chondroitin sulfate proteoglycan), HER-1 (human epidermal growth factor 1), HER-2 (human epidermal growth factor 2), HER-3 (human epidermal growth factor 3), CD19, CD20, CD22, CD33, CD38, CD52Flt3, folate receptor 1 (FOLR1), human trophoblast cell-surface antigen 2 (Trop-2) cancer antigen 12-5 (CA-12-5), human leukocyte antigen-antigen D related (HLA-DR), MUC-1 (Mucin-1), A33-antigen, PSMA (prostate-specific membrane antigen), FMS-like tyrosine kinase 3 (FLT-3), PSMA (prostate specific membrane antigen), PSCA (prostate stem cell antigen), transferrin-receptor, TNC (tenascin), carbon anhydrase IX (CA-IX), and/or peptides bound to a molecule of the human major histocompatibility complex (MHC).

The sequence(s) of the (human) members of the A33-antigen, BCMA (B-cell maturation antigen), cancer antigen 12-5 (CA-12-5), carbon anhydrase IX (CA-IX), CD19, CD20, CD22, CD33, CD38, CEA (carcinoembryonic antigen), EpCAM (epithelial cell adhesion molecule), FAP (fibroblast activation protein), FMS-like tyrosine kinase 3 (FLT-3), folate receptor 1 (FOLR1), HER-1 (human epidermal growth factor 1), HER-2 (human epidermal growth factor 2), HER-3 (human epidermal growth factor 3), human leukocyte antigen-antigen D related (HLA-DR), MSLN (mesothelin), MCSP (melanoma chondroitin sulfate proteoglycan), MUC-1 (Mucin-1), PSMA (prostate specific membrane antigen), PSMA (prostate-specific membrane antigen), PSCA (prostate stem cell antigen), p95 (p95HER2), transferrin-receptor, TNC (tenascin), human trophoblast cell-surface antigen 2 (Trop-2) are available in the UniProtKB/Swiss-Prot database and can be retrieved from http://www.uniprot.org/uniprot/?query=reviewed %3Ayes. These (protein) sequences also relate to annotated modified sequences. The present invention also provides techniques and methods wherein homologous sequences, and also genetic allelic variants and the like of the concise sequences provided herein are used. Preferably such variants and the like of the concise sequences herein are used. Preferably, such variants are genetic variants. The skilled person may easily deduce the relevant coding region of these (protein) sequences in these databank entries, which may also comprise the entry of genomic DNA as well as mRNA/cDNA. The sequence(s) of the (human) FAP (fibroblast activation protein) can be obtained from the Swiss-Prot database entry Q12884 (entry version 168, sequence version 5); The sequence(s) of the (human) CEA (carcinoembryonic antigen) can be obtained from the Swiss-Prot database entry P06731 (entry version 171, sequence version 3); the sequence(s) of the (human) EpCAM (Epithelial cell adhesion molecule) can be obtained from the Swiss-Prot database entry P16422 (entry version 117, sequence version 2); the sequence(s) of the (human) MSLN (mesothelin) can be obtained from the UniProt Entry number Q13421 (version number 132; sequence version 2); the sequence(s) of the (human) FMS-like tyrosine kinase 3 (FLT-3) can be obtained from the Swiss-Prot database entry P36888 (primary citable accession number) or Q13414 (secondary accession number) with the version number 165 and the sequence version 2; the sequences of (human) MCSP (melanoma chondroitin sulfate proteoglycan) can be obtained from the UniProt Entry number Q6UVK1 (version number 118; sequence version 2); the sequence(s) of the (human) folate receptor 1 (FOLR1) can be obtained from the UniProt Entry number P15328 (primary citable accession number) or Q53EW2 (secondary accession number) with the version number 153 and the sequence version 3; the sequence(s) of the (human) trophoblast cell-surface antigen 2 (Trop-2) can be obtained from the UniProt Entry number P09758 (primary citable accession number) or Q15658 (secondary accession number) with the version number 172 and the sequence version 3; the sequence(s) of the (human) PSCA (prostate stem cell antigen) can be obtained from the UniProt Entry number O43653 (primary citable accession number) or Q6UW92 (secondary accession number) with the version number 134 and the sequence version 1; the sequence(s) of the (human) HER-1 (Epidermal growth factor receptor) can be obtained from the Swiss-Prot database entry P00533 (entry version 177, sequence version 2); the sequence(s) of the (human) HER-2 (Receptor tyrosine-protein kinase erbB-2) can be obtained from the Swiss-Prot database entry P04626 (entry version 161, sequence version 1); the sequence(s) of the (human) HER-3 (Receptor tyrosine-protein kinase erbB-3) can be obtained from the Swiss-Prot database entry P21860 (entry version 140, sequence version 1); the sequence(s) of the (human) CD20 (B-lymphocyte antigen CD20) can be obtained from the Swiss-Prot database entry P11836 (entry version 117, sequence version 1); the sequence(s) of the (human) CD22 (B-lymphocyte antigen CD22) can be obtained from the Swiss-Prot database entry P20273 (entry version 135, sequence version 2); the sequence(s) of the (human) CD33 (B-lymphocyte antigen CD33) can be obtained from the Swiss-Prot database entry P20138 (entry version 129, sequence version 2); the sequence(s) of the (human) CA-12-5 (Mucin 16) can be obtained from the Swiss-Prot database entry Q8WXI7 (entry version 66, sequence version 2); the sequence(s) of the (human) HLA-DR can be obtained from the Swiss-Prot database entry Q29900 (entry version 59, sequence version 1); the sequence(s) of the (human) MUC-1 (Mucin-1) can be obtained from the Swiss-Prot database entry P15941 (entry version 135, sequence version 3); the sequence(s) of the (human) A33 (cell surface A33 antigen) can be obtained from the Swiss-Prot database entry Q99795 (entry version 104, sequence version 1); the sequence(s) of the (human) PSMA (Glutamate carboxypeptidase 2) can be obtained from the Swiss-Prot database entry Q04609 (entry version 133, sequence version 1), the sequence(s) of the (human) transferrin receptor can be obtained from the Swiss-Prot database entries Q9UP52 (entry version 99, sequence version 1) and P02786 (entry version 152, sequence version 2); the sequence of the (human) TNC (tenascin) can be obtained from the Swiss-Prot database entry P24821 (entry version 141, sequence version 3); or the sequence(s) of the (human) CA-IX (carbonic anhydrase IX) can be obtained from the Swiss-Prot database entry Q16790 (entry version 115, sequence version 2).

Therapeutic Use and Methods of Treatment

The molecules or constructs (i.e., antigen binding receptors, transduced T cells and kits) provided herein are particularly useful in medical settings, in particular for treatment of a malignant disease. For examples a tumor may be treated with a transduced T cell expressing an antigen binding receptor of the present invention in conjunction with a therapeutic antibody specific to the tumor cell and comprising a mutated Fc domain. Accordingly, in certain embodiments, the antigen binding receptor, the transduced T cell or the kit are used in the treatment of a malignant disease, in particular wherein the malignant disease is selected from cancer of epithelial, endothelial or mesothelial origin and cancer of the blood.

The tumor specificity of the treatment is provided by the therapeutic antibody comprising a mutated Fc domain, wherein the antibody is administered before, simultaneously with or after administration of transduced T cell expressing an antigen binding receptor of the invention. In this context, the transduced T cells are universal T cells since they are not specific for a given tumor but can be targeted to any tumor depending on the therapeutic antibody comprising the mutated Fc domain used according to the invention.

In this context the malignant disease may be a cancer/carcinoma of epithelial, endothelial or mesothelial origin or a cancer of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitourinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

For example, tumorous diseases and/or lymphomas may be treated with a specific construct directed against these medical indication(s). The indication for a transduced T cell of the present invention combined with a therapeutic antibody comprising a mutated Fc domain is given by specificity of the therapeutic antibody to a tumor antigen. For example, gastrointestinal cancer, pancreatic cancer, cholangiocellular cancer, lung cancer, breast cancer, ovarian cancer, skin cancer and/or oral cancer may be treated with an antibody comprising a mutated Fc domain wherein the antibody is directed against (human) EpCAM (as the tumor-specific antigen naturally occurring on the surface of a tumor cell).

Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic antibody comprising a mutated Fc domain wherein the antibody is directed against HER1, preferably human HER1. Furthermore, gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against MCSP, preferably human MCSP. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against FOLR1, preferably human FOLR1. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against Trop-2, preferably human Trop-2. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against PSCA, preferably human PSCA. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against EGFRvII, preferably human EGFRvIII. Gastrointestinal cancer, pancreatic cancer, cholangiocellular cancer, lung cancer, breast cancer, ovarian cancer, skin cancer, glioblastoma and/or oral cancer may be treated with a transduced T cell of the present invention administered before, simultaneously with or after administration of a therapeutic antibody comprising a mutated Fc domain wherein the antibody is directed against MSLN, preferably human MSLN. Gastric cancer, breast cancer and/or cervical cancer may be treated with a transduced T cell of the present invention administered before, simultaneously with or after administration of a therapeutic antibody comprising a mutated Fc domain wherein the antibody is directed against HER2, preferably human HER2. Gastric cancer and/or lung cancer may be treated with a transduced T cell of the present invention administered before, simultaneously with or after administration of a therapeutic antibody comprising a mutated Fc domain wherein the antibody is directed against HER3, preferably human HER3. B-cell lymphoma and/or T cell lymphoma may be treated with a transduced T cell of the present invention administered before, simultaneously with or after administration of a therapeutic antibody comprising a mutated Fc domain wherein the antibody is directed against CD20, preferably human CD20. B-cell lymphoma and/or T cell lymphoma may be treated with a transduced T cell of the present invention administered before, simultaneously with or after administration of a therapeutic antibody comprising a mutated Fc domain wherein the antibody is directed against CD22, preferably human CD22. Myeloid leukemia may be treated with a transduced T cell of the present invention administered before, simultaneously with or after administration of a therapeutic antibody comprising a mutated Fc domain wherein the antibody is directed against CD33, preferably human CD33. Ovarian cancer, lung cancer, breast cancer and/or gastrointestinal cancer may be treated with a transduced T cell of the present invention administered before, simultaneously with or after administration of a therapeutic antibody comprising a mutated Fc domain wherein the antibody is directed against CA12-5, preferably human CA12-5. Gastrointestinal cancer, leukemia and/or nasopharyngeal carcinoma may be treated with a transduced T cell of the present invention administered before, simultaneously with or after administration of a therapeutic antibody comprising a mutated Fc domain wherein the antibody is directed against HLA-DR, preferably human HLA-DR. Colon cancer, breast cancer, ovarian cancer, lung cancer and/or pancreatic cancer may be with a transduced T cell of the present invention administered before, simultaneously with or after administration of a therapeutic antibody comprising a mutated Fc domain wherein the antibody is directed against MUC-1, preferably human MUC-1. Colon cancer may be treated with a transduced T cell of the present invention administered before, simultaneously with or after administration of a therapeutic antibody comprising a mutated Fc domain wherein the antibody is directed against A33, preferably human A33. Prostate cancer may be treated with a transduced T cell of the present invention administered before, simultaneously with or after administration of a therapeutic antibody comprising a mutated Fc domain wherein the antibody is directed against PSMA, preferably human PSMA. Gastrointestinal cancer, pancreatic cancer, cholangiocellular cancer, lung cancer, breast cancer, ovarian cancer, skin cancer and/or oral cancer may be treated with a transduced T cell of the present invention administered before, simultaneously with or after administration of a therapeutic antibody comprising a mutated Fc domain wherein the antibody is directed against the transferrin receptor, preferably the human transferring receptor. Pancreatic cancer, lunger cancer and/or breast cancer may be treated with a transduced T cell of the present invention administered before, simultaneously with or after administration of a therapeutic antibody comprising a mutated Fc domain wherein the antibody is directed against the transferrin receptor, preferably the human transferring receptor. Renal cancer may be with a transduced T cell of the present invention administered before, simultaneously with or after administration of a therapeutic antibody comprising a mutated Fc domain wherein the antibody is directed against CA-IX, preferably human CA-IX.

Accordingly, the invention also relates to a method for the treatment of a disease, a malignant disease such as cancer of epithelial, endothelial or mesothelial origin and/or cancer of blood. In the context of the present invention, said subject is a human.

In the context of the present invention a particular method for the treatment of a disease comprises the steps of
   (a) isolating T cells, preferably CD8+ T cells, from a subject;
   (b) transducing said isolated T cells, preferably CD8+ T cells, with an antigen binding receptor as described herein; and
   (c) administering the transduced T cells, preferably CD8+ T cells, to said subject.

In the context of the present invention, said transduced T cells, preferably CD8+ T cells, and/or therapeutic antibody/antibodies are co-administered to said subject by intravenous infusion.

Moreover, in the context of the present invention the present invention, provides a method for the treatment of a disease comprising the steps of
(a) isolating T cells, preferably CD8+ T cells, from a subject;
(b) transducing said isolated T cells, preferably CD8+ T cells, with an antigen binding receptor as described herein;
(c) optionally co-transducing said isolated T cells, preferably CD8+ T cells, with a T cell receptor;
(d) expanding the T cells, preferably CD8+ T cells, by anti-CD3 and anti-CD28 antibodies; and
(e) administering the transduced T cells, preferably CD8+ T cells, to said subject.

The above mentioned step (d) (referring to the expanding step of the T cells such as TIL by anti-CD3 and/or anti-CD28 antibodies) may also be performed in the presence of (stimulating) cytokines such as interleukin-2 and/or interleukin-15 (IL-15). In the context of the present invention, the above mentioned step (d) (referring to the expanding step of the T cells such as TIL by anti-CD3 and/or anti-CD28 antibodies) may also be performed in the presence of interleukin-12 (IL-12), interleukin-7 (IL-7) and/or interleukin-21 (IL-21).

The method for the treatment, in addition, comprise the administration of the antibody used according to the present invention. Said antibody may be administered before, simultaneously with or after the transduced T cells are to be administered. In the context of the present invention the administration of the transduced T cells will be performed by intravenous infusion. In the context of the present invention, transduced T cells are isolated/obtained from the subject to be treated.

Compositions

Furthermore, the invention provides compositions (medicaments) comprising (an) antibody molecule(s) with (a) mutated Fc domain(s), (a) transduced T cell(s) comprising an antigen binding receptor of the invention, (a) nucleic acid molecule(s) and (a) vector(s) encoding the antigen binding receptors according to the invention, and/or and kits comprising one or more of said compositions. In the context of the present invention, the composition is a pharmaceutical composition further comprising, optionally, suitable formulations of carrier, stabilizers and/or excipients. Accordingly, in the context of the present invention a pharmaceutical composition (medicament) is provided that comprises an antibody molecule comprising a mutated Fc domain as defined herein which is to be administered in combination with a transduced T cell comprising an antigen binding receptor as described herein and/or a composition comprising said transduced T cell, wherein said antibody molecule is to be administered before, simultaneously with or after administration of transduced T cells comprising an antigen binding receptor of the invention.

In accordance with this invention, the term "pharmaceutical composition" relates to a composition for administration to a patient, preferably a human patient. Furthermore, in the context of the present invention that patient suffers from a disease, wherein said disease is a malignant disease, especially cancers/carcinomas of epithelial, endothelial or mesothelial origin or a cancer of the blood. In the context of the present invention the cancers/carcinomas is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

In a preferred embodiment, the pharmaceutical composition/medicament comprises an antibody and/or a transduced T cell as defined herein for parenteral, transdermal, intraluminal, intraarterial, intravenous, intrathecal administration or by direct injection into the tissue or tumor. In the context of the present invention the composition/medicament comprises an antibody comprising a mutated Fc domain as defined herein that is to be administered before, simultaneously with or after administration of transduced T cells comprising an antigen binding receptor as defined herein. In the context of the present invention the pharmaceutical composition/medicament comprising an antibody as defined herein is to be administered in combination with a composition/medicament comprising a transduced T cell comprising an antigen binding receptor as defined herein, wherein said T cell was obtained from a subject to be treated.

The use of the term "in combination" does not restrict the order in which the components of the treatment regimen are to be administered to the subject. Accordingly, the pharmaceutical composition/medicament described herein encompass the administration of an antibody as defined herein before, simultaneously with or after administration of transduced T cells comprising an antigen binding receptor of the present invention. "In combination" as used herein also does not restrict the timing between the administration of an antibody as defined herein before and the transduced T cells comprising an antigen binding receptor as defined herein. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

In the context of the present invention the term "in combination" also encompasses the situation where the antibody as defined herein and the transduced T cells comprising an antigen binding receptor according to the invention are pre-incubated together before administration to the subject. Thus, the two components may be pre-incubated before administration, for example, for 1 minute, 5 minutes, 10 minutes, 15 minutes, 30 minutes, 45 minutes or 1 hour or for any suitable time readily determined by one skilled in the art. The invention, in another preferred embodiment, relates to a treatment regimen, in which the antibody as defined herein and the transduced T cells comprising an antigen binding receptor as defined herein, are to be administered simultaneously with/concurrently. In the context of the present invention, the antibody as defined herein may be administered after the transduced T cells comprising an antigen binding receptor has been administered.

Further, "in combination" as used herein does not restrict the disclosed treatment regimens to the administration of an antibody as defined herein and transduced T cells, preferably CD8+ T cells, comprising an antigen binding receptor of the invention in immediate sequence (i.e., the administration of one of the two components, followed (after a certain time interval) by the administration of the other without the administration and/or practice of any other treatment protocol in between. Therefore, the present treatment regimens also encompass the separate administration of an antibody molecule as defined herein and transduced T cells, preferably CD8+ T cells, comprising an antigen binding receptor according to the invention, wherein the administrations are separated by one or more treatment protocols necessary and/or suitable for the treatment or prevention of the disease, or a symptom thereof. Examples of such intervening treatment protocols include but are not limited to, administration of pain medications; administration of chemotherapeutics, surgical handling of the disease or a symptom thereof.

Accordingly, the treatment regimens as disclosed herein encompass the administration of an antibody as defined herein and transduced T cells, preferably CD8+ T cells, comprising an antigen binding receptor as defined herein together with none, one, or more than one treatment protocol suitable for the treatment or prevention of a disease, or a symptom thereof, as described herein or as known in the art.

It is particular envisaged, that said pharmaceutical composition(s)/medicament(s) is (are) to be administered to a patient via infusion or injection. In the context of the present invention the transduced T cells comprising an antigen binding receptor as described herein is to be administered to a patient via infusion or injection. Administration of the suitable compositions/medicaments may be affected by different ways, intravenous, intraperitoneal, subcutaneous, intramuscular, topical or intradermal administration.

The pharmaceutical composition/medicament of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 µg to 5 g units per day. However, a more preferred dosage for continuous infusion might be in the range of 0.01 µg to 2 mg, preferably 0.01 µg to 1 mg, more preferably 0.01 µg to 100 g, even more preferably 0.01 µg to 50 µg and most preferably 0.01 µg to 10 µg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule.

The compositions of the invention may be administered locally or systematically. Administration will generally be parenterally, e.g., intravenously; transduced T cells may also be administered directed to the target site, e.g., by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous antibody constructs or nucleic acid molecules or vectors encoding the same (as described in this invention), and/or cells, further biologically active agents, depending on the intended use of the pharmaceutical composition. Such agents might be drugs acting on the gastro-intestinal system, drugs acting as cytostatica, drugs preventing hyperurikemia, drugs inhibiting immunereactions (e.g. corticosteroids), drugs acting on the circulatory system and/or agents such as T cell co-stimulatory molecules or cytokines known in the art.

Possible indication for administration of the composition(s)/medicament(s) of the invention are malignant diseases such as cancer of epithelial, endothelial or mesothelial origin and cancer of the blood, especially epithelial cancers/carcinomas such as breast cancer, colon cancer, prostate cancer, head and neck cancer, skin cancer (melanoma), cancers of the genitor-urinary tract, e.g., ovarial cancer, testis cancer, endothelial cancer, cervix cancer and kidney cancer, lung cancer, gastric cancer, cancer of the bile duct, esophagus cancer, cancer of the salivatory glands and cancer of the thyroid gland or other tumorous diseases like haematological tumors, gliomas, sarcomas or osteosarcomas.

The invention further envisages the co-administration protocols with other compounds, e.g., molecules capable of providing an activation signal for immune effector cells, for cell proliferation or for cell stimulation. Said molecule may be, e.g., a further primary activation signal for T cells (e.g. a further costimulatory molecule: molecules of B7 family, Ox40L, 4.1 BBL, CD40L, anti-CTLA-4, anti-PD-1), or a further cytokine interleukin (e.g., IL-2).

The composition of the invention as described above may also be a diagnostic composition further comprising, optionally, means and methods for detection.

Accordingly, in preferred embodiments, provided are the kit, the antigen binding receptors or the transduced T cell as described herein for use as a medicament. In the context of the present invention, the antigen binding receptor according to the invention for use as a medicament is provided, wherein one or more antibodies comprising a mutated Fc domain as described herein is/are to be administered before, simultaneously with or after administration of transduced T cells, preferably CD8+ T cells, comprising and/or expressing an antigen binding receptor as defined herein and wherein said T cells, preferably CD8+ T cells, were obtained from a subject to be treated. Said medicament may be employed in a method of treatment of malignant diseases especially cancers/carcinomas of epithelial, endothelial or mesothelial origin or of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in the context of the present invention the antibody as described herein comprising a mutated Fc domain binds to a tumor-specific antigen naturally occurring on the surface of a tumor cell, wherein said antibody molecule is to be administered before, simultaneously with or after administration of transduced T cells, preferably CD8+ T cells, from said subject comprising an antigen binding receptor as defined herein. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in accordance to the invention, a molecule or construct (i.e., an antibody molecule described herein) comprising one or two binding domains directed to/binding to/interacting with a tumor antigen, preferably a human tumor antigen, (as the tumor-specific antigen naturally occurring on the surface of a tumor cell) and comprising a mutated Fc domain, wherein the herein defined extracellular domains of the antigen binding receptor of the present invention is directed to/binding to/interacting with the mutated Fc domain, is provided for in the treatment of gastrointestinal cancer, pancreatic cancer, cholangiocellular cancer, lung cancer, breast cancer, ovarian cancer, skin cancer and/or oral cancer. Thus, in the context of the present invention an antibody molecule comprising two binding domains directed to/binding to/interacting with a tumor antigen, preferably a human tumor antigen, and comprising a mutated Fc domain, wherein the herein defined extracellular domains of the antigen binding receptor is directed to/binding to/interacting with the mutated Fc domain, for use in the treatment of epithelial, endothelial or mesothelial origin and cancer of the blood is provided.

In one embodiment, provided is (i) an antibody, comprising two binding domains directed to/binding to/interacting with a tumor antigen, preferably a human tumor antigen, and a mutated Fc domain; and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer and/or oral cancer.

In one embodiment, provided is (i) an antibody, comprising one or two binding domain(s) against HER1, preferably human HER1, and a mutated Fc domain, and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer and/or oral cancer.

In one embodiment, provided is (i) an antibody, comprising one or two binding domain(s) against HER2, preferably human HER2, and a mutated Fc domain, and (ii) the antigen binding receptor according to the invention directed to/binding to/interacting with the mutated Fc domain, for use in the treatment of gastric cancer, breast cancer and/or cervical cancer.

In one embodiment, provided is (i) an antibody, comprising one or two binding domain(s) against HER3, preferably human HER3, and a mutated Fc domain, and (ii) the antigen binding receptor according to the invention directed to/binding to/interacting with the mutated Fc domain, for use in the treatment of gastric cancer and/or lung cancer.

In one embodiment, provided is (i) an antibody, comprising one or two binding domain(s) against CEA, preferably human CEA, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against p95, preferably human p95, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against BCMA, preferably human BCMA, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against MSLN, preferably human MSLN, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against MCSP, preferably human MCSP, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD19, preferably human CD19, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD20, preferably human CD20, and a mutated Fc domain, and (ii) the antigen binding receptor according to the invention directed to/binding to/interacting with the mutated Fc domain, for use in the treatment of B-cell lymphoma and/or T cell lymphoma.

In one embodiment, provided is (i) an antibody, comprising one or two binding domain(s) against CD22, preferably human CD22, and a mutated Fc domain, and (ii) the antigen binding receptor according to the invention directed to/binding to/interacting with the mutated Fc domain, for use in the treatment of B-cell lymphoma and/or T cell lymphoma.

In one embodiment, provided is (i) an antibody, comprising one or two binding domain(s) against CD38, preferably human CD38, and a mutated Fc domain, and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against CD52Flt3, preferably human CD52Flt3, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against FolR1, preferably human FolR1, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against Trop-2, preferably human Trop-2, and a mutated Fc domain; and (ii) the antigen binding receptor according to the invention directed to/binding to/interacting with the mutated Fc domain, for use in the treatment of gastrointestinal cancer, pancreatic cancer, cholangiocellular cancer, lung cancer, breast cancer, ovarian cancer, skin cancer, glioblastoma and/or oral cancer.

In one embodiment, provided is (i) an antibody, comprising one or two binding domain(s) against CA-12-5, preferably human CA-12-5, and a mutated Fc domain; and (ii) the antigen binding receptor according to the invention directed to/binding to/interacting with the mutated Fc domain, for use in the treatment of ovarian cancer, lung cancer, breast cancer and/or gastrointestinal cancer.

In one embodiment, provided is (i) an antibody, comprising one or two binding domain(s) against HLA-DR, preferably human HLA-DR, and a mutated Fc domain; and (ii) the antigen binding receptor according to the invention directed to/binding to/interacting with the mutated Fc domain, for use in the treatment of gastrointestinal cancer, leukemia and/or nasopharyngeal carcinoma.

In one embodiment, provided (i) is an antibody, comprising one or two binding domain(s) against MUC-1, preferably human MUC-1, and a mutated Fc domain; and (ii) the antigen binding receptor according to the invention directed to/binding to/interacting with the mutated Fc domain, for use in the treatment cancer of colon cancer, breast cancer, ovarian cancer, lung cancer and/or pancreatic cancer.

In one embodiment, provided is (i) an antibody molecule, comprising one or two binding domain(s) against A33, preferably human A33, and a mutated Fc domain; and (ii) the antigen binding receptor according to the invention directed to/binding to/interacting with the mutated Fc domain, for use in the treatment of colon cancer.

In one embodiment, provided is (i) an antibody, comprising one or two binding domain(s) against PSMA, preferably human PSMA, and a mutated Fc domain; and (ii) the antigen binding receptor according to the invention directed to/binding to/interacting with the mutated Fc domain, for use in the treatment of prostate cancer.

In one embodiment, provided is (i) an antibody molecule, comprising one or two binding domain(s) against PSCA, preferably human PSCA, and a mutated Fc domain; and (ii) the antigen binding receptor according to the invention directed to/binding to/interacting with the mutated Fc domain, for use in the treatment cancer of epithelial, endothelial or mesothelial origin and cancer of the blood.

In one embodiment, provided is (i) an antibody molecule, comprising one or two binding domain(s) against transferrin-receptor, preferably human transferring-receptor, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody, comprising one or two binding domain(s) against tenascin, preferably human tenascin, and a mutated Fc domain; and (ii) the antigen binding receptor according to the invention directed to/binding to/interacting with the mutated Fc domain, for use in the treatment of cancer of epithelial, endothelial or mesothelial origin and cancer of the blood.

In one embodiment, provided is (i) an antibody molecule, comprising one or two binding domain(s) against CA-IX, preferably human XA-IX, and a mutated Fc domain; and (ii) the antigen binding receptor according to the invention directed to/binding to/interacting with the mutated Fc domain, for use in the treatment of renal cancer.

EXEMPLARY EMBODIMENTS

1. An antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain.

2. The antigen binding receptor of embodiment 1, wherein Fc receptor binding of the mutated Fc domain is reduced compared to Fc receptor binding of the non-mutated parent Fc domain, particularly wherein the Fc receptor is a Fcγ receptor or neonatal Fc receptor (FcRn).

3. The antigen binding receptor of any one of embodiments 1 or 2, wherein Fc receptor binding is measured by Surface Plasmon Resonance (SPR) at 25° C.

4. The antigen binding receptor of any one of embodiments 1 to 3, wherein the antigen binding moiety is a scFv, a Fab, crossFab or a scFab.

5. The antigen binding receptor of any one of embodiments 1 to 4, wherein the anchoring transmembrane domain is a transmembrane domain selected from the group consisting of the CD8, the CD3z, the FCGR3A, the NKG2D, the CD27, the CD28, the CD137, the OX40, the ICOS, the DAP10 or the DAP12 transmembrane domain or a fragment thereof.

6. The antigen binding receptor of any one of embodiments 1 to 5, wherein the anchoring transmembrane domain is the CD28 transmembrane domain, in particular wherein the anchoring transmembrane domain comprises the amino acid sequence of SEQ ID NO:11.

7. The antigen binding receptor of any one of embodiments 1 to 6 further comprising at least one stimulatory signaling domain and/or at least one co-stimulatory signaling domain.

8. The antigen binding receptor of any one of embodiments 1 to 7, wherein the at least one stimulatory signaling domain is individually selected from the group consisting of the intracellular domain of CD3z, of FCGR3A and of NKG2D, or fragments thereof.

9. The antigen binding receptor of any one of embodiments 1 to 8, wherein the at least one stimulatory signaling domain is the intracellular domain of CD3z or a fragment thereof, in particular wherein the at least one stimulatory signaling domain comprises the amino acid sequence of SEQ ID NO:13.

10. The antigen binding receptor of any one of embodiments 1 to 9, wherein the at least one co-stimulatory signaling domain is individually selected from the group consisting of the intracellular domain of CD27, of CD28, of CD137, of OX40, of ICOS, of DAP10 and of DAP12, or fragments thereof.

11. The antigen binding receptor of any one of embodiments 1 to 10, wherein the at least one co-stimulatory signaling domain is the CD28 intracellular domain or a fragment thereof, in particular, wherein the at least one co-stimulatory signaling domain comprises the amino acid sequence of SEQ ID NO:12.

12. The antigen binding receptor of any one of embodiments 1 to 11, wherein the antigen binding receptor comprises one stimulatory signaling domain comprising the intracellular domain of CD3z, or a fragment thereof, and wherein the antigen binding receptor comprises one co-stimulatory signaling domain comprising the intracellular domain of CD28, or a fragment thereof.

13. The antigen binding receptor of embodiment 12, wherein the stimulatory signaling domain comprises the amino acid sequence of SEQ ID NO:13 and the co-stimulatory signaling domain comprises the amino acid sequence of SEQ ID NO:12.

14. The antigen binding receptor of any one of embodiments 1 to 13, wherein the extracellular domain is connected to the anchoring transmembrane domain, optionally through a peptide linker.

15. The antigen binding receptor of embodiment 14, wherein the peptide linker comprises the amino acid sequence GGGGS (SEQ ID NO:17).

16. The antigen binding receptor of any one of embodiments 1 to 15, wherein the anchoring transmembrane domain is connected to a co-signaling domain or to a signaling domain, optionally through a peptide linker.

17. The antigen binding receptor of any one of embodiments 1 to 16, wherein the signaling and/or co-signaling domains are connected, optionally through at least one peptide linker.

18. The antigen binding receptor of any one of embodiments 1 to 17, wherein the antigen binding moiety is a scFv fragment, wherein the scFv fragment is connected at the C-terminus to the N-terminus of the anchoring transmembrane domain, optionally through a peptide linker.

19. The antigen binding receptor of any one of embodiments 1 to 17, wherein the antigen binding moiety is a Fab fragment or a crossFab fragment, wherein the Fab or crossFab fragment is connected at the C-terminus of the heavy chain to the N-terminus of the anchoring transmembrane domain, optionally through a peptide linker.

20. The antigen binding receptor of any one of embodiments 7 to 19, wherein the antigen binding receptor comprises one co-signaling domain, wherein the co-signaling domain is connected at the N-terminus to the C-terminus of the anchoring transmembrane domain.

21. The antigen binding receptor of embodiment 20, wherein the antigen binding receptor additionally comprises one stimulatory signaling domain, wherein the stimulatory signaling domain is connected at the N-terminus to the C-terminus of the co-stimulatory signaling domain.

22. The antigen binding receptor of any one of embodiments 1 to 21, wherein the non-mutated parent Fc domain is an IgG1 or an IgG4 Fc domain, particularly a human IgG1 Fc domain.

23. The antigen binding receptor of any one of embodiments 1 to 22, wherein the mutated Fe domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

24 The antigen binding receptor of any one of embodiments 1 to 23, wherein the mutant Fc domain comprises an amino acid substitution at a position selected from the group consisting of residue 117, 118, 136, 180, 193, 212, 214, and 318 of human IgG1 Fc (SEQ ID NO: 130), in particular wherein the amino acid mutation is L117A, L118A, I136A, N180A, H193A, P212G, P214G and/or H318A.

25. The antigen binding receptor of any one of embodiments 1 to 24, wherein the mutated Fc domain comprises at least one amino acid mutation at a position selected from the group consisting of L234, L235 and P329 according to EU numbering, in particular the amino acid mutations L234A, L235A and P329G ("PGLALA").

26. The antigen binding receptor of any one of embodiments 1 to 25, wherein the mutated Fc domain comprises the amino acid mutation P329G according to EU numbering, wherein Fcγ receptor binding of the mutated Fc domain is reduced compared to Fcγ receptor binding of the non-mutated parent Fc domain, in particular wherein the Fcγ receptor is human FcγRIIIa and/or FcγRIIa.

27 The antigen binding receptor of any one of embodiments 1 to 26, wherein the mutant Fc domain comprises an amino acid substitution at position 212 of human IgG1 Fc (SEQ ID NO: 130), in particular wherein the amino acid mutation is P212G.

28. The antigen binding receptor of any one of embodiments 1 to 24, wherein the mutated Fc domain comprises at least one amino acid mutation at a position selected from the group consisting of I253, H310 and H435 according to EU numbering, in particular the amino acid mutations I253A, H310A and H435A ("AAA"), wherein FcRn binding of the mutated Fc domain is reduced compared to FcRn binding of the non-mutated parent Fc domain.

29 The antigen binding receptor of any one of embodiments 1 to 24 or 28, wherein the mutant Fc domain comprises an amino acid substitution at positions 136, 193, and 318 of human IgG1 Fc (SEQ ID NO: 130), in particular wherein the amino acid mutation is I136A, H193A, and H318A ("AAA").

30. The antigen binding receptor of any one of embodiments 1 to 27, wherein the at least one antigen binding moiety is capable of specific binding to a mutated Fc domain comprising the P329G mutation but not capable of specific binding to the non-mutated parent Fc domain, wherein the antigen binding moiety comprises:
  (i) a heavy chain variable region (VH) comprising
    (a) the heavy chain complementarity-determining region (CDR H) 1 amino acid sequence RYWMN (SEQ ID NO:1);
    (b) the CDR H2 amino acid sequence EITPDSSTI-NYTPSLKD (SEQ ID NO:2); and
    (c) the CDR H3 amino acid sequence PYDYGAWFAS (SEQ ID NO:3); and (ii) a light chain variable region (VL) comprising
  (d) the light chain complementary-determining region (CDR L) 1 amino acid sequence RSSTGAVTTSNYAN (SEQ ID NO:4);
  (e) the CDR L2 amino acid sequence GTNKRAP (SEQ ID NO:5); and
  (f) the CDR L3 amino acid sequence ALWYSNHWV (SEQ ID NO:6).

31. The antigen binding receptor of any one of embodiments 1 to 27 or 30, wherein the at least one antigen binding moiety is capable of specific binding to a mutated Fc domain comprising the P329G mutation but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to an amino acid sequence selected from the group consisting of SEQ ID NO:8 and SEQ ID NO:32, and a light chain variable region (VL) comprising an amino acid sequence that is at least about 95%, 96%, 97%, 98%, 99% or 100% identical to an amino acid sequence selected from the group consisting of SEQ ID NO:9 and SEQ ID NO:33.

32. The antigen binding receptor of embodiment 1 to 27, 30 or 31, wherein the at least one antigen binding moiety comprises the heavy chain variable region (VH) of SEQ ID NO:8 and the light chain variable region (VL) of SEQ ID NO:9.

33. The antigen binding receptor of any one of embodiments 1 to 27 or 30 to 32, wherein the at least one antigen binding moiety is a scFv capable of specific binding to a mutated Fc domain comprising the P329G mutation but not capable of specific binding to the non-mutated parent Fc domain, wherein the antigen binding receptor comprises an amino acid sequence that is at least about 95%, 96%, 97%, 98%, 99% or 100% identical to an amino acid sequence selected from the group consisting of SEQ ID NO:7 and SEQ ID NO:31.

34. The antigen binding receptor of embodiment 33, comprising the amino acid sequence of SEQ ID NO:7.

35. The antigen binding receptor of any one of embodiments 1 to 27 or 30 to 32, wherein the at least one antigen binding moiety is a Fab fragment capable of specific binding to a mutated Fc domain comprising the P329G mutation but not capable of specific binding to the non-mutated parent Fc domain, wherein the antigen binding receptor comprises
  a) a heavy chain fusion polypeptide that is at least about 95%, 96%, 97%, 98%, 99% or 100% identical to an amino acid sequence selected from the group consisting of SEQ ID NO:39 and SEQ ID NO:48; and
  b) a light chain polypeptide that is at least about 95%, 96%, 97%, 98%, 99% or 100% identical to an amino acid sequence selected from the group consisting of SEQ ID NO:41 and SEQ ID NO:50.

36. The antigen binding receptor of embodiment 35, comprising
  a) the heavy chain fusion polypeptide of SEQ ID NO:39; and
  b) the light chain polypeptide of SEQ ID NO:41.

37. The antigen binding receptor of any one of embodiments 1 to 24 or 28 to 29, wherein the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises:
  (i) a heavy chain variable region (VH) comprising
    (a) the heavy chain complementarity-determining region (CDR H) 1 amino acid sequence SYGMS (SEQ ID NO:53);
    (b) the CDR H2 amino acid sequence SSGGSY (SEQ ID NO:54); and
    (c) the CDR H3 amino acid sequence LGMITTGYAMDY (SEQ ID NO:55); and
  (ii) a light chain variable region (VL) comprising
    (d) the light chain complementary-determining region (CDR L) 1 amino acid sequence RSSQTIVHSTGHTYLE (SEQ ID NO:56);
    (e) the CDR L2 amino acid sequence KVSNRFS (SEQ ID NO:57); and
    (f) the CDR L3 amino acid sequence FQGSHVPYT (SEQ ID NO:58).

38. The antigen binding receptor of any one of embodiments 1 to 24, 28, 29 or 37, wherein the at least one antigen binding moiety is capable of specific binding to a mutated Fc domain comprising the I253A, H310A and H435A ("AAA") mutations but not capable of specific binding to the non-mutated parent Fc domain, wherein the antigen binding moiety comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence of SEQ ID NO:62.

39. The antigen binding receptor of embodiment 1 to 24, 28, 29 or 37 to 38, wherein the at least one antigen binding moiety comprises
  a) the heavy chain variable region (VH) of SEQ ID NO:61; and
  b) the light chain variable region (VL) of SEQ ID NO:62.

40. The antigen binding receptor of any one of embodiments 1 to 24, 28, 29 or 37 to 39, wherein the at least one antigen binding moiety is a scFv capable of specific binding to a mutated Fc domain comprising the I253A, H310A and H435A ("AAA") mutations but not capable of specific binding to the non-mutated parent Fc domain, wherein the antigen binding receptor comprises an amino acid sequence that is at least about 95%, 96%, 97%, 98%, 99% or 100% identical to the amino acid sequence of SEQ ID NO:59.

41. The antigen binding receptor of embodiment 40, comprising the amino acid sequence of SEQ ID NO:59.

42. The antigen binding receptor of any one of embodiments 1 to 27 or 30 to 32, wherein the at least one antigen binding moiety is a Fab fragment capable of specific binding to a mutated Fc domain comprising the P329G mutation but not capable of specific binding to the non-mutated parent Fc domain, wherein the antigen binding receptor comprises
  a) a heavy chain fusion polypeptide that is at least about 95%, 96%, 97%, 98%, 99% or 100% identical to the amino acid sequence of SEQ ID NO:39; and
  b) a light chain polypeptide that is at least about 95%, 96%, 97%, 98%, 99% or 100% identical to the amino acid sequence of SEQ ID NO:41.

43. The antigen binding receptor of embodiment 42, comprising
  a) the heavy chain fusion polypeptide of SEQ ID NO:39; and
  b) the light chain polypeptide of SEQ ID NO:41.

44. An isolated polynucleotide encoding the antigen binding receptor of any one of embodiments 1 to 43.

45. An isolated polynucleotide encoding a heavy chain fusion polypeptide or a light chain polypeptide of the antigen binding receptor of any one of embodiments 1 to 32, 35 to 39 and 42 to 43.

46. A composition encoding the antigen binding receptor of any one of embodiments 1 to 32, 35 to 39 and 42 to 43, comprising a first isolated polynucleotide encoding a heavy chain fusion polypeptide, and a second isolated polynucleotide encoding a light chain polypeptide.

47. A polypeptide encoded by the polynucleotide of any one of embodiments 44 or 45 or by the composition of embodiment 46.

48. A vector, particularly an expression vector, comprising the polynucleotide of embodiment 44 or the polynucleotides of embodiment 45.

49. A transduced T cell comprising the polynucleotide of embodiment 44, the composition of embodiment 46 or the vector of embodiment 48.

50. A transduced T cell capable of expressing the antigen binding receptor of any one of embodiments 1 to 43.

51. The transduced T cell of any one of embodiments 49 or 50, wherein the transduced T cell is co-transduced with a T cell receptor (TCR) capable of specific binding of a target antigen.

52. A kit comprising
(A) a transduced T cell capable of expressing the antigen binding receptor of any one of embodiments 1 to 43; and
(B) an antibody comprising a mutated Fc domain;
wherein the antigen binding receptor is capable of specific binding to the mutated Fc domain but not capable of specific binding to the non-mutated parent Fc domain.

53. A kit comprising
(A) an isolated polynucleotide encoding the antigen binding receptor of any one of embodiments 1 to 43; and
(B) an antibody comprising a mutated Fc domain;
wherein the antigen binding receptor is capable of specific binding to the mutated Fc domain but not capable of specific binding to the non-mutated parent Fc domain.

54. A kit comprising
(A) the composition of embodiment 46 or the vector of embodiment 48 encoding the antigen binding receptor of any one of embodiments 1 to 43; and
(B) an antibody comprising a mutated Fc domain;
wherein the antigen binding receptor is capable of specific binding to the mutated Fc domain but not capable of specific binding to the non-mutated parent Fc domain.

55. The kit of any one of embodiments 52 to 54, wherein the non-mutated parent Fc domain is an IgG1 or an IgG4 Fc domain, particularly a human IgG1 Fc domain.

56. The kit of any one of embodiments 52 to 55, wherein Fc receptor binding of the mutated Fc domain is reduced compared to Fc receptor binding of the non-mutated parent Fc domain, particularly wherein the Fc receptor is a Fcγ receptor or neonatal Fc receptor (FcRn).

57. The kit of embodiment 56, wherein Fc receptor binding is measured by Surface Plasmon Resonance (SPR) at 25° C.

58. The kit of any one of embodiments 52 to 57, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

59. The kit of any one of embodiments 52 to 58, wherein the mutated Fc domain comprises at least one amino acid mutation at a position selected from the group consisting of L234, L235 and P329 according to EU numbering, in particular the amino acid mutations L234A, L235A and P329G ("PGLALA").

60. The kit of any one of embodiments 52 to 59, wherein the mutated Fc domain comprises the amino acid mutation P329G according to EU numbering.

61. The kit of any one of embodiments 52 to 60, wherein the mutated Fc domain comprises at least one amino acid mutation at a position selected from the group consisting of I253, H310 and H435 according to EU numbering, in particular the amino acid mutations I253A, H310A and H435A ("AAA").

62. The kit of any one of embodiments 52 to 61, wherein the antibody comprising the mutated Fc domain is capable of specific binding to an antigen on the surface of a tumor cell, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

63. The kit of any one of embodiments 52 to 62, wherein the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

64. The kit of any one of embodiments 52 to 63 for use as a medicament.

65. The antigen binding receptor of any one of embodiments 1 to 43 or the transduced T cell of any one of embodiments 49 to 51 for use as a medicament, wherein a transduced T cell expressing the antigen binding receptor is administered before, simultaneously with or after administration of an antibody comprising a mutated Fc domain wherein the antigen binding receptor is capable of specific binding to the mutated Fc domain but not capable of specific binding to the non-mutated parent Fc domain.

66. The kit of any one of embodiments 52 to 63 for use in the treatment of a disease, in particular for use in the treatment of a malignant disease.

67. The antigen binding receptor of any one of embodiments 1 to 43 or the transduced T cell of any one of embodiments 49 to 51 for use in the treatment of a malignant disease, wherein the treatment comprises administration of a transduced T cell expressing the antigen binding receptor before, simultaneously with or after administration of an antibody comprising a mutated Fc domain wherein the antigen binding receptor is capable of specific binding to the mutated Fc domain but not capable of specific binding to the non-mutated parent Fc domain.

68. The antigen binding receptor, the transduced T cell or the kit for use according to embodiment 66 or 67, wherein said malignant disease is selected from cancer of epithelial, endothelial or mesothelial origin and cancer of the blood.

69. The antigen binding receptor, the transduced T cell or the kit for use according to embodiments 66 to 68, wherein the antibody comprising the mutated Fc domain is capable of specific binding to an antigen on the surface of tumor cells, in particular wherein the antigen is selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX, and/or to a peptide bound to a molecule of the human major histocompatibility complex (MHC).

70. The antigen binding receptor, the transduced T cell or the kit for use according to embodiments 66 to 69, wherein the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1) and tenascin (TNC).

71. The antigen binding receptor, the transduced T cell or the kit for use according to any one of embodiments 66 to 70, wherein the transduced T cell is derived from a cell isolated from the subject to be treated.

72. The antigen binding receptor, the transduced T cell or the kit for use according to any one of embodiments 66 to 70, wherein the transduced T cell is not derived from a cell isolated from the subject to be treated.

73. A method of treating a disease in a subject, comprising administering to the subject a transduced T cell capable of expressing the antigen binding receptor of any one of embodiments 1 to 43 and administering before, simultaneously with or after administration of the transduced T cell a therapeutically effective amount of an antibody comprising a mutated Fc domain, wherein the antigen binding receptor is capable of specific binding to the mutated Fc domain but not capable of specific binding to the non-mutated parent Fc domain.

74. The method of embodiment 73, additionally comprising isolating a T cell from the subject and generating the transduced T cell by transducing the isolated T cell with the polynucleotide of embodiment 44, the composition of embodiment 46 or the vector of embodiment 48.

75. The method of embodiment 74, wherein the T cell is transduced with a retroviral or lentiviral vector construct or with a non-viral vector construct.

76. The method of embodiment 75, wherein the non-viral vector construct is a sleeping beauty minicircle vector.

77. The method of any one of embodiments 73 to 76, wherein the transduced T cell is administered to the subject by intravenous infusion.

78. The method of any one of embodiments 73 to 77, wherein the transduced T cell is contacted with anti-CD3 and/or anti-CD28 antibodies prior to administration to the subject.

79. The method of any one of embodiments 73 to 78, wherein the transduced T cell is contacted with at least one cytokine prior to administration to the subject, preferably with interleukin-2 (IL-2), interleukin-7 (IL-7), interleukin-15 (IL-15), and/or interleukin-21, or variants thereof.

80. The method of any one of embodiments 73 to 79, wherein the disease is a malignant disease.

81. The method of any one of embodiments 73 to 79, wherein the disease is selected from cancer of epithelial, endothelial or mesothelial origin and cancer of the blood.

82. A method for inducing lysis of a target cell, comprising contacting the target cell with a transduced T cell capable of expressing the antigen binding receptor of any one of embodiments 1 to 43 in the presence of an antibody comprising a mutated Fc domain wherein the antigen binding receptor is capable of specific binding to the mutated Fc domain but not capable of specific binding to the non-mutated parent Fc domain.

83. The method of embodiment 82, wherein the target cell is a cancer cell.

84. The method of any one of embodiments 82 or 83, wherein the target cell expresses an antigen selected from the group consisting of FAP, CEA, p95, BCMA, EpCAM, MSLN, MCSP, HER-1, HER-2, HER-3, CD19, CD20, CD22, CD33, CD38, CD52Flt3, FOLR1, Trop-2, CA-12-5, HLA-DR, MUC-1 (mucin), A33-antigen, PSMA, PSCA, transferrin-receptor, TNC (tenascin) and CA-IX.

85. The method of any one of embodiments 82 to 84, wherein the target cell expresses an antigen selected from the group consisting of fibroblast activation protein (FAP), carcinoembryonic antigen (CEA), mesothelin (MSLN), CD20, folate receptor 1 (FOLR1), and tenascin (TNC).

86. Use of the antigen binding receptor of any one of embodiments 1 to 43, the polynucleotides of any one of embodiments 44 and 45 or the transduced T cell of any one of embodiments 49 to 51 for the manufacture of a medicament.

87. The use of embodiment 86, wherein the medicament is for treatment of a malignant disease.

88. The use of embodiment 86, wherein the medicament is for treatment of a disease.

89. The use of embodiment 87, characterized in that said malignant disease is selected from cancer of epithelial, endothelial or mesothelial origin and cancer of the blood.

90. The use of embodiment 88, characterized in that said disease is selected from cancer of epithelial, endothelial or mesothelial origin and cancer of the blood.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.gov/PubMed/medline.html. Further databases and addresses, such as http://www.ncbi.nlm-.nih.gov/, http://www.infobiogen.fr/, http://www.fmi.ch/biology/research_tools.html, http://www.tigr.org/, are known to the person skilled in the art and can also be obtained using, e.g., http://www.lycos.com.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE and size exclusion chromatography (SEC).

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Antibody Production

The Pro329Gly, Leu234Ala and Leu235Ala mutations were introduced in the constant region to abrogate binding to Fc gamma receptors according to the method described in International Patent Appl. Publ. No. WO2012/130831A1. Accordingly, the I253A, H310A and H435A ("AAA") mutations were introduced in the constant region to abrogate binding to FcRn. The respective antibodies were produced by co-transfecting HEK293-EBNA cells with the mammalian expression vectors using polyethylenimine. The cells were transfected with the corresponding expression vectors for heavy and light chains in a 1:1 ratio.

Lentiviral Transduction of Jurkat NFAT T Cells

To produce lentiviral vectors, respective DNA sequences for the correct assembly of the antigen binding receptor were cloned in frame in a lentiviral polynucleotide vector under a constitutively active human cytomegalovirus immediate early promoter (CMV). The retroviral vector contained a woodchuck hepatitis virus posttranscriptional regulatory element (WPRE), a central polypurine tract (cPPT) element, a pUC origin of replication and a gene encoding for antibiotic resistance facilitating the propagation and selection in bacteria.

To produce functional virus particles, Lipofectamine LTX™ based transfection was performed using 60-70% confluent Hek293T cells (ATCC CRL3216) and CAR containing vectors as well as pCMV-VSV-G:pRSV-REV: pCgpV transfer vectors at 3:1:1:1 ratio. After 48 h supernatant was collected, centrifuge for 5 minutes at 250 g to remove cell debris and filtrated through 0.45 or 0.22 µm polyethersulfon filter. Concentrated virus particles (Lenti-x-Concentrator, Takara) were used to transduce Jurkat NFAT cells (Signosis). Positive transduced cells were sorted as pool or single clones using FACSARIA sorter (BD Bioscience). After cell expansion to appropriate density Jurkat NFAT T cells were used for experiments.

Example 1

Figure 6A:
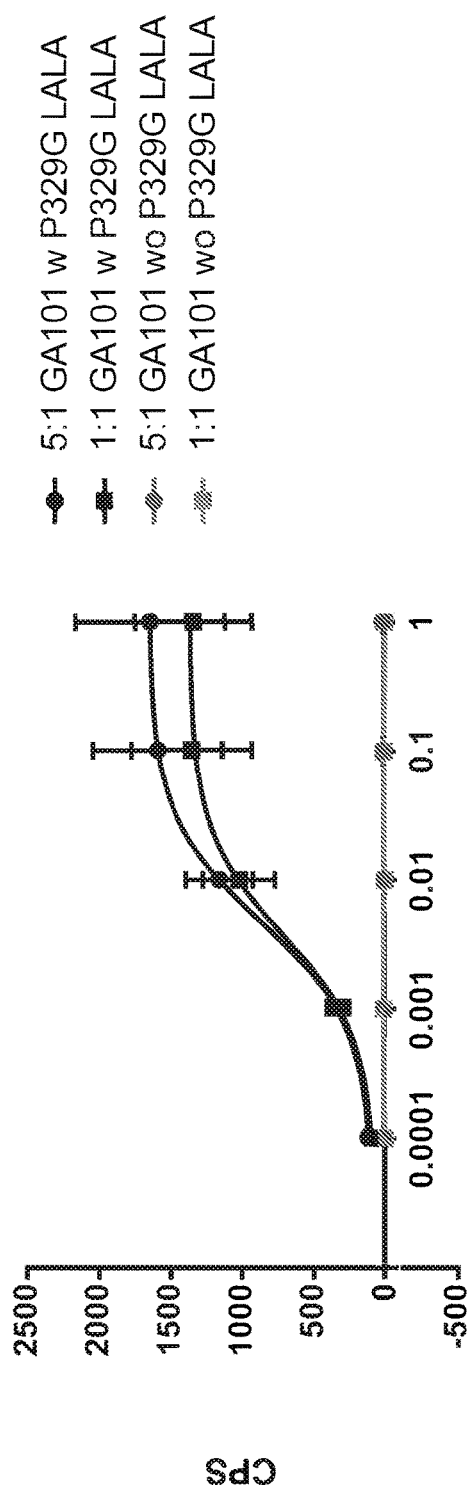
FIG. 6A and FIG. 6B depict the Jurkat NFAT T cell reporter assay using CD20 expressing SUDHDL4 tumor cells as target cells. An anti-CD20 IgG antibody (GA101) harboring the P329G mutation was used, which on one hand recognizes the tumor associated antigen and on the other hand is recognized by Jurkat NFAT T cells expressing antigen binding receptors according to the invention.
Figure 6B:
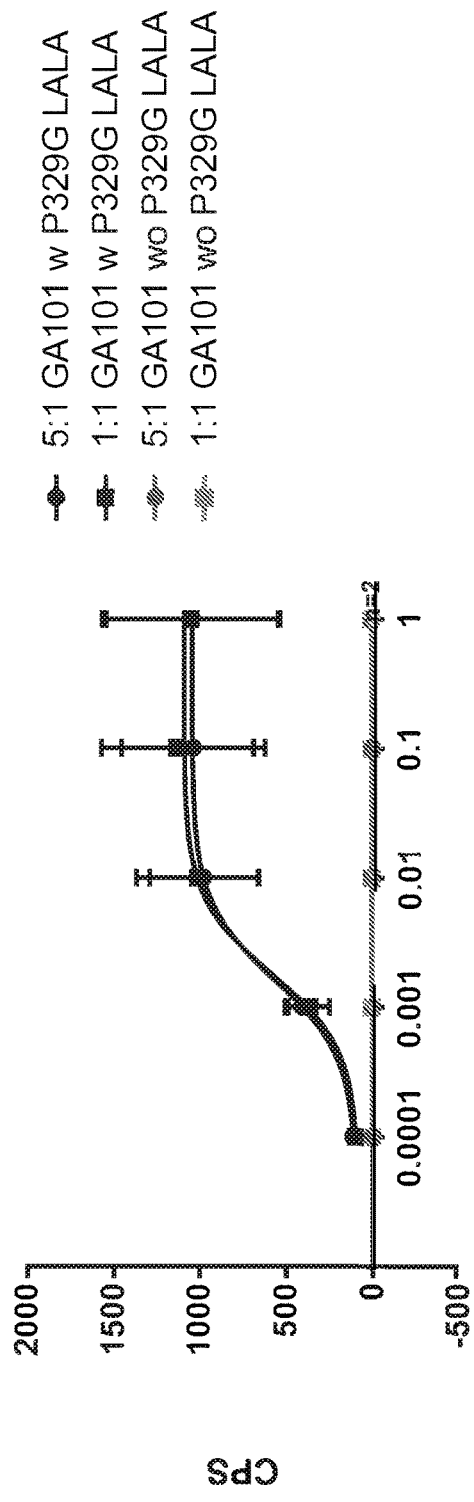

Described herein is a Jurkat NFAT T cell reporter assay using CD20 expressing SUDHDL4 tumor cells as target cells and a sorted pool of Anti-P329G-ds-Fab-CD28ATD-CD28CSD-CD3zSSD expressing Jurkat NFAT T cells (FIG. 6A) or a pool of Anti-P329G-ds-scFv-CD28ATD-CD28CSD-CD3zSSD expressing Jurkat NFAT T cells (FIG. 6B) as target cells. GA101 IgG with P329G LALA mutation was used as IgG, which on one hand recognizes the tumor antigen and on the other hand is recognized by the transduced Jurkat NFAT T cells. As positive control a 96 well plate (Cellstar Greiner-bio-one, CAT-No. 655185) was coated with 10 µg/ml CD3 antibody (from Biolegend®) in phosphate buffered saline (PBS) either for 4° C. over night or for at least 1 h at 37° C. The CD3 coated wells were washed twice with PBS, after the final washing step PBS was fully removed. Effector cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to $1 \times 10^6$ viable cells/ml in growth medium. Target cells and effector cells were plated in either 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and effector cells in a ratio 5:1 (dots) or 1:1 (squares) for 20 h the graphs show a dose-dependent activation of Anti-P329G-ds-Fab-CD28ATD-CD28CSD-CD3zSSD expressing Jurkat NFAT T cells as well as Anti-P329G-ds-scFv-CD28ATD-CD28CSD-CD3zSSD expressing Jurkat NFAT T cells when GA101 IgG with P329G LALA mutation was used as antibody (FIGS. 6A and 6B, depicted in black). If the GA101 IgG without P329G LALA mutation (FIGS. 6A and 6B, depicted in grey) was used, no activation of the transduced Jurkat NFAT T cells was detectable. Each point represents the mean value of biological duplicates, each performed as technical duplicate. All values are depicted as baseline corrected. Standard deviation is indicated by error bars.

Example 2

Described herein is a Jurkat NFAT T cell reporter assay using CD20 expressing SUDHDL4 (FIGS. 7C and 7D) or WSUDLCL2 (FIGS. 7A and 7B) tumor cells as target cells and single clone Jurkat NFAT cells expressing Anti-P329G-ds-Fab-CD28ATD-CD28CSD-CD3zSSD as target cells. GA101 IgG with P329G LALA mutation was used as IgG which on one hand recognizes the tumor antigen and on the other hand is recognized by the Jurkat NFAT T cells. Effector cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to $1 \times 10^6$ viable cells/ml in growth medium. Target cells and effector cells were plated in either 10:1, 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®).

To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and effector cells in a ratio 10:1 (dots), 5:1 (squares) or 1:1 (triangles) for 20 h the graphs show a GA101 IgG with P329G LALA dose-dependent activation of Anti-P329G-ds-Fab-CD28ATD-CD28CSD-CD3zSSD expressing Jurkat NFAT T cells (FIGS. 7A-7D, depicted in black). If the GA101 IgG without P329G LALA mutation (FIGS. 7A-7D, depicted in grey) was used, then only little activation of the transduced Jurkat NFAT T cells was detectable at the highest antibody concentration of 1 μg/ml. Each point represents the mean value of technical duplicate. All values are depicted as baseline corrected. Standard deviation is indicated by error bars.

Example 3

Described herein is a Jurkat NFAT T cell reporter assay performed using adherent FAP expressing NIH/3T3-huFAP cl 19 tumor cells as target cells. As effector cells a sorted pool of Anti-P329G-ds-Fab-CD28ATD-CD28CSD-CD3zSSD expressing Jurkat NFAT T cells (FIG. 8A) or Anti-P329G-ds-scFv-CD28ATD-CD28CSD-CD3zSSD expressing Jurkat NFAT T cells (FIG. 8C) were used. FAP 4B9 IgG with P329G LALA mutation was used as IgG which on one hand recognizes the tumor antigen and on the other hand is recognized by the Jurkat NFAT T cells. IgG DP47/vk3 harboring P329G LALA mutation was included as isotype control. As positive control wells of a 96 well plate (Greiner-bio-one, CAT-No. 655185) were coated with 10 μg/ml CD3 antibody (from Biolegend®) in phosphate buffered saline (PBS) for at least 1 h at 37° C. The CD3 coated wells were washed twice with PBS, after the final washing step PBS was fully removed. Adherent NIH/3T3-huFAP cl 19 target cells were washed once with PBS and detached using Trypsin. Detached cells were resuspended in DMEM+4.5 g LD-Glucose+L-Glutamine+25 mM HEPES+10% FCS and 1% Glutamax. Effector cells or Jurkat NFAT wild type T cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the effector cells, to $1 \times 10^6$ viable cells/ml in growth medium. Target cells and effector cells were plated in 5:1 E:T ratio (110.000 cells per well in total) in triplicates in a 96-well suspension culture plate (Greiner-bio one). As a next step a serial dilution of an antibody with P329G LALA mutation, targeting the antigen of interest, was prepared in growth medium using a 2 ml deep well plate (Axygen®). To obtain final concentrations ranging from 1 μg/ml to 0.0001 μg/ml, in a final volume of 200 ul per well, a 50 μl aliquot of the different dilutions was pipetted to the respective wells. The 96-well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Figure 8A:
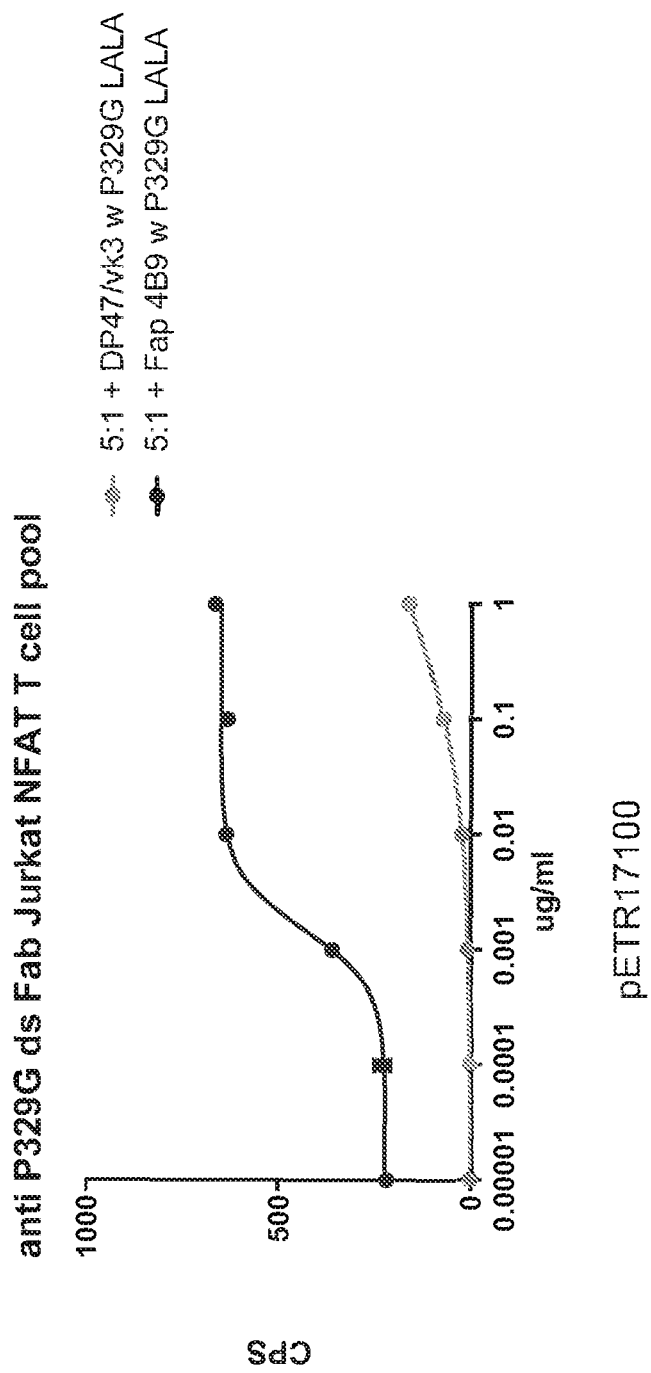
FIGS. 8A-8D depict the Jurkat NFAT T cell reporter assay performed using adherent FAP expressing NIH/3T3-huFAP cl 19 tumor cells as target cells. The anti-FAP IgG antibody clone 4B9 harboring the P329G mutation was used which the tumor associated antigen and is recognized by the Jurkat NFAT T cells expressing antigen binding receptors according to the invention. IgG DP47/vk3 harboring P329G mutation was included as isotype control.
Figure 8B:
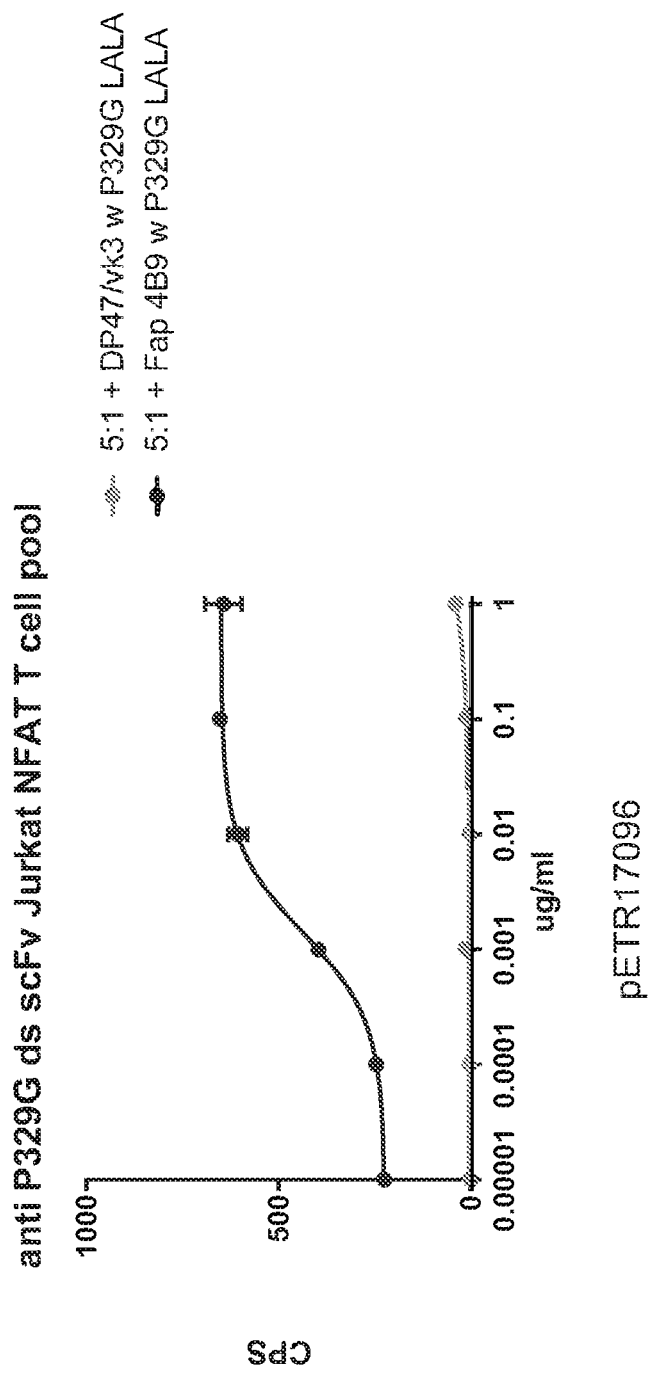
Figure 8C:
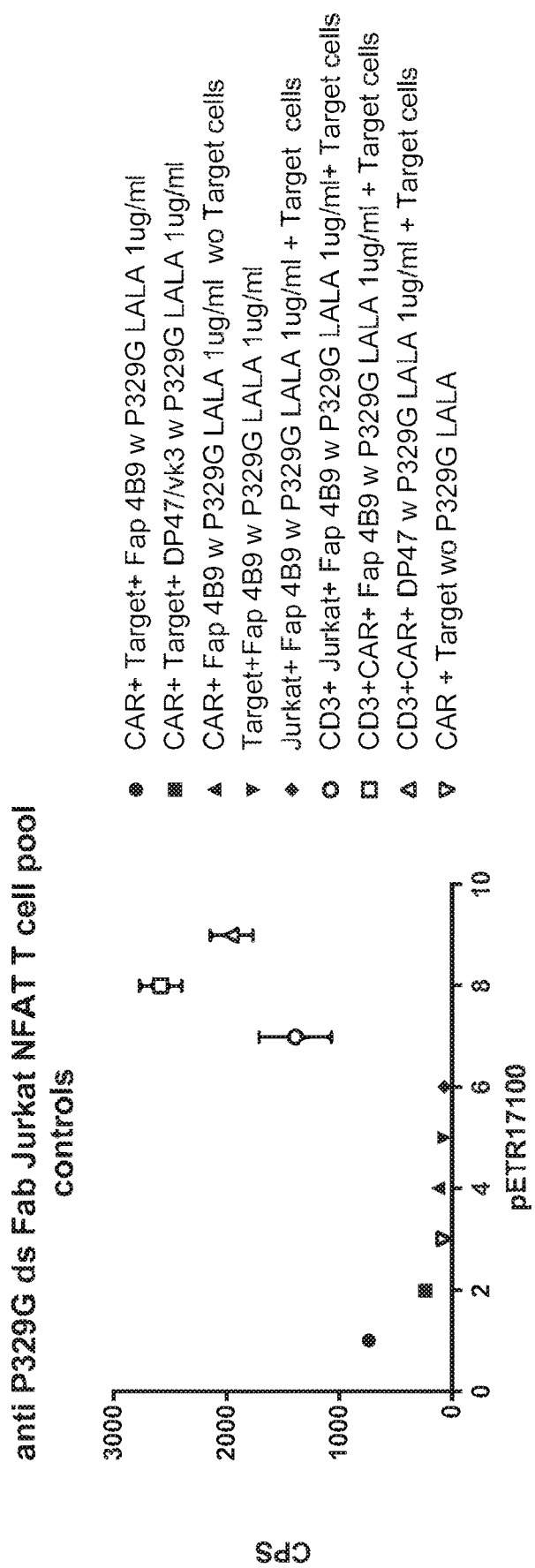
Figure 8D:
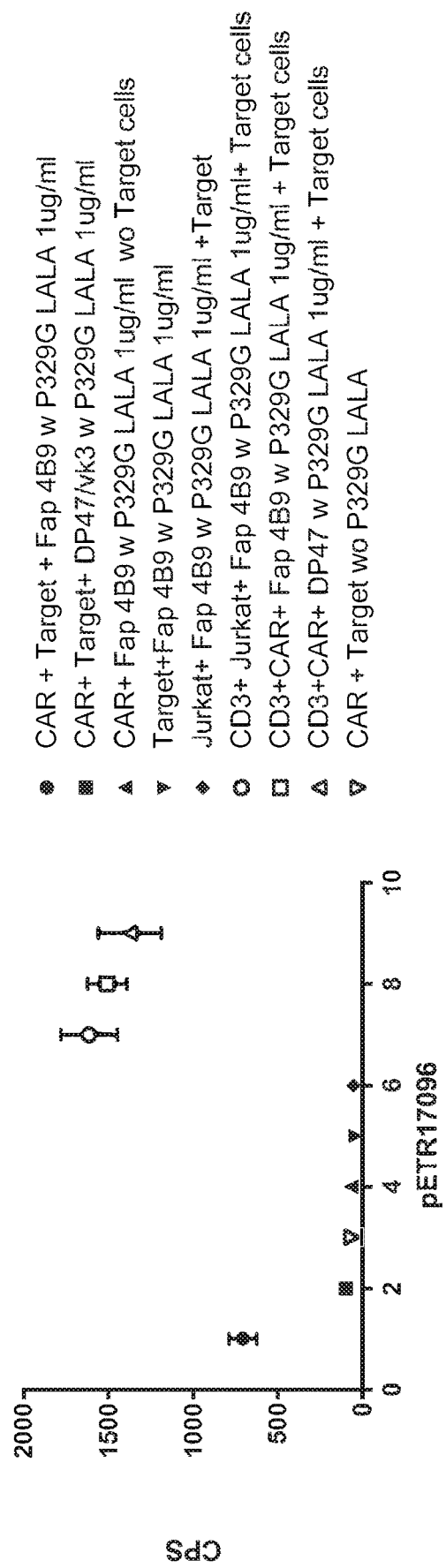

FIGS. 8B and 8D, represent data of Anti-P329G-ds-Fab-CD28ATD-CD28CSD-CD3zSSD expressing Jurkat NFAT T cells (FIG. 8D) or Anti-P329G-ds-scFv-CD28ATD-CD28CSD-CD3zSSD expressing Jurkat NFAT T cells (FIG. 8B) both co-cultivated with target cells and 1 μg/ml of FAP 4B9 antibody compared to different control conditions. Upon incubation with 1 μg/ml FAP 4B9 P329G LALA, Jurkat NFAT T cells (FIGS. 8B and 8D black triangle) as well as target cells only (FIGS. 8B and 8D upside down black triangle) do not show any detectable luminescence signal.

Also Jurkat NFAT T cells show no luminescence signal upon co-cultivation with target cells and 1 μg/ml of FAP 4B9 antibody (FIG. 8B and FIG. 8D black diamond). Whereas CD3 dependent activation of Jurkat NFAT cells co-cultivated with target cells and 1 μg/ml of FAP 4B9 antibody proofs their functionality through a detectable luminescence signal (withe dots). CD3 dependent activation of Anti-P329G-ds-Fab-CD28ATD-CD28CSD-CD3zSSD expressing Jurkat NFAT T cells (FIG. 8B white squares) and activation of Anti-P329G-ds-scFv-CD28ATD-CD28CSD-CD3zSSD expressing Jurkat NFAT T cells (FIG. 8D depicted in white squares) co-cultivated with target cells and 1 μg/ml of FAP 4B9 antibody shows the highest luminescence signals of all, since it combines the CAR mediated activation with CD3 mediated activation. CD3 mediated luminescence signal is also visible when CARs are incubated with target cells and 1 μg/ml of DP47/vk3 antibody (FIG. 8B and FIG. 8D upside down white triangles). Each point represents the mean value of technical triplicates. All values are depicted as baseline corrected. Standard deviation is indicated by error bars.

Example 4

Described herein is a Jurkat NFAT T cell reporter assay using adherent CEA expressing MKN45 tumor cells as target cells. As effector cells a sorted pool of Anti-P329G-ds-Fab-CD28ATD-CD28CSD-CD3zSSD expressing Jurkat NFAT T cells (FIG. 9A) or Anti-P329G-ds-scFv-CD28ATD-CD28CSD-CD3zSSD expressing Jurkat NFAT T cells (FIG. 9C) were used. Either CEA A5B7 IgG or CEA T84 LCHA IgG both with P329G LALA mutation were used. Further IgG DP47/vk3 harboring P329G LALA mutation was included as isotype control. As positive control wells of a 96 well plate (Greiner-bio-one, CAT-No. 655185) were coated with 10 μg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine+25 mM HEPES+10% FCS and 1% Glutamax.

Effector cells or Jurkat NFAT wild type cells were counted and checked for their viability using Cedex HiRes. The cell number was adjusted to 1×10$^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to 1×10$^6$ viable cells/ml in RPMI-1640+10% FCS+1% Glutamax.

Target cells and effector cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% CO$_2$ in a humidity atmosphere.

After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Figure 9A:
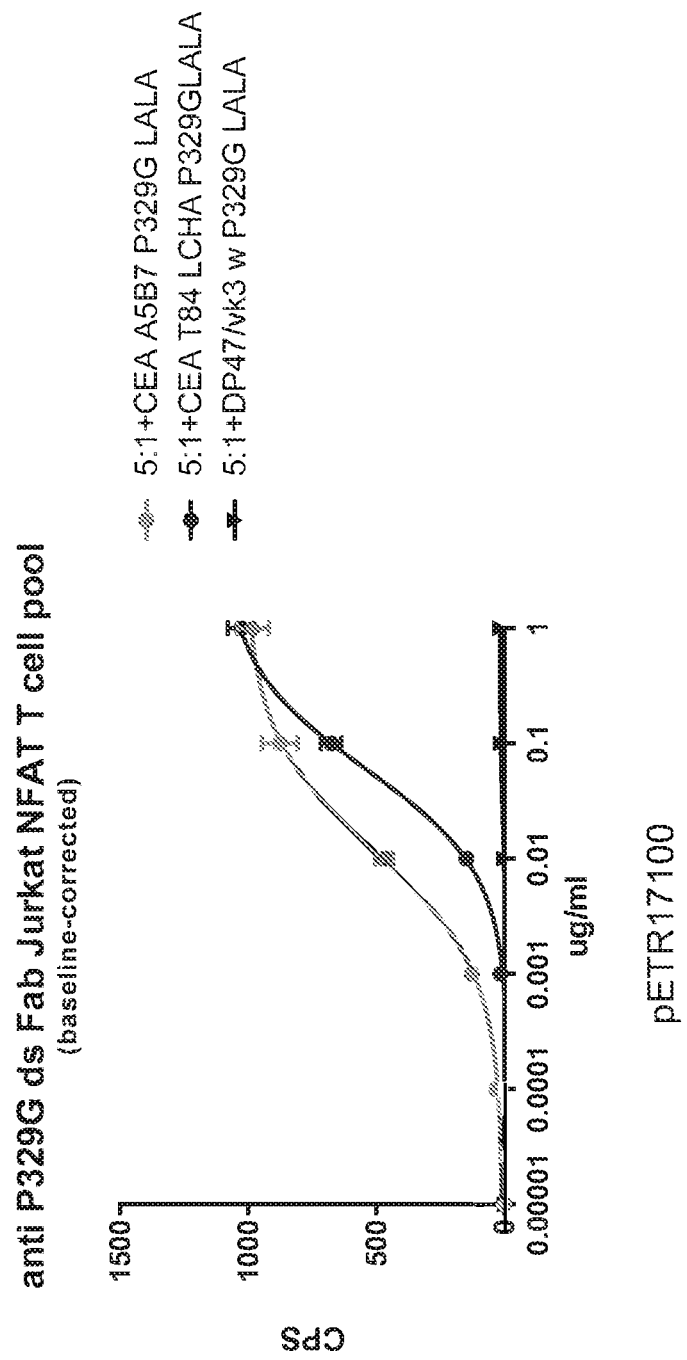
Figure 9C:
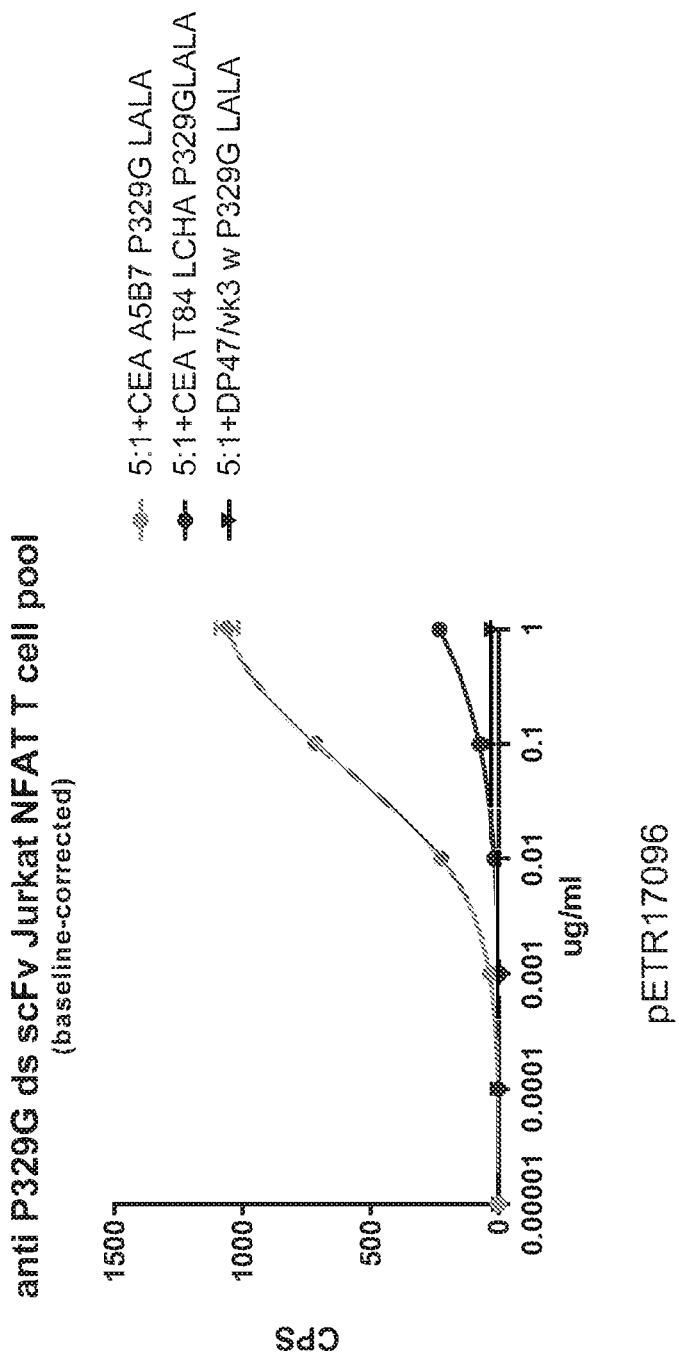

Upon co-cultivation of target and effector cells in a ratio 5:1 (FIGS. 9A and 9C, dots) for 20 h the graphs show a dose-dependent activation of Anti-P329G-ds-Fab-CD28ATD-CD28CSD-CD3zSSD expressing Jurkat NFAT T cells as well Anti-P329G-ds-scFv-CD28ATD-CD28CSD-CD3zSSD expressing Jurkat NFAT T cells when CEA A5B7 with P329G LALA mutation was used as antibody (FIGS. 9A and 9C grey dots). The use of CEA T84 LCHA with P329G LALA mutation showed only for Anti-P329G-ds-Fab-CD28ATD-CD28CSD-CD3zSSD expressing Jurkat NFAT T cells a dose dependent activation (FIG. 9A black dots). Whereas, when using the antibody with P329G LALA mutation an activation of Anti-P329G-ds-scFv-CD28ATD-CD28CSD-CD3zSSD expressing Jurkat NFAT T cells was detectable only at the highest antibody concentration of 1 μg/ml.

If the control antibody DP47/vk3 IgG with P329G LALA mutation (FIGS. 9A and 9C, black triangles) was used, no activation of Anti-P329G-ds-scFv-CD28ATD-CD28CSD-CD3zSSD Jurkat NFAT T cells or Anti-P329G-ds-Fab-CD28ATD-CD28CSD-CD3zSSD expressing Jurkat NFAT T cells was detectable. Each point represents the mean value of technical triplicates. Standard deviation is indicated by error bars.

Figure 9D:
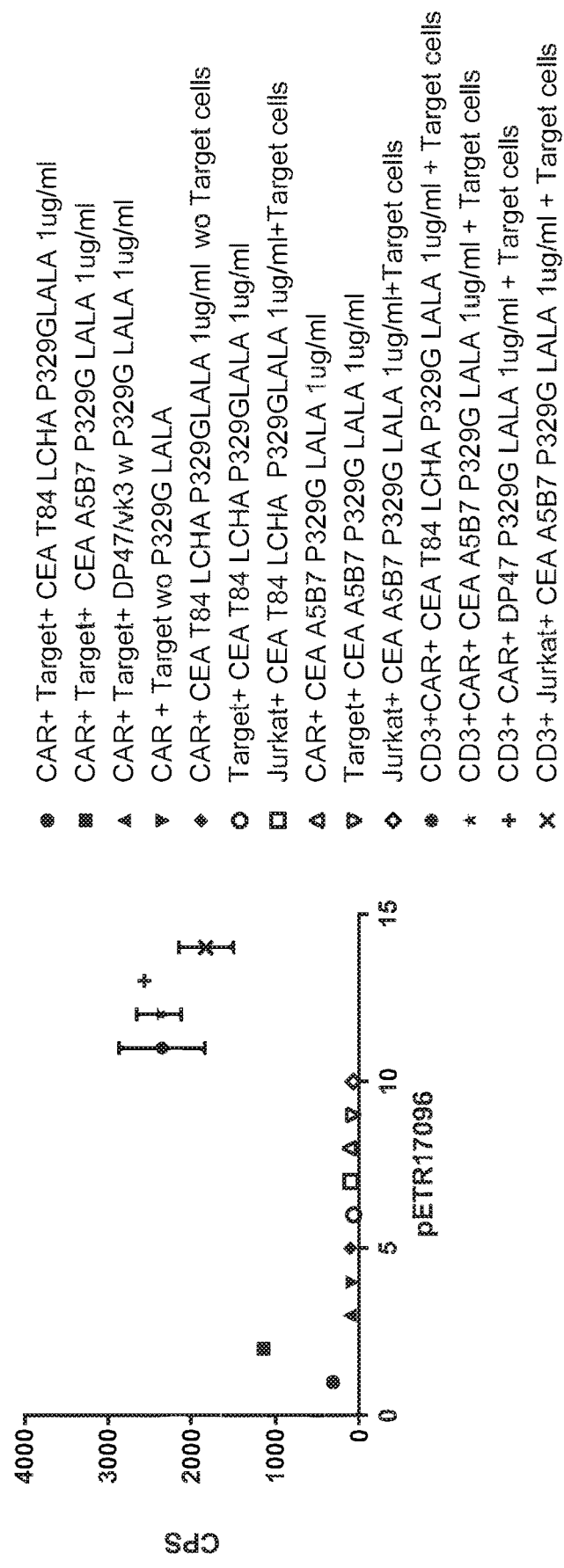

FIGS. 9B and 9D, represent data of Anti-P329G-ds-Fab-CD28ATD-CD28CSD-CD3zSSD expressing Jurkat NFAT T cells (FIG. 9B) or Anti-P329G-ds-scFv-CD28ATD-CD28CSD-CD3zSSD expressing Jurkat NFAT T cells (FIG. 9D) both co-cultivated with target cells and 1 μg/ml of CEA T8 LCHA P329G LALA or CEA A5B7 P329G LALA antibody compared to different control conditions.

Upon incubation with 1 μg/ml CEA T8 LCHA P329G LALA, Jurkat NFAT CAR T cells alone (FIGS. 9B and 9D black diamond) as well as target cells alone (FIGS. 9B and 9D white circle) do not show any detectable luminescence signal.

Also Jurkat NFAT T cells do not show a detectable luminescence signal upon co-cultivation with target cells and 1 μg/ml IgG (FIG. 9B and FIG. 9D white square and white diamond). Whereas CD3 dependent activation of Jurkat NFAT T cells co-cultivated with target cells and 1 μg/ml IgG proofs their functionality through a detectable luminescence signal (FIGS. 9B and 9D grey cross).

CD3 dependent activation of Anti-P329G-ds-Fab-CD28ATD-CD28CSD-CD3zSSD Jurkat NFAT T cells (FIG. 9B black star and grey star) and activation of Anti-P329G-ds-scFv-CD28ATD-CD28CSD-CD3zSSD expressing NFAT T cells (FIG. 9D black star and grey star) co-cultivated with target cells and 1 μg/ml IgG show the highest luminescence signals of all, since CAR mediated activation and CD3 mediated activation is combined. CD3 mediated luminescence signal is also visible when CARs are incubated with target cells and 1 μg/ml of DP47/vk3 antibody (FIG. 9B and FIG. 9D, grey plus). Each point represents the mean value of technical triplicates. Standard deviation is indicated by error bars.

Example 5

Described herein is a Jurkat NFAT T cell reporter assay using adherent CEA expressing MKN45 tumor cells as target cells. As effector cells, a sorted pool of Anti-P329G-ds-Fab-CD28ATD-CD28CSD-CD3zSSD expressing Jukat NFAT T cells (FIG. 10C) or Anti-P329G-ds-scFv-CD28ATD-CD28CSD-CD3zSSD expressing Jurkat NFAT T cells (FIG. 10A) were used. Either CH1A1A 98 99 or CEA hMN14 IgG both with P329G LALA mutation were used.

Further IgG DP47/vk3 harboring P329G LALA mutation was included as isotype control.

As positive control wells of a 96-well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine+25 mM HEPES+10% FCS and 1% Glutamax.

Effector cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to $1 \times 10^6$ viable cells/ml in RPMI-1640+10% FCS+1% Glutamax.

Target cells and effector cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon 20 h co-cultivation of target cells and Anti-P329G-ds-scFv-CD28ATD-CD28CSD-CD3zSSD expressing Jurkat NFAT T cells in a ratio 5:1 (FIG. 10A black and grey dots) no activation is detectable, when the CEA hMN14 antibody or the CH1A1A 98 99 antibody was used as (FIGS. 9A and 9B, grey dots). Anti-P329G-ds-Fab-CD28ATD-CD28CSD-CD3zSSD expressing Jurkat NFAT T cells show little activation at 0.1 and 1 µg/ml of both CEA hMN14 antibody or the CH1A1A 98 99 antibodies (FIG. 10C black and grey dots).

If the control antibody DP47/vk3 IgG with P329G LALA mutation (FIGS. 10A and 10C, black triangles) was used, neither the activation of Anti-P329G-ds-scFv-CD28ATD-CD28CSD-CD3zSSD expressing Jurkat NFAT T cells nor Anti-P329G-ds-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

Figure 10A:
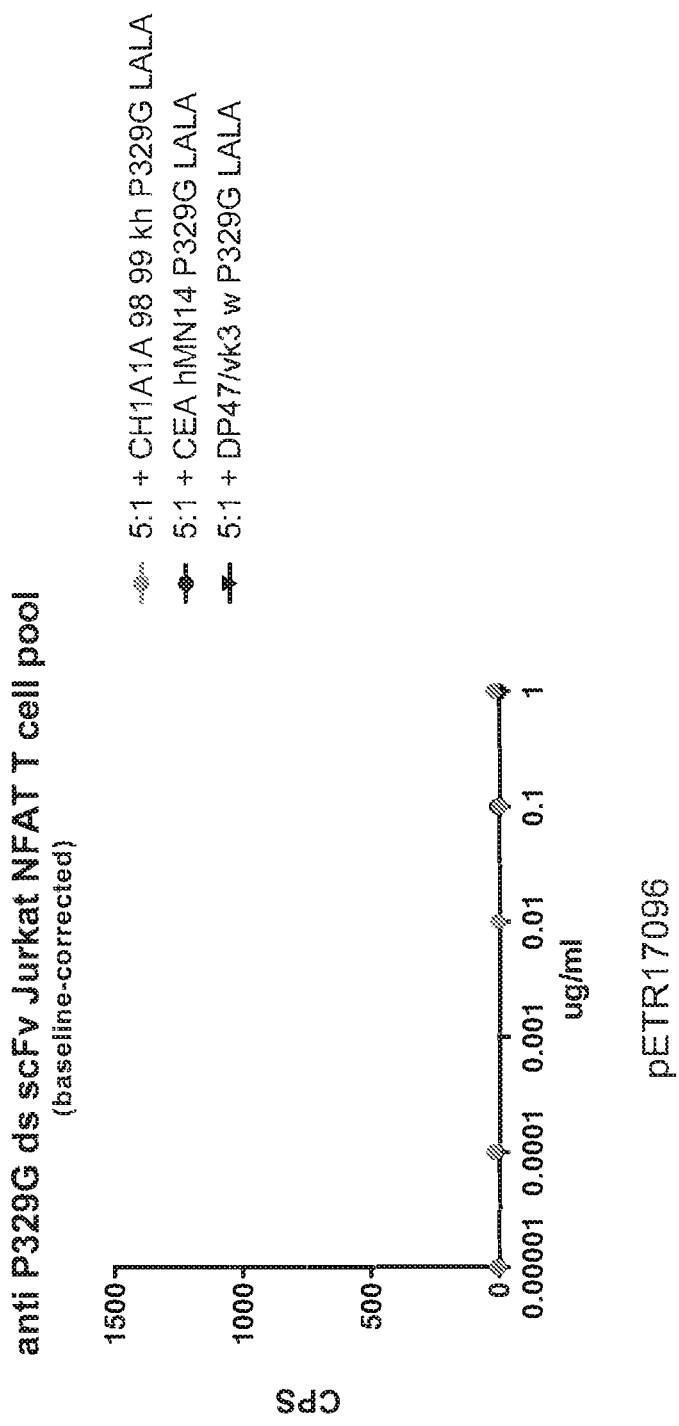
FIGS. 10A-10D depict the Jurkat NFAT T cell reporter assay using adherent CEA expressing MKN45 tumor cells as target cells. Either the anti-CEA clone CH1A1A 98 99 or the anti-CEA IgG clone hMN14 IgG both harboring the P329G mutation were used which recognize the tumor associated antigen and are recognized by the Jurkat NFAT T cells expressing antigen binding receptors according to the invention. Further IgG DP47/vk3 harboring P329G mutation was included as isotype control.
Figure 10B:
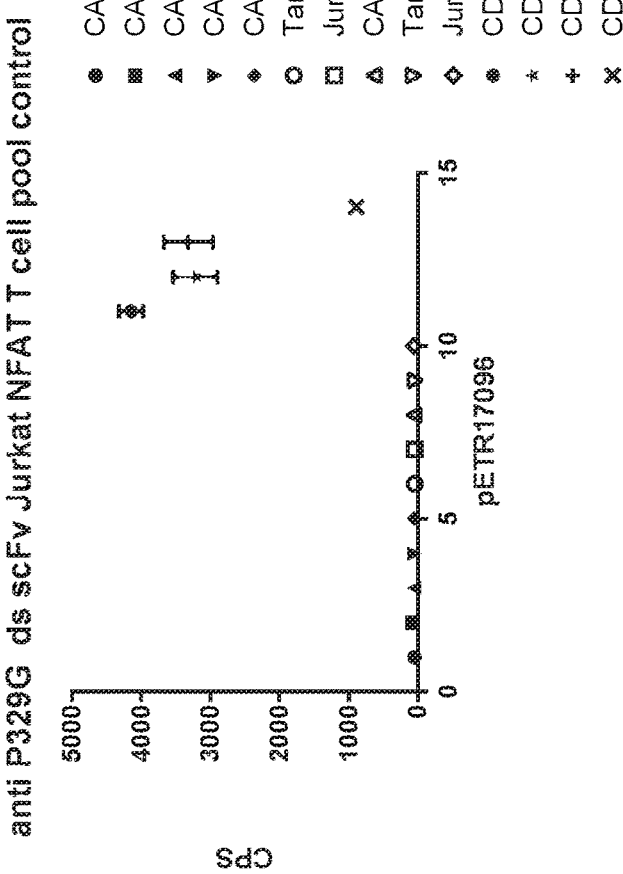
Figure 10C:
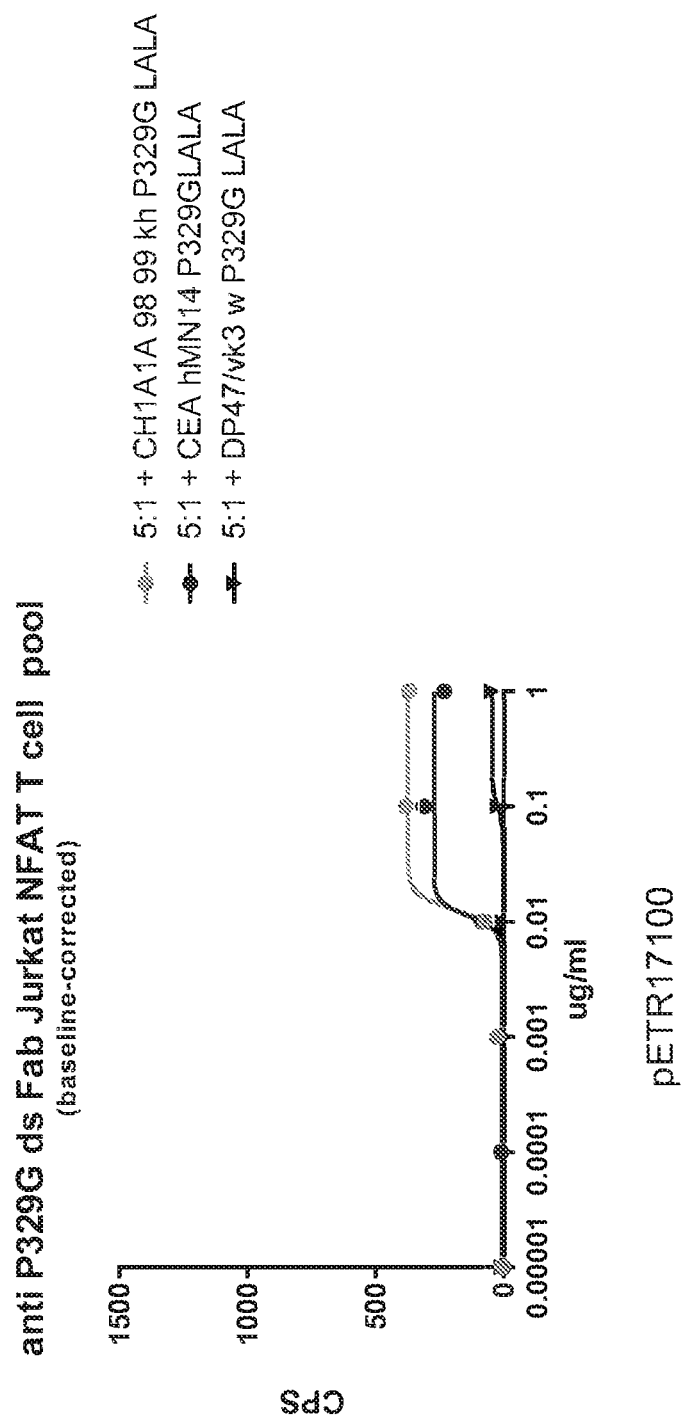
Figure 10D:
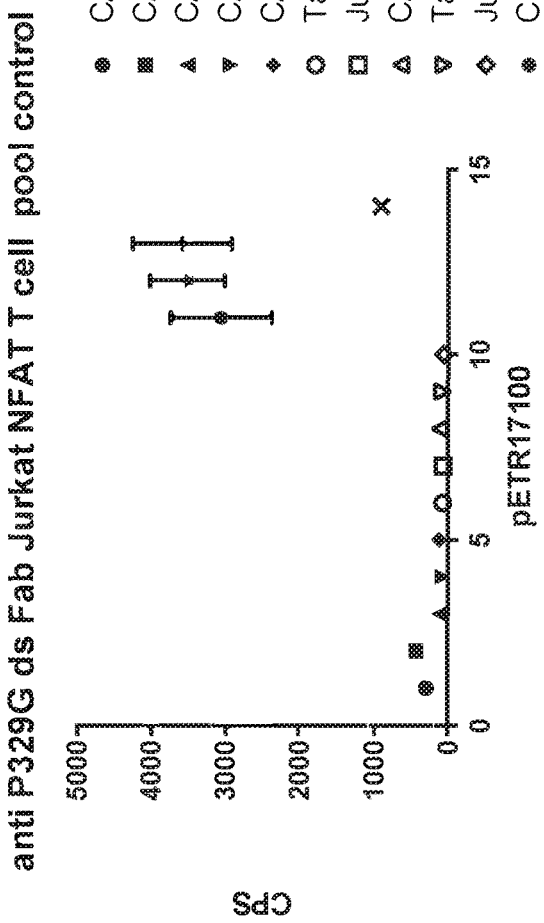

FIGS. 10B and 10D, represent data of Anti-P329G-ds-Fab-CD28ATD-CD28CSD-CD3zSSD expressing Jurkat NFAT T cells (Figure D) or Anti-P329G-ds-scFv-CD28ATD-CD28CSD-CD3zSSD expressing NFAT T cells (FIG. 9D) both co-cultivated with target cells and 1 µg/ml of CEA hMN14 antibody or the CH1A1A 98 99 antibody compared to different control conditions.

All performed control experiments do not show any detectable luminescence signal, except those where CD3 was used as an activation stimulus. Each point represents the mean value of technical triplicates. Standard deviation is indicated by error bars.

Example 6

Described herein is a Jurkat NFAT T cell reporter assay using adherent TNC expressing CT26TNC cl 19 tumor cells as target cells. As effector cells, a sorted pool of Anti-P329G-ds-Fab-CD28ATD-CD28CSD-CD3zSSD expressing Jurkat NFAT T cells (FIG. 11C) or Anti-P329G-ds-scFv-CD28ATD-CD28CSD-CD3zSSD expressing Jurkat NFAT T cells (FIG. 11A) were used. TNCA2B10 with P329G LALA mutation was used as IgG. Further IgG DP47/vk3 harboring P329G LALA mutation was included as isotype control.

As positive control wells of a 96 well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 µg/ml Puromycin.

Effector cells or Jurkat NFAT wild type T cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to $1 \times 10^6$ viable cells/ml in RPMI-1640+10% FCS+1% Glutamax.

Target cells and effector cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and effector cells in a ratio 5:1 (FIGS. 11A and 11C black dots) for 20 h the graphs show a dose-dependent activation of Anti-P329G-ds-Fab-CD28ATD-CD28CSD-CD3zSSD expressing Jurkat NFAT T cells as well as of Anti-P329G-ds-scFv-CD28ATD-CD28CSD-CD3zSSD expressing Jurkat NFAT T cells when TNC A2B10 with P329G LALA mutation was used as antibody. If the control antibody DP47/vk3 IgG with P329G LALA mutation (FIGS. 11A and 11C black dots) was used, neither the activation of Anti-P329G-ds-scFv-CD28ATD-CD28CSD-CD3zSSD expressing Jurkat NFAT T cells nor Anti-P329G-ds-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

Figure 11A:
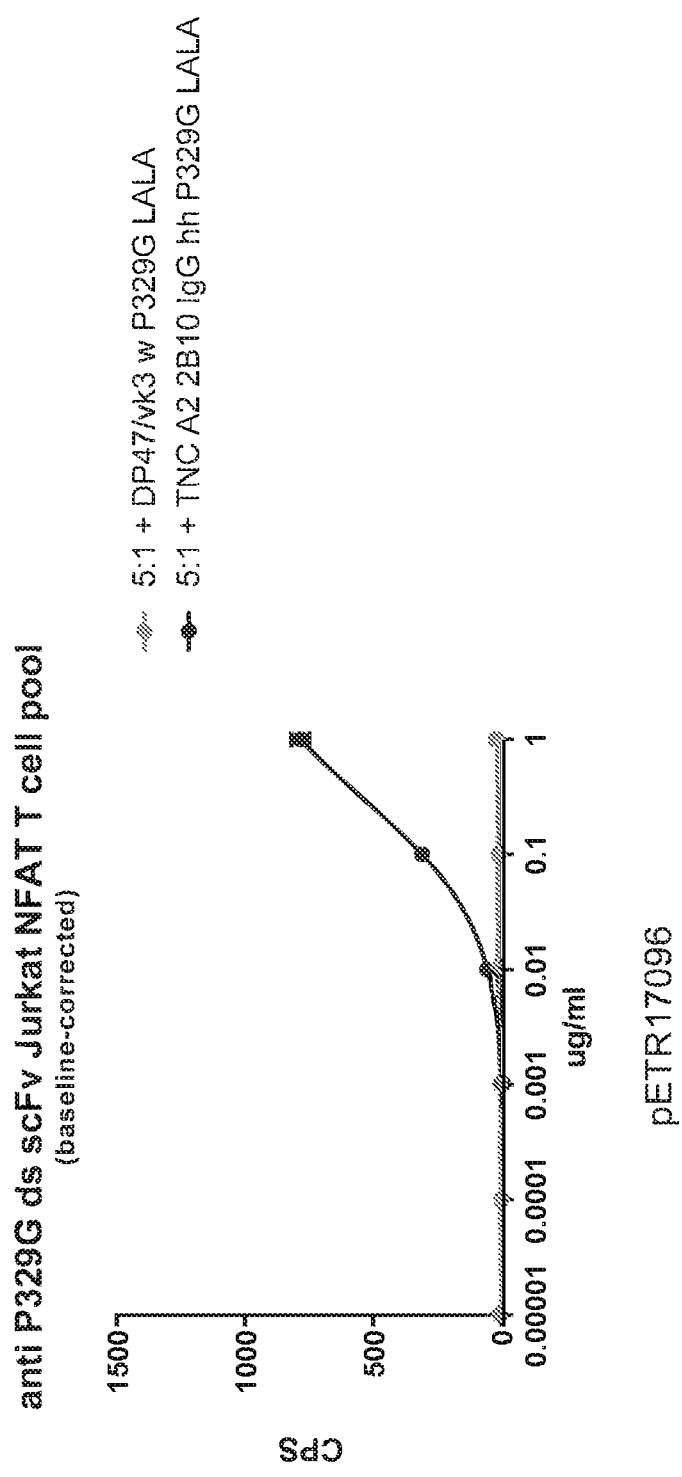
FIGS. 11A-11D depict the Jurkat NFAT T cell reporter assay using adherent TNC expressing CT26TNC cl 19 tumor cells as target cells. The anti-TNC IgG clone A2B10 harboring the P329G mutation was used as IgG antibody which recognizes the tumor associated antigen and is recognized by the Jurkat NFAT T cells expressing antigen binding receptors according to the invention. Further IgG DP47/vk3 harboring P329G mutation was included as isotype control.
Figure 11B:
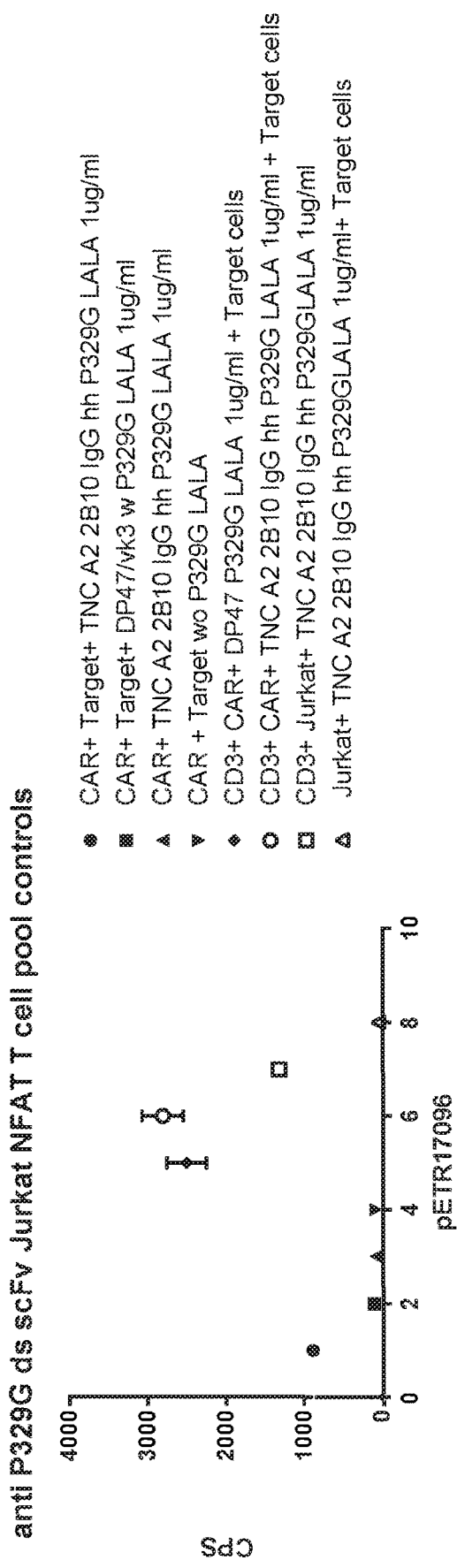
Figure 11C:
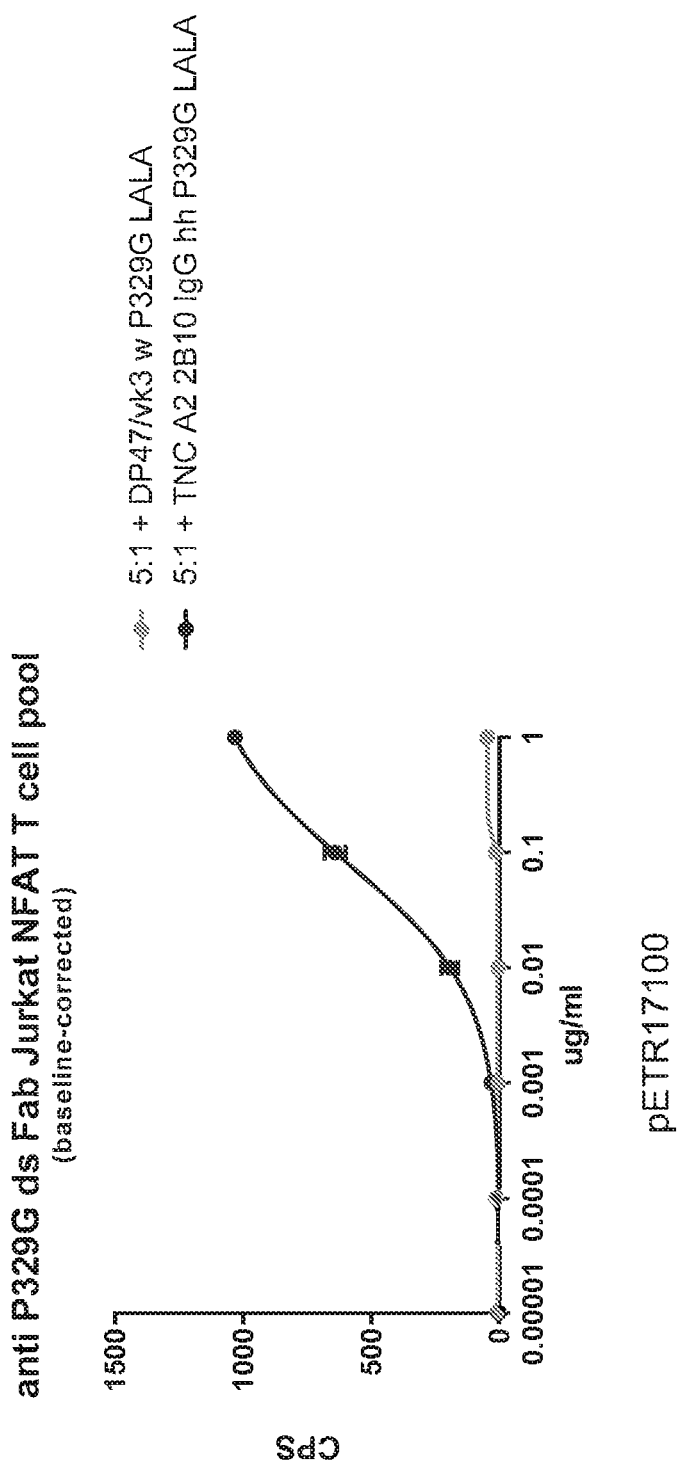
Figure 11D:
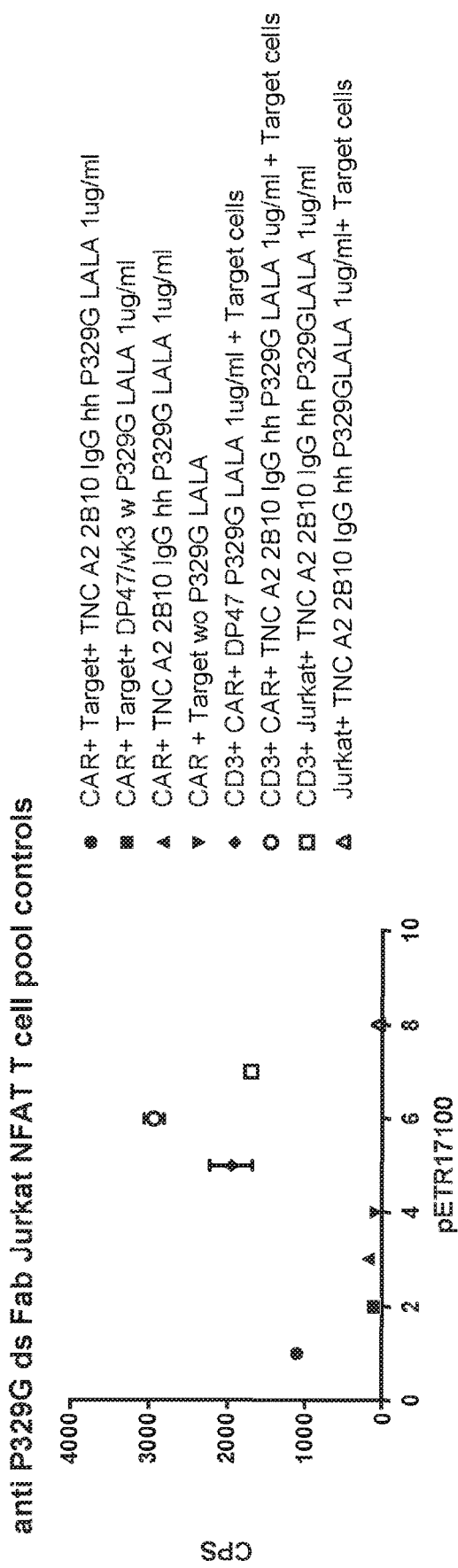

FIGS. 11B and 11D, represent data of Anti-P329G-ds-Fab-CD28ATD-CD28CSD-CD3zSSD expressing Jurkat NFAT T cells (FIG. 11D) or Anti-P329G-ds-scFv-CD28ATD-CD28CSD-CD3zSSD expressing Jurkat NFAT T cells (FIG. 11B) both co-cultivated with target cells and 1 µg/ml of TNC A2B10 compared to different control conditions.

Jurkat NFAT T cells do not show any detectable luminescence signal upon co-cultivation with target cells and 1 µg/ml IgG (FIG. 11B and FIG. 11D white triangle). Whereas CD3 dependent activation of Jurkat NFAT cells co-cultivated with target cells and 1 µg/ml IgG proofs their functionality through a detectable luminescence signal (FIG. 11B and FIG. 11D white square).

CD3 dependent activation of Anti-P329G-ds-Fab-CD28ATD-CD28CSD-CD3zSSD expressing Jurkat NFAT T cells (FIG. 11B white circle) and activation of Anti-P329G-ds-scFv-CD28ATD-CD28CSD-CD3zSSD expressing Jurkat NFAT T cells (FIG. 11D white circle) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 µg/ml of DP47/vk3 antibody (FIG. 11B and FIG. 11D, black diamond). Each point represents the mean value of technical triplicates. Standard deviation is indicated by error bars.

Example 7

Figure 12A:
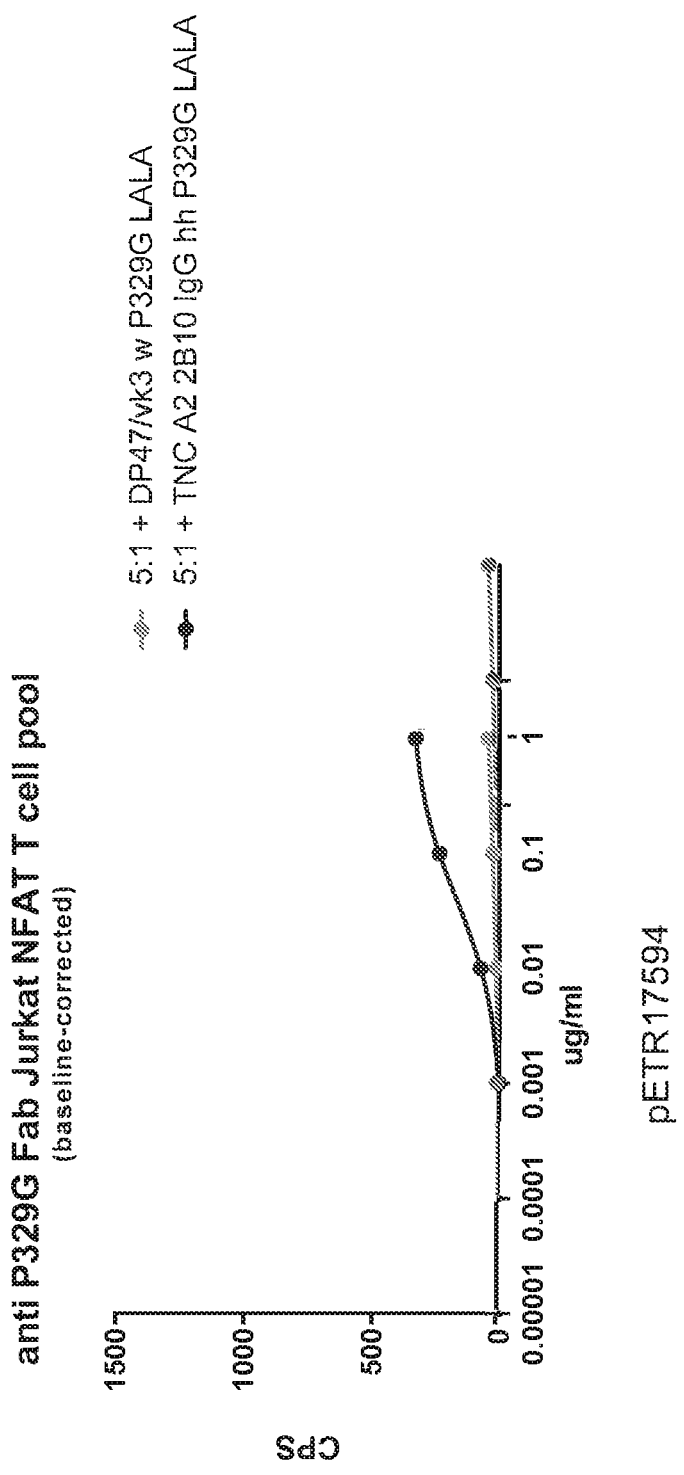
FIG. 12A and FIG. 12B depict the Jurkat NFAT T cell reporter assay using adherent TNC expressing CT26TNC cl 19 tumor cells as target cells. The anti-TNC IgG clone A2B10 harboring the P329G mutation was used which recognizes the tumor associated antigen and is recognized by the Jurkat NFAT T cells expressing antigen binding receptors according to the invention. Further IgG DP47/vk3 harboring P329G mutation was included as isotype control. A sorted pool of anti-P329G-Fab-CD28ATD-CD28CSD-CD3zSSD expressing Jurkat NFAT T cells was used as effector cells.

Described herein is a Jurkat NFAT T cell reporter assay using adherent TNC expressing CT26TNC cl 19 tumor cells as target cells. As effector cells, a sorted pool of Anti-P329G-Fab-CD28ATD-CD28CSD-CD3zSSD expressing Jurkat NFAT T cells (FIG. 12A) was used.

TNCA2B10 with P329G LALA mutation was used as IgG. Further IgG DP47/vk3 harboring P329G LALA mutation was included as isotype control.

As positive control wells of a 96-well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+15 µg/ml Puromycin.

Effector cells or Jurkat NFAT wild type cells were counted and checked for their viability using Cedex HiRes. The cell number was adjusted to 1×10⁶ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the effector cells, to 1×10⁶ viable cells/ml in RPMI-1640+10% FCS+1% Glutamax.

Target cells and effector cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and effector cells in a ratio 5:1 (FIG. 12A black dots) for 20 h the graphs show a dose-dependent activation of Anti-P329G-Fab-CD28ATD-CD28CSD-CD3zSSD expressing Jurkat NFAT T cells beginning with 0.01 µg/ml of TNC A2B10 with P329G LALA mutation. If the control antibody DP47/vk3 IgG with P329G LALA mutation (FIGS. 12A and 12C grey dots) was used, no activation of Anti-P329G-Fab-CD28ATD-CD28CSD-CD3zSSD expressing Jurkat NFAT T cells was detectable. Each point represents the mean value of technical triplicates. All values are depicted as baseline corrected. Standard deviation is indicated by error bars.

Figure 12B:
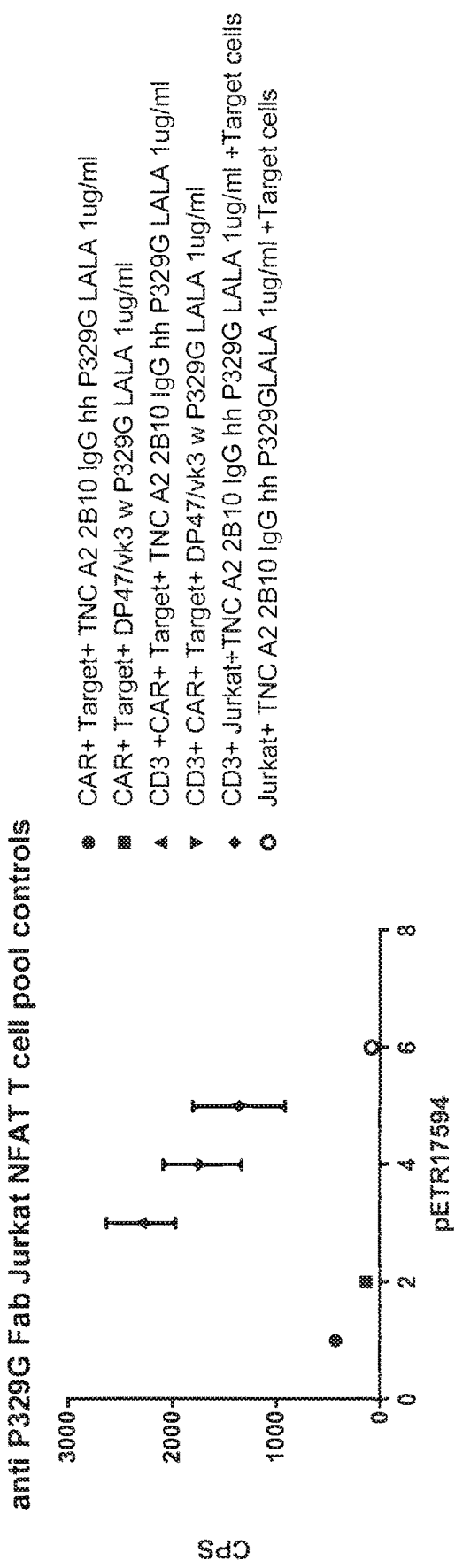

FIG. 12B, represents data of Anti-P329G-Fab-CD28ATD-CD28CSD-CD3zSSD expressing Jurkat NFAT T cells co-cultivated with target cells and 1 µg/ml of TNC A2B10 antibody compared to different control conditions.

Anti-P329G-Fab-CD28ATD-CD28CSD-CD3zSSD expressing Jurkat NFAT T cells incubated with target cells but without antibody (FIG. 12B black square) as well as Jurkat NFAT cells incubated with target cells and 1 µg/ml of TNC A2B10 antibody (FIG. 12B white dots) show no detectable luminescence signal. Whereas Jurkat NFAT cells co-cultured with target cells and 1 µg/ml of TNC A2B10 plated in CD3 coated wells, show a clear luminescence signal.

Further Anti-P329G-CD28ATD-CD28CSD-CD3zSSD Fab expressing Jurkat NFAT T cells incubated with target cells and either 1 µg/ml of TNC A2B10 or 1 µg/ml DP47/vk3 antibody, in CD3 coated wells, show a high luminescence signal. Each point represents the mean value of technical triplicates. Standard deviation is indicated by error bars.

Example 8

Figure 13A:
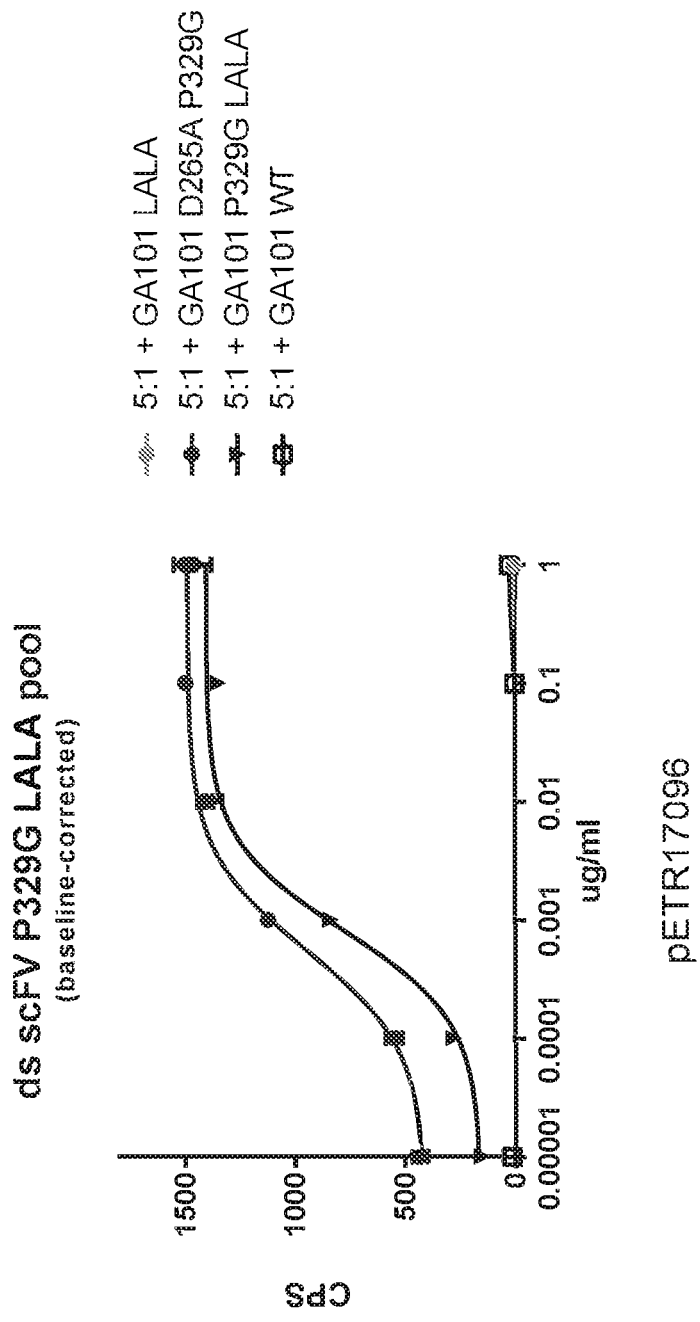
FIG. 13A and FIG. 13B depict the Jurkat NFAT T cell reporter assay using CD20 tumor cells as target cells. Either an anti-CD20 IgG antibody (GA101) harboring the P329G and the LALA mutation, a P329G and D265A mutation, the LALA mutation alone or no mutation at all were used in order to detect the tumor associated antigen and is recognized by the Jurkat NFAT T cells expressing antigen binding receptors according to the invention.
Figure 13B:
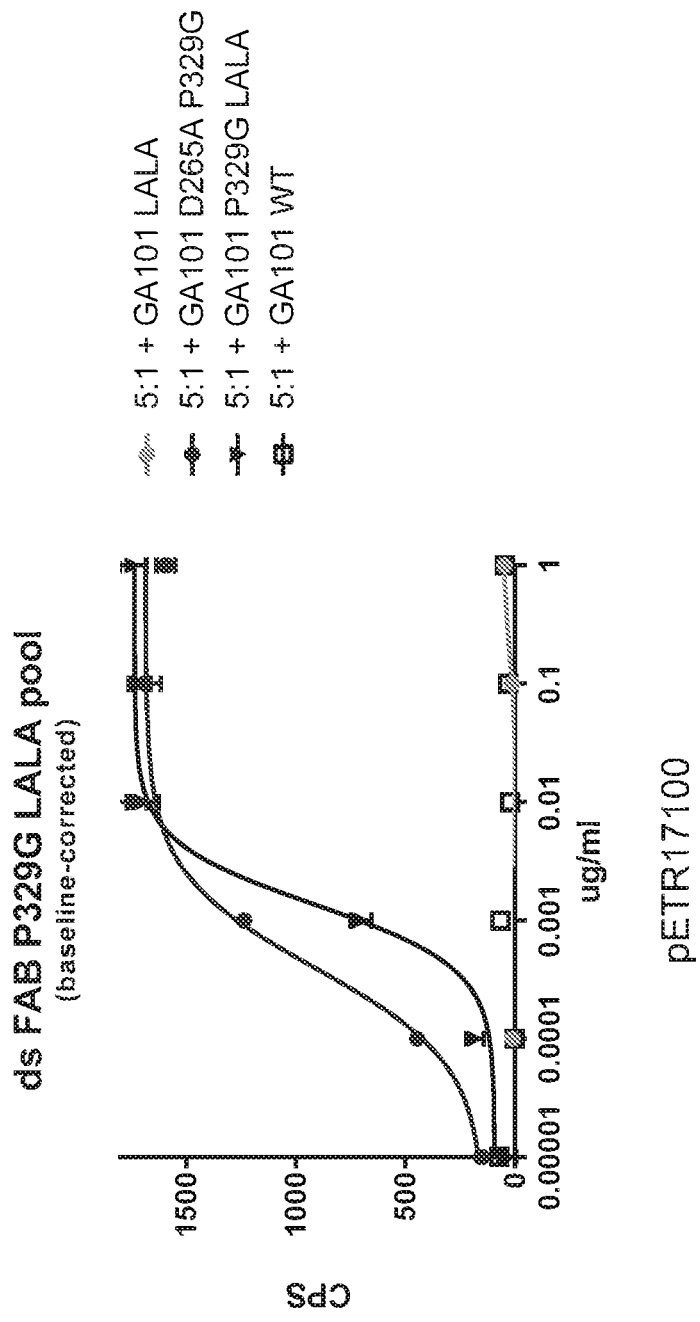

Described herein is a Jurkat NFAT T cell reporter assay using CD20 expressing SUDHDL4 tumor cells as target cells and a pool of Jurkat NFAT cells expressing anti-P329G-ds-scFv-CD28ATD-CD28CSD-CD3zSSD (FIG. 13A) or anti-P329G-ds-Fab-CD28ATD-CD28CSD-CD3zSSD as (FIG. 13B) as effector cells. Either GA101 IgG with P329G LALA, a D265A P329G mutation, a LALA mutation only or no mutation at all was used as IgG which on one hand recognizes the tumor antigen and on the other hand is recognized by the Jurkat NFAT T cells. Effector cells were counted and checked for their viability using Cedex HiRes. The cell number was adjusted to 1×10⁶ viable cells/ml. An appropriate aliquot of the cell suspension was pelleted at 210 g for 5 min at room temperature (RT) and resuspended in fresh RPMI-160+10% FCS+1% Glutamax. Target cells expressing the antigen of interest, were counted and checked for their viability as well. The cell number was adjusted, analog as described for the effector cells, to 1×10⁶ viable cells/ml in growth medium. Target cells and effector cells were plated in 5:1 E:T ratio (110.000 cells per well in total) in triplicates in a 96-well suspension culture plate (Greiner-bio one). As a next step a serial dilution of the different antibodies, targeting the antigen of interest, were prepared in growth medium using a 2 ml deep well plate (Axygen®).

To obtain final concentrations ranging from 1 µg/ml to 10 µg/ml in a final volume of 200 µl per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96 well plate (Greiner-bio-one) and 100 µl ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. The graphs show an dose dependent activation of the target cells only when the antibodies are used that harbor a P329G mutation or the P329G and the LALA mutation but not the LALA mutation alone. Further, no activation of the effector cells is detectable if the GA101 wild type antibody is used.

Example 9

Figure 14A:
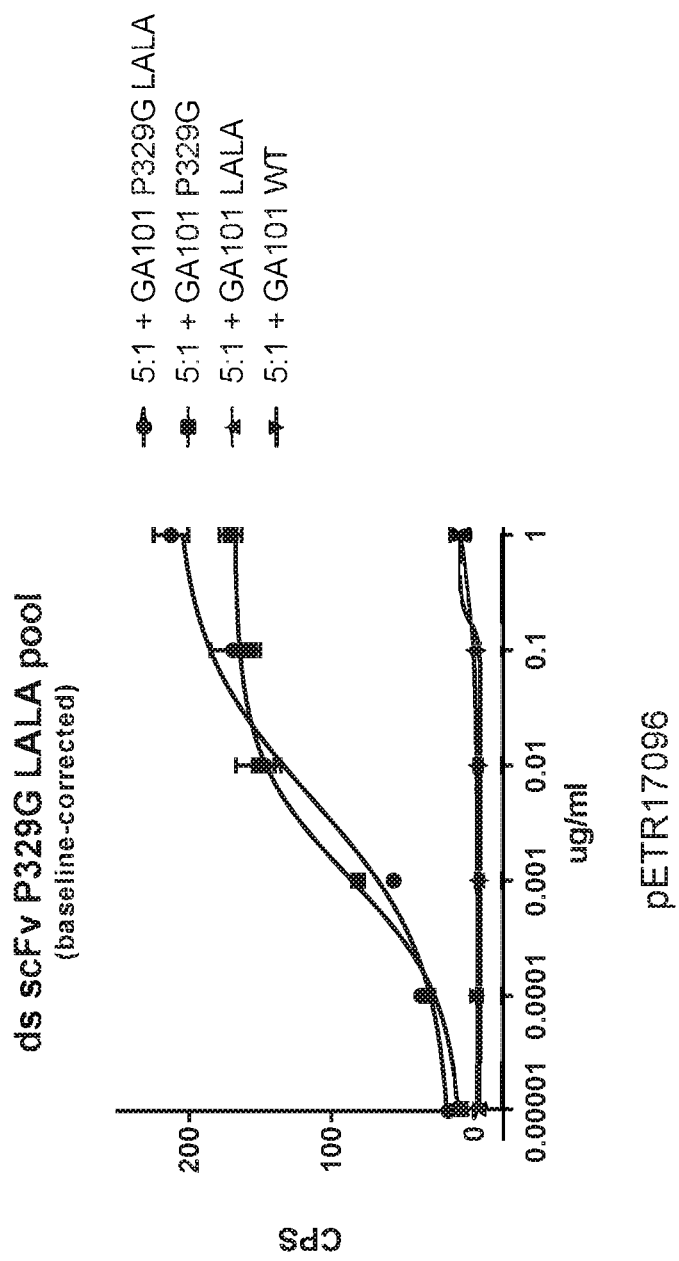
FIG. 14A and FIG. 14B depict the Jurkat NFAT T cell reporter assay using CD20 tumor cells as target cells. Either an anti-CD20 IgG antibody (GA101) harboring the P329G and the LALA mutation, a P329G mutation alone, the LALA mutation alone or no mutation at all were used in order to detect the tumor associated antigen and is recognized by the Jurkat NFAT T cells expressing antigen binding receptors according to the invention.
Figure 14B:
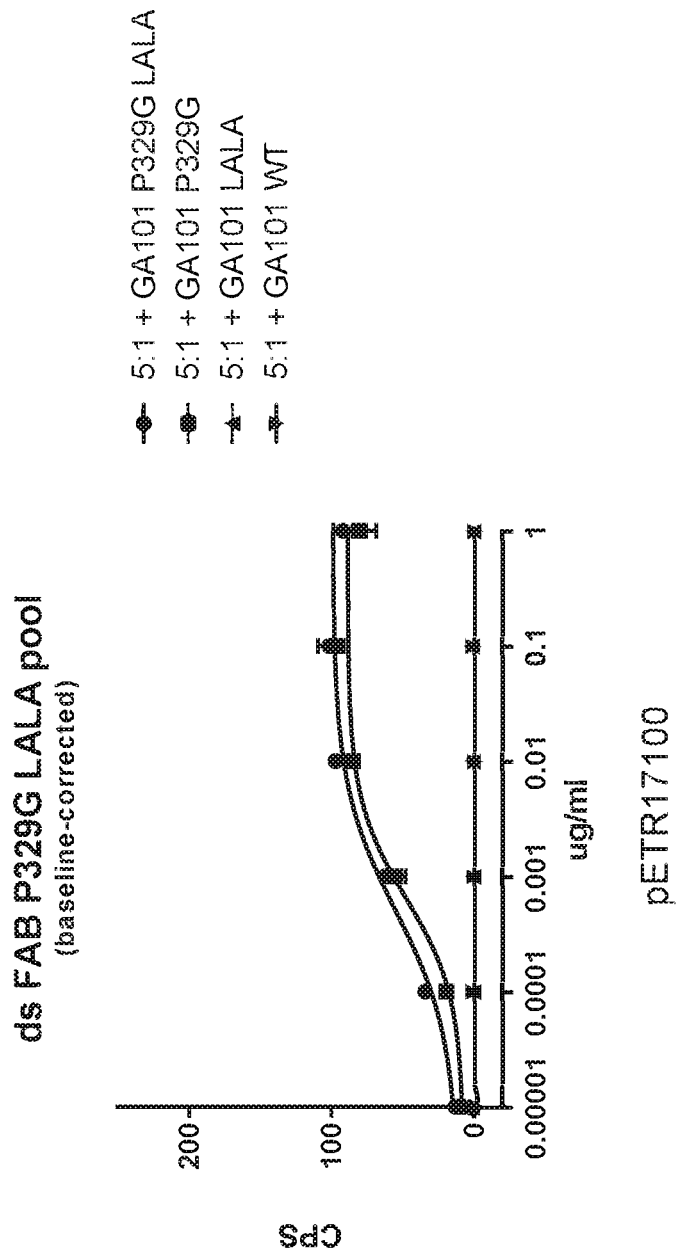

Described herein is a Jurkat NFAT T cell reporter assay using CD20 expressing SUDHDL4 tumor cells as target cells and a pool of Jurkat NFAT cells expressing anti-P329G-ds-scFv-CD28ATD-CD28CSD-CD3zSSD (FIG. 14A) or anti-P329G-ds-Fab-CD28ATD-CD28CSD-CD3zSSD as (FIG. 14B) as effector cells. Either GA101 IgG with P329G LALA, a P329G mutation alone, a LALA mutation only or no mutation at all was used as IgG which on one hand recognizes the tumor antigen and on the other hand is recognized by the Jurkat NFAT T cells. Effector cells were counted and checked for their viability using Cedex HiRes. The cell number was adjusted to 1×10⁶ viable cells/ml. An appropriate aliquot of the cell suspension was pelleted at 210 g for 5 min at room temperature (RT) and resuspended in fresh RPMI-160+10% FCS+1% Glutamax. Target cells expressing the antigen of interest, were counted and checked for their viability as well. The cell number was adjusted, analog as described for the effector cells, to 1×10⁶ viable cells/ml in growth medium. Target cells and effector cells were plated in 5:1 E:T ratio (110.000 cells per well in total) in triplicates in a 384-well plate. As a next step a serial dilution of the different antibodies, targeting the antigen of interest, were prepared in growth medium using a 96 well plate. To obtain final concentrations ranging from 1 µg/ml to 10 µg/ml in a final volume of 30 µl per well, a 10 µl aliquot of the different dilutions was pipetted to the respective wells. The 384 well plate was centrifuged for 2 min at 190 g and RT. Sealed with Parafilm®, the plate was incubated at 37° C. and 5% C02 in a humidity atmosphere. After 20 h incubation, 6 µl of ONE-Glo™ Luciferase Assay (Promega) was added and the readout was performed immediately using a Tecan® Spark10M plate reader, 1 sec/well as detection time. The graphs show a dose dependent activation of the target cells only when the antibodies are used that harbor a P329G mutation or the P329G and the LALA mutation but not the LALA mutation alone. Further, no activation of the effector cells is detectable if the GA101 wild type antibody is used.

EXEMPLARY SEQUENCES

TABLE 2

Anti-P329G-ds-scFv amino acid sequences:

| Construct | Amino acid sequence | SEQ ID NO |
| --- | --- | --- |
| Anti-P329G CDR H1 Kabat | RYWMN | 1 |
| Anti-P329G CDR H2 Kabat | EITPDSSTINYTPSLKD | 2 |
| Anti-P329G CDR H3 Kabat | PYDYGAWFAS | 3 |
| Anti-P329G CDR L1 Kabat | RSSTGAVTTSNYAN | 4 |
| Anti-P329G CDR L2 Kabat | GTNKRAP | 5 |
| Anti-P329G CDR L3 Kabat | ALWYSNHWV | 6 |
| Anti-P329G-ds-scFv-CD28ATD-CD28CSD-CD3zSSD fusion PETR17096 | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQTEDEAIY FCALWYSNHWVFGCGTKLTVLGGGGSFWVLVVVGGV LACYSLLVTVAFIIFWVRSKRSRLLHSDYMNMTPRRPG | 7 |

TABLE 2-continued

Anti-P329G-ds-scFv amino acid sequences:

| Construct | Amino acid sequence | SEQ ID NO |
|---|---|---|
| | PTRKHYQPYAPPRDFAAYRSRVKFSRSADAPAYQQGQ NQLYNELNLGRREEYDVLDKRRGRDPEMGGKPRRKNP QEGLYNELQKDKMAEAYSEIGMKGERRRGKGHDGLY QGLSTATKDTYDALHMQALPPR | |
| Anti-P329G-ds VH | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSA | 8 |
| Anti-P329G-ds VL | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGCGTKLTVL | 9 |
| Anti-P329G-ds-scFv | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQTEDEAIY FCALWYSNHWVFGCGTKLTVL | 10 |
| CD28ATD | FWVLVVVGGVLACYSLLVTVAFIIFWV | 11 |
| CD28CSD | RSKRSRLLHSDYMNMTPRRPGPTRKHYQPYAPPRDFA AYRS | 12 |
| CD3zSSD | RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALP PR | 13 |
| CD28ATD-CD28CSD-CD3zSSD | FWVLVVVGGVLACYSLLVTVAFIIFWVRSKRSRLLHSD YMNMTPRRPGPTRKHYQPYAPPRDFAAYRSRVKFSRS ADAPAYQQGQNQLYNELNLGRREEYDVLDKRRGRDP EMGGKPRRKNPQEGLYNELQKDKMAEAYSEIGMKGE RRRGKGHDGLYQGLSTATKDTYDALHMQALPPR | 14 |
| eGFP | VSKGEELFTGVVPILVELDGDVNGHKFSVSGEGEGDAT YGKLTLKFICTTGKLPVPWPTLVTTLTYGVQCFSRYPD HMKQHDFFKSAMPEGYVQERTIFFKDDGNYKTRAEVK FEGDTLVNRIELKGIDFKEDGNILGHKLEYNYNSHNVYI MADKQKNGIKVNFKIRHNIEDGSVQLADHYQQNTPIG DGPVLLPDNHYLSTQSALSKDPNEKRDHMVLLEFVTA AGITLGMDELYK | 15 |
| (G4S)4 linker | GGGGSGGGGSGGGGSGGGGS | 16 |
| G4S linker | GGGGS | 17 |
| T2A linker | GEGRGSLLTCGDVEENPGP | 18 |

TABLE 3 anti-P329G-ds-scFv DNA sequences:

| Construct | DNA sequence | SEQ ID NO |
|---|---|---|
| Anti-P329G-ds-scFv-CD28ATD-CD28CSD-CD3zSSD fusion PETR17096 | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGTGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC | 19 |

TABLE 3-continued anti-P329G-ds-scFv DNA sequences:

| Construct | DNA sequence | SEQ ID NO |
|---|---|---|
| | GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCTGTGGCACCAAGCTG ACCGTGCTGGGAGGGGCGGATCCTTCTGGGTGCTG GTGGTGGTGGGCGGCGTGCTGGCCTGCTACAGCCTG CTGGTGACCGTGGCCTTCATCATCTTCTGGGTGAGGA GCAAGAGGAGCAGGCTGCTGCACAGCGACTACATGA ACATGACCCCCAGGAGGCCCGGCCCCACCAGGAAGC ACTACCAGCCCTACGCCCCCCCCAGGGACTTCGCCG CCTACAGGAGCAGGGTGAAGTTCAGCAGGAGCGCCG ACGCCCCCGCCTACCAGCAGGGCCAGAACCAGCTGT ATAACGAGCTGAACCTGGGCAGGAGGGAGGAGTAC GACGTGCTGGACAAGAGGAGGGGCAGGGACCCCGA GATGGGCGGCAAGCCCAGGAGGAAGAACCCCCAGG AGGGGCCTGTATAACGAGCTGCAGAAGGACAAGATGG CCGAGGCCTACAGCGAGATCGGCATGAAGGGCGAG AGGAGGAGGGGCAAGGGCCACGACGGCCTGTACCA GGGCCTGAGCACCGCCACCAAGGACACCTACGACGC CCTGCACATGCAGGCCCTGCCCCCCAGG | |
| Anti-P329G-ds VH | GAGGTGAAGCTGCTGGAGAGCGGCGGCGGCCTGGTG CAGCCCGGCGGCAGCCTGAAGCTGAGCTGCGCCGCC AGCGGCTTCGACTTCAGCAGGTACTGGATGAACTGG GTGAGGCAGGCCCCCGGCAAGTGTCTGGAGTGGATC GGCGAGATCACCCCCGACAGCAGCACCATCAACTAC ACCCCCAGCCTGAAGGACAAGTTCATCATCAGCAGG GACAACGCCAAGAACACCCTGTACCTGCAGATGATC AAGGTGAGGAGCGAGGACACCGCCCTGTACTACTGC GTGAGGCCCTACGACTACGGCGCCTGGTTCGCCAGC TGGGGCCAGGGCACCCTGGTGACCGTGAGCGCC | 20 |
| Anti-P329G-ds VL | CAGGCCGTGGTGACCCAGGAGAGCGCCCTGACCACC AGCCCCGGCGAGACCGTGACCCTGACCTGCAGGAGC AGCACCGGCGCCGTGACCACCAGCAACTACGCCAAC TGGGTGCAGGAGAAGCCCGACCACCTGTTCACCGGC CTGATCGGCGGCACCAACAAGAGGGCCCCCGGCGTG CCCGCCAGGTTCAGCGGCAGCCTGATCGGCGACAAG GCCGCCCTGACCATCACCGGCGCCCAGACCGAGGAC GAGGCCATCTACTTCTGCGCCCTGTGGTACAGCAACC ACTGGGTGTTCGGCTGTGGCACCAAGCTGACCGTGC TG | 21 |
| Anti-P329G-ds-scFv | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGTGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGCGGAAGTGGTG GCGGGGAAGCGGCGGGGGTGGCAGCGGAGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCTGTGGCACCAAGCTG ACCGTGC | 22 |

TABLE 3-continued anti-P329G-ds-scFv DNA sequences:

| Construct | DNA sequence | SEQ ID NO |
|---|---|---|
| IRES EV71, internal ribosomal entry side | CCCGAAGTAACTTAGAAGCTGTAAATCAACGATCAA TAGCAGGTGTGGCACACCAGTCATACCTTGATCAAG CACTTCTGTTTCCCCGGACTGAGTATCAATAGGCTGC TCGCGCGGCTGAAGGAGAAAACGTTCGTTACCCGAC CAACTACTTCGAGAAGCTTAGTACCACCATGAACGA GGCAGGGTGTTTCGCTCAGCACAACCCCAGTGTAGA TCAGGCTGATGAGTCACTGCAACCCCCATGGGCGAC CATGGCAGTGGCTGCGTTGGCGGCCTGCCCATGGAG AAATCCATGGGACGCTCTAATTCTGACATGGTGTGA AGTGCCTATTGAGCTAACTGGTAGTCCTCCGGCCCCT GATTGCGGCTAATCCTAACTGCGGAGCACATGCTCA CAAACCAGTGGGTGGTGTGTCGTAACGGGCAACTCT GCAGCGGAACCGACTACTTTGGGTGTCCGTGTTTCCT TTTATTCCTATATTGGCTGCTTATGGTGACAATCAAA AAGTTGTTACCATATAGCTATTGGATTGGCCATCCGG TGTGCAACAGGGCAACTGTTTACCTATTTATTGGTTT TGTACCATTATCACTGAAGTCTGTGATCACTCTCAAA TTCATTTTGACCCTCAACACAATCAAAC | 23 |
| CD28ATD | TTTTGGGTGCTGGTGGTGGTTGGTGGAGTCCTGGCTT GCTATAGCTTGCTAGTAACAGTGGCCTTTATTATTTT CTGGGTG | 24 |
| CD28CSD | AGGAGTAAGAGGAGCAGGCTCCTGCACAGTGACTAC ATGAACATGACTCCCCGCCGCCCCGGGCCCACCCGC AAGCATTACCAGCCCTATGCCCCACCACGCGACTTC GCAGCCTATCGCTCC | 25 |
| CD3zSSD | AGAGTGAAGTTCAGCAGGAGCGCAGACGCCCCCGCG TACCAGCAGGGCCAGAACCAGCTCTATAACGAGCTC AATCTAGGACGAAGAGAGGAGTACGATGTTTTGGAC AAGAGACGTGGCCGGGACCCTGAGATGGGGGGAAA GCCGAGAAGGAAGAACCCTCAGGAAGGCCTGTACA ATGAACTGCAGAAAGATAAGATGGCGGAGGCCTACA GTGAGATTGGGATGAAAGGCGAGCGCCGGAGGGGC AAGGGGCACGATGGCCTTTACCAGGGTCTCAGTACA GCCACCAAGGACACCTACGACGCCCTTCACATGCAG GCCCTGCCCCCTCGC | 26 |
| CD28ATD-CD28CSD-CD3zSSD | TTCTGGGTGCTGGTGGTGGTGGGCGGCGTGCTGGCCT GCTACAGCCTGCTGGTGACCGTGGCCTTCATCATCTT CTGGGTGAGGAGCAAGAGGAGCAGGCTGCTGCACA GCGACTACATGAACATGACCCCCAGGAGGCCCGGCC CCACCAGGAAGCACTACCAGCCCTACGCCCCCCCCA GGGACTTCGCCGCCTACAGGAGCAGGGTGAAGTTCA GCAGGAGCGCCGACGCCCCCGCCTACCAGCAGGGCC AGAACCAGCTGTATAACGAGCTGAACCTGGGCAGGA GGGAGGAGTACGACGTGCTGGACAAGAGGAGGGGC AGGGACCCCGAGATGGGCGGCAAGCCCAGGAGGAA GAACCCCCAGGAGGGCCTGTATAACGAGCTGCAGAA GGACAAGATGGCCGAGGCCTACAGCGAGATCGGCAT GAAGGGCGAGAGGAGGAGGGGCAAGGGCCACGACG GCCTGTACCAGGGCCTGAGCACCGCCACCAAGGACA CCTACGACGCCCTGCACATGCAGGCCCTGCCCCCCA GG | 27 |
| T2A element | TCCGGAGAGGGCAGAGGAAGTCTTCTAACATGCGGT GACGTGGAGGAGAATCCCGGCCCTAGG | 28 |
| eGFP | GTGAGCAAGGGCGAGGAGCTGTTCACCGGGGTGGTG CCCATCCTGGTCGAGCTGGACGGCGACGTAAACGGC CACAAGTTCAGCGTGTCCGGCGAGGGCGAGGGCGAT GCCACCTACGGCAAGCTGACCCTGAAGTTCATCTGC ACCACCGGCAAGCTGCCCGTGCCCTGGCCCACCCTC GTGACCACCCTGACCTACGGCGTGCAGTGCTTCAGC CGCTACCCCGACCACATGAAGCAGCACGACTTCTTC AAGTCCGCCATGCCCGAAGGCTACGTCCAGGAGCGC ACCATCTTCTTCAAGGACGACGGCAACTACAAGACC CGCGCCGAGGTGAAGTTCGAGGGCGACACCCTGGTG AACCGCATCGAGCTGAAGGGCATCGACTTCAAGGAG GACGGCAACATCCTGGGGCACAAGCTGGAGTACAAC TACAACAGCCACAACGTCTATATCATGGCCGACAAG CAGAAGAACGGCATCAAGGTGAACTTCAAGATCCGC CACAACATCGAGGACGGCAGCGTGCAGCTCGCCGAC | 29 |

TABLE 3-continued anti-P329G-ds-scFv DNA sequences:

| Construct | DNA sequence | SEQ ID NO |
|---|---|---|
| | CACTACCAGCAGAACACCCCCATCGGCGACGGCCCC GTGCTGCTGCCCGACAACCACTACCTGAGCACCCAG TCCGCCCTGAGCAAAGACCCCAACGAGAAGCGCGAT CACATGGTCCTGCTGGAGTTCGTGACCGCCGCCGGG ATCACTCTCGGCATGGACGAGCTGTACAAGTGA | |
| Anti-P329G-ds-scFv-CD28ATD-CD28CSD-CD3zSSD-eGFP fusion PETR17096 | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGTGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCTGTGGCACCAAGCTG ACCGTGCTGGGAGGGGCGGATCCTTCTGGGTGCTG GTGGTGGTGGGCGGCGTGCTGGCCTGCTACAGCCTG CTGGTGACCGTGGCCTTCATCATCTTCTGGGTGAGGA GCAAGAGGAGCAGGCTGCTGCACAGCGACTACATGA ACATGACCCCCAGGAGGCCCGGCCCCACCAGGAAGC ACTACCAGCCCTACGCCCCCCCCAGGGACTTCGCCG CCTACAGGAGCAGGGTGAAGTTCAGCAGGAGCGCCG ACGCCCCCGCCTACCAGCAGGGCCAGAACCAGCTGT ATAACGAGCTGAACCTGGGCAGGAGGGAGGAGTAC GACGTGCTGGACAAGAGGAGGGGCAGGGACCCCGA GATGGGCGGCAAGCCCAGGAGGAAGAACCCCCAGG AGGGCCTGTATAACGAGCTGCAGAAGGACAAGATGG CCGAGGCCTACAGCGAGATCGGCATGAAGGGCGAG AGGAGGAGGGGCAAGGGCCACGACGGCCTGTACCA GGGCCTGAGCACCGCCACCAAGGACACCTACGACGC CCTGCACATGCAGGCCCTGCCCCCAGGTCCGGAGA GGGCAGAGGAAGTCTTCTAACATGCGGTGACGTGGA GGAGAATCCCGGCCCTAGGGTGAGCAAGGGCGAGG AGCTGTTCACCGGGGTGGTGCCCATCCTGGTCGAGCT GGACGGCGACGTAAACGGCCACAAGTTCAGCGTGTC CGGCGAGGGCGAGGGCGATGCCACCTACGGCAAGCT GACCCTGAAGTTCATCTGCACCACCGGCAAGCTGCC CGTGCCCTGGCCCACCCTCGTGACCACCCTGACCTAC GGCGTGCAGTGCTTCAGCCGCTACCCCGACCACATG AAGCAGCACGACTTCTTCAAGTCCGCCATGCCCGAA GGCTACGTCCAGGAGCGCACCATCTTCTTCAAGGAC GACGGCAACTACAAGACCCGCGCCGAGGTGAAGTTC GAGGGCGACACCCTGGTGAACCGCATCGAGCTGAAG GGCATCGACTTCAAGGAGGACGGCAACATCCTGGGG CACAAGCTGGAGTACAACTACAACAGCCACAACGTC TATATCATGGCCGACAAGCAGAAGAACGGCATCAAG GTGAACTTCAAGATCCGCCACAACATCGAGGACGGC AGCGTGCAGCTCGCCGACCACTACCAGCAGAACACC CCCATCGGCGACGGCCCCGTGCTGCTGCCCGACAAC CACTACCTGAGCACCCAGTCCGCCCTGAGCAAAGAC CCCAACGAGAAGCGCGATCACATGGTCCTGCTGGAG TTCGTGACCGCCGCCGGGATCACTCTCGGCATGGAC GAGCTGTACAAGTGA | 30 |

TABLE 4

| Anti-P329G-scFv amino acid sequences: | | |
|---|---|---|
| Construct | Amino acid sequence | SEQ ID NO |
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-scFv-CD28ATD-CD28CSD-CD3zSSD fusion | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQTEDEAIY FCALWYSNHWVFGGGTKLTVLGGGGSFWVLVVVGGV LACYSLLVTVAFIIFWVRSKRSRLLHSDYMNMTPRRPG PTRKHYQPYAPPRDFAAYRSRVKFSRSADAPAYQQGQ NQLYNELNLGRREEYDVLDKRRGRDPEMGGKPRRKNP QEGLYNELQKDKMAEAYSEIGMKGERRRGKGHDGLY QGLSTATKDTYDALHMQALPPR | 31 |
| Anti-P329G VH | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSA | 32 |
| Anti-P329G VL | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGGGTKLTVL | 33 |
| Anti-P329G-scFv | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAGGGGGGGGSGGGGSGGGGSQAVVTQESALT TSPGETVTLTCRSSTGAVTTSNYANWVQEKPDHLFTGL IGGTNKRAPGVPARFSGSLIGDKAALTITGAQTEDEAIY FCALWYSNHWVFGGGTKLTVL | 34 |
| CD28ATD | see Table 2 | 11 |
| CD28CSD | see Table 2 | 12 |
| CD3zSSD | see Table 2 | 13 |
| CD28ATD-CD28CDS-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |

TABLE 5

Anti-P329G-scFv DNA sequences:

| Construct | DNA sequence | SEQ ID NO |
|---|---|---|
| Anti-P329G-scFv-CD28ATD-CD28CSD-CD3zSSD fusion | ATGGGATGGAGCTGTATCATCCTCTTCTTGGTAGCAACAGCTACCGGTGTGCATTCCGAGGTGAAGCTGCTGGAGAGCGGCGGCGGCCTGGTGCAGCCCGGCGGCAGCCTGAAGCTGAGCTGCGCCGCCAGCGGCTTCGACTTCAGCAGGTACTGGATGAACTGGGTGAGGCAGGCCCCCGGCAAGGGTCTGGAGTGGATCGGCGAGATCACCCCCGACAGCAGCACCATCAACTACACCCCCAGCCTGAAGGACAAGTTCATCATCAGCAGGGACAACGCCAAGAACACCCTGTACCTGCAGATGATCAAGGTGAGGAGCGAGGACACCGCCCTGTACTACTGCGTGAGGCCCTACGACTACGGCGCCTGGTTCGCCAGCTGGGGCCAGGGCACCCTGGTGACCGTGAGCGCCGGAGGGGCGGAAGTGGTGGCGGGGGAAGCGGCGGGGGTGGCAGCGGAGGGGGCGGATCTCAGGCCGTGGTGACCCAGGAGAGCGCCCTGACCACCAGCCCCGGCGAGACCGTGACCCTGACCTGCAGGAGCAGCACCGGCGCCGTGACCACCAGCAACTACGCCAACTGGGTGCAGGAGAAGCCCGACCACCTGTTCACCGGCCTGATCGGCGGCACCAACAAGAGGGCCCCCGGCGTGCCCGCCAGGTTCAGCGGCAGCCTGATCGGCGACAAGGCCGCCCTGACCATCACCGGCGCCCAGACCGAGGACGAGGCCATCTACTTCTGCGCCCTGTGGTACAGCAACCACTGGGTGTTCGGCGGTGGCACCAAGCTGACCGTGCTGGGAGGGGCGGATCCTTCTGGGTGCTGGTGGTGGTGGGCGGCGTGCTGGCCTGCTACAGCCTGCTGGTGACCGTGGCCTTCATCATCTTCTGGGTGAGGAGCAAGAGGAGCAGGCTGCTGCACAGCGACTACATGAACATGACCCCCAGGAGGCCCGGCCCCACCAGGAAGCACTACCAGCCCTACGCCCCCCCCAGGGACTTCGCCGCCTACAGGAGCAGGGTGAAGTTCAGCAGGAGCGCCGACGCCCCCGCCTACCAGCAGGGCCAGAACCAGCTGTATAACGAGCTGAACCTGGGCAGGAGGGAGGAGTACGACGTGCTGGACAAGAGGAGGGGCAGGGACCCCGAGATGGGCGGCAAGCCCAGGAGGAAGAACCCCCAGGAGGGCCTGTATAACGAGCTGCAGAAGGACAAGATGGCCGAGGCCTACAGCGAGATCGGCATGAAGGGCGAGAGGAGGAGGGGCAAGGGCCACGACGGCCTGTACCAGGGCCTGAGCACCGCCACCAAGGACACCTACGACGCCCTGCACATGCAGGCCCTGCCCCCCAGG | 35 |
| Anti-P329G VH | GAGGTGAAGCTGCTGGAGAGCGGCGGCGGCCTGGTGCAGCCCGGCGGCAGCCTGAAGCTGAGCTGCGCCGCCAGCGGCTTCGACTTCAGCAGGTACTGGATGAACTGGGTGAGGCAGGCCCCCGGCAAGGGTCTGGAGTGGATCGGCGAGATCACCCCCGACAGCAGCACCATCAACTACACCCCCAGCCTGAAGGACAAGTTCATCATCAGCAGGGACAACGCCAAGAACACCCTGTACCTGCAGATGATCAAGGTGAGGAGCGAGGACACCGCCCTGTACTACTGCGTGAGGCCCTACGACTACGGCGCCTGGTTCGCCAGCTGGGGCCAGGGCACCCTGGTGACCGTGAGCGCC | 36 |
| Anti-P329G VL | CAGGCCGTGGTGACCCAGGAGAGCGCCCTGACCACCAGCCCCGGCGAGACCGTGACCCTGACCTGCAGGAGCAGCACCGGCGCCGTGACCACCAGCAACTACGCCAACTGGGTGCAGGAGAAGCCCGACCACCTGTTCACCGGCCTGATCGGCGGCACCAACAAGAGGGCCCCCGGCGTGCCCGCCAGGTTCAGCGGCAGCCTGATCGGCGACAAGGCCGCCCTGACCATCACCGGCGCCCAGACCGAGGACGAGGCCATCTACTTCTGCGCCCTGTGGTACAGCAACCACTGGGTGTTCGGCGGTGGCACCAAGCTGACCGTGCTG | 37 |
| CD28ATD | see Table 3 | 24 |
| CD28CSD | see Table 3 | 25 |
| CD3zSSD | see Table 3 | 26 |
| CD28ATD-CD28CSD-CD3zSSD | see Table 3 | 27 |
| T2A element | see Table 3 | 28 |
| eGFP | see Table 3 | 29 |

TABLE 5-continued

Anti-P329G-scFv DNA sequences:

| Construct | DNA sequence | SEQ ID NO |
|---|---|---|
| Anti-P329G-scFv-CD28ATD-CD28CSD-CD3zSSD-eGFP fusion | ATGGGATGGAGCTGTATCATCCTCTTCTTGGTAGCAACAGCTACCGGTGTGCATTCCGAGGTGAAGCTGCTGGAGAGCGGCGGCGGCCTGGTGCAGCCCGGCGGCAGCCTGAAGCTGAGCTGCGCCGCCAGCGGCTTCGACTTCAGCAGGTACTGGATGAACTGGGTGAGGCAGGCCCCCGGCAAGGGTCTGGAGTGGATCGGCGAGATCACCCCCGACAGCAGCACCATCAACTACACCCCCAGCCTGAAGGACAAGTTCATCATCAGCAGGGACAACGCCAAGAACACCCTGTACCTGCAGATGATCAAGGTGAGGAGCGAGGACACCGCCCTGTACTACTGCGTGAGGCCCTACGACTACGGCGCCTGGTTCGCCAGCTGGGGCCAGGGCACCCTGGTGACCGTGAGCGCCGGAGGGGCGGAAGTGGTGGCGGGGGAAGCGGCGGGGTGGCAGCGGAGGGGCGGATCTCAGGCCGTGGTGACCCAGGAGAGCGCCCTGACCACCAGCCCCGGCGAGACCGTGACCCTGACCTGCAGGAGCAGCACCGGCGCCGTGACCACCAGCAACTACGCCAACTGGGTGCAGGAGAAGCCCGACCACCTGTTCACCGGCCTGATCGGCGGCACCAACAAGAGGGCCCCCGGCGTGCCCGCCAGGTTCAGCGGCAGCCTGATCGGCGACAAGGCCGCCCTGACCATCACCGGCGCCCAGACCGAGGACGAGGCCATCTACTTCTGCGCCCTGTGGTACAGCAACCACTGGGTGTTCGGCGGTGGCACCAAGCTGACCGTGCTGGGAGGGGCGGATCCTTCTGGGTGCTGGTGGTGGTGGGCGGCGTGCTGGCCTGCTACAGCCTGCTGGTGACCGTGGCCTTCATCATCTTCTGGGTGAGGAGCAAGAGGAGCAGGCTGCTGCACAGCGACTACATGAACATGACCCCCAGGAGGCCCGGCCCCACCAGGAAGCACTACCAGCCCTACGCCCCCCCCAGGGACTTCGCCGCCTACAGGAGCAGGGTGAAGTTCAGCAGGAGCGCCGACGCCCCCGCCTACCAGCAGGGCCAGAACCAGCTGTATAACGAGCTGAACCTGGGCAGGAGGGAGGAGTACGACGTGCTGGACAAGAGGAGGGGCAGGGACCCCGAGATGGGCGGCAAGCCCAGGAGGAAGAACCCCCAGGAGGGCCTGTATAACGAGCTGCAGAAGGACAAGATGGCCGAGGCCTACAGCGAGATCGGCATGAAGGGCGAGAGGAGGAGGGGCAAGGGCCACGACGGCCTGTACCAGGGCCTGAGCACCGCCACCAAGGACACCTACGACGCCCTGCACATGCAGGCCCTGCCCCCCAGGTCCGGAGAGGGCAGAGGAAGTCTTCTAACATGCGGTGACGTGGAGGAGAATCCCGGCCCTAGGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAACGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAACCACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACAAGTGA | 38 |

TABLE 6

Anti-P329G-ds-Fab amino acid sequences

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |

TABLE 6-continued

Anti-P329G-ds-Fab amino acid sequences

| Construct | Amino acid sequence | SEQ ID NO |
|---|---|---|
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-ds-Fab-heavy chain-CD28ATD-CD28CSD-CD3zSSD fusion PETR17100 | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCGGGGS FWVLVVVGGVLACYSLLVTVAFIIFWVRSKRSRLLHSD YMNMTPRRPGPTRKHYQPYAPPRDFAAYRSRVKESRS ADAPAYQQGQNQLYNELNLGRREEYDVLDKRRGRDP EMGGKPRRKNPQEGLYNELQKDKMAEAYSEIGMKGE RRRGKGHDGLYQGLSTATKDTYDALHMQALPPR | 39 |
| Anti-P329G-ds-Fab heavy chain | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 40 |
| Anti-P329G-ds-Fab light chain | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGCGTKLTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 41 |
| Anti-P329G-ds VL | see Table 2 | 9 |
| CL | RTVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 42 |
| Anti-P329G-ds VH | see Table 2 | 8 |
| CH1 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC | 43 |
| CD28ATD-CD28CSD-CD3zSSD | see Table 2 | 14 |

TABLE 7

Anti-P329G-ds-Fab DNA sequences:

| Construct | DNA Sequence | SEQ ID NO |
|---|---|---|
| Anti-P329G-ds-Fab-heavy chain-CD28ATD-CD28CSD-CD3zSSD fusion PETR17100 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCT GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG | 44 |

TABLE 7-continued

Anti-P329G-ds-Fab DNA sequences:

| Construct | DNA Sequence | SEQ ID NO |
|---|---|---|
| | AAGGTGGATAACGCCCTCCAATCGGGTAACTCCCAG<br>GAGAGTGTCACAGAGCAGGACAGCAAGGACAGCAC<br>CTACAGCCTCAGCAGCACCCTGACGCTGAGCAAAGC<br>AGACTACGAGAAACACAAAGTCTACGCCTGCGAAGT<br>CACCCATCAGGGCCTGAGCTCGCCCGTCACAAAGAG<br>CTTCAACAGGGGAGAGTGTTAGGAATTCCCCGAAGT<br>AACTTAGAAGCTGTAAATCAACGATCAATAGCAGGT<br>GTGGCACACCAGTCATACCTTGATCAAGCACTTCTGT<br>TTCCCCGGACTGAGTATCAATAGGCTGCTCGCGCGG<br>CTGAAGGAGAAAACGTTCGTTACCCGACCAACTACT<br>TCGAGAAGCTTAGTACCACCATGAACGAGGCAGGGT<br>GTTTCGCTCAGCACAACCCCAGTGTAGATCAGGCTG<br>ATGAGTCACTGCAACCCCCATGGGCGACCATGGCAG<br>TGGCTGCGTTGGCGGCCTGCCCATGGAGAAATCCAT<br>GGGACGCTCTAATTCTGACATGGTGTGAAGTGCCTAT<br>TGAGCTAACTGGTAGTCCTCCGGCCCCTGATTGCGGC<br>TAATCCTAACTGCGGAGCACATGCTCACAAACCAGT<br>GGGTGGTGTGTCGTAACGGGCAACTCTGCAGCGGAA<br>CCGACTACTTTGGGTGTCCGTGTTTCCTTTTATTCCTA<br>TATTGGCTGCTTATGGTGACAATCAAAAAGTTGTTAC<br>CATATAGCTATTGGATTGGCCATCCGGTGTGCAACA<br>GGGCAACTGTTTACCTATTTATTGGTTTTGTACCATT<br>ATCACTGAAGTCTGTGATCACTCTCAAATTCATTTTG<br>ACCCTCAACACAATCAAACGCCACCATGGGATGGAG<br>CTGTATCATCCTCTTCTTGGTAGCAACAGCTACCGGT<br>GTGCACTCCGAGGTGAAGCTGCTGGAGAGCGGCGGC<br>GGCCTGGTGCAGCCCGGCGGCAGCCTGAAGCTGAGC<br>TGCGCCGCCAGCGGCTTCGACTTCAGCAGGTACTGG<br>ATGAACTGGGTGAGGCAGGCCCCCGGCAAGTGTCTG<br>GAGTGGATCGGCGAGATCACCCCCGACAGCAGCACC<br>ATCAACTACACCCCCAGCCTGAAGGACAAGTTCATC<br>ATCAGCAGGGACAACGCCAAGAACACCCTGTACCTG<br>CAGATGATCAAGGTGAGGAGCGAGGACACCGCCCTG<br>TACTACTGCGTGAGGCCCTACGACTACGGCGCCTGG<br>TTCGCCAGCTGGGGCCAGGGCACCCTGGTGACCGTG<br>AGCGCCGCTAGCACCAAGGGCCCCTCCGTGTTCCCC<br>CTGGCCCCCAGCAGCAAGAGCACCAGCGGCGGCACA<br>GCCGCTCTGGGCTGCCTGGTCAAGGACTACTTCCCCG<br>AGCCCGTGACCGTGTCCTGGAACAGCGGAGCCCTGA<br>CCTCCGGCGTGCACACCTTCCCCGCCGTGCTGCAGAG<br>TTCTGGCCTGTATAGCCTGAGCAGCGTGGTCACCGTG<br>CCTTCTAGCAGCCTGGGCACCCAGACCTACATCTGCA<br>ACGTGAACCACAAGCCCAGCAACACCAAGGTGGACA<br>AGAAGGTGGAGCCCAAGAGCTGCGGAGGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGG | |
| Anti-P329G-ds VL | see Table 3 | 21 |
| CL | CGTACGGTGGCTGCACCATCTGTCTTCATCTTCCCGC<br>CATCTGATGAGCAGTTGAAATCTGGAACTGCCTCTGT<br>TGTGTGCCTGCTGAATAACTTCTATCCCAGAGAGGCC<br>AAAGTACAGTGGAAGGTGGATAACGCCCTCCAATCG<br>GGTAACTCCCAGGAGAGTGTCACAGAGCAGGACAGC<br>AAGGACAGCACCTACAGCCTCAGCAGCACCCTGACG<br>CTGAGCAAAGCAGACTACGAGAAACACAAAGTCTAC<br>GCCTGCGAAGTCACCCATCAGGGCCTGAGCTCGCCC<br>GTCACAAAGAGCTTCAACAGGGGAGAGTGTTAG | 45 |

TABLE 7-continued

Anti-P329G-ds-Fab DNA sequences:

| Construct | DNA Sequence | SEQ ID NO |
|---|---|---|
| Anti-P329G-ds VH | see Table 3 | 20 |
| CH1 | GCTAGCACCAAGGGCCCCTCCGTGTTCCCCCTGGCCC CCAGCAGCAAGAGCACCAGCGGCGGCACAGCCGCTC TGGGCTGCCTGGTCAAGGACTACTTCCCCGAGCCCGT GACCGTGTCCTGGAACAGCGGAGCCCTGACCTCCGG CGTGCACACCTTCCCCGCCGTGCTGCAGAGTTCTGGC CTGTATAGCCTGAGCAGCGTGGTCACCGTGCCTTCTA GCAGCCTGGGCACCCAGACCTACATCTGCAACGTGA ACCACAAGCCCAGCAACACCAAGGTGGACAAGAAG GTGGAGCCCAAGAGCTGC | 46 |
| CD28ATD-CD28CSD-CD3zSSD | see Table 3 | 27 |
| Anti-P329G-ds-Fab-heavy chain-CD28ATD-CD28CSD-CD3ZSSD-eGFP fusion PETR17100 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCT GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT CACCCATCAGGGCCTGAGCTCGCCCGTCACAAAGAG CTTCAACAGGGGAGAGTGTTAGGAATTCCCCGAAGT AACTTAGAAGCTGTAAATCAACGATCAATAGCAGGT GTGGCACACCAGTCATACCTTGATCAAGCACTTCTGT TTCCCCGGACTGAGTATCAATAGGCTGCTCGCGCGG CTGAAGGAGAAAACGTTCGTTACCCGACCAACTACT TCGAGAAGCTTAGTACCACCATGAACGAGGCAGGGT GTTTCGCTCAGCACAACCCCAGTGTAGATCAGGCTG ATGAGTCACTGCAACCCCCATGGGACCATGGCAG TGGCTGCGTTGGCGGCCTGCCCATGGAGAAATCCAT GGGACGCTCTAATTCTGACATGGTGTGAAGTGCCTAT TGAGCTAACTGGTAGTCCTCCGGCCCCTGATTGCGGC TAATCCTAACTGCGGAGCACATGCTCACAAACCAGT GGGTGGTGTGTCGTAACGGGCAACTCTGCAGCGGAA CCGACTACTTTGGGTGTCCGTGTTTCCTTTTATTCCTA TATTGGCTGCTTATGGTGACAATCAAAAAGTTGTTAC CATATAGCTATTGGATTGGCCATCCGGTGTGCAACA GGGCAACTGTTTACCTATTTATTGGTTTTGTACCATT ATCACTGAAGTCTGTGATCACTCTCAAATTCATTTTG ACCCTCAACACAATCAAACGCCACCATGGGATGGAG CTGTATCATCCTCTTCTTGGTAGCAACAGCTACCGGT GTGCACTCCGAGGTGAAGCTGCTGGAGAGCGGCGGC GGCCTGGTGCAGCCCGGCGGCAGCCTGAAGCTGAGC TGCGCCGCCAGCGGCTTCGACTTCAGCAGGTACTGG ATGAACTGGGTGAGGCAGGCCCCCGGCAAGTGTCTG GAGTGGATCGGCGAGATCACCCCCGACAGCAGCACC ATCAACTACACCCCCAGCCTGAAGGACAAGTTCATC ATCAGCAGGGACAACGCCAAGAACACCCTGTACCTG CAGATGATCAAGGTGAGGAGCGAGGACACCGCCCTG TACTACTGCGTGAGGCCCTACGACTACGGCGCCTGG TTCGCCAGCTGGGGCCAGGGCACCCTGGTGACCGTG AGCGCCGCTAGCACCAAGGGCCCCTCCGTGTTCCCC CTGGCCCCCAGCAGCAAGAGCACCAGCGGCGGCACA GCCGCTCTGGGCTGCCTGGTCAAGGACTACTTCCCCG AGCCCGTGACCGTGTCCTGGAACAGCGGAGCCCTGA CCTCCGGCGTGCACACCTTCCCCGCCGTGCTGCAGAG TTCTGGCCTGTATAGCCTGAGCAGCGTGGTCACCGTG CCTTCTAGCAGCCTGGGCACCCAGACCTACATCTGCA ACGTGAACCACAAGCCCAGCAACACCAAGGTGGACA AGAAGGTGGAGCCCAAGAGCTGCGAGGGGCGGA TCCTTCTGGGTGCTGGTGGTGGTGGGCGGCGTGCTGG CCTGCTACAGCCTGCTGGTGACCGTGGCCTTCATCAT CTTCTGGGTGAGGAGCAAGAGGAGCAGGCTGCTGCA | 47 |

TABLE 7-continued

Anti-P329G-ds-Fab DNA sequences:

| Construct | DNA Sequence | SEQ ID NO |
|---|---|---|
| | CAGCGACTACATGAACATGACCCCCAGGAGGCCCGG | |
| | CCCCACCAGGAAGCACTACCAGCCCTACGCCCCCCC | |
| | CAGGGACTTCGCCGCCTACAGGAGCAGGGTGAAGTT | |
| | CAGCAGGAGCGCCGACGCCCCCGCCTACCAGCAGGG | |
| | CCAGAACCAGCTGTATAACGAGCTGAACCTGGGCAG | |
| | GAGGGAGGAGTACGACGTGCTGGACAAGAGGAGGG | |
| | GCAGGGACCCCGAGATGGGCGGCAAGCCCAGGAGG | |
| | AAGAACCCCCAGGAGGGCCTGTATAACGAGCTGCAG | |
| | AAGGACAAGATGGCCGAGGCCTACAGCGAGATCGG | |
| | CATGAAGGGCGAGAGGAGGAGGGGCAAGGGCCACG | |
| | ACGGCCTGTACCAGGGCCTGAGCACCGCCACCAAGG | |
| | ACACCTACGACGCCCTGCACATGCAGGCCCTGCCCC | |
| | CCAGGTCCGGAGAGGGCAGAGGAAGTCTTCTAACAT | |
| | GCGGTGACGTGGAGGAGAATCCCGGCCCTAGGGTGA | |
| | GCAAGGGCGAGGAGCTGTTCACCGGGGTGGTGCCCA | |
| | TCCTGGTCGAGCTGGACGGCGACGTAAACGGCCACA | |
| | AGTTCAGCGTGTCCGGCGAGGGCGAGGGCGATGCCA | |
| | CCTACGGCAAGCTGACCCTGAAGTTCATCTGCACCA | |
| | CCGGCAAGCTGCCCGTGCCCTGGCCCACCCTCGTGA | |
| | CCACCCTGACCTACGGCGTGCAGTGCTTCAGCCGCTA | |
| | CCCCGACCACATGAAGCAGCACGACTTCTTCAAGTC | |
| | CGCCATGCCCGAAGGCTACGTCCAGGAGCGCACCAT | |
| | CTTCTTCAAGGACGACGGCAACTACAAGACCCGCGC | |
| | CGAGGTGAAGTTCGAGGGCGACACCCTGGTGAACCG | |
| | CATCGAGCTGAAGGGCATCGACTTCAAGGAGGACGG | |
| | CAACATCCTGGGGCACAAGCTGGAGTACAACTACAA | |
| | CAGCCACAACGTCTATATCATGGCCGACAAGCAGAA | |
| | GAACGGCATCAAGGTGAACTTCAAGATCCGCCACAA | |
| | CATCGAGGACGGCAGCGTGCAGCTCGCCGACCACTA | |
| | CCAGCAGAACACCCCCATCGGCGACGGCCCCGTGCT | |
| | GCTGCCCGACAACCACTACCTGAGCACCCAGTCCGC | |
| | CCTGAGCAAAGACCCCAACGAGAAGCGCGATCACAT | |
| | GGTCCTGCTGGAGTTCGTGACCGCCGCCGGGATCAC | |
| | TCTCGGCATGGACGAGCTGTACAAGTGA | |

TABLE 8

Anti-P329G-Fab amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-Fab-heavy chain-CD28ATD-CD28CSD-CD3zSSD fusion PETR17594 | EVKLLESGGGLVQPGGSLKLSCAASGFDFSR YWMNWVRQAPGKGLEWIGEITPDSSTINYTP SLKDKFIISRDNAKNTLYLQMIKVRSEDTAL YYCVRPYDYGAWFASWGQGTLVTVSAASTKG PSVFPLAPSSKSTSGGTAALGCLVKDYFPEP VTVSWNSGALTSGVHTFPAVLQSSGLYSLSS VVTVPSSSLGTQTYICNVNHKPSNTKVDKKV EPKSCGGGGSFWVLVVVGGVLACYSLLVTVA FIIFWVRSKRSRLLHSDYMNMTPRRPGPTRK HYQPYAPPRDFAAYRSRVKFSRSADAPAYQQ GQNQLYNELNLGRREEYDVLDKRRGRDPEMG GKPRRKNPQEGLYNELQKDKMAEAYSEIGMK GERRRGKGHDGLYQGLSTATKDTYDALHMQA LPPR | 48 |
| Anti-P329G-Fab heavy chain | EVKLLESGGGLVQPGGSLKLSCAASGFDFSR YWMNWVRQAPGKGLEWIGEITPDSSTINYTP SLKDKFIISRDNAKNTLYLQMIKVRSEDTAL YYCVRPYDYGAWFASWGQGTLVTVSAASTKG PSVFPLAPSSKSTSGGTAALGCLVKDYFPEP VTVSWNSGALTSGVHTFPAVLQSSGLYSLSS VVTVPSSSLGTQTYICNVNHKPSNTKVDKKV EPKSC | 49 |
| Anti-P329G-Fab light chain | QAVVTQESALTTSPGETVTLTCRSSTGAVTT SNYANWVQEKPDHLFTGLIGGTNKRAPGVPA RFSGSLIGDKAALTITGAQTEDEAIYFCALW YSNHWVFGGGTKLTVLRTVAAPSVFIFPPSD EQLKSGTASVVCLLNNFYPREAKVQWKVDNA LQSGNSQESVTEQDSKDSTYSLSSTLTLSKA | 50 |

TABLE 8-continued

Anti-P329G-Fab amino acid sequences:

| Construct | Amino acid sequence | SEQ ID NO |
|---|---|---|
|  | DYEKHKVYACEVTHQGLSSPVTKSFNRGEC |  |
| Anti-P329G VL | see Table 4 | 33 |
| CL | see Table 6 | 42 |

TABLE 8-continued

Anti-P329G-Fab amino acid sequences:

| Construct | Amino acid sequence | SEQ ID NO |
|---|---|---|
| Anti-P329G VH | see Table 4 | 32 |
| CH1 | see Table 6 | 43 |
| CD28ATD-CD28CSD-CD3zSSD | see Table 2 | 14 |

TABLE 9

Anti-P329G-Fab DNA sequences:

| Construct | DNA Sequence | SEQ ID NO |
|---|---|---|
| Anti-P329G-Fab-heavy chain-CD28ATD-CD28CSD-CD3zSSD fusion PETR17594 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCG GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT CACCCATCAGGGCCTGAGCTCGCCCGTCACAAAGAG CTTCAACAGGGGAGAGTGTTAGGAATTCCCCGAAGT AACTTAGAAGCTGTAAATCAACGATCAATAGCAGGT GTGGCACACCAGTCATACCTTGATCAAGCACTTCTGT TTCCCCGGACTGAGTATCAATAGGCTGCTCGCGCGG CTGAAGGAGAAAACGTTCGTTACCCGACCAACTACT TCGAGAAGCTTAGTACCACCATGAACGAGGCAGGGT GTTTCGCTCAGCACAACCCCAGTGTAGATCAGGCTG ATGAGTCACTGCAACCCCCATGGGCGACCATGGCAG TGGCTGCGTTGGCGGCCTGCCCATGGAGAAATCCAT GGGACGCTCTAATTCTGACATGGTGTGAAGTGCCTAT TGAGCTAACTGGTAGTCCTCCGGCCCCTGATTGCGGC TAATCCTAACTGCGGAGCACATGCTCACAAACCAGT GGGTGGTGTGTCGTAACGGGCAACTCTGCAGCGGAA CCGACTACTTTGGGTGTCCGTGTTTCCTTTTATTCCTA TATTGGCTGCTTATGGTGACAATCAAAAAGTTGTTAC CATATAGCTATTGGATTGGCCATCCGGTGTGCAACA GGGCAACTGTTTACCTATTTATTGGTTTTGTACCATT ATCACTGAAGTCTGTGATCACTCTCAAATTCATTTTG ACCCTCAACACAATCAAACGCCACCATGGGATGGAG CTGTATCATCCTCTTCTTGGTAGCAACAGCTACCGGT GTGCACTCCGAGGTGAAGCTGCTGGAGAGCGGCGGC GGCCTGGTGCAGCCCGGCGGCAGCCTGAAGCTGAGC TGCGCCGCCAGCGGCTTCGACTTCAGCAGGTACTGG ATGAACTGGGTGAGGCAGGCCCCCGGCAAGGGTCTG GAGTGGATCGGCGAGATCACCCCCGACAGCAGCACC ATCAACTACACCCCCAGCCTGAAGGACAAGTTCATC ATCAGCAGGGACAACGCCAAGAACACCCTGTACCTG CAGATGATCAAGGTGAGGAGCGAGGACACCGCCCTG TACTACTGCGTGAGGCCCTACGACTACGGCGCCTGG TTCGCCAGCTGGGGCCAGGGCACCCTGGTGACCGTG AGCGCCGCTAGCACCAAGGGCCCCTCCGTGTTCCCC CTGGCCCCCAGCAGCAAGAGCACCAGCGGCGGCACA GCCGCTCTGGGCTGCCTGGTCAAGGACTACTTCCCCG AGCCCGTGACCGTGTCCTGGAACAGCGGAGCCCTGA CCTCCGGCGTGCACACCTTCCCCGCCGTGCTGCAGAG TTCTGGCCTGTATAGCCTGAGCAGCGTGGTCACCGTG CCTTCTAGCAGCCTGGGCACCCAGACCTACATCTGCA | 51 |

TABLE 9-continued

Anti-P329G-Fab DNA sequences:

| Construct | DNA Sequence | SEQ ID NO |
|---|---|---|
| | ACGTGAACCACAAGCCCAGCAACACCAAGGTGGACA<br>AGAAGGTGGAGCCCAAGAGCTGCGGAGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGG | |
| Anti-P329G VL | see Table 5 | 37 |
| CL | see Table 7 | 45 |
| Anti-P329G VH | see Table 5 | 36 |
| CH1 | see Table 7 | 46 |
| CD28ATD-CD28CSD-CD3zSSD | see Table 3 | 27 |
| Anti-P329G-Fab-heavy chain-CD28ATD-CD28CSD-CD3zSSD-eGFP fusion PETR17594 | ATGGGATGGAGCTGTATCATCCTCTTCTTGGTAGCAA<br>CAGCTACGGGTGTGCATTCCCAGGCCGTGGTGACCC<br>AGGAGAGCGCCCTGACCACCAGCCCCGGCGAGACCG<br>TGACCCTGACCTGCAGGAGCAGCACCGGCGCCGTGA<br>CCACCAGCAACTACGCCAACTGGGTGCAGGAGAAGC<br>CCGACCACCTGTTCACCGGCCTGATCGGCGGCACCA<br>ACAAGAGGGCCCCCGGCGTGCCCGCCAGGTTCAGCG<br>GCAGCCTGATCGGCGACAAGGCCGCCCTGACCATCA<br>CCGGCGCCCAGACCGAGGACGAGGCCATCTACTTCT<br>GCGCCCTGTGGTACAGCAACCACTGGGTGTTCGGCG<br>GTGGCACCAAGCTGACCGTGCTGCGCTACGGTGGCTG<br>CACCATCTGTCTTCATCTTCCCGCCATCTGATGAGCA<br>GTTGAAATCTGGAACTGCCTCTGTTGTGTGCCTGCTG<br>AATAACTTCTATCCCAGAGAGGCCAAAGTACAGTGG<br>AAGGTGGATAACGCCCTCCAATCGGGTAACTCCCAG<br>GAGAGTGTCACAGAGCAGGACAGCAAGGACAGCAC<br>CTACAGCCTCAGCAGCACCCTGACGCTGAGCAAAGC<br>AGACTACGAGAAACACAAAGTCTACGCCTGCGAAGT<br>CACCCATCAGGGCCTGAGCTCGCCCGTCACAAAGAG<br>CTTCAACAGGGGAGAGTGTTAGGAATTCCCCGAAGT<br>AACTTAGAAGCTGTAAATCAACGATCAATAGCAGGT<br>GTGGCACACCAGTCATACCTTGATCAAGCACTTCTGT<br>TTCCCCGGACTGAGTATCAATAGGCTGCTCGCGCGG<br>CTGAAGGAGAAAACGTTCGTTACCCGACCAACTACT<br>TCGAGAAGCTTAGTACCACCATGAACGAGGCAGGGT<br>GTTTCGCTCAGCACAACCCCAGTGTAGATCAGGCTG<br>ATGAGTCACTGCAACCCCATGGGCGACCATGGCAG<br>TGGCTGCGTTGGCGGCCTGCCCATGGAGAAATCCAT<br>GGGACGCTCTAATTCTGACATGGTGTGAAGTGCCTAT<br>TGAGCTAACTGGTAGTCCTCCGGCCCCTGATTGCGGC<br>TAATCCTAACTGCGGAGCACATGCTCACAAACCAGT<br>GGGTGGTGTGTCGTAACGGGCAACTCTGCAGCGGAA<br>CCGACTACTTTGGGTGTCCGTGTTTCCTTTTATTCCTA<br>TATTGGCTGCTTATGGTGACAATCAAAAAGTTGTTAC<br>CATATAGCTATTGGATTGGCCATCCGGTGTGCAACA<br>GGGCAACTGTTTACCTATTTATTGGTTTTGTACCATT<br>ATCACTGAAGTCTGTGATCACTCTCAAATTCATTTTG<br>ACCCTCAACACAATCAAACGCCACCATGGGATGGAG<br>CTGTATCATCCTCTTCTTGGTAGCAACAGCTACCGGT<br>GTGCACTCCGAGGTGAAGCTGCTGGAGAGCGGCGGC<br>GGCCTGGTGCAGCCCGGCGGCAGCCTGAAGCTGAGC<br>TGCGCCGCCAGCGGCTTCGACTTCAGCAGGTACTGG<br>ATGAACTGGGTGAGGCAGGCCCCCGGCAAGGGTCTG<br>GAGTGGATCGGCGAGATCACCCCCGACAGCAGCACC<br>ATCAACTACACCCCCAGCCTGAAGGACAAGTTCATC<br>ATCAGCAGGGACAACGCCAAGAACACCCTGTACCTG | 52 |

TABLE 9-continued

Anti-P329G-Fab DNA sequences:

| Construct | DNA Sequence | SEQ ID NO |
|---|---|---|
| | CAGATGATCAAGGTGAGGAGCGAGGACACCGCCCTG<br>TACTACTGCGTGAGGCCCTACGACTACGGCGCCTGG<br>TTCGCCAGCTGGGGCCAGGGCACCCTGGTGACCGTG<br>AGCGCCGCTAGCACCAAGGGCCCCTCCGTGTTCCCC<br>CTGGCCCCCAGCAGCAAGAGCACCAGCGGCACA<br>GCCGCTCTGGGCTGCCTGGTCAAGGACTACTTCCCCG<br>AGCCCGTGACCGTGTCCTGGAACAGCGGAGCCCTGA<br>CCTCCGGCGTGCACACCTTCCCCGCCGTGCTGCAGAG<br>TTCTGGCCTGTATAGCCTGAGCAGCGTGGTCACCGTG<br>CCTTCTAGCAGCCTGGGCACCCAGACCTACATCTGCA<br>ACGTGAACCACAAGCCCAGCAACACCAAGGTGGACA<br>AGAAGGTGGAGCCCAAGAGCTGCGGAGGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CAGGTCCGGAGAGGGCAGAGGAAGTCTTCTAACAT<br>GCGGTGACGTGGAGGAGAATCCCGGCCCTAGGGTGA<br>GCAAGGGCGAGGAGCTGTTCACCGGGGTGGTGCCCA<br>TCCTGGTCGAGCTGGACGGCGACGTAAACGGCCACA<br>AGTTCAGCGTGTCCGGCGAGGGCGAGGGCGATGCCA<br>CCTACGGCAAGCTGACCCTGAAGTTCATCTGCACCA<br>CCGGCAAGCTGCCCGTGCCCTGGCCCACCCTCGTGA<br>CCACCCTGACCTACGGCGTGCAGTGCTTCAGCCGCTA<br>CCCCGACCACATGAAGCAGCACGACTTCTTCAAGTC<br>CGCCATGCCCGAAGGCTACGTCCAGGAGCGCACCAT<br>CTTCTTCAAGGACGACGGCAACTACAAGACCCGCGC<br>CGAGGTGAAGTTCGAGGGCGACACCCTGGTGAACCG<br>CATCGAGCTGAAGGGCATCGACTTCAAGGAGGACGG<br>CAACATCCTGGGGCACAAGCTGGAGTACAACTACAA<br>CAGCCACAACGTCTATATCATGGCCGACAAGCAGAA<br>GAACGGCATCAAGGTGAACTTCAAGATCCGCCACAA<br>CATCGAGGACGGCAGCGTGCAGCTCGCCGACCACTA<br>CCAGCAGAACACCCCCATCGGCGACGGCCCCGTGCT<br>GCTGCCCGACAACCACTACCTGAGCACCCAGTCCGC<br>CCTGAGCAAAGACCCCAACGAGAAGCGCGATCACAT<br>GGTCCTGCTGGAGTTCGTGACCGCCGCCGGGATCAC<br>TCTCGGCATGGACGAGCTGTACAAGTGA | |

TABLE 10

Anti-AAA-scFv amino acid sequences

| Construct | Amino acid sequence | SEQ ID NO |
|---|---|---|
| Anti-AAA CDR H1 Kabat | SYGMS | 53 |
| Anti-AAA CDR H2 Kabat | SSGGSY | 54 |
| Anti-AAA CDR H3 Kabat | LGMITTGYAMDY | 55 |
| Anti-AAA CDR L1 Kabat | RSSQTIVHSTGHTYLE | 56 |
| Anti-AAA CDR L2 Kabat | KVSNRFS | 57 |
| Anti-AAA CDR L3 Kabat | FQGSHVPYT | 58 |

TABLE 10-continued

Anti-AAA-scFv amino acid sequences

| Construct | Amino acid sequence | SEQ ID NO |
|---|---|---|
| Anti-AAA-scFv-CD28ATD-CD28CSD-CD3zSSD fusion | MNFGLSLVFLALILKGVQCEVQLVESGGDLVKP GGSLKLSCAASGFTFSSYGMSWVRQTPDKRLEW VATISSGGSYIYYPDSVKGRFTISRDNAKNTLY LQMSSLKSEDTAMYYCARLGMITTGYAMDYWGQ GTSVTVSSGGGGSGGGGSGGGGSGGGGSDVLMT QTPLSLPVSLGDQASISCRSSQTIVHSTGHTYL EWFLQKPGQSPKLLIYKVSNRFSGVPDRFSGSG SGTDFTLKISRVEAEDLGVYYCFQGSHVPYTFG GGTKLEIKGGGGSFWVLVVVGGVLACYSLLVTV AFIIFWVRSKRSLLHSDYMNMTPRRPGPTRKH YQPYAPPRDFAAYRSRVKFSRSADAPAYQQGQN QLYNELNLGRREEYDVLDKRRGRDPEMGGKPRR KNPQEGLYNELQKDKMAEAYSEIGMKGERRRGK GHDGLYQGLSTATKDTYDALHMQALPPR | 59 |
| Anti-AAA-scFv | MNFGLSLVFLALILKGVQCEVQLVESGGDLVKP GGSLKLSCAASGFTFSSYGMSWVRQTPDKRLEW VATISSGGSYIYYPDSVKGRFTISRDNAKNTLY LQMSSLKSEDTAMYYCARLGMITTGYAMDYWGQ GTSVTVSSGGGGSGGGGSGGGGSGGGGSDVLMT QTPLSLPVSLGDQASISCRSSQTIVHSTGHTYL EWFLQKPGQSPKLLIYKVSNRFSGVPDRFSGSG SGTDFTLKISRVEAEDLGVYYCFQGSHVPYTFG GGTKLEIK | 60 |
| Anti-AAA VH | MNFGLSLVFLALILKGVQCEVQLVESGGDLVKP GGSLKLSCAASGFTFSSYGMSWVRQTPDKRLEW VATISSGGSYIYYPDSVKGRFTISRDNAKNTLY LQMSSLKSEDTAMYYCARLGMITTGYAMDYWGQ GTSVTVSS | 61 |
| Anti-AAA VL | DVLMTQTPLSLPVSLGDQASISCRSSQTIVHST GHTYLEWFLQKPGQSPKLLIYKVSNRFSGVPDR FSGSGSGTDFTLKISRVEAEDLGVYYCFQGSHV PYTFGGGTKLEIK | 62 |

TABLE 11

Anti-AAA-Fab amino acid sequences

| Construct | Protein Sequence | SEQ ID NO |
|---|---|---|
| Anti-AAA CDR H1 Kabat | see Table 10 | 53 |
| Anti-AAA CDR H2 Kabat | see Table 10 | 54 |
| Anti-AAA CDR H3 Kabat | see Table 10 | 55 |
| Anti-AAA CDR L1 Kabat | see Table 10 | 56 |
| Anti-AAA CDR L2 Kabat | see Table 10 | 57 |
| Anti-AAA CDR L3 Kabat | see Table 10 | 58 |
| Anti-AAA-Fab heavy chain-CD28ATD-CD28CSD-CD3zSSD fusion | MNFGLSLVFLALILKGVQCEVQLVESGGDLVK PGGSLKLSCAASGFTFSSYGMSWVRQTPDKRL EWVATISSGGSYIYYPDSVKGRFTISRDNAKN TLYLQMSSLKSEDTAMYYCARLGMITTGYAMD YWGQGTSVTVSSASTKGPSVFPLAPSSKSTSG GTAALGCLVKDYFPEPVTVSWNSGALTSGVHT FPAVLQSSGLYSLSSVVTVPSSLGTQTYICN VNHKPSNTKVDKKVEPKSCGGGGSFWVLVVVG GVLACYSLLVTVAFIIFWVRSKRSLLHSDYM NMTPRRPGPTRKHYQPYAPPRDFAAYRSRVKF SRSADAPAYQQGQNQLYNELNLGRREEYDVLD KRRGRDPEMGGKPRRKNPQEGLYNELQKDKMA EAYSEIGMKGERRRGKHDGLYQGLSTATKDT YDALHMQALPPR | 63 |
| Anti-AAA-Fab heavy chain | MNFGLSLVFLALILKGVQCEVQLVESGGDLVK PGGSLKLSCAASGFTFSSYGMSWVRQTPDKRL EWVATISSGGSYIYYPDSVKGRFTISRDNAKN TLYLQMSSLKSEDTAMYYCARLGMITTGYAMD WYGQGTSVTVSSASTKGPSVFPLAPSSKSTSG GTAALGCLVKDYFPEPVTVSWNSGALTSGVHT FPAVLQSSGLYSLSSVVTVPSSLGTQTYICN PVNHKSNTKVDKKVEPKSC | 64 |
| Anti-AAA-Fab light chain | DVLMTQTPLSLPVSLGDQASISCRSSQTIVHS TGHTYLEWFLQKPGQSPKLLIYKVSNRFSGVP DRFSGSGSGTDFTLKISRVEAEDLGVYYCFQG SHVPYTFGGGTKLEIKRTVAAPSVFIFPPSDE QLKSGTASVVCLLNNFYPREAKVQWKVDNALQ SGNSQESVTEQDSKDSTYSLSSTLTLSKADYE KHKVYACEVTHQGLSSPVTKSFNRGEC | 65 |
| Anti-AAA VL | see Table 10 | 62 |
| CL | see Table 6 | 42 |
| Anti-AAA VH | see Table 10 | 61 |
| CH1 | see Table 6 | 43 |

TABLE 12

| Construct | Amino acid sequence | SEQ ID NO |
|---|---|---|
| Human CD27 | ATGGCGCGCCCGCATCCGTGGTGGCTGTGCGTGCTG GGCACCCTGGTGGGCCTGAGCGCGACCCCGGCGCCG AAAAGCTGCCCGGAACGCCATTATTGGGCGCAGGGC AAACTGTGCTGCCAGATGTGCGAACCGGGCACCTTT CTGGTGAAAGATTGCGATCAGCATCGCAAAGCGGCG | 66 |

TABLE 12-continued

| Construct | Amino acid sequence | SEQ ID NO |
|---|---|---|
| | CAGTGCGATCCGTGCATTCCGGGCGTGAGCTTTAGCC<br>CGGATCATCATACCCGCCCGCATTGCGAAAGCTGCC<br>GCCATTGCAACAGCGGCCTGCTGGTGCGCAACTGCA<br>CCATTACCGCGAACGCGGAATGCGCGTGCCGCAACG<br>GCTGGCAGTGCCGCGATAAAGAATGCACCGAATGCG<br>ATCCGCTGCCGAACCCGAGCCTGACCGCGCGCAGCA<br>GCCAGGCGCTGAGCCCGCATCCGCAGCCGACCCATC<br>TGCCGTATGTGAGCGAAATGCTGGAAGCGCGCACCG<br>CGGGCCATATGCAGACCCTGGCGGATTTTCGCCAGC<br>TGCCGGCGCGCACCCTGAGCACCCATTGGCCGCCGC<br>AGCGCAGCCTGTGCAGCAGCGATTTTATTCGCATTCT<br>GGTGATTTTTAGCGGCATGTTTCTGGTGTTTACCCTG<br>GCGGGCGCGCTGTTTCTGCATCAGCGCCGCAAATAT<br>CGCAGCAACAAAGGCGAAAGCCCGGTGGAACCGGC<br>GGAACCGTGCCATTATAGCTGCCCGCGCGAAGAAGA<br>AGGCAGCACCATTCCGATTCAGGAAGATTATCGCAA<br>ACCGGAACCGGCGTGCAGCCCG | |
| Human CD27 | MARPHPWWLCVLGTLVGLSATPAPKSCPERHYWAQG<br>KLCCQMCEPGTFLVKDCDQHRKAAQCDPCIPGVSFSPD<br>HHTRPHCESCRHCNSGLLVRNCTITANAECACRNGWQ<br>CRDKECTECDPLPNPSLTARSSQALSPHPQPTHLPYVSE<br>MLEARTAGHMQTLADFRQLPARTLSTHWPPQRSLCSS<br>DFIRILVIFSGMFLVFTLAGALFLHQRRKYRSNKGESPV<br>EPAEPCHYSCPREEEGSTIPIQEDYRKPEPACSP | 67 |
| Murine CD27 | ATGGCGTGGCCGCCGCCGTATTGGCTGTGCATGCTG<br>GGCACCCTGGTGGGCCTGAGCGCGACCCTGGCGCCG<br>AACAGCTGCCCGGATAAACATTATTGGACCGGCGGC<br>GGCCTGTGCTGCCGCATGTGCGAACCGGGCACCTTTT<br>TTGTGAAAGATTGCGAACAGGATCGCACCGCGGCGC<br>AGTGCGATCCGTGCATTCCGGGCACCAGCTTTAGCCC<br>GGATTATCATACCCGCCCGCATTGCGAAAGCTGCCG<br>CCATTGCAACAGCGGCTTTCTGATTCGCAACTGCACC<br>GTGACCGCGAACGCGGAATGCAGCTGCAGCAAAAAC<br>TGGCAGTGCCGCGATCAGGAATGCACCGAATGCGAT<br>CCGCCGCTGAACCCGGCGCTGACCCGCCAGCCGAGC<br>GAAACCCCGAGCCCGCAGCCGCCGCCGACCCATCTG<br>CCGCATGGCACCGAAAAACCGAGCTGGCCGCTGCAT<br>CGCCAGCTGCCGAACAGCACCGTGTATAGCCAGCGC<br>AGCAGCCATCGCCCGCTGTGCAGCAGCGATTGCATT<br>CGCATTTTTGTGACCTTTAGCAGCATGTTTCTGATTTT<br>TGTGCTGGGCGCGATTCTGTTTTTTCATCAGCGCCGC<br>AACCATGGCCCGAACGAAGATCGCCAGGCGGTGCCG<br>GAAGAACCGTGCCCGTATAGCTGCCCGCGCGAAGAA<br>GAAGGCAGCGCGATTCCGATTCAGGAAGATTATCGC<br>AAACCGGAACCGGCGTTTTATCCG | 68 |
| Murine CD27 | MAWPPPYWLCMLGTLVGLSATLAPNSCPDKHYWTGG<br>GLCCRMCEPGTFFVKDCEQDRTAAQCDPCIPGTSFSPD<br>YHTRPHCESCRHCNSGFLIRNCTVTANAECSCSKNWQC<br>RDQECTECDPPLNPALTRQPSETPSPQPPPTHLPHGTEK<br>PSWPLHRQLPNSTVYSQRSSHRPLCSSDCIRIFVTFSSMF<br>LIFVLGAILFFHQRRNHGPNEDRQAVPEEPCPYSCPREE<br>EGSAIPIQEDYRKPEPAFYP | 69 |
| Human CD28 | ATGCTGCGCCTGCTGCTGGCGCTGAACCTGTTTCCGA<br>GCATTCAGGTGACCGGCAACAAAATTCTGGTGAAAC<br>AGAGCCCGATGCTGGTGGCGTATGATAACGCGGTGA<br>ACCTGAGCTGCAAATATAGCTATAACCTGTTTAGCCG<br>CGAATTTCGCGCGAGCCTGCATAAAGGCCTGGATAG<br>CGCGGTGGAAGTGTGCGTGGTGTATGGCAACTATAG<br>CCAGCAGCTGCAGGTGTATAGCAAAACCGGCTTTAA<br>CTGCGATGGCAAACTGGGCAACGAAAGCGTGACCTT<br>TTATCTGCAGAACCTGTATGTGAACCAGACCGATATT<br>TATTTTTGCAAAATTGAAGTGATGTATCCGCCGCCGT<br>ATCTGGATAACGAAAAAAGCAACGGCACCATTATTC<br>ATGTGAAAGGCAAACATCTGTGCCCGAGCCCGCTGT<br>TCCGGGCCCGAGCAAACGTTTTGGGTGCTGGTGGT<br>GGTGGGCGGCGTGCTGGCGTGCTATAGCCTGCTGGT<br>GACCGTGGCGTTTATTATTTTTTGGGTGCGCAGCAAA<br>CGCAGCCGCCTGCTGCATAGCGATTATATGAACATG<br>ACCCCGCGCCGCCCGGGCCCGACCCGCAAACATTAT<br>CAGCCGTATGCGCCGCCGCGCGATTTTGCGGCGTATC<br>GCAGC | 70 |

TABLE 12-continued

| Construct | Amino acid sequence | SEQ ID NO |
|---|---|---|
| Human CD28 | MLRLLLALNLFPSIQVTGNKILVKQSPMLVAYDNAVNL SCKYSYNLFSREFRASLHKGLDSAVEVCVVYGNYSQQ LQVYSKTGFNCDGKLGNESVTFYLQNLYVNQTDIYFC KIEVMYPPPYLDNEKSNGTIIHVKGKHLCPSPLFPGPSK PFWVLVVVGGVLACYSLLVTVAFIIFWVRSKRSRLLHS DYMNMTPRRPGPTRKHYQPYAPPRDFAAYRS | 71 |
| Murine CD28 | ATGACCCTGCGCCTGCTGTTTCTGGCGCTGAACTTTT TTAGCGTGCAGGTGACCGAAAACAAAATTCTGGTGA AACAGAGCCCGCTGCTGGTGGTGGATAGCAACGAAG TGAGCCTGAGCTGCCGCTATAGCTATAACCTGCTGGC GAAAGAATTTCGCGCGAGCCTGTATAAAGGCGTGAA CAGCGATGTGGAAGTGTGCGTGGGCAACGGCAACTT TACCTATCAGCCGCAGTTTCGCAGCAACGCGGAATTT AACTGCGATGGCGATTTTGATAACGAAACCGTGACC TTTCGCCTGTGGAACCTGCATGTGAACCATACCGATA TTTATTTTTGCAAAATTGAATTTATGTATCCGCCGCC GTATCTGGATAACGAACGCAGCAACGGCACCATTAT TCATATTAAAGAAAAACATCTGTGCCATACCCAGAG CAGCCCGAAACTGTTTTGGGCGCTGGTGGTGGTGGC GGGCGTGCTGTTTTGCTATGGCCTGCTGGTGACCGTG GCGCTGTGCGTGATTTGGACCAACAGCCGCCGCAAC CGCCTGCTGCAGAGCGATTATATGAACATGACCCCG CGCCGCCCGGGCCTGACCCGCAAACCGTATCAGCCG TATGCGCCGGCGCGCGATTTTGCGGCGTATCGCCCG | 72 |
| Murine CD28 | MTLRLLFLALNFFSVQVTENKILVKQSPLLVVDSNEVSL SCRYSYNLLAKEFRASLYKGVNSDVEVCVGNGNFTYQ PQFRSNAEFNCDGDFDNETVTFRLWNLHVNHTDIYFCK IEFMYPPPYLDNERSNGTIIHIKEKHLCHTQSSPKLFWAL VVVAGVLFCYGLLVTVALCVIWTNSRRNRLLQSDYMN MTPRRPGLTRKPYQPYAPARDFAAYRP | 73 |
| Human CD137 | ATGGGAAACAGCTGTTACAACATAGTAGCCACTCTG TTGCTGGTCCTCAACTTTGAGAGGACAAGATCATTGC AGGATCCTTGTAGTAACTGCCCAGCTGGTACATTCTG TGATAATAACAGGAATCAGATTTGCAGTCCCTGTCCT CCAAATAGTTTCTCCAGCGCAGGTGGACAAAGGACC TGTGACATATGCAGGCAGTGTAAAGGTGTTTTCAGG ACCAGGAAGGAGTGTTCCTCCACCAGCAATGCAGAG TGTGACTGCACTCCAGGGTTTCACTGCCTGGGGGCA GGATGCAGCATGTGTGAACAGGATTGTAAACAAGGT CAAGAACTGACAAAAAAAGGTTGTAAAGACTGTTGC TTTGGGACATTTAACGATCAGAAACGTGGCATCTGTC GACCCTGGACAAACTGTTCTTTGGATGGAAAGTCTGT GCTTGTGAATGGGACGAAGGAGAGGGACGTGGTCTG TGGACCATCTCCAGCCGACCTCTCTCCGGGAGCATCC TCTGTGACCCCGCCTGCCCCTGCGAGAGAGCCAGGA CACTCTCCGCAGATCATCTCCTTCTTTCTTGCGCTGA CGTCGACTGCGTTGCTCTTCCTGCTGTTCTTCCTCACG CTCCGTTTCTCTGTTGTTAAACGGGGCAGAAAGAAA CTCCTGTATATATTCAAACAACCATTTATGAGACCAG TACAAACTACTCAAGAGGAAGATGGCTGTAGCTGCC GATTTCCAGAAGAAGAAGAAGGAGGATGTGAACTGT GA | 74 |
| Human CD137 | MGNSCYNIVATLLLVLNFERTRSLQDPCSNCPAGTFCD NNRNQICSPCPPNSESSAGGQRTCDICRQCKGVFRTRKE CSSTSNAECDCTPGFHCLGAGCSMCEQDCKQGQELTK KGCKDCCFGTFNDQKRGICRPWTNCSLDGKSVLVNGT KERDVVCGPSPADLSPGASSVTPPAPAREPGHSPQIISFF LALTSTALLFLLFFLTLRFSVVKRGRKKLLYIFKQPFMR PVQTTQEEDGCSCRFPEEEEGGCEL | 75 |
| Murine CD137 | ATGGGCAACAACTGCTATAACGTGGTGGTGATTGTG CTGCTGCTGGTGGGCTGCGAAAAAGTGGGCGCGGTG CAGAACAGCTGCGATAACTGCCAGCCGGGCACCTTT TGCCGCAAATATAACCCGGTGTGCAAAAGCTGCCCG CCGAGCACCTTTAGCAGCATTGGCGGCCAGCCGAAC TGCAACATTTGCCGCGTGTGCGCGGGCTATTTTCGCT TTAAAAAATTTTGCAGCAGCACCCATAACGCGGAAT GCGAATGCATTGAAGGCTTTCATTGCCTGGGCCCGC AGTGCACCCGCTGCGAAAAAGATTGCCGCCCGGGCC AGGAACTGACCAAACAGGGCTGCAAAACCTGCAGCC TGGGCACCTTTAACGATCAGAACGGCACCGGCGTGT GCCGCCCGTGGACCAACTGCAGCCTGGATGGCCGCA | 76 |

TABLE 12-continued

| Construct | Amino acid sequence | SEQ ID NO |
|---|---|---|
| | GCGTGCTGAAAACCGGCACCACCGAAAAAGATGTGG<br>TGTGCGGCCCGCCGGTGGTGAGCTTTAGCCCGAGCA<br>CCACCATTAGCGTGACCCCGGAAGGCGGCCCGGGCG<br>GCCATAGCCTGCAGGTGCTGACCCTGTTTCTGGCGCT<br>GACCAGCGCGCTGCTGCTGGCGCTGATTTTTATTACC<br>CTGCTGTTTAGCGTGCTGAAATGGATTCGCAAAAAA<br>TTTCCGCATATTTTTAAACAGCCGTTTAAAAAAACCA<br>CCGGCGCGGCGCAGGAAGAAGATGCGTGCAGCTGCC<br>GCTGCCCGCAGGAAGAAGAAGGCGGCGGCGGCGGC<br>TATGAACTG | |
| Murine CD137 | MGNNCYNVVVIVLLLVGCEKVGAVQNSCDNCQPGTF<br>CRKYNPVCKSCPPSTFSSIGGQPNCNICRVCAGYFRFKK<br>FCSSTHNAECECIEGFHCLGPQCTRCEKDCRPGQELTK<br>QGCKTCSLGTFNDQNGTGVCRPWTNCSLDGRSVLKTG<br>TTEKDVVCGPPVVSFSPSTTISVTPEGGPGGHSLQVLTL<br>FLALTSALLLALIFITLLFSVLKWIRKKFPHIFKQPFKKTT<br>GAAQEEDACSCRCPQEEEGGGGGYEL | 77 |
| Human OX40 | ATGTGCGTGGGCGCGCGCCGCCTGGGCCGCGGCCCG<br>TGCGCGGCGCTGCTGCTGCTGGGCCTGGGCCTGAGC<br>ACCGTGACCGGCCTGCATTGCGTGGGCGATACCTAT<br>CCGAGCAACGATCGCTGCTGCCATGAATGCCGCCCG<br>GGCAACGGCATGGTGAGCCGCTGCAGCCGCAGCCAG<br>AACACCGTGTGCCGCCCGTGCGGCCCGGGCTTTTATA<br>ACGATGTGGTGAGCAGCAAACCGTGCAAACCGTGCA<br>CCTGGTGCAACCTGCGCAGCGGCAGCGAACGCAAAC<br>AGCTGTGCACCGCGACCCAGGATACCGTGTGCCGCT<br>GCCGCGCGGGCACCCAGCCGCTGGATAGCTATAAAC<br>CGGGCGTGGATTGCGCGCCGTGCCCGCCGGGCCATT<br>TTAGCCCGGGCGATAACCAGGCGTGCAAACCGTGGA<br>CCAACTGCACCCTGGCGGGCAAACATACCCTGCAGC<br>CGGCGAGCAACAGCAGCGATGCGATTTGCGAAGATC<br>GCGATCCGCCGGCGACCCAGCCGCAGGAAACCCAGG<br>GCCCGCCGGCGCGCCCGATTACCGTGCAGCCGACCG<br>AAGCGTGGCCGCGCACCAGCCAGGGCCCGAGCACCC<br>GCCCGGTGGAAGTGCCGGGCGGCCGCGCGGTGGCGG<br>CGATTCTGGGCCTGGGCGTGCTGGGCCTGCTGG<br>GCCCGCTGGCGATTCTGCTGGCGCTGTATCTGCTGCG<br>CCGCGATCAGCGCCTGCCGCCGGATGCGCATAAACC<br>GCCGGGCGGCGGCAGCTTTCGCACCCCGATTCAGGA<br>AGAACAGGCGGATGCGCATAGCACCCTGGCGAAAAT<br>T | 78 |
| Human OX40 | MCVGARRLGRGPCAALLLLGLGLSTVTGLHCVGDTYP<br>SNDRCCHECRPGNGMVSRCSRSQNTVCRPCGPGFYND<br>VVSSKPCKPCTWCNLRSGSERKQLCTATQDTVCRCRA<br>GTQPLDSYKPGVDCAPCPPGHFSPGDNQACKPWTNCT<br>LAGKHTLQPASNSSDAICEDRDPPATQPQETQGPPARPI<br>TVQPTEAWPRTSQGPSTRPVEVPGGRAVAAILGLGLVL<br>GLLGPLAILLALYLLRRDQRLPPDAHKPPGGGSFRTPIQ<br>EEQADAHSTLAKI | 79 |
| Murine OX40 | ATGTATGTGTGGGTGCAGCAGCCGACCGCGCTGCTG<br>CTGCTGGCGCTGACCCTGGGCGTGACCGCGCGCCGC<br>CTGAACTGCGTGAAACATACCTATCCGAGCGGCCAT<br>AAATGCTGCCGCGAATGCCAGCCGGGCCATGGCATG<br>GTGAGCCGCTGCGATCATACCCGCGATACCCTGTGC<br>CATCCGTGCGAAACCGGCTTTTATAACGAAGCGGTG<br>AACTATGATACCTGCAAACAGTGCACCCAGTGCAAC<br>CATCGCAGCGGCAGCGAACTGAAACAGAACTGCACC<br>CCGACCCAGGATACCGTGTGCCGCTGCCGCCCGGGC<br>ACCCAGCCGCGCCAGGATAGCGGCTATAAACTGGGC<br>GTGGATTGCGTGCCGTGCCCGCCGGGCCATTTTAGCC<br>CGGGCAACAACCAGGCGTGCAAACCGTGGACCAACT<br>GCACCCTGAGCGGCAAACAGACCCGCCATCCGGCGA<br>GCGATAGCCTGGATGCGGTGTGCGAAGATCGCAGCC<br>TGCTGGCGACCCTGCTGTGGGAAACCCAGCGCCCGA<br>CCTTTCGCCCGACCACCGTGCAGAGCACCACCGTGT<br>GGCCGCGCACCAGCGAACTGCCGAGCCCGCCGACCC<br>TGGTGACCCCGGAAGGCCCGGCGTTTGCGGTGCTGC<br>TGGGCCTGGGCCTGGGCCTGCTGGCGCCGCTGACCG<br>TGCTGCTGGCGCTGTATCTGCTGCGCAAAGCGTGGC<br>GCCTGCCGAACACCCCGAAACCGTGCTGGGGCAACA<br>GCTTTCGCACCCCGATTCAGGAAGAACATACCGATG<br>CGCATTTTACCCTGGCGAAAATT | 80 |

TABLE 12-continued

| Construct | Amino acid sequence | SEQ ID NO |
|---|---|---|
| Murine OX40 | MYVWVQQPTALLLLALTLGVTARRLNCVKHTYPSGH KCCRECQPGHGMVSRCDHTRDTLCHPCETGFYNEAVN YDTCKQCTQCNHRSGSELKQNCTPTQDTVCRCRPGTQ PRQDSGYKLGVDCVPCPPGHFSPGNNQACKPWTNCTL SGKQTRHPASDSLDAVCEDRSLLATLLWETQRPTFRPT TVQSTTVWPRTSELPSPPTLVTPEGPAFAVLLGLGLGLL APLTVLLALYLLRKAWRLPNTPKPCWGNSFRTPIQEEH TDAHFTLAKI | 81 |
| Human ICOS | ATGAAAAGCGGCCTGTGGTATTTTTTCTGTTTTGCC TGCGCATTAAAGTGCTGACCGGCGAAATTAACGGCA GCGCGAACTATGAAATGTTTATTTTTCATAACGGCGG CGTGCAGATTCTGTGCAAATATCCGGATATTGTGCAG CAGTTTAAAATGCAGCTGCTGAAAGGCGGCCAGATT CTGTGCGATCTGACCAAAACCAAAGGCAGCGGCAAC ACCGTGAGCATTAAAAGCCTGAAATTTTGCCATAGC CAGCTGAGCAACAACAGCGTGAGCTTTTTTCTGTATA ACCTGGATCATAGCCATGCGAACTATTATTTTTGCAA CCTGAGCATTTTTGATCCGCCGCCGTTTAAAGTGACC CTGACCGGCGGCTATCTGCATATTTATGAAAGCCAG CTGTGCTGCCAGCTGAAATTTTGGCTGCCGATTGGCT GCGCGGCGTTTGTGGTGGTGTGCATTCTGGGCTGCAT TCTGATTTGCTGGCTGACCAAAAAAAAATATAGCAG CAGCGTGCATGATCCGAACGGCGAATATATGTTTAT GCGCGCGGTGAACACCGCGAAAAAAAGCCGCCTGAC CGATGTGACCCTG | 82 |
| Human ICOS | MKSGLWYFFLFCLRIKVLTGEINGSANYEMFIFHNGGV QILCKYPDIVQQFKMQLLKGGQILCDLTKTKGSGNTVSI KSLKFCHSQLSNNSVSFFLYNLDHSHANYYFCNLSIFDP PPFKVTLTGGYLHIYESQLCCQLKFWLPIGCAAFVVVCI LGCILICWLTKKKYSSSVHDPNGEYMFMRAVNTAKKS RLTDVTL | 83 |
| Murine ICOS | ATGAAACCGTATTTTTGCCGCGTGTTTGTGTTTTGCTT TCTGATTCGCCTGCTGACCGGCGAAATTAACGGCAG CGCGGATCATCGCATGTTTAGCTTTCATAACGGCGGC GTGCAGATTAGCTGCAAATATCCGGAAACCGTGCAG CAGCTGAAAATGCGCCTGTTTCGCGAACGCGAAGTG CTGTGCGAACTGACCAAAACCAAAGGCAGCGGCAAC GCGGTGAGCATTAAAAACCCGATGCTGTGCCTGTAT CATCTGAGCAACAACAGCGTGAGCTTTTTTCTGAACA ACCCGGATAGCAGCCAGGGCAGCTATTATTTTTGCA GCCTGAGCATTTTTGATCCGCCGCCGTTTCAGGAACG CAACCTGAGCGGCGGCTATCTGCATATTTATGAAAG CCAGCTGTGCTGCCAGCTGAAACTGTGGCTGCCGGT GGGCTGCGCGGCGTTTGTGGTGGTGCTGCTGTTTGGC TGCATTCTGATTATTTGGTTTAGCAAAAAAAAATATG GCAGCAGCGTGCATGATCCGAACAGCGAATATATGT TTATGGCGGCGGTGAACACCAACAAAAAAAGCCGCC TGGCGGGCGTGACCAGC | 84 |
| Murine ICOS | MKPYFCRVFVFCFLIRLLTGEINGSADHRMFSFHNGGV QISCKYPETVQQLKMRLFREREVLCELTKTKGSGNAVS IKNPMLCLYHLSNNSVSFFLNNPDSSQGSYYFCSLSIFDP PPFQERNLSGGYLHIYESQLCCQLKLWLPVGCAAFVVV LLFGCILIIWFSKKKYGSSVHDPNSEYMFMAAVNTNKK SRLAGVTS | 85 |
| Human DAP10 | ATGATTCATCTGGGCCATATTCTGTTTCTGCTGCTGC TGCCGGTGGCGGCGGCGCAGACCACCCCGGGCGAAC GCAGCAGCCTGCCGGCGTTTTATCCGGGCACCAGCG GCAGCTGCAGCGGCTGCGGCAGCCTGAGCCTGCCGC TGCTGGCGGGCCTGGTGGCGGCGGATGCGGTGGCGA GCCTGCTGATTGTGGGCGCGGTGTTTCTGTGCGCGCG CCCGCGCCGCAGCCCGGCGCAGGAAGATGGCAAAGT GTATATTAACATGCCGGGCCGCGGC | 86 |
| Human DAP10 | MIHLGHILFLLLLPVAAAQTTPGERSSLPAFYPGTSGSCS GCGSLSLPLLAGLVAADAVASLLIVGAVFLCARPRRSP AQEDGKVYINMPGRG | 87 |
| Murine DAP10 | ATGGATCCGCCGGGCTATCTGCTGTTTCTGCTGCTGC TGCCGGTGGCGGCGAGCCAGACCAGCGCGGGCAGCT GCAGCGGCTGCGGCACCCTGAGCCTGCCGCTGCTGG | 88 |

TABLE 12-continued

| Construct | Amino acid sequence | SEQ ID NO |
|---|---|---|
| | CGGGCCTGGTGGCGGCGGATGCGGTGATGAGCCTGC<br>TGATTGTGGGCGTGGTGTTTGTGTGCATGCGCCCGCA<br>TGGCCGCCCGGCGCAGGAAGATGGCCGCGTGTATAT<br>TAACATGCCGGGCCGCGGC | |
| Murine DAP10 | MDPPGYLLFLLLLPVAASQTSAGSCSGCGTLSLPLLAGL<br>VAADAVMSLLIVGVVFVCMRPHGRPAQEDGRVYINMP<br>GRG | 89 |
| Human DAP12 | ATGGGGGGACTTGAACCCTGCAGCAGGCTCCTGCTC<br>CTGCCTCTCCTGCTGGCTGTAAGTGGTCTCCGTCCTG<br>TCCAGGCCCAGGCCCAGAGCGATTGCAGTTGCTCTA<br>CGGTGAGCCCGGGCGTGCTGGCAGGGATCGTGATGG<br>GAGACCTGGTGCTGACAGTGCTCATTGCCCTGGCCGT<br>GTACTTCCTGGGCCGGCTGGTCCCTCGGGGCGAGG<br>GGCTGCGGAGGCAGCGACCCGGAAACAGCGTATCAC<br>TGAGACCGAGTCGCCTTATCAGGAGCTCCAGGGTCA<br>GAGGTCGGATGTCTACAGCGACCTCAACACACAGAG<br>GCCGTATTACAAATGA | 90 |
| Human DAP12 | MGGLEPCSRLLLLPLLLAVSGLRPVQAQAQSDCSCSTV<br>SPGVLAGIVMGDLVLTVLIALAVYFLGRLVPRGRGAAE<br>AATRKQRITETESPYQELQGQRSDVYSDLNTQRPYYK | 91 |
| Murine DAP12 | ATGGGGGCTCTGGAGCCCTCCTGGTGCCTTCTGTTCC<br>TTCCTGTCCTCCTGACTGTGGGAGGATTAAGTCCCGT<br>ACAGGCCCAGAGTGACACTTTCCCAAGATGCGACTG<br>TTCTTCCGTGAGCCCTGGTGTACTGGCTGGGATTGTT<br>CTGGGTGACTTGGTGTTGACTCTGCTGATTGCCCTGG<br>CTGTGTACTCTCTGGGCCGCCTGGTCTCCCGAGGTCA<br>AGGGACAGCGGAAGGGACCCGGAAACAACACATTG<br>CTGAGACTGAGTCGCCTTATCAGGAGCTTCAGGGTC<br>AGAGACCAGAAGTATACAGTGACCTCAACACACAGA<br>GGCAATATTACAGATGA | 92 |
| Murine DAP12 | MGALEPSWCLLFLPVLLTVGGLSPVQAQSDTFPRCDCS<br>SVSPGVLAGIVLGDLVLTLLIALAVYSLGRLVSRGQGT<br>AEGTRKQHIAETESPYQELQGQRPEVYSDLNTQRQYYR | 93 |
| Human CD3z | MKWKALFTAAILQAQLPITEAQSFGLLDPKLCYLLDGI<br>LFIYGVILTALFLRVKFSRSADAPAYQQGQNQLYNELN<br>LGRREEYDVLDKRRGRDPEMGGKPQRRKNPQEGLYNE<br>LQKDKMAEAYSEIGMKGERRRGKGHDGLYQGLSTAT<br>KDTYDALHMQALPPR | 94 |
| Human CD3z | ATGAAGTGGAAGGCGCTTTTCACCGCGGCCATCCTG<br>CAGGCACAGTTGCCGATTACAGAGGCACAGAGCTTT<br>GGCCTGCTGGATCCCAAACTCTGCTACCTGCTGGATG<br>GAATCCTCTTCATCTATGGTGTCATTCTCACTGCCTT<br>GTTCCTGAGAGTGAAGTTCAGCAGGAGCGCAGAGCC<br>CCCCGCGTACCAGCAGGGCCAGAACCAGCTCTATAA<br>CGAGCTCAATCTAGGACGAAGAGAGGAGTACGATGT<br>TTTGGACAAGAGACGTGGCCGGGACCCTGAGATGGG<br>GGGAAAGCCGAGAAGGAAGAACCCTCAGGAAGGCC<br>TGTACAATGAACTGCAGAAAGATAAGATGGCGGAGG<br>CCTACAGTGAGATTGGGATGAAAGGCGAGCGCCGGA<br>GGGGCAAGGGGCACGATGGCCTTTACCAGGGTCTCA<br>GTACAGCCACCAAGGACACCTACGACGCCCTTCACA<br>TGCAGGCCCTGCCCCCTCGCTAA | 95 |
| Murine CD3z | MKWKVSVLACILHVRFPGAEAQSFGLLDPKLCYLLDGI<br>LFIYGVIITALYLRAKFSRSAETAANLQDPNQLYNELNL<br>GRREEYDVLEKKRARDPEMGGKQQRRRNPQEGVYNA<br>LQKDKMAEAYSEIGTKGERRRGKGHDGLYQGLSTATK<br>DTYDALHMQTLAPR | 96 |
| Murine CD3z | ATGAAGTGGAAAGTGTCTGTTCTCGCCTGCATCCTCC<br>ACGTGCGGTTCCCAGGAGCAGAGGCACAGAGCTTTG<br>GTCTGCTGGATCCCAAACTCTGCTACTTGCTAGATGG<br>AATCCTCTTCATCTACGGAGTCATCATCACAGCCCTG<br>TACCTGAGAGCAAAATTCAGCAGGAGTGCAGAGACT<br>GCTGCCAACCTGCAGGACCCCAACCAGCTCTACAAT<br>GAGCTCAATCTAGGGCGAAGAGAGGAATATGACGTC<br>TTGGAGAAGAAGCGGGCTCGGGATCCAGAGATGGG<br>AGGCAAACAGCAGAGGAGGAGGAACCCCCAGGAAG<br>GCGTATACAATGCACTGCAGAAAGACAAGATGGCAG | 97 |

TABLE 12-continued

| Construct | Amino acid sequence | SEQ ID NO |
|---|---|---|
| | AAGCCTACAGTGAGATCGGCACAAAAGGCGAGAGG<br>CGGAGAGGCAAGGGGCACGATGGCCTTTACCAGGGT<br>CTCAGCACTGCCACCAAGGACACCTATGATGCCCTG<br>CATATGCAGACCCTGGCCCCTCGCTAA | |
| Human FCGR3A | MWQLLLPTALLLLVSAGMRTEDLPKAVVFLEPQWYRV<br>LEKDSVTLKCQGAYSPEDNSTQWFHNESLISSQASSYFI<br>DAATVDDSGEYRCQTNLSTLSDPVQLEVHIGWLLLQAP<br>RWVFKEEDPIHLRCHSWKNTALHKVTYLQNGKGRKYF<br>HHNSDFYIPKATLKDSGSYFCRGLFGSKNVSSETVNITI<br>TQGLAVSTISSFFPPGYQVSFCLVMVLLFAVDTGLYFSV<br>KTNIRSSTRDWKDHKFKWRKDPQDK | 98 |
| Human FCGR3A | ATGTGGCAGCTGCTGCTGCCGACCGCGCTGCTGCTGC<br>TGGTGAGCGCGGGCATGCGCACCGAAGATCTGCCGA<br>AAGCGGTGGTGTTTCTGGAACCGCAGTGGTATCGCG<br>TGCTGGAAAAAGATAGCGTGACCCTGAAATGCCAGG<br>GCGCGTATAGCCCGGAAGATAACAGCACCCAGTGGT<br>TTCATAACGAAAGCCTGATTAGCAGCCAGGCGAGCA<br>GCTATTTTATTGATGCGGCGACCGTGGATGATAGCG<br>GCGAATATCGCTGCCAGACCAACCTGAGCACCCTGA<br>GCGATCCGGTGCAGCTGGAAGTGCATATTGGCTGGC<br>TGCTGCTGCAGGCGCCGCGCTGGGTGTTTAAGGAAG<br>AAGATCCGATTCATCTGCGCTGCCATAGCTGGAAAA<br>ACACCGCGCTGCATAAAGTGACCTATCTGCAGAACG<br>GCAAAGGCCGCAAATATTTTCATCATAACAGCGATT<br>TTTATATTCCGAAAGCGACCCTGAAAGATAGCGGCA<br>GCTATTTTTGCCGCGGCCTGTTTGGCAGCAAAAACGT<br>GAGCAGCGAAACCGTGAACATTACCATTACCCAGGG<br>CCTGGCGGTGAGCACCATTAGCAGCTTTTTTCCGCCG<br>GGCTATCAGGTGAGCTTTTGCCTGGTGATGGTGCTGC<br>TGTTTGCGGTGGATACCGGCCTGTATTTTAGCGTGAA<br>AACCAACATTCGCAGCAGCACCCGCGATTGGAAAGA<br>TCATAAATTTAAATGGCGCAAAGATCCGCAGGATAA<br>A | 99 |
| Murine FCGR3A | MFQNAHSGSQWLLPPLTILLLFAFADRQSAALPKAVVK<br>LDPPWIQVLKEDMVTLMCEGTHNPGNSSTQWFHNGRS<br>IRSQVQASYTFKATVNDSGEYRCQMEQTRLSDPVDLG<br>VISDWLLLQTPQRVFLEGETITLRCHSWRNKLLNRISFF<br>HNEKSVRYHHYKSNFSIPKANHSHSGDYYCKGSLGSTQ<br>HQSKPVTITVQDPATTSSISLVWYHTAFSLVMCLLFAV<br>DTGLYFYVRRNLQTPREYWRKSLSIRKHQAPQDK | 100 |
| Murine FCGR3A | ATGTTTCAGAATGCACACTCTGGAAGCCAATGGCTA<br>CTTCCACCACTGACAATTCTGCTGCTGTTTGCTTTTGC<br>AGACAGGCAGAGTGCAGCTCTTCCGAAGGCTGTGGT<br>GAAACTGGACCCCCCATGGATCCAGGTGCTCAAGGA<br>AGACATGGTGACACTGATGTGCGAAGGGACCCACAA<br>CCCTGGGAACTCTTCTACCCAGTGGTTCCACAACGGG<br>AGGTCCATCCGGAGCCAGGTCCAAGCCAGTTACACG<br>TTTAAGGCCACAGTCAATGACAGTGGAGAATATCGG<br>TGTCAAATGGAGCAGACCCGCCTCAGCGACCCTGTA<br>GATCTGGGAGTGATTTCTGACTGGCTGCTGCTCCAGA<br>CCCCTCAGCGGGTGTTTCTGGAAGGGGAAACCATCA<br>CGCTAAGGTGCCATAGCTGGAGGAACAAACTACTGA<br>ACAGGATCTCATTCTTCCATAATGAAAAATCCGTGA<br>GGTATCATCACTACAAAAGTAATTTCTCTATCCCAAA<br>AGCCAACCACAGTCACAGTGGGGACTACTACTGCAA<br>AGGAAGTCTAGGAAGTACACAGCACCAGTCCAAGCC<br>TGTCACCATCACTGTCCAAGATCCAGCAACTACATCC<br>TCCATCTCTCTAGTCTGGTACCACACTGCTTTCTCCCT<br>AGTGATGTGCCTCCTGTTTGCAGTGGACACGGGCCTT<br>TATTTCTACGTACGGAGAAATCTTCAAACCCCCGAGG<br>GAGTACTGGAGGAAGTCCCTGTCAATCAGAAAGCAC<br>CAGGCTCCTCAAGACAAGTGA | 101 |
| Human NKG2D | MGWIRGRRSRHSWEMSEFHNYNLDLKKSDFSTRWQK<br>QRCPVVKSKCRENASPFFFCCFIAVAMGIRFIIMVAIWS<br>AVFLNSLFNQEVQIPLTESYCGPCPKNWICYKNNCYQF<br>FDESKNWYESQASCMSQNASLLKVYSKEDQDLLKLVK<br>SYHWMGLVHIPTNGSWQWEDGSILSPNLLTIIEMQKGD<br>CALYASSFKGYIENCSTPNTYICMQRTV | 102 |
| Human NKG2D | ATGGGCTGGATTCGCGGCCGCCGCAGCCGCCATAGC<br>TGGGAAATGAGCGAATTTCATAACTATAACCTGGAT | 103 |

TABLE 12-continued

| Construct | Amino acid sequence | SEQ ID NO |
|---|---|---|
| | CTGAAAAAAAGCGATTTTAGCACCCGCTGGCAGAAA CAGCGCTGCCCGGTGGTGAAAAGCAAATGCCGCGAA AACGCGAGCCCGTTTTTTTTTGCTGCTTTATTGCGGT GGCGATGGGCATTCGCTTTATTATTATGGTGGCGATT TGGAGCGCGGTGTTTCTGAACAGCCTGTTTAACCAG GAAGTGCAGATTCCGCTGACCGAAAGCTATTGCGGC CCGTGCCCGAAAAACTGGATTTGCTATAAAAACAAC TGCTATCAGTTTTTTGATGAAAGCAAAAACTGGTATG AAAGCCAGGCGAGCTGCATGAGCCAGAACGCGAGC CTGCTGAAAGTGTATAGCAAAGAAGATCAGGATCTG CTGAAACTGGTGAAAAGCTATCATTGGATGGGCCTG GTGCATATTCCGACCAACGGCAGCTGGCAGTGGGAA GATGGCAGCATTCTGAGCCCGAACCTGCTGACCATT ATTGAAATGCAGAAAGGCGATTGCGCGCTGTATGCG AGCAGCTTTAAAGGCTATATTGAAAACTGCAGCACC CCGAACACCTATATTTGCATGCAGCGCACCGTG | |
| Murine NKG2D | MALIRDRKSHHSEMSKCHNYDLKPAKWDTSQEQQKQ RLALTTSQPGENGIIRGRYPIEKLKISPMFVVRVLAIALA IRFTLNTLMWLAIFKETFQPVLCNKEVPVSSREGYCGPC PNNWICHRNNCYQFFNEEKTWNQSQASCLSQNSSLLKI YSKEEQDFLKLVKSYHWMGLVQIPANGSWQWEDGSS LSYNQLTLVEIPKGSCAVYGSSFKAYTEDCANLNTYIC MKRAV | 104 |
| Murine NKG2D | ATGGCGCTGATTCGCGATCGCAAAAGCCATCATAGC GAAATGAGCAAATGCCATAACTATGATCTGAAACCG GCGAAATGGGATACCAGCCAGGAACAGCAGAAACA GCGCCTGGCGCTGACCACCAGCCAGCCGGGCGAAAA CGGCATTATTCGCGGCCGCTATCCGATTGAAAAACT GAAAATTAGCCCGATGTTTGTGGTGCGCGTGCTGGC GATTGCGCTGGCGATTCGCTTTACCCTGAACACCCTG ATGTGGCTGGCGATTTTTAAAGAAACCTTTCAGCCGG TGCTGTGCAACAAAGAAGTGCCGGTGAGCAGCCGCG AAGGCTATTGCGGCCCGTGCCCGAACAACTGGATTT GCCATCGCAACAACTGCTATCAGTTTTTTAACGAAGA AAAAACCTGGAACCAGAGCCAGGCGAGCTGCCTGAG CCAGAACAGCAGCCTGCTGAAAATTTATAGCAAAGA AGAAACAGGATTTTCTGAAACTGGTGAAAAGCTATCA TTGGATGGGCCTGGTGCAGATTCCGGCGAACGGCAG CTGGCAGTGGGAAGATGGCAGCAGCCTGAGCTATAA CCAGCTGACCCTGGTGGAAATTCCGAAAGGCAGCTG CGCGGTGTATGGCAGCAGCTTTAAAGCGTATACCGA AGATTGCGCGAACCTGAACACCTATATTTGCATGAA ACGCGCGGTG | 105 |
| CD28 YMNM | YMNM | 106 |
| CD28 PYAP | PYAP | 107 |
| CD28 FMNM | FMNM | 108 |
| CD28 AYAA | AYAA | 109 |
| Signal peptide | ATMGWSCIILFLVATATGVHS | 110 |
| Signal peptide DNA sequence | ATGGGATGGAGCTGTATCATCCTCTTCTTGGTAGCAA CAGCTACCGGTGTGCACTCC | 111 |
| Anti-CD20 (GA101) heavy chain | QVQLVQSGAEVKKPGSSVKVSCKASGYAFSYSWINWV RQAPGQGLEWMGRIFPGDGDTDYNGKFKGRVTITADK STSTAYMELSSLRSEDTAVYYCARNVFDGYWLVYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPELLGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALPAPIEKTI SKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 112 |

TABLE 12-continued

| Construct | Amino acid sequence | SEQ ID NO |
|---|---|---|
| Anti-CD20 (GA101) light chain | DIVMTQTPLSLPVTPGEPASISCRSSKSLLHSNGITYLYW YLQKPGQSPQLLIYQMSNLVSGVPDRFSGSGSGTDFTL KISRVEAEDVGVYYCAQNLELPYTFGGGTKVEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC | 113 |
| Anti-FAP(4B9) PGLALA heavy chain | EVQLLESGGGLVQPGGSLRLSCAASGFTFSSYAMSWVR QAPGKGLEWVSAIIGSGASTYYADSVKGRFTISRDNSK NTLYLQMNSLRAEDTAVYYCAKGWFGGFNYWGQGTL VTVSSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSCDKTHTCP PCPAPEAAGGPSVFLFPPKPKDTLMISRTPEVTCVVVDV SHEDPEVKFNWYVDGVEVHNAKTKPREEQYNSTYRV VSVLTVLHQDWLNGKEYKCKVSNKALGAPIEKTISKA KGQPREPQVYTLPPSRDELTKNQVSLTCLVKGFYPSDIA VEWESNGQPENNYKTTPPVLDSDGSFFLYSKLTVDKSR WQQGNVFSCSVMHEALHNHYTQKSLSLSPGK | 114 |
| Anti-FAP(4B9) light chain | EIVLTQSPGTLSLSPGERATLSCRASQSVTSSYLAWYQQ KPGQAPRLLINVGSRRATGIPDRFSGSGSGTDFTLTISRL EPEDFAVYYCQQGIMLPPTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 115 |
| Anti-CEA (A5B7) PGLALA heavy chain | EVQLVESGGGLVQPGRSLRLSCAASGFTVSSYWMHWV RQAPGKGLEWVGFIRNKANGGTTEYAASVKGRFTISR DDSKNTLYLQMNSLRAEDTAVYYCARDRGLRFYFDY WGQGTTVTVSSASTKGPSVFPLAPSSKSTSGGTAALGC LVKDYFPEPVTVSWNSGALTSGVHTFPAVLQSSGLYSL SSVVTVPSSSLGTQTYICNVNHKPSNTKVDKKVEPKSC DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK | 116 |
| Anti-CEA (A5B7) light chain | QAVLTQPASLSASPGASASLTCTLRRGINVGAYSIYWY QQKPGSPPQYLLRYKSDSDKQQGSGVSSRFSASKDASA NAGILLISGLQSEDEADYYCMIWHSGASAVFGGGTKLT VLRTVAAPSVFIFPPSDEQLKSGTASVVCLLNNFYPREA KVQWKVDNALQSGNSQESVTEQDSKDSTYSLSSTLTLS KADYEKHKVYACEVTHQGLSSPVTKSFNRGEC | 117 |
| Anti-CEA (T84.66LCHA) PGLALA heavy chain | QVQLVQSGAEVKKPGSSVKVSCKASGFNIKDTYMHW VRQAPGQGLEWMGRIDPANGNSKYVPKFQGRVTITAD TSTSTAYMELSSLRSEDTAVYYCAPFGYYVSDYAMAY WGQGTLVTVSSASTKGPSVFPLAPSSKSTSGGTAALGC LVKDYFPEPVTVSWNSGALTSGVHTFPAVLQSSGLYSL SSVVTVPSSSLGTQTYICNVNHKPSNTKVDKKVEPKSC DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK | 118 |
| Anti-CEA (T84.66LCHA) light chain | EIVLTQSPATLSLSPGERATLSCRAGESVDIFGVGFLHW YQQKPGQAPRLLIYRASNRATGIPARFSGSGSGTDFLT ISSLEPEDFAVYYCQQTNEDPYTFGQGTKLEIKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC | 119 |
| Anti-CEA (CH1A1A98/992F1) PGLALA heavy chain | QVQLVQSGAEVKKPGASVKVSCKASGYTFTEFGMNW VRQAPGQGLEWMGWINTKTGEATYVEEFKGRVTFTTD TSTSTAYMELRSLRSDDTAVYYCARWDFAYYVEAMD YWGQGTTVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKKVEPKS CDKTHTCPPCPAPEAAGGPSVFLFPPKPKDTLMISRTPE | 120 |

TABLE 12-continued

| Construct | Amino acid sequence | SEQ ID NO |
|---|---|---|
| | VTCVVVDVSHEDPEVKFNWYVDGVEVHNAKTKPREE QYNSTYRVVSVLTVLHQDWLNGKEYKCKVSNKALGA PIEKTISKAKGQPREPQVCTLPPSRDELTKNQVSLSCAV KGFYPSDIAVEWESNGQPENNYKTTPPVLDSDGSFFLV SKLTVDKSRWQQGNVFSCSVMHEALHNHYTQKSLSLS PGK | |
| Anti-CEA (CH1A1A98/992F1) light chain | DIQMTQSPSSLSASVGDRVTITCKASAAVGTYVAWYQ QKPGKAPKLLIYSASYRKRGVPSRFSGSGSGTDFTLTISS LQPEDFATYYCHQYYTYPLFTFGQGTKLEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | 121 |
| Anti-CEA (hMN14) PGLALA heavy chain | EVQLVESGGGVVQPGRSLRLSCSASGFDFTTYWMSWV RQAPGKGLEWIGEIHPDSSTINYAPSLKDRFTISRDNAK NTLFLQMDSLRPEDTGVYFCASLYFGFPWFAYWGQGT PVTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPEAAGGPSVFLFPPKPKDTLMISRTPEVTCVVVD VSHEDPEVKFNWYVDGVEVHNAKTKPREEQYNSTYR VVSVLTVLHQDWLNGKEYKCKVSNKALGAPIEKTISK AKGQPREPQVYTLPPSRDELTKNQVSLTCLVKGFYPSDI AVEWESNGQPENNYKTTPPVLDSDGSFFLYSKLTVDKS RWQQGNVFSCSVMHEALHNHYTQKSLSLSPGK | 122 |
| Anti-CEA (hMN14) light chain | DIQLTQSPSSLSASVGDRVTITCKASQDVGTSVAWYQQ KPGKAPKLLIYWTSTRHTGVPSRFSGSGSGTDFTLTISSL QPEDIATYYCQQYSLYRSFGQGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | 123 |
| Anti-TNC (2B10) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARLYGYAYYGAFDYW GQGTTVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPEAAGGPSVFLFPPKPKDTLMISRTPEVTC VVVDVSHEDPEVKFNWYVDGVEVHNAKTKPREEQYN STYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPGK | 124 |
| Anti-TNC (2B10) light chain | DIQMTQSPSSLSASVGDRVTITCRASQGIRNDLGWYQQ KPGKAPKRLIYAASSLQSGVPSRFSGSGSGTEFTLTISSL QPEDFATYYCLQNGLQPATFGQGTKVEIKRTVAAPSVF IFPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 125 |
| Anti-HER2 (PER) PG LALA heavy chain 1 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAPIEKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 126 |
| Anti-HER2 (PER) light chain 1 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 127 |

TABLE 12-continued

| Construct | Amino acid sequence | SEQ ID NO |
|---|---|---|
| Anti-HER2 (PER) PG LALA heavy chain 2 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAPIEKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 128 |
| Anti-HER2 (PER) light chain 2 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 129 |
| Human IgG1 Fc | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTV LHQDWLNGKEYKCKVSNKALPAPIEKTISKAKGQPREP QVYTLPPSRDELTKNQVSLTCLVKGFYPSDIAVEWESN GQPENNYKTTPPVLDSDGSFFLYSKLTVDKSRWQQGN VFSCSVMHEALHNHYTQKSLSLSPGK | 130 |

What is claimed is:

1. A transduced T cell capable of expressing an antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutation P329G according to EU numbering, wherein the antigen binding moiety is capable of specific binding to the mutated Fc domain comprising the P329G mutation but not capable of specific binding to the non-mutated parent Fc domain, and wherein the antigen binding moiety comprises:

(A)
  (i) a heavy chain variable region (VH) comprising:
    (a) the heavy chain complementarity-determining region (CDR H) 1 amino acid sequence RYWMN (SEQ ID NO:1);
    (b) the CDR H2 amino acid sequence EITPDSSTI-NYTPSLKD (SEQ ID NO:2); and
    (c) the CDR H3 amino acid sequence PYDGAW-FAS (SEQ ID NO:3); and
  (ii) a light chain variable region (VL) comprising:
    (d) the light chain complementarity-determining region (CDR L) 1 amino acid sequence RSST-GAVTTSNYAN (SEQ ID NO:4);
    (e) the CDR L2 amino acid sequence GTNKRAP (SEQ ID NO:5); and
    (f) the CDR L3 amino acid sequence ALWYSNHWV (SEQ ID NO:6); or
(B)
  (i) a VH comprising the amino acid sequence of SEQ ID NO:8; and
  (ii) a VL comprising the amino acid sequence of SEQ ID NO:9.

2. The transduced T cell of claim 1, wherein the anchoring transmembrane domain is a transmembrane domain selected from the group consisting of the CD8, the CD3z, the FCGR3A, the NKG2D, the CD27, the CD28, the CD137, the OX40, the ICOS, the DAP10, and the DAP12 transmembrane domain, or a fragment thereof.

3. The transduced T cell of claim 2, wherein the anchoring transmembrane domain is the CD28 transmembrane domain, or a fragment thereof.

4. The transduced T cell of claim 1, wherein the antigen binding moiety is a scFv, a Fab, a crossFab, or a scFab.

5. The transduced T cell of claim 4, wherein the scFv, the Fab, the crossFab, or the scFab is humanized.

6. The transduced T cell of claim 4, wherein the antigen binding moiety is a scFv comprising the amino acid sequence of SEQ ID NO:10.

7. The transduced T cell of claim 4, wherein the antigen binding moiety is a scFv, wherein the scFv is connected at the C-terminus to the N-terminus of the anchoring transmembrane domain.

8. The transduced T cell of claim 7, wherein the scFv is connected to the anchoring transmembrane domain through a peptide linker.

9. The transduced T cell of claim 4, wherein the antigen binding moiety is a Fab or a crossFab, wherein the Fab or the crossFab is connected at the C-terminus of the heavy chain to the N-terminus of the anchoring transmembrane domain.

10. The transduced T cell of claim 9, wherein the Fab or the crossFab is connected to the anchoring transmembrane domain through a peptide linker.

11. The transduced T cell of claim 1, wherein the mutated Fc domain further comprises at least one amino acid mutation at a position selected from the group consisting of L234, L235, P331, and N297, according to EU numbering.

12. The transduced T cell of claim 11, wherein the amino acid mutation is L234A, L235A, P331S, and/or N297A.

13. The transduced T cell of claim 1, further comprising at least one stimulatory signaling domain and/or at least one co-stimulatory signaling domain.

14. The transduced T cell of claim 13, wherein the at least one stimulatory signaling domain is individually selected from the group consisting of the intracellular domain of CD3z, of FCGR3A, and of NKG2D, or fragments thereof.

15. The transduced T cell of claim 14, wherein the at least one stimulatory signaling domain is the intracellular domain of CD3z, or a fragment thereof.

16. The transduced T cell of claim 13, wherein the at least one co-stimulatory signaling domain is individually selected from the group consisting of the intracellular domain of CD27, of CD28, of CD137, of OX40, of ICOS, of DAP10, and of DAP12, or fragments thereof.

17. The transduced T cell of claim 16, wherein the at least one co-stimulatory signaling domain is the intracellular domain of CD28, or a fragment thereof.

18. The transduced T cell of claim 13, wherein the antigen binding receptor comprises one stimulatory signaling domain comprising the intracellular domain of CD3z, or a fragment thereof, and one co-stimulatory signaling domain comprising the intracellular domain of CD28, or a fragment thereof.

19. A transduced T cell capable of expressing an antigen binding receptor comprising an anchoring transmembrane domain and an extracellular domain comprising an antigen binding moiety, wherein the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutations I253A, H310A, and H435A according to EU numbering, wherein the antigen binding moiety is capable of specific binding to the mutated Fc domain comprising the I253A, H310A, and H435A mutations but not capable of specific binding to the non-mutated parent Fc domain, and wherein the antigen binding moiety comprises:
(A)
  (i) a heavy chain variable region (VH) comprising:
    (a) the heavy chain complementarity-determining region (CDR H) 1 amino acid sequence SYGMS (SEQ ID NO:53);
    (b) the CDR H2 amino acid sequence SSGGSY (SEQ ID NO:54); and
    (c) the CDR H3 amino acid sequence LGMITTG-YAMDY (SEQ ID NO:55); and
  (ii) a light chain variable region (VL) comprising:
    (d) the light chain complementary-determining region (CDR L) 1 amino acid sequence RSSQ-TIVHSTGHTYLE (SEQ ID NO:56);
    (e) the CDR L2 amino acid sequence KVSNRFS (SEQ ID NO:57); and
    (f) the CDR L3 amino acid sequence FQGSHVPYT (SEQ ID NO:58); or
(B)
  (i) a VH comprising the amino acid sequence of SEQ ID NO: 61; and
  (ii) a VL comprising the amino acid sequence of SEQ ID NO: 62.

20. An isolated polynucleotide encoding an antigen binding receptor comprising an anchoring transmembrane domain and an extracellular domain comprising an antigen binding moiety, wherein the antigen binding moiety is capable of specific binding to a mutated fragment crystallizable (Fc) domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutation P329G according to EU numbering, wherein the antigen binding moiety is capable of specific binding to the mutated Fc domain comprising the P329G mutation but not capable of specific binding to the non-mutated parent Fc domain, and wherein the antigen binding moiety comprises:
(A)
  (i) a heavy chain variable region (VH) comprising:
    (a) the heavy chain complementarity-determining region (CDR H) 1 amino acid sequence RYWMN (SEQ ID NO:1);
    (b) the CDR H2 amino acid sequence EITPDSSTI-NYTPSLKD (SEQ ID NO:2); and
    (c) the CDR H3 amino acid sequence PYDYGAW-FAS (SEQ ID NO:3); and
  (ii) a light chain variable region (VL) comprising:
    (d) the light chain complementary-determining region (CDR L) 1 amino acid sequence RSST-GAVTTSNYAN (SEQ ID NO:4);
    (e) the CDR L2 amino acid sequence GTNKRAP (SEQ ID NO:5); and
    (f) the CDR L3 amino acid sequence ALWYSNHWV (SEQ ID NO:6); or
(B)
  (i) a VH comprising the amino acid sequence of SEQ ID NO:8; and
  (ii) a VL comprising the amino acid sequence of SEQ ID NO:9.

21. An isolated polynucleotide encoding an antigen binding receptor comprising an anchoring transmembrane domain and an extracellular domain comprising an antigen binding moiety, wherein the antigen binding moiety is capable of specific binding to a mutated Fc domain but not capable of specific binding to the non-mutated parent Fc domain, wherein the mutated Fc domain comprises at least one amino acid substitution compared to the non-mutated parent Fc domain, wherein the mutated Fc domain comprises the amino acid mutations I253A, H310A, and H435A according to EU numbering, wherein the antigen binding moiety is capable of specific binding to the mutated Fc domain comprising the I253A, H310A, and H435A mutations but not capable of specific binding to the non-mutated parent Fc domain, and wherein the antigen binding moiety comprises:
(A)
  (i) a heavy chain variable region (VH) comprising:
    (a) the heavy chain complementarity-determining region (CDR H) 1 amino acid sequence SYGMS (SEQ ID NO:53);
    (b) the CDR H2 amino acid sequence SSGGSY (SEQ ID NO:54); and
    (c) the CDR H3 amino acid sequence LGMITTG-YAMDY (SEQ ID NO:55); and
  (ii) a light chain variable region (VL) comprising:
    (d) the light chain complementary-determining region (CDR L) 1 amino acid sequence RSSQ-TIVHSTGHTYLE (SEQ ID NO:56);
    (e) the CDR L2 amino acid sequence KVSNRFS (SEQ ID NO:57); and
    (f) the CDR L3 amino acid sequence FQGSHVPYT (SEQ ID NO:58); or
(B)
  (i) a VH comprising the amino acid sequence of SEQ ID NO: 61; and
  (ii) a VL comprising the amino acid sequence of SEQ ID NO: 62.

22. A vector comprising the polynucleotide of claim 20.

23. A vector comprising the polynucleotide of claim 21.

24. A kit comprising:
(i) the transduced T cell of claim 1; and
(ii) an antibody comprising a mutated Fc domain,
wherein the antigen binding receptor expressed by the transduced T cell is capable of specific binding to the mutated Fc domain but not capable of specific binding to the non-mutated parent Fc domain.

25. The kit of claim 24, wherein the antibody comprising the mutated Fc domain is capable of specific binding to an antigen selected from the group consisting of fibroblast activation protein (FAP), carcinoembryonic antigen (CEA), mesothelin (MSLN), CD20, folate receptor 1 (FOLR1), and tenascin (TNC).

26. A kit comprising:
(i) the transduced T cell of claim 19; and
(ii) an antibody comprising a mutated Fc domain,
wherein the antigen binding receptor expressed by the transduced T cell is capable of specific binding to the mutated Fc domain but not capable of specific binding to the non-mutated parent Fc domain.

27. A kit comprising:
(i) the isolated polynucleotide of claim 20; and
(ii) an antibody comprising a mutated Fc domain,
wherein the antigen binding receptor encoded by the isolated polynucleotide is capable of specific binding to the mutated Fc domain but not capable of specific binding to the non-mutated parent Fc domain.

28. A kit comprising:
(i) the isolated polynucleotide of claim 21; and
(ii) an antibody comprising a mutated Fc domain,
wherein the antigen binding receptor encoded by the isolated polynucleotide is capable of specific binding to the mutated Fc domain but not capable of specific binding to the non-mutated parent Fc domain.

* * * * *